(12) United States Patent
Akerström et al.

(10) Patent No.: US 6,187,548 B1
(45) Date of Patent: Feb. 13, 2001

(54) METHODS USING HUMAN CALCIUM SENSOR PROTEIN, FRAGMENTS THEREOF AND DNA ENCODING SAME

(75) Inventors: Göran Akerström; Claes Juhlin; Lars Rask; Göran Hjälm, all of Uppsala (SE); Clarence C. Morse, Royersford, PA (US); Edward M. Murray, Drexel Hill, PA (US); Gregg R. Crumley, Philadelphia, PA (US)

(73) Assignee: Rhone-Poulenc Rorer Pharmaceuticals Inc., Collegeville, PA (US)

(*) Notice: Under 35 U.S.C. 154(b), the term of this patent shall be extended for 0 days.

(21) Appl. No.: 08/652,877

(22) Filed: May 23, 1996

Related U.S. Application Data

(63) Continuation-in-part of application No. PCT/US95/15203, filed on Nov. 22, 1995, which is a continuation-in-part of application No. 08/487,314, filed on Jun. 7, 1995, which is a continuation-in-part of application No. 08/344,836, filed on Nov. 23, 1994, now abandoned, which is a continuation-in-part of application No. PCT/SE94/00483, filed on May 23, 1993.

(30) Foreign Application Priority Data

May 23, 1993 (SE) .................................... 9301764

(51) Int. Cl.⁷ .......................... G01N 33/53; G01N 33/567
(52) U.S. Cl. ........................... 435/7.2; 435/7.1; 435/7.21; 436/501; 436/503
(58) Field of Search ........................... 435/7.1, 7.2, 7.21; 436/501, 503

(56) References Cited

FOREIGN PATENT DOCUMENTS 358977 3/1990 (EP) .

OTHER PUBLICATIONS

Kounnas et al., *JBC*, vol. 267, pp. 21162–21166, 1992.
Kounnas et al., *JBC*, vol. 270, pp. 13070–13075, Jun. 2, 1995.
Juhlin, C. et al., 500–Kilodalton Calcium Sensor Regulating Cytoplasmic Ca2+ in CytotrophoblastCells of Human Placenta, The Journal of Biological Chemistry 265, 8275–8279 (1990).
Saito, A. et al., Complete Cloning and Sequencing of Rat gp330/"Megalin," a Dinstinctive Member of the Low Density Liproprotein Receptor Gene Family, Proceedings of the National Academy of Science 91, 9725–9729 (1994).
Raychowdhury, R. et al., Autoimmune Target in Heymann Nephritis is a Glycoprotein with Homology to the LDL Receptor, Science 244, 1163–1165 (1989).
Juhlin, C. et al., Monoclonal Antibodies with Exclusive Reactivity Against Parathyroid Cells and Tubule cells of the Kidney, Proceedings of the National Academy of Science 84, 2990–2994 (1987).
Lundgren, S. et al., A Protein Involved in Calcium Sensing of the Human Parathyroid and Placental Cytotrophoblast Cells Belongs to the LDL–Receptor Protein Superfamily, Experimental Cell Research 212, 344–350 (1994).
Brown, E. et al., Molecular Mechanisms Underlysing the Sensing of Extracellular Ca2+ by Parathryroid and Kidney Cells, Europearn Journal of Endocrinology 132, 523–531 (1995).
Moestrup, S., The alpha2–Macroglobulin Receptor and Epithelial Glycoprotein–330: Two Giant Receptors Mediating Endocytosis of Multiple Ligands, Biochimica et Biophysica Acta 1197 197–213 (1994).
Farquhar, M. et al., gp330 and RAP: The Heymann Nephritis Antigenic Complex, Annals New York Academy of Sciences 737, 96–113 (1994).
Kounnas, m. et al., An Overview of the Structure and Function of Glycoprotein 330, a Receptor Related to the alpha2–macroglobulin Receptor, Annals New York Academy of Sciences 737, 114–123 (1994).
Moestrup, S. et al., Binding and Endocytosis of Proteins Mediated by Epithelial gp330, Annals New York Academy of Sciences 737, 124–137 (1994).
Zlokovic et al., Glycoprotein 330/megalin: Probable role in receptor–mediated transport of apolipoprotein J alone and in a complex with Alzheimer disease amyloid β at the blood–brain and blood–cerebrospinal fluid barriers, Proc. Natl. Acad. Sci., USA 93, 4229–4234 (1996).

*Primary Examiner*—Anthony C. Caputa
*Assistant Examiner*—Stephen Gucker
(74) *Attorney, Agent, or Firm*—Finnegan, Henderson, Farabow, Garrett & Dunner, L.L.P.

(57) ABSTRACT

The present invention relates to the isolation of a cDNA clone encoding the calcium sensor in human placenta and subsequent Northern blots confirming the mRNA expression also in human parathyroid and kidney tubule cells. Close sequence similarity is demonstrated with the rat *Heymann nephritis* antigen, a glycoprotein of the kidney tubule brush border with calcium binding ability. Immunohistochemistry substantiates a tissue distribution of the calcium sensor protein similar to that previously described for the Heymann antigen. It is proposed that the identified calcium sensor protein constitutes a universal sensor for recognition of variation in extracellular calcium, and that it plays a key role for calcium regulation via different organ systems. The calcium sensor protein belongs to the LDL-superfamily of glycoproteins, claimed to function primarily as protein receptors, but with functionally important calcium binding capacity.

2 Claims, 16 Drawing Sheets

292: X-A-M-N-P-Y-S-L-D-I-F-E-D-Q-L-Y-W
293: X-V-M-Q-P-D-G-I-A-X-D-W-V

```
                    27                                                                54
AAA TAC GTA ATG CAG CCA GAT GGA ATA GCA GTG GAC TGG GTT GGA AGG CAT ATT
 K   Y   V   M   Q   P   D   G   I   A   V   D   W   V   G   R   H   I
                                         81                                          108
TAC TGG TCA GAT GTC AAG AAT AAA CGC ATT GAG GTG GCT AAA CTT GAT GGA AGG
                                        135                                          162
TAC AGA AAG TGG CTG ATT TCC ACT GAC CTG GAC CAA CCA GCT GCT ATT GCT GTG
 Y   R   K   W   L   I   S   T   D   L   D   Q   P   A   A   I   A   V
                                        189                                          216
AAT CCC AAA CTA GGG CTT ATG TTC TGG ACT GAC TGG GGA AAG GAA CCT AAA ATC
 N   P   K   L   G   L   M   F   W   T   D   W   G   K   E   P   K   I
                                        243                                          270
GAG TCT GCC TGG ATG AAT GGA GAG GAC CGC AAC ATC CTG GTT TTC GAG GAC CTT
 E   S   A   W   M   N   G   E   D   R   N   I   L   V   F   E   D   L
                                        297                                          324
GGT TGG CCA ACT GGC CTT TCT ATC GAT TAT TTG AAC AAT GAC CGA ATC TAC TGG
 G   W   P   T   G   L   S   I   D   Y   L   N   N   D   R   I   Y   W
                                        351                                          378
AGT GAC TTC AAG GAG GAC GTT ATT GAA ACC ATA AAA TAT GAT GGG ACT GAT AGG
 S   D   F   K   E   D   V   I   E   T   I   K   Y   D   G   T   D   R
                                        405                                          432
AGA GTC ATT GCA AAG GAA GCA ATG AAC CCT TAC AGC CTG GAC ATC TTT GAA GAC
 R   V   I   A   K   E   A   M   N   P   Y   S   L   D   I   F   E   D
                                        459                                          486
CAG TTA TAC TGG ATA TCT AAG GAA AAG GGA GAA GTA TGG AAA CAA AAT AAA TTT
 Q   L   Y   W   I   S   K   E   K   G   E   V   W   K   Q   N   K   F
                                        513                                          540
GGG CAA GGA AAG AAA GAG AAA ACG CTG GTA GTG AAC CCT TGG CTC ACT CAA GTT
 G   Q   G   K   K   E   K   T   L   V   V   N   P   W   L   T   Q   V
                                        567                                          594
CGA ATC TTT CAT CAA CTC AGA TAC AAT AAG TCA GTG CCC AAC CTT TGC AAA CAG
 R   I   F   H   Q   L   R   Y   N   K   S   V   P   N   L   C   K   Q
                                        621                                          648
ATC TGC AGC CAC CTC TGC CTT CTG AGA CCT GGA GGA TAC AGC TGT GCC TGT CCC
 I   C   S   H   L   C   L   L   R   P   G   G   Y   S   C   A   C   P
                                        675                                          702
CAA GGC TCC AGC TTT ATA GAG GGG AGC ACC ACT GAG TGT GAT GCA GCC ATC GAA
 Q   G   S   S   F   I   E   G   S   T   T   E   C   D   A   A   I   E
                                        729                                          756
CTG CCT ATC AAC CTG CCC CCC CCA TGC AGG TGC ATG CAC GGA GGA AAT TGC TAT
 L   P   I   N   L   P   P   P   C   R   C   M   H   G   G   N   C   Y
                                        783
TTT GAT GAG ACT GAC CTC CCC AAA TGC AAG TGT CCT AGC GGC TAC ACC
 F   D   E   T   D   L   P   K   C   K   C   P   S   G   Y   T
```

FIG. 3

```
CA-SEN    KYVMQPDGIAVDWVGRHIYWSDVKNKRIEVAKLDGRYRKWLISTDLDQPAAIAVNPKLGL
HEYMANN   XXXXX***L*************ANSQ*****T**********T*Q***************
LDL-RRP   TGLSN***L******GNL**C*KGRDT***S**N*A**TV*V*SG*RE*R*LV*DVQN*Y
LDL-RC    RDIQA***L****IHSN***T*SVLGTVS**DTK*VK**T*FRENGSK*R**V*D*VH*F

CA-SEN    MFWTDWGKEPKIESAWMNGEDRNILVFEDLGWPTGLSIDYLNNDRIYWSDFKEDVIETIK
HEYMANN   *****Q**Q***********H*SV**S*N**W*N********D**V****S******A**
LDL-RRP   LY*****DHSL*GRIG*D*SS*SVI*DTKITW*N**TL**VTE-****A*AR**Y**FAS
LDL-RC    *Y*****TPA**KKGGL**V*IYS**T*NIQW*N*ITL*L*SG-*L**V*S*LHS*SS*D

CA-SEN    YDGTDRRVIAKEAMN---PYSLDIFEDQLYWI-SKEKGEVWKQNKFGQGKKEKTLVVNPW
HEYMANN   *******L*IN***K---*F*******K***VAXXXXXXXXXR*****KEN***V******
LDL-RRP   L**SN*H*VLSQD--IPHIFA*TL*YVTDWET*S-INRAH*TTGTN*TLLISTLHR
LDL-RC    *N*GN*KT*LEDEKRLAH*FAV*KVF*TDIINEA-IFSA*RLTGSDVNLLAENLLS

CA-SEN    LTQVRIFHQLRYNKSVPNLCKQI------CSHLCLLRPGG------YSCACPQGSSFIEG
HEYMANN   *****XXXXXXXXXXXXXX***V------***********------*********D*VT*
LDL-RRP   PMDLHV**A**-QPD***--HPCKVNNGG**N****S***GHK-----****TNF-YLGS
LDL-RC    PEDMVL**N*T-QPRGV*W*ERTTLSNGG*QY***PA*QINPHSPKFT****D*M-LLAR

CA-SEN    STTECDAAIELPINL--PPPC-----RCMHGGNCYFDETDLPKC---KCPSGYT
HEYMANN   **VQ*XXXXXX*VTM--****-----************NE****---**S***S
LDL-RRP   DGRT*VSNCTASQFVCKNDK*IPFWWK*DTEDD*GDHSDEP*D*PEF**RP*QF
LDL-RC    DMRS*LTEA*AAV---ATQETSTVRLKVSSTAVRTQHT*TR*V-------PDTS
```

```
CAA GGC TGT GAG GAG AGG ACA TGC CAT CCT GTG GGG GAT TTC CGC TGT    48
Gln Gly Cys Glu Glu Arg Thr Cys His Pro Val Gly Asp Phe Arg Cys
 1           5                  10                  15
AAA ACT CAC CAC TGC ATC CCT CTT CGT TGG CAG TGT GAT GGG CAA AAT    96
Lys Thr His His Cys Ile Pro Leu Arg Trp Gln Cys Asp Gly Gln Asn
             20                  25                  30
GAC TGT GGA GAT AAC TCA GAT GAG GAA AAC TGT GCT CCC CGG GAG TGC   144
Asp Cys Gly Asp Asn Ser Asp Glu Glu Asn Cys Ala Pro Arg Glu Gys
         35                  40                  45
ACA GAG AGC GAG TTT CGA TGT GTC AAT CAG CAG TGC ATT CCC TCG CGA   192
Thr Glu Ser Glu Phe Arg Cys Val Asn Gln Gln Cys Ile Pro Ser Arg
     50                  55                  60
TGG ATC TGT GAC CAT TAC AAC GAC TGT GGG GAC AAC TCA GAT GAA CGG   240
Trp Ile Cys Asp His Tyr Asn Asp Cys Gly Asp Asn Ser Asp Glu Arg
 65                  70                  75                  80
GAC TGT GAG ATG AGG ACC TGC CAT CCT GAA TAT TTT GAG TGT ACA AGT   288
Asp Cys Glu Met Arg Thr Cys His Pro Glu Tyr Phe Gln Cys Thr Ser
                 85                  90                  95
GGA CAT TGT GTA CAC AGT GAA CTG AAA TGC GAT GGA TCC GCT GAC TGT   336
Gly His Cys Val His Ser Glu Leu Lys Cys Asp Gly Ser Ala Asp Cys
            100                 105                 110
TTG GAT GCG TCT GAT GAA GCT GAT TGT CCC ACA CGC TTT CCT GAT GGT   384
Leu Asp Ala Ser Asp Glu Ala Asp Cys Pro Thr Arg Phe Pro Asp Gly
        115                 120                 125
GCA TAC TGC CAG GCT ACT ATG TTC GAA TGC AAA AAC CAT GTT TGT ATC   432
Ala Tyr Cys Gln Ala Thr Met Phe Glu Cys Lys Asn His Val Cys Ile
    130                 135                 140
CCG CCA TAT TGG AAA TGT GAT GGC GAT GAT GAC TGT GGC GAT GGT TCA   480
Pro Pro Tyr Trp Lys Cys Asp Gly Asp Asp Asp Cys Gly Asp Gly Ser
145                 150                 155                 160
GAT GAA GAA CTT CAC CTG TGC TTG GAT GTT CCC TGT AAT TCA CCA AAC   528
Asp Glu Glu Leu His Leu Cys Leu Asp Val Pro Cys Asn Ser Pro Asn
                165                 170                 175
CGT TTC CGG TGT GAC AAC AAT CGC TGC ATT TAT AGT CAT GAG GTG TGC   576
Arg Phe Arg Cys Asp Asn Asn Arg Cys Ile Tyr Ser His Glu Val Cys
            180                 185                 190
AAT GGT GTG GAT GAC TGT GGA GAT GGA ACT GAT GAG ACA GAG GAG CAC   624
Asn Gly Val Asp Asp Cys Gly Asp Gly Thr Asp Glu Thr Glu Glu His
        195                 200                 205
TGT AGA AAA CCG ACC CCT AAA CCT TGT ACA GAA TAT GAA TAT AAG TGT   672
Cys Arg Lys Pro Thr Pro Lys Pro Cys thr Glu Tyr Glu Tyr Lys Cys
    210                 215                 220
```

*FIG. 6*

```
GGC AAT GGG CAT TGC ATT CCA CAT GAC AAT GTG TGT GAT GAT GCC GAT    720
Gly Asn Gly His Cys Ile Pro His Asp Asn Val Cys Asp Asp Ala Asp
225             230                 235                 240
GAC TGT GGT GAC TGG TCC GAT GAA CTG GGT TGC AAT AAA GGA AAA GAA    768
Asp Cys Gly Asp Trp Ser Asp Glu Leu Gly Cys Asn Lys Gly Lys Glu
                245                 250                 255
AGA ACA TGT GCT GAA AAT ATA TGC GAG CAA AAT TGT ACC CAA TTA AAT    816
Arg Thr Cys Ala Glu Asn Ile Cys Glu Gln Asn Cys Thr Gln Leu Asn
                260                 265                 270
GAA GGA GGA TTT ATC TGC TCC TGT ACA GCT GGG TTC GAA ACC AAT GTT    864
Glu Gly Gly Phe Ile Cys Ser Cys Thr Ala Gly Phe Glu Thr Asn Val
                275                 280                 285
TTT GAC AGA ACC TCC TGT CTA GAT ATC AAT GAA TGT GAA CAA TTT GGG    912
Phe Asp Arg Thr Ser Cys Leu Asp Ile Asn Glu Cys Glu Gln Phe Gly
            290                 295                 300
ACT TGT CCC CAG CAC TGC AGA AAT ACC AAA GGA AGT TAT GAG TGT GTC    960
Thr Cys Pro Gln His Cys Arg Asn Thr Lys Gly Ser Tyr Glu Cys Val
305             310                 315                 320
TGT GCT GAT GGC TTC ACG TCT ATG AGT GAC CGC CCT GGA AAA CGA TGT   1008
Cys Ala Asp Gly Phe Thr Ser Met Ser Asp Arg Pro Gly Lys Arg Cys
                325                 330                 335
GCA GCT GAG GGT AGC TCT CCT TTG TTG CTA CTG CCT GAC AAT GTC CGA   1056
Ala Ala Glu Gly Ser Ser Pro Leu Leu Leu Leu Pro Asp Asn Val Arg
                340                 345                 350
ATT CGA AAA TAT AAT CTC TCA TCT GAG AGG TTC TCA GAG TAT CTT CAA   1104
Ile Arg Lys Tyr Asn Leu Ser Ser Glu Arg Phe Ser Glu Tyr Leu Gln
                355                 360                 365
GAT GAG GAA TAT ATC CAA GCT GTT GAT TAT GAT TGG GAT CCC AAG GAC   1152
Asp Glu Glu Tyr Ile Gln Ala Val Asp Tyr Asp Trp Asp Pro Lys Asp
            370                 375                 380
ATA GGC CTC AGT GTT GTG TAT TAC ACT GTG CGA GGG GAG GGC TCT AGG   1200
Ile Gly Leu Ser Val Val Tyr Tyr Thr Val Arg Gly Glu Gly Ser Arg
385             390                 395                 400
TTT GGT GCT ATC AAA CGT GCC TAC ATC CCC AAC TTT GAA TCC GGC CGC   1248
Phe Gly Ala Ile Lys Arg Ala Tyr Ile Pro Asn Phe Glu Ser Gly Arg
                405                 410                 415
AAT AAT CTT GTG CAG GAA GTT GAC CTG AAA CTG AAA TAC GTA ATG CAG   1296
Asn Asn Leu Val Gln Glu Val Asp Leu Lys Leu Lys Tyr Val Met Gln
                420                 425                 430
CCA GAT GGA ATA GCA GTG GAC TGG GTT GGA AGG CAT ATT TAC TGG TCA   1344
Pro Asp Gly Ile Ala Val Asp Trp Val Gly Arg His Ile Tyr Trp Ser
            435                 440                 445
GAT GTC AAG AAT AAA CGC ATT GAG GTG GCT AAA CTT GAT GGA AGG TAC   1392
```

*FIG. 6 CONT.*

```
                Asp Val Lys Asn Lys Arg Ile Glu Val Ala Lys Leu Asp Gly Arg Tyr
                    450                 455                 460
AGA AAG TGG CTG ATT TCC ACT GAC CTG GAC CAA CCA GCT GCT ATT GCT            1440
Arg Lys Trp Leu Ile Ser Thr Asp Leu Asp Gln Pro Ala Ala Ile Ala
465                 470                 475                 480
GTG AAT CCC AAA CTA GGG CTT ATG TTC TGG ACT GAC TGG GGA AAG GAA            1488
Val Asn Pro Lys Leu Gly Leu Met Phe Trp Thr Asp Trp Gly Lys Glu
                    485                 490                 495
CCT AAA ATC GAG TCT GCC TGG ATG AAT GGA GAG GAC CGC AAC ATC CTG            1536
Pro Lys Ile Glu Ser Ala Trp Met Asn Gly Glu Asp Arg Asn Ile Leu
                500                 505                 510
GTT TTC GAG GAC CTT GGT TGG CCA ACT GGC CTT TCT ATC GAT TAT TTG            1584
Val Phe Glu Asp Leu Gly Trp Pro Thr Gly Leu Ser Ile Asp Tyr Leu
            515                 520                 525
AAC AAT GAC CGA ATC TAC TGG AGT GAC TTC AAG GAG GAC GTT ATT GAA            1632
Asn Asn Asp Arg Ile Tyr Trp Ser Asp Phe Lys Glu Asp Val Ile Glu
            530                 535                 540
ACC ATA AAA TAT GAT GGG ACT GAT AGG AGA GTC ATT GCA AAG GAA GCA            1680
Thr Ile Lys Tyr Asp Gly Thr Asp Arg Arg Val Ile Ala Lys Glu Ala
545                 550                 555                 560
ATG AAC CCT TAC AGC CTG GAC ATC TTT GAA GAC CAG TTA TAC TGG ATA            1728
Met Asn Pro Tyr Ser Leu Asp Ile Phe Glu Asp Gln Leu Tyr Trp Ile
                565                 570                 575
TCT AAG GAA AAG GGA GAA GTA TGG AAA CAA AAT AAA TTT GGG CAA GGA            1776
Ser Lys Glu Lys Gly Glu Val Trp Lys Gln Asn Lys Phe Gly Gln Gly
                580                 585                 590
AAG AAA GAG AAA ACG CTG GTA GTG AAC CCT TGG CTC ACT CAA GTT CGA            1824
Lys Lys Glu Lys Thr Leu Val Val Asn Pro Trp Leu Thr Gln Val Arg
                595                 600                 605
ATC TTT CAT CAA CTC AGA TAC AAT AAG TCA GTG CCC AAC CTT TGC AAA            1872
Ile Phe His Gln Leu Arg Tyr Asn Lys Ser Val Pro Asn Leu Cys Lys
610                 615                 620
CAG ATC TGC AGC CAC CTC TGC CTT CTG AGA CCT GGA GGA TAC AGC TGT            1920
Gln Ile Cys Ser His Leu Cys Leu Leu Arg Pro Gly Gly Tyr Ser Cys
625                 630                 635                 640
GCC TGT CCC CAA GGC TCC AGC TTT ATA GAG GGG AGC ACC ACT GAG TGT            1968
Ala Cys Pro Gln Gly Ser Ser Phe Ile Glu Gly Ser Thr Thr Glu Cys
                645                 650                 655
GAT GCA GCC ATC GAA CTG CCT ATC AAC CTG CCC CCC CCA TGC AGG TGC            2016
Asp Ala Ala Ile Glu Leu Pro Ile Asn Leu Pro Pro Pro Cys Arg Cys
                660                 665                 670
ATG CAC GGA GGA AAT TGC TAT TTT GAT GAG ACT GAC CTC CCC AAA TGC            2064
Met His Gly Gly Asn Cys Tyr Phe Asp Glu Thr Asp Leu Pro Lys Cys
            675                 680                 685
```

*FIG. 6 CONT.*

| | | | | | | | | | | | | | | | |
|---|---|---|---|---|---|---|---|---|---|---|---|---|---|---|---|
| AAG | TGT | CCT | AGC | GGC | TAC | ACC | GGA | AAA | TAT | TGT | GAA | ATG | GCG | TTT | TCA | 2112 |
| Lys | Cys | Pro | Ser | Gly | Tyr | Thr | Gly | Lys | Tyr | Cys | Glu | Met | Ala | Phe | Ser | |
| | 690 | | | | 695 | | | | | 700 | | | | | | |
| AAA | GGC | ATC | TCT | CCA | GGA | ACA | ACC | GCA | GTA | GCT | GTG | CTG | TTG | ACA | ATC | 2160 |
| Lys | Gly | Ile | Ser | Pro | Gly | Thr | Thr | Ala | Val | Ala | Val | Leu | Leu | Thr | Ile | |
| 705 | | | | | 710 | | | | 715 | | | | | | 720 | |
| CTC | TTG | ATC | GTC | GTA | ATT | GGA | GCT | CTG | GCA | ATT | GCA | GGA | TTC | TTC | CAC | 2208 |
| Leu | Leu | Ile | Val | Val | Ile | Gly | Ala | Leu | Ala | Ile | Ala | Gly | Phe | Phe | His | |
| | | | | 725 | | | | 730 | | | | | | 735 | | |
| TAT | AGA | AGG | ACC | GGC | TCC | CTT | TTG | CCT | GCT | CTG | CCC | AAG | CTG | CCA | AGC | 2256 |
| Tyr | Arg | Arg | Thr | Gly | Ser | Leu | Leu | Pro | Ala | Leu | Pro | Lys | Leu | Pro | Ser | |
| | | | 740 | | | | | 745 | | | | | 750 | | | |
| TTA | AGC | AGT | CTC | GTC | AAG | CCC | TCT | GAA | AAT | GGG | AAT | GGG | GTG | ACC | TTC | 2304 |
| Leu | Ser | Ser | Leu | Val | Lys | Pro | Ser | Glu | Asn | Gly | Asn | Gly | Val | Thr | Phe | |
| | | 755 | | | | | 760 | | | | | 765 | | | | |
| AGA | TCA | GGG | GCA | GAT | CTT | AAC | ATG | GAT | ATT | GGA | GTG | TCT | GGT | TTT | GGA | 2352 |
| Arg | Ser | Gly | Ala | Asp | Leu | Asn | Met | Asp | Ile | Gly | Val | Ser | Gly | Phe | Gly | |
| | 770 | | | | | 775 | | | | | 780 | | | | | |
| CCT | GAG | ACT | GCT | ATT | GAC | AGG | TCA | ATG | GCA | ATG | AGT | GAA | GAC | TTT | GTC | 2400 |
| Pro | Glu | Thr | Ala | Ile | Asp | Arg | Ser | Met | Ala | Met | Ser | Glu | Asp | Phe | Val | |
| 785 | | | | | 790 | | | | | 795 | | | | | 800 | |
| ATG | GAA | ATG | GGG | AAG | CAG | CCC | ATA | ATA | TTT | GAA | AAC | CCA | ATG | TAC | TCA | 2448 |
| Met | Glu | Met | Gly | Lys | Gln | Pro | Ile | Ile | Phe | Glu | Asn | Pro | Met | Tyr | Ser | |
| | | | | 805 | | | | | 810 | | | | | 815 | | |
| GCC | AGA | GAC | AGT | GCT | GTC | AAA | GTG | GTT | CAG | CCA | ATC | CAG | GTG | ACT | GTA | 2496 |
| Ala | Arg | Asp | Ser | Ala | Val | Lys | Val | Val | Gln | Pro | Ile | Gln | Val | Thr | Val | |
| | | | 820 | | | | | 825 | | | | | 830 | | | |
| TCT | GAA | AAT | GTG | GAT | AAT | AAG | AAT | TAT | GGA | AGT | CCC | ATA | AAC | CCT | TCT | 2544 |
| Ser | Glu | Asn | Val | Asp | Asn | Lys | Asn | Tyr | Gly | Ser | Pro | Ile | Asn | Pro | Ser | |
| | | 835 | | | | | 840 | | | | | 845 | | | | |
| GAG | ATA | GTT | CCA | GAG | ACA | AAC | CCA | ACT | TCA | CCA | GCT | GCT | GAT | GGA | ACT | 2592 |
| Glu | Ile | Val | Pro | Glu | Thr | Asn | Pro | Thr | Ser | Pro | Ala | Ala | Asp | Gly | Thr | |
| | 850 | | | | | 855 | | | | | 860 | | | | | |
| CAG | GTG | ACA | AAA | TGG | AAT | CTC | TTC | AAA | CGA | AAA | TCT | AAA | CAA | ACT | ACC | 2640 |
| Gln | Val | Thr | Lys | Trp | Asn | Leu | Phe | Lys | Arg | Lys | Ser | Lys | Gln | Thr | Thr | |
| 865 | | | | | 870 | | | | | 875 | | | | | 880 | |
| AAC | TTT | GAA | AAT | CCA | ATC | TAT | GCA | CAG | ATG | GAG | AAC | GAG | CAA | AAG | GAA | 2688 |
| Asn | Phe | Glu | Asn | Pro | Ile | Tyr | Ala | Gln | Met | Glu | Asn | Glu | Gln | Lys | Glu | |
| | | | | 885 | | | | | 890 | | | | | 895 | | |
| AGT | GTT | GCT | GCG | ACA | CCA | CCT | CCA | TCA | CCT | TCG | CTC | CCT | GCT | AAG | CCT | 2736 |
| Ser | Val | Ala | Ala | Thr | Pro | Pro | Pro | Ser | Pro | Ser | Leu | Pro | Ala | Lys | Pro | |
| | | | 900 | | | | | 905 | | | | | 910 | | | |
| AAG | CCT | CCT | TCG | AGA | AGA | GAC | CCA | ACT | CCA | ACC | TAT | TCT | GCA | ACA | GAA | 2784 |

*FIG. 6 CONT.*

```
Lys Pro Pro Ser Arg Arg Asp Pro Thr Pro Thr Tyr Ser Ala Thr Glu
        915                 920             925

GAC ACT TTT AAA GAC ACC GCA AAT CTT GTT AAA GAA GAC TCT GAA GTA        2832
Asp Thr Phe Lys Asp Thr Ala Asn Leu Val Lys Glu Asp Ser Glu Val
        930                 935             940

TAG                                                                    2835
 *
945
```

FIG. 6 CONT.

RRTGSLLPALPKLPSLSSLVKPSENGNGVTFRSGADLNMDIGVSGFGPETAID
RSMAMSEDFVMEMGKQPIIFENPMYSARDSAVKVVQPIQVTVSENVDNKN
YGSPINPSEIVPETNPTSPAADGTQVTKWNLFKRKSKQTTNFENPIYAOMENE
QKESVAATPPPSPSLPAKPKPPSRRDPTPTYSATEDTFKDTANLVKEDSEV

SEQUENCE ALIGNMENT OF SH3-BINDING MOTIFS

Table 5. Sequence Alignment of SH3-Binding Motifs

| SH3-Binding Motif | $P_{-5}$ | $P_{-4}$ | $P_{-3}$ | $P_{-2}$ | $P_{-1}$ | $P_0$ | $P_1$ | $P_2$ | $P_3$ | $P_4$ | $P_5$ |
|---|---|---|---|---|---|---|---|---|---|---|---|
| PI3K library consensus | | | R | X | L | P | P | R | P | X | X |
| Src library consensus | | | R | X | L | P | P | L | P | R | ∅ |
| Murine 38P1(267-277) | | P | T | M | P | P | P | L | P | P | V | P |
| Murine 38P2-40(2-12) | | P | A | Y | P | P | P | P | V | P | V | P |
| Mouse Sos1(1146-1156) | | E | V | P | V | P | P | P | V | P | P | R |
| Mouse Sos1(1174-1184) | | H | L | D | S | P | P | A | l | P | P | R |
| Mouse Sos1(1285-1295) | | H | S | l | A | G | P | P | V | P | P | R |
| Human dynamin(785-795) | | A | P | A | V | P | P | A | R | P | G | S |
| Human dynamin(811-821) | | G | A | P | P | V | P | S | R | P | G | A |
| Human PI3Kp85(91-101) | | P | P | R | P | L | P | V | A | P | G | S |
| Human PI3Kp85(303-313) | | P | A | P | A | L | P | P | K | P | P | K |
| Human GTPase-activated protein CDC42(250-260) | A | P | K | P | M | P | P | R | P | P | L |
| Mouse formin(873-883) | | P | P | T | P | P | P | L | P | P | P | L |
| Rat muscarinic acetylcholine receptor(277-287) | P | A | L | P | P | P | P | R | P | V | P |
| v-Fgr(12-22) | | R | P | R | P | L | P | P | L | P | P | T |
| Human HK2(63-103) | | G | V | R | P | L | P | P | L | P | D | P |
| Human proacrosin(333-343) | P | P | R | P | L | P | P | R | P | P | A |
| SH3-binding site consensus | | | X | p | ∅ | P | p | X | P | | |

Capital letters represent amino acid residues in the SH3-binding motifs.
X represents nonconserved residues, ∅ represents hydrophobic residues, and p
represents residues that tend to be proline. Amino acids that are completely
conserved are boxed. In the case of 38P1, the amino acid position numbers count
from the beginning of the partial cDNA sequence reported by Ciochetti et al. (1992).

```
    x p ∅ P p x P  - SH3 CONSENSUS
    p s L P a k P  - CAS - PEP-1
      s l L P a l P  - CAS - PEP-2
    p a L P k l P  - CAS - PEP-3
```

FIG. 7

CAS-CYP-SH3BR + SH3s

RRTGSLLPALPKLPSLSSLVKPSENGNGVTFRSGADLNMDIGVSGFGPETAID
RSMAMSEDFVMEMGKQPIIFENPMYSARDSAVKVVQPIQVTVSENVDNKN
YGSPINPSEIVPETNPTSPAADGTQVTKWNLFKRKSKQTTNFE̱NPIYAOMENE
QKESVAATPPPSPSLPAKPKPPSRRDPTPTYSATEDTFKDTANLVKEDSEV

<u>pTyr PEPTIDE SPECIFICITY OF SH2 DOMAINS
OF p85 C-TERMINAL SH2</u>

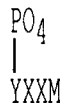

| Binding Sites in Proteins | | |
|---|---|---|
| Sequence | Protein | Tyr Location |
| <u>Known binding sites</u> | | |
| ES<u>D</u>GGYMDMSK<u>DE</u>SV<u>D</u>YVPMLD | Human PDGF receptor β | (Y740. Y751) |
| E<u>EEEE</u>YMPM<u>E</u>DLYLD/LP | Mouse polyoma MT | (Y315) |
| QGV<u>D</u>TYVEMRP | Mouse colony-stimulating factor 1 receptor | (Y721) |
| <u>D</u>STN<u>E</u>YMDMKP | Human c-Kit | (Y721) |
| <u>Possible sites on proteins known to bind p85</u> | | |
| GPGG<u>D</u>YAAMGACPASE<u>Q</u>GYEEMRA | Human ErbB3 | (Y1257.Y1270) |
| TP<u>DEDY</u>EYMNRQR<u>D</u>GGGPGG<u>D</u>YAAMGA | Human ErbB3 | (Y1241.Y1257) |
| CTI<u>D</u>VYMVMVK | Human ErbB3 | (Y922) |
| SPSSGYMPMNQ | Human ErbB3 | (Y1.035) |
| <u>DEDEE</u>YEYMNR | Human ErbB3 | (Y1.178) |
| L<u>EE</u>LGYEYMDV | Human ErbB3 | (Y1.203) |
| <u>EE</u>LSNYICMGG | Rat insulin receptor substrate 1 | (Y460) |
| VSI<u>EE</u>YTEMMP | Rat insulin receptor substrate 1 | (Y546) |
| HT<u>DD</u>GYMPMSP | Rat insulin receptor substrate 1 | (Y608) |
| KGNG<u>D</u>YMPMSP | Rat insulin receptor substrate 1 | (Y628) |
| V<u>D</u>PNGYMMMSP | Rat insulin receptor substrate 1 | (Y658) |
| PCTG<u>D</u>YMNMSP | Rat insulin receptor substrate 1 | (Y727) |
| TGS<u>EE</u>YMNMDL | Rat insulin receptor substrate 1 | (Y939) |
| NSRG<u>D</u>YMTMQI | Rat insulin receptor substrate 1 | (Y987) |
| VAPVSYADMRT | Rat insulin receptor substrate 1 | (Y1.010) |
| <u>ERENE</u>YMPMAPQIHLYSQ/RE | Hamster polyoma MT | (298) |
| LSNPTYSVMRS | Mouse polyoma MT | (Y250) |
| CPEKVYELMRA | Mouse v-Abl oncoprotein | (Y355) |

FIG. 9

Other possible sites

| | | |
|---|---|---|
| NTTVDYVYMSHGDNGDYVYMN | Human papaloma virus 11 E5b | (Y59.Y70) |
| NCNDDYVTMHYTTDGDYIYMN | Human papaloma type 6b E5b | (Y57.Y68) |
| YVNDIYLYMRHLEREFKVRTDYMAMQE | Stamsh G2 cyclin B | (Y149.Y165) |
| NQEEAYVTMSS | Human Il-7 receptor | (Y449) |
| FIASKYEDMYP | Human G2 cyclin b | (Y255) |
| LGSQSYEDMRG | Mouse B cell CD 19 | (Y493) |
| EDADSYENMDK | Mouse B cell CD 19 | (Y522) |
| ELQDDYEDMME | Human red cell band 3 | (Y8) |
| AACVVYEDMSH | Human T cell CD7 | (Y222) |
| APPEEYVPMVK | Chick pp125 | (Y926) |
| IDSCTYEAMYN | Human c-cbl proto-oncogene | (Y731) |
| VAVAEYEIMEQ | Chicken dystrophin | (Y974) |
| MSVESYEEMKM | Aspergillus kinesin-like Birnc | (Y462) |
| HQTREYESMIE | C. elegans kinesin-like Unc-104 | (Y633) |
| TLQNEYELMRE | Human Rb-associated protein 110 | (Y692) |
| GGEEIYVVMLG | Rat s-myc proto-oncogene | (Y247) |
| LEGEHYINMAV | Avian EB virus sea oncoprotein | (Y331) |
| EITEQYIYMVM | Mouse Esk STY kinase | (Y596) |
| TEQYIYMVMEC | Mouse Esk STY kinase | (Y598) |

FIG. 9 (cont.)

| | | |
|---|---|---|
| SEQ ID NO: 83 | CAC AGG GCA TGG | amino acid 1287 (Ala) |
| SEQ ID NO: 89 | CAC AGG GCA TGG | |
| SEQ ID NO: 85 | CAC AGG SCA TGG | S=G or C (gives Ala or Pro) |

| | | |
|---|---|---|
| SEQ ID NO: 83 | CAA TGC GCA TCT | amino acid 2872 (Ala) |
| SEQ ID NO: 89 | CAA TGC GCA TCT | |
| SEQ ID NO: 85 | CAA TGC ACA TCT | (gives Thr) |

| | | |
|---|---|---|
| SEQ ID NO: 83 | GAT CCC AAG GAC | amino acid 4094 (Lys) |
| SEQ ID NO: 89 | GAT CCC GAG GAC | |
| SEQ ID NO: 85 | GAT CCC RAG GAC | R=A or G (gives Lys or Glu) |
| SEQ ID NO: 87 | GAT CCC GAG GAC | |

| | | |
|---|---|---|
| SEQ ID NO: 83 | CCT AAA ATC GAG | amino acid 4210 (Ile) |
| SEQ ID NO: 89 | CCT AAA CTC GAG | |
| SEQ ID NO: 85 | CCT AAA MTC GAG | M=A or C (gives Ile or Leu) |
| SEQ ID NO: 87 | CCT AAA MTC GAG | |

FIG. 12

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
      (A) LENGTH: 17 amino acids
      (B) TYPE: amino acid
      (C) STRANDEDNESS:
      (D) TOPOLOGY: linear (ii) MOLECULE TYPE: peptide (v) FRAGMENT TYPE: internal (xi) SEQUENCE DESCRIPTION: SEQ ID NO:1:

Xaa Ala Met Asn Pro Tyr Ser Leu Asp Ile Phe Glu Asp Gln Leu Tyr
1               5                  10                  15

Trp (2) INFORMATION FOR SEQ ID NO:2:

(i) SEQUENCE CHARACTERISTICS:
      (A) LENGTH: 13 amino acids
      (B) TYPE: amino acid
      (C) STRANDEDNESS:
      (D) TOPOLOGY: linear (ii) MOLECULE TYPE: peptide (v) FRAGMENT TYPE: internal (xi) SEQUENCE DESCRIPTION: SEQ ID NO:2:

```
Xaa Val Met Gln Pro Asp Gly Ile Ala Xaa Asp Trp Val
1               5                   10
```

(2) INFORMATION FOR SEQ ID NO:3:

(i) SEQUENCE CHARACTERISTICS:
        (A) LENGTH: 804 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..804

(xi) SEQUENCE DESCRIPTION: SEQ ID NO:3:

```
AAA TAC GTA ATG CAG CCA GAT GGA ATA GCA GTG GAC TGG GTT GGA AGG      48
Lys Tyr Val Met Gln Pro Asp Gly Ile Ala Val Asp Trp Val Gly Arg
 1               5                  10                  15

CAT ATT TAC TGG TCA GAT GTC AAG AAT AAA CGC ATT GAG GTG GCT AAA      96
His Ile Tyr Trp Ser Asp Val Lys Asn Lys Arg Ile Glu Val Ala Lys
                20                  25                  30

CTT GAT GGA AGG TAC AGA AAG TGG CTG ATT TCC ACT GAC CTG GAC CAA     144
Leu Asp Gly Arg Tyr Arg Lys Trp Leu Ile Ser Thr Asp Leu Asp Gln
             35                  40                  45

CCA GCT GCT ATT GCT GTG AAT CCC AAA CTA GGG CTT ATG TTC TGG ACT     192
Pro Ala Ala Ile Ala Val Asn Pro Lys Leu Gly Leu Met Phe Trp Thr
 50                  55                  60

GAC TGG GGA AAG GAA CCT AAA ATC GAG TCT GCC TGG ATG AAT GGA GAG     240
Asp Trp Gly Lys Glu Pro Lys Ile Glu Ser Ala Trp Met Asn Gly Glu
 65                  70                  75                  80

GAC CGC AAC ATC CTG GTT TTC GAG GAC CTT GGT TGG CCA ACT GGC CTT     288
Asp Arg Asn Ile Leu Val Phe Glu Asp Leu Gly Trp Pro Thr Gly Leu
                 85                  90                  95

TCT ATC GAT TAT TTG AAC AAT GAC CGA ATC TAC TGG AGT GAC TTC AAG     336
Ser Ile Asp Tyr Leu Asn Asn Asp Arg Ile Tyr Trp Ser Asp Phe Lys
            100                 105                 110

GAG GAC GTT ATT GAA ACC ATA AAA TAT GAT GGG ACT GAT AGG AGA GTC     384
Glu Asp Val Ile Glu Thr Ile Lys Tyr Asp Gly Thr Asp Arg Arg Val
        115                 120                 125

ATT GCA AAG GAA GCA ATG AAC CCT TAC AGC CTG GAC ATC TTT GAA GAC     432
Ile Ala Lys Glu Ala Met Asn Pro Tyr Ser Leu Asp Ile Phe Glu Asp
    130                 135                 140

CAG TTA TAC TGG ATA TCT AAG GAA AAG GGA GAA GTA TGG AAA CAA AAT     480
Gln Leu Tyr Trp Ile Ser Lys Glu Lys Gly Glu Val Trp Lys Gln Asn
145                 150                 155                 160

AAA TTT GGG CAA GGA AAG AAA GAG AAA ACG CTG GTA GTG AAC CCT TGG     528
Lys Phe Gly Gln Gly Lys Lys Glu Lys Thr Leu Val Val Asn Pro Trp
                165                 170                 175

CTC ACT CAA GTT CGA ATC TTT CAT CAA CTC AGA TAC AAT AAG TCA GTG     576
Leu Thr Gln Val Arg Ile Phe His Gln Leu Arg Tyr Asn Lys Ser Val
            180                 185                 190

CCC AAC CTT TGC AAA CAG ATC TGC AGC CAC CTC TGC CTT CTG AGA CCT     624
Pro Asn Leu Cys Lys Gln Ile Cys Ser His Leu Cys Leu Leu Arg Pro
        195                 200                 205

GGA GGA TAC AGC TGT GCC TGT CCC CAA GGC TCC AGC TTT ATA GAG GGG     672
Gly Gly Tyr Ser Cys Ala Cys Pro Gln Gly Ser Ser Phe Ile Glu Gly
    210                 215                 220

AGC ACC ACT GAG TGT GAT GCA GCC ATC GAA CTG CCT ATC AAC CTG CCC     720
```

```
Ser Thr Thr Glu Cys Asp Ala Ala Ile Glu Leu Pro Ile Asn Leu Pro
225                 230                 235                 240

CCC CCA TGC AGG TGC ATG CAC GGA GGA AAT TGC TAT TTT GAT GAG ACT        768
Pro Pro Cys Arg Cys Met His Gly Gly Asn Cys Tyr Phe Asp Glu Thr
                245                 250                 255

GAC CTC CCC AAA TGC AAG TGT CCT AGC GGC TAC ACC                        804
Asp Leu Pro Lys Cys Lys Cys Pro Ser Gly Tyr Thr
            260                 265
```

(2) INFORMATION FOR SEQ ID NO:4:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO:4:

```
Lys Tyr Val Met Gln Pro Asp Gly Ile Ala Val Asp Trp Val Gly Arg
  1               5                  10                  15

His Ile Tyr Trp Ser Asp Val Lys Asn Lys Arg Ile Glu Val Ala Lys
             20                  25                  30

Leu Asp Gly Arg Tyr Arg Lys Trp Leu Ile Ser Thr Asp Leu Asp Gln
         35                  40                  45

Pro Ala Ala Ile Ala Val Asn Pro Lys Leu Gly Leu Met Phe Trp Thr
     50                  55                  60

Asp Trp Gly Lys Glu Pro Lys Ile Glu Ser Ala Trp Met Asn Gly Glu
 65                  70                  75                  80

Asp Arg Asn Ile Leu Val Phe Glu Asp Leu Gly Trp Pro Thr Gly Leu
                 85                  90                  95

Ser Ile Asp Tyr Leu Asn Asn Asp Arg Ile Tyr Trp Ser Asp Phe Lys
            100                 105                 110

Glu Asp Val Ile Glu Thr Ile Lys Tyr Asp Gly Thr Asp Arg Arg Val
        115                 120                 125

Ile Ala Lys Glu Ala Met Asn Pro Tyr Ser Leu Asp Ile Phe Glu Asp
    130                 135                 140

Gln Leu Tyr Trp Ile Ser Lys Glu Lys Gly Glu Val Trp Lys Gln Asn
145                 150                 155                 160

Lys Phe Gly Gln Gly Lys Lys Glu Lys Thr Leu Val Val Asn Pro Trp
                165                 170                 175

Leu Thr Gln Val Arg Ile Phe His Gln Leu Arg Tyr Asn Lys Ser Val
            180                 185                 190

Pro Asn Leu Cys Lys Gln Ile Cys Ser His Leu Cys Leu Leu Arg Pro
        195                 200                 205

Gly Gly Tyr Ser Cys Ala Cys Pro Gln Gly Ser Ser Phe Ile Glu Gly
    210                 215                 220

Ser Thr Thr Glu Cys Asp Ala Ala Ile Glu Leu Pro Ile Asn Leu Pro
225                 230                 235                 240

Pro Pro Cys Arg Cys Met His Gly Gly Asn Cys Tyr Phe Asp Glu Thr
                245                 250                 255

Asp Leu Pro Lys Cys Lys Cys Pro Ser Gly Tyr Thr
            260                 265
```

(2) INFORMATION FOR SEQ ID NO:5:

(i) SEQUENCE CHARACTERISTICS:
        (A) LENGTH: 269 amino acids

```
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Xaa Xaa Xaa Xaa Xaa Pro Asp Gly Leu Ala Val Asp Trp Val Gly Arg
1               5                   10                  15

His Ile Tyr Trp Ser Asp Ala Asn Ser Gln Arg Ile Glu Val Ala Thr
                20                  25                  30

Leu Asp Gly Arg Tyr Arg Lys Trp Leu Ile Thr Thr Gln Leu Asp Gln
            35                  40                  45

Pro Ala Ala Ile Ala Val Asn Pro Lys Leu Gly Leu Met Phe Trp Thr
        50                  55                  60

Asp Gln Gly Lys Gln Pro Lys Ile Glu Ser Ala Trp Met Asn Gly Glu
65                  70                  75                  80

His Arg Ser Val Leu Val Ser Glu Asn Leu Gly Trp Pro Asn Gly Leu
                85                  90                  95

Ser Ile Asp Tyr Leu Asn Asp Asp Arg Val Tyr Trp Ser Asp Ser Lys
                100                 105                 110

Glu Asp Val Ile Glu Ala Ile Lys Tyr Asp Gly Thr Asp Arg Arg Leu
                115                 120                 125

Ile Ile Asn Glu Ala Met Lys Pro Phe Ser Leu Asp Ile Phe Glu Asp
130                 135                 140

Lys Leu Tyr Trp Val Ala Xaa Xaa Xaa Xaa Xaa Xaa Xaa Arg Gln
145                 150                 155                 160

Asn Lys Phe Gly Lys Glu Asn Lys Glu Lys Val Leu Val Val Asn Pro
                165                 170                 175

Trp Leu Thr Gln Val Arg Xaa Xaa Xaa Xaa Xaa Xaa Xaa Xaa Xaa
                180                 185                 190

Xaa Xaa Xaa Xaa Cys Lys Gln Val Cys Ser His Leu Cys Leu Leu Arg
            195                 200                 205

Pro Gly Gly Tyr Ser Cys Ala Cys Pro Gln Gly Ser Asp Phe Val Thr
        210                 215                 220

Gly Ser Thr Val Gln Cys Xaa Xaa Xaa Xaa Xaa Xaa Pro Val Thr Met
225                 230                 235                 240

Pro Pro Pro Cys Arg Cys Met His Gly Gly Asn Cys Tyr Phe Asp Glu
                245                 250                 255

Asn Glu Leu Pro Lys Cys Lys Cys Ser Ser Gly Tyr Ser
                260                 265

(2) INFORMATION FOR SEQ ID NO:6:

(i) SEQUENCE CHARACTERISTICS:
        (A) LENGTH: 280 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Arg Asp Ile Gln Ala Pro Asp Gly Leu Ala Val Asp Trp Ile His Ser
1               5                   10                  15

Asn Ile Tyr Trp Thr Asp Ser Val Leu Gly Thr Val Ser Val Ala Asp
                20                  25                  30

Thr Lys Gly Val Lys Arg Lys Thr Leu Phe Arg Glu Asn Gly Ser Lys
```

```
                35                  40                  45
Pro Arg Ala Ile Val Val Asp Pro Val His Gly Phe Met Tyr Trp Thr
            50                  55                  60
Asp Trp Gly Thr Pro Ala Lys Ile Lys Lys Gly Gly Leu Asn Gly Val
65                  70                  75                  80
Asp Ile Tyr Ser Leu Val Thr Glu Asn Ile Gln Trp Pro Asn Gly Ile
                85                  90                  95
Thr Leu Asp Leu Leu Ser Gly Arg Leu Tyr Trp Val Asp Ser Lys Leu
            100                 105                 110
His Ser Ile Ser Ser Ile Asp Tyr Asn Gly Gly Asn Arg Lys Thr Ile
            115                 120                 125
Leu Glu Asp Glu Lys Arg Leu Ala His Pro Phe Ser Leu Ala Val Phe
            130                 135                 140
Glu Asp Lys Val Phe Trp Thr Asp Ile Ile Asn Glu Ala Ile Phe Ser
145                 150                 155                 160
Ala Asn Arg Leu Thr Gly Ser Asp Val Asn Leu Leu Ala Glu Asn Leu
                165                 170                 175
Leu Ser Pro Glu Asp Met Val Leu Phe His Asn Leu Thr Gln Pro Arg
            180                 185                 190
Gly Val Asn Trp Cys Glu Arg Thr Thr Leu Ser Asn Gly Gly Cys Gln
            195                 200                 205
Tyr Leu Cys Leu Pro Ala Pro Gln Ile Asn Pro His Ser Pro Lys Phe
            210                 215                 220
Thr Cys Ala Cys Pro Asp Gly Met Leu Leu Ala Arg Asp Met Arg Ser
225                 230                 235                 240
Cys Leu Thr Glu Ala Glu Ala Val Ala Thr Gln Glu Thr Ser Thr
                245                 250                 255
Val Arg Leu Lys Val Ser Ser Thr Ala Val Arg Thr Gln His Thr Thr
            260                 265                 270
Thr Arg Pro Val Pro Asp Thr Ser
            275                 280

(2) INFORMATION FOR SEQ ID NO:7:

(i) SEQUENCE CHARACTERISTICS:
        (A) LENGTH: 281 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Thr Gly Leu Ser Asn Pro Asp Gly Leu Ala Val Asp Trp Val Gly Gly
1               5                   10                  15
Asn Leu Tyr Trp Cys Asp Lys Gly Arg Asp Thr Ile Glu Val Ser Lys
                20                  25                  30
Leu Asn Gly Ala Tyr Arg Thr Val Leu Val Ser Ser Gly Leu Arg Glu
            35                  40                  45
Pro Arg Ala Leu Val Val Asp Val Gln Asn Gly Tyr Leu Tyr Trp Thr
            50                  55                  60
Asp Trp Gly Asp His Ser Leu Ile Gly Arg Ile Gly Met Asp Gly Ser
65                  70                  75                  80
Ser Arg Ser Val Ile Val Asp Thr Lys Ile Thr Trp Pro Asn Gly Leu
                85                  90                  95
Thr Leu Asp Tyr Val Thr Glu Arg Ile Tyr Trp Ala Asp Ala Arg Glu
```

```
                    100                 105                 110
Asp Tyr Ile Glu Phe Ala Ser Leu Asp Gly Ser Asn Arg His Val Val
            115                 120                 125

Leu Ser Gln Asp Ile Pro His Ile Phe Ala Leu Thr Leu Phe Glu Asp
        130                 135                 140

Tyr Val Tyr Trp Thr Asp Trp Glu Thr Lys Ser Ile Asn Arg Ala His
145                 150                 155                 160

Lys Thr Thr Gly Thr Asn Lys Thr Leu Leu Ile Ser Thr Leu His Arg
                165                 170                 175

Pro Met Asp Leu His Val Phe His Ala Leu Arg Gln Pro Asp Val Pro
            180                 185                 190

Asn His Pro Cys Lys Val Asn Asn Gly Gly Cys Ser Asn Leu Cys Leu
            195                 200                 205

Leu Ser Pro Gly Gly His Lys Cys Ala Cys Pro Thr Asn Phe Tyr
    210                 215                 220

Leu Gly Ser Asp Gly Arg Thr Cys Val Ser Asn Cys Thr Ala Ser Gln
225                 230                 235                 240

Phe Val Cys Lys Asn Asp Lys Cys Ile Pro Phe Trp Trp Lys Cys Asp
                245                 250                 255

Thr Glu Asp Asp Cys Gly Asp His Ser Asp Glu Pro Pro Asp Cys Pro
            260                 265                 270

Glu Phe Lys Cys Arg Pro Gly Gln Phe
            275                 280
```

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (ix) FEATURE:
        (A) NAME/KEY: modified_base
        (B) LOCATION: 7
        (D) OTHER INFORMATION: /mod_base= i (ix) FEATURE:
        (A) NAME/KEY: modified_base
        (B) LOCATION: 28
        (D) OTHER INFORMATION: /mod_base= i (ix) FEATURE:
        (A) NAME/KEY: modified_base
        (B) LOCATION: 31
        (D) OTHER INFORMATION: /mod_base= i (ix) FEATURE:
        (A) NAME/KEY: modified_base
        (B) LOCATION: 37
        (D) OTHER INFORMATION: /mod_base= i (ix) FEATURE:
        (A) NAME/KEY: modified_base
        (B) LOCATION: 46
        (D) OTHER INFORMATION: /mod_base= i (xi) SEQUENCE DESCRIPTION: SEQ ID NO:8:

```
CCARTANAGC TGRTCCTCRA AGATRTCNAG NGARTANGGR TTCATNGC          48
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

```
GCGGAATTCG TNATGCARCC NGAYGG                                       26
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

```
ATAGGATCCT GRTCYTCRAA DATRTC                                       26
```

(2) INFORMATION FOR SEQ ID NO:11:

(i) SEQUENCE CHARACTERISTICS:
        (A) LENGTH: 2835 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..2835

(xi) SEQUENCE DESCRIPTION: SEQ ID NO:11:

```
CAA GGC TGT GAG GAG AGG ACA TGC CAT CCT GTG GGG GAT TTC CGC TGT     48
Gln Gly Cys Glu Glu Arg Thr Cys His Pro Val Gly Asp Phe Arg Cys
 1               5                  10                  15

AAA ACT CAC CAC TGC ATC CCT CTT CGT TGG CAG TGT GAT GGG CAA AAT     96
Lys Thr His His Cys Ile Pro Leu Arg Trp Gln Cys Asp Gly Gln Asn
             20                  25                  30

GAC TGT GGA GAT AAC TCA GAT GAG GAA AAC TGT GCT CCC CGG GAG TGC    144
Asp Cys Gly Asp Asn Ser Asp Glu Glu Asn Cys Ala Pro Arg Glu Cys
         35                  40                  45

ACA GAG AGC GAG TTT CGA TGT GTC AAT CAG CAG TGC ATT CCC TCG CGA    192
Thr Glu Ser Glu Phe Arg Cys Val Asn Gln Gln Cys Ile Pro Ser Arg
     50                  55                  60

TGG ATC TGT GAC CAT TAC AAC GAC TGT GGG GAC AAC TCA GAT GAA CGG    240
Trp Ile Cys Asp His Tyr Asn Asp Cys Gly Asp Asn Ser Asp Glu Arg
 65                  70                  75                  80
```

```
GAC TGT GAG ATG AGG ACC TGC CAT CCT GAA TAT TTT CAG TGT ACA AGT         288
Asp Cys Glu Met Arg Thr Cys His Pro Glu Tyr Phe Gln Cys Thr Ser
                 85                  90                  95

GGA CAT TGT GTA CAC AGT GAA CTG AAA TGC GAT GGA TCC GCT GAC TGT         336
Gly His Cys Val His Ser Glu Leu Lys Cys Asp Gly Ser Ala Asp Cys
                100                 105                 110

TTG GAT GCG TCT GAT GAA GCT GAT TGT CCC ACA CGC TTT CCT GAT GGT         384
Leu Asp Ala Ser Asp Glu Ala Asp Cys Pro Thr Arg Phe Pro Asp Gly
                115                 120                 125

GCA TAC TGC CAG GCT ACT ATG TTC GAA TGC AAA AAC CAT GTT TGT ATC         432
Ala Tyr Cys Gln Ala Thr Met Phe Glu Cys Lys Asn His Val Cys Ile
        130                 135                 140

CCG CCA TAT TGG AAA TGT GAT GGC GAT GAT GAC TGT GGC GAT GGT TCA         480
Pro Pro Tyr Trp Lys Cys Asp Gly Asp Asp Asp Cys Gly Asp Gly Ser
145                 150                 155                 160

GAT GAA GAA CTT CAC CTG TGC TTG GAT GTT CCC TGT AAT TCA CCA AAC         528
Asp Glu Glu Leu His Leu Cys Leu Asp Val Pro Cys Asn Ser Pro Asn
                165                 170                 175

CGT TTC CGG TGT GAC AAC AAT CGC TGC ATT TAT AGT CAT GAG GTG TGC         576
Arg Phe Arg Cys Asp Asn Asn Arg Cys Ile Tyr Ser His Glu Val Cys
                180                 185                 190

AAT GGT GTG GAT GAC TGT GGA GAT GGA ACT GAT GAG ACA GAG GAG CAC         624
Asn Gly Val Asp Asp Cys Gly Asp Gly Thr Asp Glu Thr Glu Glu His
                195                 200                 205

TGT AGA AAA CCG ACC CCT AAA CCT TGT ACA GAA TAT GAA TAT AAG TGT         672
Cys Arg Lys Pro Thr Pro Lys Pro Cys Thr Glu Tyr Glu Tyr Lys Cys
210                 215                 220

GGC AAT GGG CAT TGC ATT CCA CAT GAC AAT GTG TGT GAT GAT GCC GAT         720
Gly Asn Gly His Cys Ile Pro His Asp Asn Val Cys Asp Asp Ala Asp
225                 230                 235                 240

GAC TGT GGT GAC TGG TCC GAT GAA CTG GGT TGC AAT AAA GGA AAA GAA         768
Asp Cys Gly Asp Trp Ser Asp Glu Leu Gly Cys Asn Lys Gly Lys Glu
                245                 250                 255

AGA ACA TGT GCT GAA AAT ATA TGC GAG CAA AAT TGT ACC CAA TTA AAT         816
Arg Thr Cys Ala Glu Asn Ile Cys Glu Gln Asn Cys Thr Gln Leu Asn
                260                 265                 270

GAA GGA GGA TTT ATC TGC TCC TGT ACA GCT GGG TTC GAA ACC AAT GTT         864
Glu Gly Gly Phe Ile Cys Ser Cys Thr Ala Gly Phe Glu Thr Asn Val
                275                 280                 285

TTT GAC AGA ACC TCC TGT CTA GAT ATC AAT GAA TGT GAA CAA TTT GGG         912
Phe Asp Arg Thr Ser Cys Leu Asp Ile Asn Glu Cys Glu Gln Phe Gly
290                 295                 300

ACT TGT CCC CAG CAC TGC AGA AAT ACC AAA GGA AGT TAT GAG TGT GTC         960
Thr Cys Pro Gln His Cys Arg Asn Thr Lys Gly Ser Tyr Glu Cys Val
305                 310                 315                 320

TGT GCT GAT GGC TTC ACG TCT ATG AGT GAC CGC CCT GGA AAA CGA TGT        1008
Cys Ala Asp Gly Phe Thr Ser Met Ser Asp Arg Pro Gly Lys Arg Cys
                325                 330                 335

GCA GCT GAG GGT AGC TCT CCT TTG TTG CTA CTG CCT GAC AAT GTC CGA        1056
Ala Ala Glu Gly Ser Ser Pro Leu Leu Leu Leu Pro Asp Asn Val Arg
                340                 345                 350

ATT CGA AAA TAT AAT CTC TCA TCT GAG AGG TTC TCA GAG TAT CTT CAA        1104
Ile Arg Lys Tyr Asn Leu Ser Ser Glu Arg Phe Ser Glu Tyr Leu Gln
                355                 360                 365

GAT GAG GAA TAT ATC CAA GCT GTT GAT TAT GAT TGG GAT CCC AAG GAC        1152
Asp Glu Glu Tyr Ile Gln Ala Val Asp Tyr Asp Trp Asp Pro Lys Asp
                370                 375                 380

ATA GGC CTC AGT GTT GTG TAT TAC ACT GTG CGA GGG GAG GGC TCT AGG        1200
Ile Gly Leu Ser Val Val Tyr Tyr Thr Val Arg Gly Glu Gly Ser Arg
385                 390                 395                 400
```

```
TTT GGT GCT ATC AAA CGT GCC TAC ATC CCC AAC TTT GAA TCC GGC CGC      1248
Phe Gly Ala Ile Lys Arg Ala Tyr Ile Pro Asn Phe Glu Ser Gly Arg
                405                 410                 415

AAT AAT CTT GTG CAG GAA GTT GAC CTG AAA CTG AAA TAC GTA ATG CAG      1296
Asn Asn Leu Val Gln Glu Val Asp Leu Lys Leu Lys Tyr Val Met Gln
            420                 425                 430

CCA GAT GGA ATA GCA GTG GAC TGG GTT GGA AGG CAT ATT TAC TGG TCA      1344
Pro Asp Gly Ile Ala Val Asp Trp Val Gly Arg His Ile Tyr Trp Ser
        435                 440                 445

GAT GTC AAG AAT AAA CGC ATT GAG GTG GCT AAA CTT GAT GGA AGG TAC      1392
Asp Val Lys Asn Lys Arg Ile Glu Val Ala Lys Leu Asp Gly Arg Tyr
    450                 455                 460

AGA AAG TGG CTG ATT TCC ACT GAC CTG GAC CAA CCA GCT GCT ATT GCT      1440
Arg Lys Trp Leu Ile Ser Thr Asp Leu Asp Gln Pro Ala Ala Ile Ala
465                 470                 475                 480

GTG AAT CCC AAA CTA GGG CTT ATG TTC TGG ACT GAC TGG GGA AAG GAA      1488
Val Asn Pro Lys Leu Gly Leu Met Phe Trp Thr Asp Trp Gly Lys Glu
                485                 490                 495

CCT AAA ATC GAG TCT GCC TGG ATG AAT GGA GAG GAC CGC AAC ATC CTG      1536
Pro Lys Ile Glu Ser Ala Trp Met Asn Gly Glu Asp Arg Asn Ile Leu
            500                 505                 510

GTT TTC GAG GAC CTT GGT TGG CCA ACT GGC CTT TCT ATC GAT TAT TTG      1584
Val Phe Glu Asp Leu Gly Trp Pro Thr Gly Leu Ser Ile Asp Tyr Leu
        515                 520                 525

AAC AAT GAC CGA ATC TAC TGG AGT GAC TTC AAG GAG GAC GTT ATT GAA      1632
Asn Asn Asp Arg Ile Tyr Trp Ser Asp Phe Lys Glu Asp Val Ile Glu
    530                 535                 540

ACC ATA AAA TAT GAT GGG ACT GAT AGG AGA GTC ATT GCA AAG GAA GCA      1680
Thr Ile Lys Tyr Asp Gly Thr Asp Arg Arg Val Ile Ala Lys Glu Ala
545                 550                 555                 560

ATG AAC CCT TAC AGC CTG GAC ATC TTT GAA GAC CAG TTA TAC TGG ATA      1728
Met Asn Pro Tyr Ser Leu Asp Ile Phe Glu Asp Gln Leu Tyr Trp Ile
                565                 570                 575

TCT AAG GAA AAG GGA GAA GTA TGG AAA CAA AAT AAA TTT GGG CAA GGA      1776
Ser Lys Glu Lys Gly Glu Val Trp Lys Gln Asn Lys Phe Gly Gln Gly
            580                 585                 590

AAG AAA GAG AAA ACG CTG GTA GTG AAC CCT TGG CTC ACT CAA GTT CGA      1824
Lys Lys Glu Lys Thr Leu Val Val Asn Pro Trp Leu Thr Gln Val Arg
        595                 600                 605

ATC TTT CAT CAA CTC AGA TAC AAT AAG TCA GTG CCC AAC CTT TGC AAA      1872
Ile Phe His Gln Leu Arg Tyr Asn Lys Ser Val Pro Asn Leu Cys Lys
    610                 615                 620

CAG ATC TGC AGC CAC CTC TGC CTT CTG AGA CCT GGA GGA TAC AGC TGT      1920
Gln Ile Cys Ser His Leu Cys Leu Leu Arg Pro Gly Gly Tyr Ser Cys
625                 630                 635                 640

GCC TGT CCC CAA GGC TCC AGC TTT ATA GAG GGG AGC ACC ACT GAG TGT      1968
Ala Cys Pro Gln Gly Ser Ser Phe Ile Glu Gly Ser Thr Thr Glu Cys
                645                 650                 655

GAT GCA GCC ATC GAA CTG CCT ATC AAC CTG CCC CCC CCA TGC AGG TGC      2016
Asp Ala Ala Ile Glu Leu Pro Ile Asn Leu Pro Pro Pro Cys Arg Cys
            660                 665                 670

ATG CAC GGA GGA AAT TGC TAT TTT GAT GAG ACT GAC CTC CCC AAA TGC      2064
Met His Gly Gly Asn Cys Tyr Phe Asp Glu Thr Asp Leu Pro Lys Cys
        675                 680                 685

AAG TGT CCT AGC GGC TAC ACC GGA AAA TAT TGT GAA ATG GCG TTT TCA      2112
Lys Cys Pro Ser Gly Tyr Thr Gly Lys Tyr Cys Glu Met Ala Phe Ser
    690                 695                 700

AAA GGC ATC TCT CCA GGA ACA ACC GCA GTA GCT GTG CTG TTG ACA ATC      2160
Lys Gly Ile Ser Pro Gly Thr Thr Ala Val Ala Val Leu Leu Thr Ile
```

-continued

| | | | | | | | | | | | | | | | |
|---|---|---|---|---|---|---|---|---|---|---|---|---|---|---|---|
| 705 | | | | | 710 | | | | | 715 | | | | | 720 |
| CTC | TTG | ATC | GTC | GTA | ATT | GGA | GCT | CTG | GCA | ATT | GCA | GGA | TTC | TTC | CAC | 2208
| Leu | Leu | Ile | Val | Val | Ile | Gly | Ala | Leu | Ala | Ile | Ala | Gly | Phe | Phe | His |
| | | | | 725 | | | | | 730 | | | | | 735 | |

```
CTC TTG ATC GTC GTA ATT GGA GCT CTG GCA ATT GCA GGA TTC TTC CAC    2208
Leu Leu Ile Val Val Ile Gly Ala Leu Ala Ile Ala Gly Phe Phe His
                725                 730                 735

TAT AGA AGG ACC GGC TCC CTT TTG CCT GCT CTG CCC AAG CTG CCA AGC    2256
Tyr Arg Arg Thr Gly Ser Leu Leu Pro Ala Leu Pro Lys Leu Pro Ser
            740                 745                 750

TTA AGC AGT CTC GTC AAG CCC TCT GAA AAT GGG AAT GGG GTG ACC TTC    2304
Leu Ser Ser Leu Val Lys Pro Ser Glu Asn Gly Asn Gly Val Thr Phe
        755                 760                 765

AGA TCA GGG GCA GAT CTT AAC ATG GAT ATT GGA GTG TCT GGT TTT GGA    2352
Arg Ser Gly Ala Asp Leu Asn Met Asp Ile Gly Val Ser Gly Phe Gly
    770                 775                 780

CCT GAG ACT GCT ATT GAC AGG TCA ATG GCA ATG AGT GAA GAC TTT GTC    2400
Pro Glu Thr Ala Ile Asp Arg Ser Met Ala Met Ser Glu Asp Phe Val
785                 790                 795                 800

ATG GAA ATG GGG AAG CAG CCC ATA ATA TTT GAA AAC CCA ATG TAC TCA    2448
Met Glu Met Gly Lys Gln Pro Ile Ile Phe Glu Asn Pro Met Tyr Ser
                805                 810                 815

GCC AGA GAC AGT GCT GTC AAA GTG GTT CAG CCA ATC CAG GTG ACT GTA    2496
Ala Arg Asp Ser Ala Val Lys Val Val Gln Pro Ile Gln Val Thr Val
            820                 825                 830

TCT GAA AAT GTG GAT AAT AAG AAT TAT GGA AGT CCC ATA AAC CCT TCT    2544
Ser Glu Asn Val Asp Asn Lys Asn Tyr Gly Ser Pro Ile Asn Pro Ser
        835                 840                 845

GAG ATA GTT CCA GAG ACA AAC CCA ACT TCA CCA GCT GCT GAT GGA ACT    2592
Glu Ile Val Pro Glu Thr Asn Pro Thr Ser Pro Ala Ala Asp Gly Thr
    850                 855                 860

CAG GTG ACA AAA TGG AAT CTC TTC AAA CGA AAA TCT AAA CAA ACT ACC    2640
Gln Val Thr Lys Trp Asn Leu Phe Lys Arg Lys Ser Lys Gln Thr Thr
865                 870                 875                 880

AAC TTT GAA AAT CCA ATC TAT GCA CAG ATG GAG AAC GAG CAA AAG GAA    2688
Asn Phe Glu Asn Pro Ile Tyr Ala Gln Met Glu Asn Glu Gln Lys Glu
                885                 890                 895

AGT GTT GCT GCG ACA CCA CCT CCA TCA CCT TCG CTC CCT GCT AAG CCT    2736
Ser Val Ala Ala Thr Pro Pro Pro Ser Pro Ser Leu Pro Ala Lys Pro
            900                 905                 910

AAG CCT CCT TCG AGA AGA GAC CCA ACT CCA ACC TAT TCT GCA ACA GAA    2784
Lys Pro Pro Ser Arg Arg Asp Pro Thr Pro Thr Tyr Ser Ala Thr Glu
        915                 920                 925

GAC ACT TTT AAA GAC ACC GCA AAT CTT GTT AAA GAA GAC TCT GAA GTA    2832
Asp Thr Phe Lys Asp Thr Ala Asn Leu Val Lys Glu Asp Ser Glu Val
    930                 935                 940

TAG                                                                2835
945
```

(2) INFORMATION FOR SEQ ID NO:12:

(i) SEQUENCE CHARACTERISTICS:
        (A) LENGTH: 944 amino acids
        (B) TYPE: amino acid
        (D) TOPOLOGY: linear (ii) MOLECULE TYPE: protein (xi) SEQUENCE DESCRIPTION: SEQ ID NO:12:

```
Gln Gly Cys Glu Glu Arg Thr Cys His Pro Val Gly Asp Phe Arg Cys
  1               5                  10                  15

Lys Thr His His Cys Ile Pro Leu Arg Trp Gln Cys Asp Gly Gln Asn
             20                  25                  30
```

-continued

```
Asp Cys Gly Asp Asn Ser Asp Glu Glu Asn Cys Ala Pro Arg Glu Cys
             35                  40                  45

Thr Glu Ser Glu Phe Arg Cys Val Asn Gln Gln Cys Ile Pro Ser Arg
     50                  55                  60

Trp Ile Cys Asp His Tyr Asn Asp Cys Gly Asp Asn Ser Asp Glu Arg
 65                  70                  75                  80

Asp Cys Glu Met Arg Thr Cys His Pro Glu Tyr Phe Gln Cys Thr Ser
                 85                  90                  95

Gly His Cys Val His Ser Glu Leu Lys Cys Asp Gly Ser Ala Asp Cys
                100                 105                 110

Leu Asp Ala Ser Asp Glu Ala Asp Cys Pro Thr Arg Phe Pro Asp Gly
            115                 120                 125

Ala Tyr Cys Gln Ala Thr Met Phe Glu Cys Lys Asn His Val Cys Ile
        130                 135                 140

Pro Pro Tyr Trp Lys Cys Asp Gly Asp Asp Asp Cys Gly Asp Gly Ser
145                 150                 155                 160

Asp Glu Glu Leu His Leu Cys Leu Asp Val Pro Cys Asn Ser Pro Asn
                165                 170                 175

Arg Phe Arg Cys Asp Asn Asn Arg Cys Ile Tyr Ser His Glu Val Cys
            180                 185                 190

Asn Gly Val Asp Asp Cys Gly Asp Gly Thr Asp Glu Thr Glu Glu His
        195                 200                 205

Cys Arg Lys Pro Thr Pro Lys Pro Cys Thr Glu Tyr Glu Tyr Lys Cys
    210                 215                 220

Gly Asn Gly His Cys Ile Pro His Asp Asn Val Cys Asp Asp Ala Asp
225                 230                 235                 240

Asp Cys Gly Asp Trp Ser Asp Glu Leu Gly Cys Asn Lys Gly Lys Glu
                245                 250                 255

Arg Thr Cys Ala Glu Asn Ile Cys Glu Gln Asn Cys Thr Gln Leu Asn
            260                 265                 270

Glu Gly Gly Phe Ile Cys Ser Cys Thr Ala Gly Phe Glu Thr Asn Val
        275                 280                 285

Phe Asp Arg Thr Ser Cys Leu Asp Ile Asn Glu Cys Glu Gln Phe Gly
    290                 295                 300

Thr Cys Pro Gln His Cys Arg Asn Thr Lys Gly Ser Tyr Glu Cys Val
305                 310                 315                 320

Cys Ala Asp Gly Phe Thr Ser Met Ser Asp Arg Pro Gly Lys Arg Cys
                325                 330                 335

Ala Ala Glu Gly Ser Ser Pro Leu Leu Leu Pro Asp Asn Val Arg
            340                 345                 350

Ile Arg Lys Tyr Asn Leu Ser Ser Glu Arg Phe Ser Glu Tyr Leu Gln
        355                 360                 365

Asp Glu Glu Tyr Ile Gln Ala Val Asp Tyr Asp Trp Asp Pro Lys Asp
    370                 375                 380

Ile Gly Leu Ser Val Val Tyr Tyr Thr Val Arg Gly Glu Gly Ser Arg
385                 390                 395                 400

Phe Gly Ala Ile Lys Arg Ala Tyr Ile Pro Asn Phe Glu Ser Gly Arg
                405                 410                 415

Asn Asn Leu Val Gln Glu Val Asp Leu Lys Leu Lys Tyr Val Met Gln
            420                 425                 430

Pro Asp Gly Ile Ala Val Asp Trp Val Gly Arg His Ile Tyr Trp Ser
        435                 440                 445

Asp Val Lys Asn Lys Arg Ile Glu Val Ala Lys Leu Asp Gly Arg Tyr
```

-continued

```
            450                 455                 460
Arg Lys Trp Leu Ile Ser Thr Asp Leu Asp Gln Pro Ala Ala Ile Ala
465                 470                 475                 480

Val Asn Pro Lys Leu Gly Leu Met Phe Trp Thr Asp Trp Gly Lys Glu
                485                 490                 495

Pro Lys Ile Glu Ser Ala Trp Met Asn Gly Glu Asp Arg Asn Ile Leu
            500                 505                 510

Val Phe Glu Asp Leu Gly Trp Pro Thr Gly Leu Ser Ile Asp Tyr Leu
            515                 520                 525

Asn Asn Asp Arg Ile Tyr Trp Ser Asp Phe Lys Glu Asp Val Ile Glu
            530                 535                 540

Thr Ile Lys Tyr Asp Gly Thr Asp Arg Arg Val Ile Ala Lys Glu Ala
545                 550                 555                 560

Met Asn Pro Tyr Ser Leu Asp Ile Phe Glu Asp Gln Leu Tyr Trp Ile
                565                 570                 575

Ser Lys Glu Lys Gly Glu Val Trp Lys Gln Asn Lys Phe Gly Gln Gly
                580                 585                 590

Lys Lys Glu Lys Thr Leu Val Val Asn Pro Trp Leu Thr Gln Val Arg
            595                 600                 605

Ile Phe His Gln Leu Arg Tyr Asn Lys Ser Val Pro Asn Leu Cys Lys
            610                 615                 620

Gln Ile Cys Ser His Leu Cys Leu Leu Arg Pro Gly Gly Tyr Ser Cys
625                 630                 635                 640

Ala Cys Pro Gln Gly Ser Ser Phe Ile Glu Gly Ser Thr Thr Glu Cys
                645                 650                 655

Asp Ala Ala Ile Glu Leu Pro Ile Asn Leu Pro Pro Pro Cys Arg Cys
                660                 665                 670

Met His Gly Gly Asn Cys Tyr Phe Asp Glu Thr Asp Leu Pro Lys Cys
            675                 680                 685

Lys Cys Pro Ser Gly Tyr Thr Gly Lys Tyr Cys Glu Met Ala Phe Ser
            690                 695                 700

Lys Gly Ile Ser Pro Gly Thr Thr Ala Val Ala Val Leu Leu Thr Ile
705                 710                 715                 720

Leu Leu Ile Val Val Ile Gly Ala Leu Ala Ile Ala Gly Phe Phe His
                725                 730                 735

Tyr Arg Arg Thr Gly Ser Leu Leu Pro Ala Leu Pro Lys Leu Pro Ser
                740                 745                 750

Leu Ser Ser Leu Val Lys Pro Ser Glu Asn Gly Asn Gly Val Thr Phe
            755                 760                 765

Arg Ser Gly Ala Asp Leu Asn Met Asp Ile Gly Val Ser Gly Phe Gly
            770                 775                 780

Pro Glu Thr Ala Ile Asp Arg Ser Met Ala Met Ser Glu Asp Phe Val
785                 790                 795                 800

Met Glu Met Gly Lys Gln Pro Ile Ile Phe Glu Asn Pro Met Tyr Ser
                805                 810                 815

Ala Arg Asp Ser Ala Val Lys Val Val Gln Pro Ile Gln Val Thr Val
                820                 825                 830

Ser Glu Asn Val Asp Asn Lys Asn Tyr Gly Ser Pro Ile Asn Pro Ser
            835                 840                 845

Glu Ile Val Pro Glu Thr Asn Pro Thr Ser Pro Ala Ala Asp Gly Thr
            850                 855                 860

Gln Val Thr Lys Trp Asn Leu Phe Lys Arg Lys Ser Lys Gln Thr Thr
865                 870                 875                 880
```

```
Asn Phe Glu Asn Pro Ile Tyr Ala Gln Met Glu Asn Glu Gln Lys Glu
            885                 890                 895

Ser Val Ala Ala Thr Pro Pro Ser Pro Ser Leu Pro Ala Lys Pro
        900                 905                 910

Lys Pro Pro Ser Arg Arg Asp Pro Thr Pro Thr Tyr Ser Ala Thr Glu
        915                 920                 925

Asp Thr Phe Lys Asp Thr Ala Asn Leu Val Lys Glu Asp Ser Glu Val
        930                 935                 940

945
```

(2) INFORMATION FOR SEQ ID NO:13:

(i) SEQUENCE CHARACTERISTICS:
        (A) LENGTH: 207 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: C-terminal (xi) SEQUENCE DESCRIPTION: SEQ ID NO:13:

```
Arg Arg Thr Gly Ser Leu Leu Pro Ala Leu Pro Lys Leu Pro Ser Leu
1                5                  10                  15

Ser Ser Leu Val Lys Pro Ser Glu Asn Gly Asn Gly Val Thr Phe Arg
            20                  25                  30

Ser Gly Ala Asp Leu Asn Met Asp Ile Gly Val Ser Gly Phe Gly Pro
        35                  40                  45

Glu Thr Ala Ile Asp Arg Ser Met Ala Met Ser Glu Asp Phe Val Met
    50                  55                  60

Glu Met Gly Lys Gln Pro Ile Ile Phe Glu Asn Pro Met Tyr Ser Ala
65                  70                  75                  80

Arg Asp Ser Ala Val Lys Val Val Gln Pro Ile Gln Val Thr Val Ser
                85                  90                  95

Glu Asn Val Asp Asn Lys Asn Tyr Gly Ser Pro Ile Asn Pro Ser Glu
            100                 105                 110

Ile Val Pro Glu Thr Asn Pro Thr Ser Pro Ala Ala Asp Gly Thr Gln
        115                 120                 125

Val Thr Lys Trp Asn Leu Phe Lys Arg Lys Ser Lys Gln Thr Thr Asn
    130                 135                 140

Phe Glu Asn Pro Ile Tyr Ala Gln Met Glu Asn Glu Gln Lys Glu Ser
145                 150                 155                 160

Val Ala Ala Thr Pro Pro Ser Pro Ser Leu Pro Ala Lys Pro Lys
                165                 170                 175

Pro Pro Ser Arg Arg Asp Pro Thr Pro Thr Tyr Ser Ala Thr Glu Asp
            180                 185                 190

Thr Phe Lys Asp Thr Ala Asn Leu Val Lys Glu Asp Ser Glu Val
        195                 200                 205
```

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:14:

Pro Ser Leu Pro Ala Lys Pro
1               5

(2) INFORMATION FOR SEQ ID NO:15:

(i) SEQUENCE CHARACTERISTICS:
             (A) LENGTH: 7 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:15:

Ser Leu Leu Pro Ala Leu Pro
1               5

(2) INFORMATION FOR SEQ ID NO:16:

(i) SEQUENCE CHARACTERISTICS:
             (A) LENGTH: 7 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:16:

Pro Ala Leu Pro Lys Leu Pro
1               5

(2) INFORMATION FOR SEQ ID NO:17:

(i) SEQUENCE CHARACTERISTICS:
             (A) LENGTH: 6412 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

GAATTCTGTC AATGAGCTGG CCTTCCTTAT AAAAGGATTT ACATTTTCTG CTTAAGAGGT     60

ATTATTTATA GTTTGAAATA TTTCTGGTGA TATTTGCGGG TGGGATCATA TGTGCTTCAT    120

TGTGCATTTT ATAAAGAACA ACAAATTCAC GGGAAGATGT GCCTTTTGAT GTTGTTGCTT    180

TGCAAATTTT GCTGAGAAGA GTCGTTGATA TTTCCTGTTG TTTAGAAGGA ATCGGCACAT    240

TTATTAGAAA TTGGTGATTG CTCTTCTTGA TGGAAAAGTG ACTCAGAATA TAGTTAAAAG    300

-continued

| | | | | |
|---|---|---|---|---|
| GTTAATGGGC | AGAACTTCCA | TGGCGCTTCT | TAGGGAGCAT | TTAATGTAGA | AGCTGTTGCA | 360 |
| AGTGCTATTG | TGGAGGGGTC | AATGTGAACG | GTGGCTGCAT | CCATCTTTTA | CTTCTTCTGG | 420 |
| GATTATCTTT | CTTCAGGTCC | GGGTGGTGCC | GAGTGCCAGT | GTCCACATGA | GGGCAACTGG | 480 |
| TATTTGGCCA | ACAACAGGAA | GCACTGCATT | GTGGACAATG | GTGAACGATG | TGGTGCATCT | 540 |
| TCCTTCACCT | GCTCCAATGG | GCGCTGCATC | TCGGAAGAGT | GGAAGTGTGA | TAATGACAAC | 600 |
| GACTGTGGGG | ATGGCAGTGA | TGAGATGGAA | AGTGTCTGTG | CACTTCACAC | CTGCTCACCG | 660 |
| ACAGCCTTCA | CCTGTGCCAA | TGGGCGATGT | GTCCAATACT | CTTACCGCTG | TGATTACTAC | 720 |
| AATGACTGTG | GTGATGGCAG | TGATGAGGCA | GGGTGCCTGT | TCAGGGACTG | CAATGCCACC | 780 |
| ACGGAGTTTA | TGTGCAATAA | CAGAAGGTGC | ATACCTCGTG | AGTTTATCTG | CAATGGTGTA | 840 |
| GACAACTGCC | ATGATAATAA | CACTTCAGAT | GAGAAAAATT | GCCCTGATCG | CACTTGCCAG | 900 |
| TCTGGATACA | CAAAATGTCA | TAATTCAAAT | ATTTGTATTC | CTCGCGTTTA | TTTGTGTGAC | 960 |
| GGAGACAATG | ACTGTGGAGA | TAACAGTGAT | GAAAACCCTA | CTTATTGCAC | CACTCACACA | 1020 |
| TGCAGCAGTG | AGTTCCAATG | CACATCTGGG | NGCTGTATTC | CTCAACATTG | GTATTGTGAT | 1080 |
| CAAGAAACAG | ATTGTTTTGA | TGCCTCTCGA | TGAACCTGCC | TCCTTGTGGT | CACTCTGAGC | 1140 |
| GAACATGCCT | AGCTGATGAG | TTCAAGTGTG | ATGGTGGGAG | GTGCATCCCA | AGCGAATGGA | 1200 |
| TCTGTGACGG | TGATAATGAC | TGTGGGGATA | TGAGTGACGA | GGATAAAAGG | CACCAGTGTC | 1260 |
| AGAATCAAAA | CTGCTCGGAT | TCCGAGTTTC | TCTGTGTAAA | TGACAGACCT | CCGGACAGGA | 1320 |
| GTGCATTCCC | CAGTCTTGGG | TCTGTGATGG | CGATGTGGAT | TGTACTGACG | GCTACATGAG | 1380 |
| AATCAGAATT | GCACCAGGAG | AACTTGCTCT | GAAAATGAAT | TCACCTGTGG | TTACGGAATG | 1440 |
| TGTATCCCAA | AGATATTGCG | AGGTGTGACC | GGCACAATGA | CTGTGGTGAC | TATAGCGACG | 1500 |
| AGAGGGCTGC | TTATACCTAG | ACTTGCCAAC | AGAATCAGTT | TCCTGTCAGA | ACGGGCGCTG | 1560 |
| CATTAGTAAA | ACCTTCGTCT | GTGATGCAGG | ATGAATCGAC | TGTGGAGACG | GATCTGATGA | 1620 |
| GCTGATGCAC | CTGTGCCACA | CCCCACGTGT | CCACCTCACG | AGTGTCAAAT | ATGACAATGG | 1680 |
| GCGCTGCATC | GAGATGATGA | AACTCTGCAA | CCACCTAGAT | GACTGTTTGG | ACAACAGCGA | 1740 |
| TGAGAAAGGC | TGTGGCATTA | ATGAATGCCA | TGACCCTTCA | ATCAGTGGCT | GCGATCACAA | 1800 |
| CTGTATAGAC | ACCTTAACCA | GTTTCTATTG | TTCCTGTCGT | CCTGGTTACA | AGCTCATGTC | 1860 |
| TGACAAGCGG | ACTTGTGTTG | ATATTGATGA | ATGCACAGAG | ATGCCTTTTG | TCTGTAGCCA | 1920 |
| GAAGTGTGAG | AATGTAATAG | GCTCCTACAT | CTGTAAGTGT | GCCCCAGGCT | ACCTCCGAGA | 1980 |
| ACCAGATGGA | AAGACCTGCC | GGCAAAACAG | TAACATCGAA | CCCTATCTCA | TTTTTAGCAA | 2040 |
| CCGTTACTAT | TTGAGAAATT | TAACTATAGA | TGGCTATTTT | TACTCCCTCA | TCTTGGAAGG | 2100 |
| ACTGGACAAT | GTTGTGGCAT | TAGATTTTGA | CCGAGTAGAG | AAGAGATTGT | ATTGGATTGA | 2160 |
| TACACAGAGG | CAAGTCATTG | AGAGAATGTT | TCTGAATAAG | ACAAACAAGG | AGACAATCAT | 2220 |
| AAACCACAGA | CTACCAGCTG | CAGAAAGTCT | GGCTGTAGAC | TGGGTTTCCA | GAAAGCTCTA | 2280 |
| CTGGTTGGAT | GCCCGCCTGG | ATGGCCTCTT | TGTCTCTGAC | CTCAATGGTG | GACACCGCCG | 2340 |
| CATGCTGGCC | CAGCACTGTG | TGGATGCCAA | CAACACCTTC | TGCTTTGATA | ATCCCAGAGG | 2400 |
| ACTTGCCCTT | CACCCTCAAT | ATGGGTACCT | CTACTGGGCA | GACTGGGGTC | ACCGCGCATA | 2460 |
| CATTGGGAGA | GTAGGCATGG | ATGGAACCAA | CAAGTCTGTG | ATACTCCACC | AAGTTAGAGT | 2520 |
| TGGCCTAATG | GCATCACCAT | TGATTACACC | AATGATCTAC | TCTACTGGGC | AGATGCCACC | 2580 |
| CTGGGTTACA | TAGAGTACTC | TGATTTGGAG | GGCCACCATC | GACACACGGT | GTATGATGGG | 2640 |
| GCACTGCCTC | ACCCTTTCGC | TATTACCATT | TTTGAAGACA | CTATTTATTG | GACAGATTGG | 2700 |

```
AATACAAGGA CAGTGGAAAA GGGAAACAAA TATGATGGAT CAAATAGACA GACACTGGTG    2760

AACACAACAC ACAGACCATT TGACATCCAT GTGTACCATC CATATAGGCA GCCCGTACCA    2820

TCCATATAGG CAGCCCATTG TGAGCAATCC CTGTGGTACC AACAATGGTG GCTGTTCTCA    2880

TCTCTGCCTC ATCAAGCCAG GAGGAAAAGG GTTCACTTGC GAGTGTCCAG ATGACTTCCG    2940

CACCCTTCAA CTGAGTGGCA GCACCTACTG CATGCCCATG TGCTCCAGCA CCCAGTTCCT    3000

GTGCGCTAAC AATGAAAAGT GCATTCCTAT CTGGTGGAAA TGTGATGGAC AGAAAGACTG    3060

CTCAGATGGC TCTGATGAAC TGGCCCTTTG CCCGCAGCGC TTCTGCCGAC TGGGACAGTT    3120

CCAGTGCAGT GACGGCAACT GCACCAGCCC GCAGACTTTA TGCAATGCTC ACCAAAATTG    3180

CCCTCGATGG TCTGATGAAG ACCGTCTTCT TTGTGAGAAT CACCACTGTG ACTCCAATGA    3240

ATGGCAGTGC GCCAACAAAC GTTGCATCCC AGAATCCTGG CAGTGTGACA CATTTAACGA    3300

CTGTGAGGAT AACTCAGATG AAGACAGTTC CCACTGTGCC AGCAGGACCT GCCGGCCGGG    3360

CCAGTTTCGG TGTGCTAATG GCCGCTGCAT CCCGCAGGCC TGGAAGTGTG ATGTGGATAA    3420

TGATTGTGGA GACCACTCGG ATGAGCCCAT TGAAGAATGC ATGAGCTCTG CCCATCTCTG    3480

TGACAACTTC ACAGAATTCA GCTGCAAAAC AAATTACCGC TGCATCCCAA AGTGGGCCGT    3540

GTGCAATGGT GTAGATGACT GCAGGGACAA CAGTGATGAG CAAGGCTGTG AGGAGAGGAC    3600

ATGCCATCCT GTGGGGGATT TCCGCTGTAA AACTCACCAC TGCATCCCTC TTCGTTGGCA    3660

GTGTGATGGG CAAAATGACT GTGGAGATAA CTCAGATGAG GAAAACTGTG CTCCCCGGGA    3720

GTGCACAGAG AGCGAGTTTC GATGTGTCAA TCAGCAGTGC ATTCCTCGC GATGGATCTG    3780

TGACCATTAC AACGACTGTG GGGACAACTC AGATGAACGG GACTGTGAGA TGAGGACCTG    3840

CCATCCTGAA TATTTTCAGT GTACAAGTGG ACATTGTGTA CACAGTGAAC TGAAATGCGA    3900

TGGATCCGCT GACTGTTTGG ATGCGTCTGA TGAAGCTGAT TGTCCCACAC GCTTTCCTGA    3960

TGGTGCATAC TGCCAGGCTA CTATGTTCGA ATGCAAAAAC CATGTTTGTA TCCCGCCATA    4020

TTGGAAATGT GATGGCGATG ATGACTGTGG CGATGGTTCA GATGAAGAAC TTCACCTGTG    4080

CTTGGATGTT CCCTGTAATT CACCAAACCG TTTCCGGTGT GACAACAATC GCTGCATTTA    4140

TAGTCATGAG GTGTGCAATG GTGTGGATGA CTGTGGAGAT GGAACTGATG AGACAGAGGA    4200

GCACTGTAGA AAACCGACCC CTAAACCTTG TACAGAATAT GAATATAAGT GTGGCAATGG    4260

GCATTGCATT CCACATGACA ATGTGTGTGA TGATGCCGAT GACTGGGTG ACTGGTCCGA    4320

TGAACTGGGT TGCAATAAAG GAAAAGAAAG AACATGTGCT GAAAATATAT GCGAGCAAAA    4380

TTGTACCCAA TTAAATGAGG AGGATTTATC TGCTCCTGTA CAGCTGGGTT CGAAACCAAT    4440

GTTTTTTGAC AGAACCTCCT GTCTAGATAT CAATGAATGT GAACAATTTG GGACTTGTCC    4500

CCAGCACTGC AGAAATACCA AAGGAAGTTA TGAGTGTGTC TGTGCTGATG GCTTCACGTC    4560

TATGAGTGAC CGCCCTGGAA AACGATGTGC AGCTGAGGGT AGCTCTCCTT TGTTGCTACT    4620

GCCTGACAAT GTCCGAATTC GAAAATATAA TCTCTCATCT GAGAGGTTCT CAGAGTATCT    4680

TCAAGATGAG GAATATATCC AAGCTGTTGA TTATGATTGG GATCCCAAGG ACATAGGCCT    4740

CAGTGTTGTG TATTACACTG TGCGAGGGGA GGGCTCTAGG TTTGGTGCTA TCAAACGTGC    4800

CTACATCCCC AACTTTGAAT CCGGCCGCAA TAATCTTGTG CAGGAAGTTG ACCTGAAACT    4860

GAAATACGTA ATGCAGCCAG ATGGAATAGC AGTGGACTGG GTTGGAAGGC ATATTTACTG    4920

GTCAGATGTC AAGAATAAAC GCATTGAGGT GGCTAAACTT GATGGAAGGT ACAGAAAGTG    4980

GCTGATTTCC ACTGACCTGG ACCAACCAGC TGCTATTGCT GTGAATCCCA AACTAGGGCT    5040
```

-continued

```
TATGTTCTGG ACTGACTGGG GAAAGGAACC TAAAATCGAG TCTGCCTGGA TGAATGGAGA      5100

GGACCGCAAC ATCCTGGTTT TCGAGGACCT TGGTTGGCCA ACTGGCCTTT CTATCGATTA      5160

TTTGAACGAC CGAATCTACT GGAGTGACTT CAAGGAGGAC GTTATTGAAA CCATAAAATA      5220

TGATGGGACT GATAGGAGAG TCATTGCAAA GGAAGCAATG AACCCTTACA GCCTGGACAT      5280

CTTTGAAGAC CAGTTATACT GGATATCTAA GGAAAAGGGA GAAGTATGGA AACAAAATAA      5340

ATTTGGGCAA GGAAAGAAAG AGAAAACGCT GGTAGTGAAC CCTTGGCTCA CTCAAGTTCG      5400

AATCTTTCAT CAACTCAGAT ACAATAAGTC AGTGCCCAAC CTTTGCAAAC AGATCTGCAG      5460

CCACCTCTGC CTTCTGAGAC CTGGAGGATA CAGCTGTGCC TGTCCCCAAG GCTCCAGCTT      5520

TATAGAGGGG AGCACCACTG AGTGTGATGC AGCCATCGAA CTGCCTATCA ACCTGCCCCC      5580

CCCATGCAGG TGCATGCACG GAGGAAATTG CTATTTTGAT GAGACTGACC TCCCCAAATG      5640

CAAGTGTCCT AGCGGCTACA CCGGAAAATA TTGTGAAATG GCGTTTTCAA AAGGCATCTC      5700

TCCAGGAACA ACCGCAGTAG CTGTGCTGTT GACAATCCTC TTGATCGTCG TAATTGGAGC      5760

TCTGGCAATT GCAGGATTCT TCCACTATAG AAGGACCGGC TCCCTTTTGC CTGCTCTGCC      5820

CAAGCTGCCA AGCTTAAGCA GTCTCGTCAA GCCCTCTGAA AATGGGAATG GGGTGACCTT      5880

CAGATCAGGG GCAGATCTTA ACATGGATAT TGGAGTGTCT GGTTTTGGAC CTGAGACTGC      5940

TATTGACAGG TCAATGGCAA TGAGTGAAGA CTTTGTCATG GAAATGGGGA AGCAGCCCAT      6000

AATATTTGAA AACCCAATGT ACTCAGCCAG AGACAGTGCT GTCAAAGTGG TTCAGCCAAT      6060

CCAGGTGACT GTATCTGAAA ATGTGGATAA TAAGAATTAT GGAAGTCCCA TAAACCCTTC      6120

TGAGATAGTT CCAGAGACAA ACCCAACTTC ACCAGCTGCT GATGGAACTC AGGTGACAAA      6180

ATGGAATCTC TTCAAACGAA AATCTAAACA AACTACCAAC TTTGAAAATC CAATCTATGC      6240

ACAGATGGAG AACGAGCAAA AGGAAAGTGT TGCTGCGACA CCACCTCCAT CACCTTCGCT      6300

CCCTGCTAAG CCTAAGCCTC CTTCGAGAAG AGACCCAACT CCAACCTATT CTGCAACAGA      6360

AGACACTTTT AAAGACACCG CAAATCTTGT TAAAGAAGAC TCTGAAGTAT AG            6412
```

(2) INFORMATION FOR SEQ ID NO:18:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:18:

```
Ala Thr Pro Pro Pro Ser Pro Ser Leu Pro Ala Lys Pro Lys Pro Pro
1               5                   10                  15

Ser Arg Arg
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:19:

Phe Glu Asn Pro Ile Tyr Ala Gln Met Glu Asn Glu
1               5                  10

(2) INFORMATION FOR SEQ ID NO:20:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:20:

Arg Xaa Leu Pro Pro Arg Pro Xaa Xaa
1               5

(2) INFORMATION FOR SEQ ID NO:21:

(i) SEQUENCE CHARACTERISTICS:
          (A) LENGTH: 9 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (ix) FEATURE:
          (A) NAME/KEY: Modified-site
          (B) LOCATION: 9
          (D) OTHER INFORMATION: /label= hydrophobic (xi) SEQUENCE DESCRIPTION: SEQ ID NO:21:

Arg Xaa Leu Pro Pro Leu Pro Arg Xaa
1               5

(2) INFORMATION FOR SEQ ID NO:22:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:22:

Pro Thr Met Pro Pro Pro Leu Pro Pro Val Pro
1               5                  10

(2) INFORMATION FOR SEQ ID NO:23:

(i) SEQUENCE CHARACTERISTICS:
          (A) LENGTH: 11 amino acids (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:23:

Pro Ala Tyr Pro Pro Pro Val Pro Val Pro
1               5                   10

(2) INFORMATION FOR SEQ ID NO:24:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:24:

Glu Val Pro Val Pro Pro Pro Val Pro Pro Arg
1               5                   10

(2) INFORMATION FOR SEQ ID NO:25:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:25:

His Leu Asp Ser Pro Pro Ala Ile Pro Pro Arg
1               5                   10

(2) INFORMATION FOR SEQ ID NO:26:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:26:

His Ser Ile Ala Gly Pro Pro Val Pro Pro Arg
1               5                   10

(2) INFORMATION FOR SEQ ID NO:27:

(i) SEQUENCE CHARACTERISTICS:

(A) LENGTH: 11 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:27:

Ala Pro Ala Val Pro Pro Ala Arg Pro Gly Ser
1               5                   10

(2) INFORMATION FOR SEQ ID NO:28:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:28:

Gly Ala Pro Pro Val Pro Ser Arg Pro Gly Ala
1               5                   10

(2) INFORMATION FOR SEQ ID NO:29:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:29:

Pro Pro Arg Pro Leu Pro Val Ala Pro Gly Ser
1               5                   10

(2) INFORMATION FOR SEQ ID NO:30:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:30:

Pro Ala Pro Ala Leu Pro Pro Lys Pro Pro Lys
1               5                   10

(2) INFORMATION FOR SEQ ID NO:31:

```
    (i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:31:

Ala Pro Lys Pro Met Pro Pro Arg Pro Pro Leu
1               5                   10

(2) INFORMATION FOR SEQ ID NO:32:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:32:

Pro Pro Thr Pro Pro Pro Leu Pro Pro Pro Leu
1               5                   10

(2) INFORMATION FOR SEQ ID NO:33:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:33:

Pro Ala Leu Pro Pro Pro Pro Arg Pro Val Pro
1               5                   10

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:34:

Arg Pro Arg Pro Leu Pro Pro Leu Pro Pro Thr
1               5                   10

(2) INFORMATION FOR SEQ ID NO:35:
```

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:35:

```
Gly Val Arg Pro Leu Pro Pro Leu Pro Asp Pro
1               5                   10
```

(2) INFORMATION FOR SEQ ID NO:36:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:36:

```
Pro Pro Arg Pro Leu Pro Pro Arg Pro Pro Ala
1               5                   10
```

(2) INFORMATION FOR SEQ ID NO:37:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (ix) FEATURE:
        (A) NAME/KEY: Modified-site
        (B) LOCATION: 3
        (D) OTHER INFORMATION: /label= hydrophobic (xi) SEQUENCE DESCRIPTION: SEQ ID NO:37:

```
Xaa Pro Xaa Pro Pro Xaa Pro
1               5
```

(2) INFORMATION FOR SEQ ID NO:38:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:38:

```
Glu Ser Asp Gly Gly Tyr Met Asp Met Ser Lys Asp Glu Ser Val Asp
1               5                   10                  15

Tyr Val Pro Met Leu Asp
            20
```

(2) INFORMATION FOR SEQ ID NO:39:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:39:

```
Glu Glu Glu Glu Glu Tyr Met Pro Met Glu Asp Leu Tyr Leu Asp Ile
1               5                   10                  15

Leu Pro
```

(2) INFORMATION FOR SEQ ID NO:40:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:40:

```
Gln Gly Val Asp Thr Tyr Val Glu Met Arg Pro
1               5                   10
```

(2) INFORMATION FOR SEQ ID NO:41:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:41:

```
Asp Ser Thr Asn Glu Tyr Met Asp Met Lys Pro
1               5                   10
```

(2) INFORMATION FOR SEQ ID NO:42:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide

```
        (iii) HYPOTHETICAL: NO (v) FRAGMENT TYPE: internal (xi) SEQUENCE DESCRIPTION: SEQ ID NO:42:

Gly Pro Gly Gly Asp Tyr Ala Ala Met Gly Ala Cys Pro Ala Ser Glu
1               5                  10                  15

Gln Gly Tyr Glu Glu Met Arg Ala
                20

(2) INFORMATION FOR SEQ ID NO:43:

(i) SEQUENCE CHARACTERISTICS:
             (A) LENGTH: 27 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:43:

Thr Pro Asp Glu Asp Tyr Glu Tyr Met Asn Arg Gln Arg Asp Gly Gly
1               5                  10                  15

Gly Pro Gly Gly Asp Tyr Ala Ala Met Gly Ala
                20                  25

(2) INFORMATION FOR SEQ ID NO:44:

(i) SEQUENCE CHARACTERISTICS:
             (A) LENGTH: 11 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:44:

Cys Thr Ile Asp Val Tyr Met Val Met Val Lys
1               5                  10

(2) INFORMATION FOR SEQ ID NO:45:

(i) SEQUENCE CHARACTERISTICS:
             (A) LENGTH: 11 amino acids
             (B) TYPE: amino acid
             (C) STRANDEDNESS:
             (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:45:

Ser Pro Ser Ser Gly Tyr Met Pro Met Asn Gln
1               5                  10

(2) INFORMATION FOR SEQ ID NO:46:
```

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:46:

Asp Glu Asp Glu Glu Tyr Glu Tyr Met Asn Arg
1               5                   10

(2) INFORMATION FOR SEQ ID NO:47:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:47:

Leu Glu Glu Leu Gly Tyr Glu Tyr Met Asp Val
1               5                   10

(2) INFORMATION FOR SEQ ID NO:48:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:48:

Glu Glu Leu Ser Asn Tyr Ile Cys Met Gly Gly
1               5                   10

(2) INFORMATION FOR SEQ ID NO:49:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:49:

Val Ser Ile Glu Glu Tyr Thr Glu Met Met Pro
1               5                   10

(2) INFORMATION FOR SEQ ID NO:50:

```
    (i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:50:

His Thr Asp Asp Gly Tyr Met Pro Met Ser Pro
1               5                   10

(2) INFORMATION FOR SEQ ID NO:51:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:51:

Lys Gly Asn Gly Asp Tyr Met Pro Met Ser Pro
1               5                   10

(2) INFORMATION FOR SEQ ID NO:52:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:52:

Val Asp Pro Asn Gly Tyr Met Met Met Ser Pro
1               5                   10

(2) INFORMATION FOR SEQ ID NO:53:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:53:

Pro Cys Thr Gly Asp Tyr Met Asn Met Ser Pro
1               5                   10
```

```
(2) INFORMATION FOR SEQ ID NO:54:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:54:

Thr Gly Ser Glu Glu Tyr Met Asn Met Asp Leu
1               5                   10

(2) INFORMATION FOR SEQ ID NO:55:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:55:

Asn Ser Arg Gly Asp Tyr Met Thr Met Gln Ile
1               5                   10

(2) INFORMATION FOR SEQ ID NO:56:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:56:

Val Ala Pro Val Ser Tyr Ala Asp Met Arg Thr
1               5                   10

(2) INFORMATION FOR SEQ ID NO:57:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:57:

Glu Arg Glu Asn Glu Tyr Met Pro Met Ala Pro Gln Ile His Leu Tyr
1               5                   10                  15
```

Ser Gln Ile Arg Glu
            20

(2) INFORMATION FOR SEQ ID NO:58:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:58:

Leu Ser Asn Pro Thr Tyr Ser Val Met Arg Ser
1               5                   10

(2) INFORMATION FOR SEQ ID NO:59:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:59:

Cys Pro Glu Lys Val Tyr Glu Leu Met Arg Ala
1               5                   10

(2) INFORMATION FOR SEQ ID NO:60:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:60:

Asn Thr Thr Val Asp Tyr Val Tyr Met Ser His Gly Asp Asn Gly Asp
1               5                   10                  15

Tyr Val Tyr Met Asn
            20

(2) INFORMATION FOR SEQ ID NO:61:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:61:

Asn Cys Asn Asp Asp Tyr Val Thr Met His Tyr Thr Thr Asp Gly Asp
1               5                   10                  15

Tyr Ile Tyr Met Asn
                20

(2) INFORMATION FOR SEQ ID NO:62:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:62:

Tyr Val Asn Asp Ile Tyr Leu Tyr Met Arg His Leu Glu Arg Glu Phe
1               5                   10                  15

Lys Val Arg Thr Asp Tyr Met Ala Met Gln Glu
                20                  25

(2) INFORMATION FOR SEQ ID NO:63:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:63:

Asn Gln Glu Glu Ala Tyr Val Thr Met Ser Ser
1               5                   10

(2) INFORMATION FOR SEQ ID NO:64:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:64:

Phe Ile Ala Ser Lys Tyr Glu Asp Met Tyr Pro
1               5                   10

(2) INFORMATION FOR SEQ ID NO:65:

(i) SEQUENCE CHARACTERISTICS:
            (A) LENGTH: 11 amino acids
            (B) TYPE: amino acid

```
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:65:

Leu Gly Ser Gln Ser Tyr Glu Asp Met Arg Gly
1               5                   10

(2) INFORMATION FOR SEQ ID NO:66:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:66:

Glu Asp Ala Asp Ser Tyr Glu Asn Met Asp Lys
1               5                   10

(2) INFORMATION FOR SEQ ID NO:67:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:67:

Glu Leu Gln Asp Asp Tyr Glu Asp Met Met Glu
1               5                   10

(2) INFORMATION FOR SEQ ID NO:68:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:68:

Ala Ala Cys Val Val Tyr Glu Asp Met Ser His
1               5                   10

(2) INFORMATION FOR SEQ ID NO:69:

(i) SEQUENCE CHARACTERISTICS:
        (A) LENGTH: 11 amino acids
```

```
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:69:

Ala Pro Pro Glu Glu Tyr Val Pro Met Val Lys
1               5                   10

(2) INFORMATION FOR SEQ ID NO:70:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:70:

Ile Asp Ser Cys Thr Tyr Glu Ala Met Tyr Asn
1               5                   10

(2) INFORMATION FOR SEQ ID NO:71:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:71:

Val Ala Val Ala Glu Tyr Glu Ile Met Glu Gln
1               5                   10

(2) INFORMATION FOR SEQ ID NO:72:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:72:

Met Ser Val Glu Ser Tyr Glu Glu Met Lys Met
1               5                   10

(2) INFORMATION FOR SEQ ID NO:73:

(i) SEQUENCE CHARACTERISTICS:
```

(A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:73:

His Gln Thr Arg Glu Tyr Glu Ser Met Ile Glu
1               5                   10

(2) INFORMATION FOR SEQ ID NO:74:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:74:

Thr Leu Gln Asn Glu Tyr Glu Leu Met Arg Glu
1               5                   10

(2) INFORMATION FOR SEQ ID NO:75:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:75:

Gly Gly Glu Glu Ile Tyr Val Val Met Leu Gly
1               5                   10

(2) INFORMATION FOR SEQ ID NO:76:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:76:

Leu Glu Gly Glu His Tyr Ile Asn Met Ala Val
1               5                   10

(2) INFORMATION FOR SEQ ID NO:77:

```
    (i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:77:

Glu Ile Thr Glu Gln Tyr Ile Tyr Met Val Met
1               5                   10

(2) INFORMATION FOR SEQ ID NO:78:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:78:

Thr Glu Gln Tyr Ile Tyr Met Val Met Glu Cys
1               5                   10

(2) INFORMATION FOR SEQ ID NO:79:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:79:

Leu Pro Ala Lys Pro
1               5

(2) INFORMATION FOR SEQ ID NO:80:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:80:

Leu Pro Ala Leu Pro
1               5

(2) INFORMATION FOR SEQ ID NO:81:
```

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:81:

Leu Pro Lys Leu Pro
1               5

(2) INFORMATION FOR SEQ ID NO:82:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:82:

Glu Asn Pro Ile Tyr Ala Gln Met Glu Asn Glu
1               5                   10

(2) INFORMATION FOR SEQ ID NO:83:

(i) SEQUENCE CHARACTERISTICS:
            (A) LENGTH: 14086 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens (ix) FEATURE:
            (A) NAME/KEY: CDS
            (B) LOCATION: 107..14074

(xi) SEQUENCE DESCRIPTION: SEQ ID NO:83:

```
TTGCAGACCT AAAGGAGCGT TCGCTAGCAG AGGCGCTGCC GGTGCGGTGT GCTACGCGCG        60

CCCACCTCCC GGGGAAGGAA CGGCGAGGCC GGGGACCGTC GCGGAG ATG GAT CGC         115
                                                 Met Asp Arg

GGG CCG GCA GCA GTG GCG TGC ACG CTG CTC CTG GCT CTC GTC GCC TGC        163
Gly Pro Ala Ala Val Ala Cys Thr Leu Leu Leu Ala Leu Val Ala Cys
    950                 955                 960

CTA GCG CCG GCC AGT GGC CAA GAA TGT GAC AGT GCG CAT TTT CGC TGT        211
Leu Ala Pro Ala Ser Gly Gln Glu Cys Asp Ser Ala His Phe Arg Cys
965                 970                 975                 980

GGA AGT GGG CAT TGC ATC CCT GCA GAC TGG AGG TGT GAT GGG ACC AAA        259
Gly Ser Gly His Cys Ile Pro Ala Asp Trp Arg Cys Asp Gly Thr Lys
                985                 990                 995
```

```
GAC TGT TCA GAT GAC GCG GAT GAA ATT GGC TGC GCT GTT GTG ACC TGC      307
Asp Cys Ser Asp Asp Ala Asp Glu Ile Gly Cys Ala Val Val Thr Cys
            1000                1005                1010

CAG CAG GGC TAT TTC AAG TGC CAG AGT GAG GGA CAA TGC ATC CCC AGC      355
Gln Gln Gly Tyr Phe Lys Cys Gln Ser Glu Gly Gln Cys Ile Pro Ser
            1015                1020                1025

TCC TGG GTG TGT GAC CAA GAT CAA GAC TGT GAT GAT GGC TCA GAT GAA      403
Ser Trp Val Cys Asp Gln Asp Gln Asp Cys Asp Asp Gly Ser Asp Glu
            1030                1035                1040

CGT CAA GAT TGC TCA CAA AGT ACA TGC TCA AGT CAT CAG ATA ACA TGC      451
Arg Gln Asp Cys Ser Gln Ser Thr Cys Ser Ser His Gln Ile Thr Cys
1045                1050                1055                1060

TCC AAT GGT CAG TGT ATC CCA AGT GAA TAC AGG TGC GAC CAC GTC AGA      499
Ser Asn Gly Gln Cys Ile Pro Ser Glu Tyr Arg Cys Asp His Val Arg
            1065                1070                1075

GAC TGC CCC GAT GGA GCT GAT GAG AAT GAC TGC CAG TAC CCA ACA TGT      547
Asp Cys Pro Asp Gly Ala Asp Glu Asn Asp Cys Gln Tyr Pro Thr Cys
            1080                1085                1090

GAG CAG CTT ACT TGT GAC AAT GGG GCC TGC TAT AAC ACC AGT CAG AAG      595
Glu Gln Leu Thr Cys Asp Asn Gly Ala Cys Tyr Asn Thr Ser Gln Lys
            1095                1100                1105

TGT GAT TGG AAA GTT GAT TGC AGG GAC TCC TCA GAT GAA ATC AAC TGC      643
Cys Asp Trp Lys Val Asp Cys Arg Asp Ser Ser Asp Glu Ile Asn Cys
            1110                1115                1120

ACT GAG ATA TGC TTG CAC AAT GAG TTT TCA TGT GGC AAT GGA GAG TGT      691
Thr Glu Ile Cys Leu His Asn Glu Phe Ser Cys Gly Asn Gly Glu Cys
1125                1130                1135                1140

ATC CCT CGT GCT TAT GTC TGT GAC CAT GAC AAT GAT TGC CAA GAC GGC      739
Ile Pro Arg Ala Tyr Val Cys Asp His Asp Asn Asp Cys Gln Asp Gly
            1145                1150                1155

AGT GAT GAA CAT GCT TGC AAC TAT CCG ACC TGC GGT GGT TAC CAG TTC      787
Ser Asp Glu His Ala Cys Asn Tyr Pro Thr Cys Gly Gly Tyr Gln Phe
            1160                1165                1170

ACT TGC CCC AGT GGC CGA TGC ATT TAT CAA AAC TGG GTT TGT GAT GGA      835
Thr Cys Pro Ser Gly Arg Cys Ile Tyr Gln Asn Trp Val Cys Asp Gly
            1175                1180                1185

GAA GAT GAC TGT AAA GAT AAT GGA GAT GAA GAT GGA TGT GAA AGC GGT      883
Glu Asp Asp Cys Lys Asp Asn Gly Asp Glu Asp Gly Cys Glu Ser Gly
            1190                1195                1200

CCT CAT GAT GTT CAT AAA TGT TCC CCA AGA GAA TGG TCT TGC CCA GAG      931
Pro His Asp Val His Lys Cys Ser Pro Arg Glu Trp Ser Cys Pro Glu
1205                1210                1215                1220

TCG GGA CGA TGC ATC TCC ATT TAT AAA GTT TGT GAT GGG ATT TTA GAT      979
Ser Gly Arg Cys Ile Ser Ile Tyr Lys Val Cys Asp Gly Ile Leu Asp
            1225                1230                1235

TGC CCA GGA AGA GAA GAT GAA AAC AAC ACT AGT ACC GGA AAA TAC TGT     1027
Cys Pro Gly Arg Glu Asp Glu Asn Asn Thr Ser Thr Gly Lys Tyr Cys
            1240                1245                1250

AGT ATG ACT CTG TGC TCT GCC TTG AAC TGC CAG TAC CAG TGC CAT GAG     1075
Ser Met Thr Leu Cys Ser Ala Leu Asn Cys Gln Tyr Gln Cys His Glu
            1255                1260                1265

ACG CCG TAT GGA GGA GCG TGT TTT TGT CCC CCA GGT TAT ATC ATC AAC     1123
Thr Pro Tyr Gly Gly Ala Cys Phe Cys Pro Pro Gly Tyr Ile Ile Asn
            1270                1275                1280

CAC AAT GAC AGC CGT ACC TGT GTT GAG TTT GAT GAT TGC CAG ATA TGG     1171
His Asn Asp Ser Arg Thr Cys Val Glu Phe Asp Asp Cys Gln Ile Trp
1285                1290                1295                1300

GGA ATT TGT GAC CAG AAG TGT GAA AGC CGA CCT GGC CGT CAC CTG TGC     1219
Gly Ile Cys Asp Gln Lys Cys Glu Ser Arg Pro Gly Arg His Leu Cys
            1305                1310                1315
```

```
CAC TGT GAA GAA GGG TAT ATC TTG GAG CGT GGA CAG TAT TGC AAA GCT       1267
His Cys Glu Glu Gly Tyr Ile Leu Glu Arg Gly Gln Tyr Cys Lys Ala
            1320                1325                1330

AAT GAT TCC TTT GGC GAG GCC TCC ATT ATC TTC TCC AAT GGT CGG GAT       1315
Asn Asp Ser Phe Gly Glu Ala Ser Ile Ile Phe Ser Asn Gly Arg Asp
            1335                1340                1345

TTG TTA ATT GGT GAT ATT CAT GGA AGG AGC TTC CGG ATC CTA GTG GAG       1363
Leu Leu Ile Gly Asp Ile His Gly Arg Ser Phe Arg Ile Leu Val Glu
            1350                1355                1360

TCT CAG AAT CGT GGA GTG GCC GTG GGT GTG GCT TTC CAC TAT CAC CTG       1411
Ser Gln Asn Arg Gly Val Ala Val Gly Val Ala Phe His Tyr His Leu
1365                1370                1375                1380

CAA AGA GTT TTT TGG ACA GAC ACC GTG CAA AAT AAG GTT TTT TCA GTT       1459
Gln Arg Val Phe Trp Thr Asp Thr Val Gln Asn Lys Val Phe Ser Val
                1385                1390                1395

GAC ATT AAT GGT TTA AAT ATC CAA GAG GTT CTC AAT GTT TCT GTT GAA       1507
Asp Ile Asn Gly Leu Asn Ile Gln Glu Val Leu Asn Val Ser Val Glu
            1400                1405                1410

ACC CCA GAG AAC CTG GCT GTG GAC TGG GTT AAT AAT AAA ATC TAT CTA       1555
Thr Pro Glu Asn Leu Ala Val Asp Trp Val Asn Asn Lys Ile Tyr Leu
            1415                1420                1425

GTG GAA ACC AAG GTC AAC CGC ATA GAT ATG GTA AAT TTG GAT GGA AGC       1603
Val Glu Thr Lys Val Asn Arg Ile Asp Met Val Asn Leu Asp Gly Ser
            1430                1435                1440

TAT CGG GTT ACC CTT ATA ACT GAA AAC TTG GGG CAT CCT AGA GGA ATT       1651
Tyr Arg Val Thr Leu Ile Thr Glu Asn Leu Gly His Pro Arg Gly Ile
1445                1450                1455                1460

GCC GTG GAC CCA ACT GTT GGT TAT TTA TTT TTC TCA GAT TGG GAG AGC       1699
Ala Val Asp Pro Thr Val Gly Tyr Leu Phe Phe Ser Asp Trp Glu Ser
                1465                1470                1475

CTT TCT GGG GAA CCT AAG CTG GAA AGG GCA TTC ATG GAT GGC AGC AAC       1747
Leu Ser Gly Glu Pro Lys Leu Glu Arg Ala Phe Met Asp Gly Ser Asn
            1480                1485                1490

CGT AAA GAC TTG GTG AAA ACA AAG CTG GGA TGG CCT GCT GGG GTA ACT       1795
Arg Lys Asp Leu Val Lys Thr Lys Leu Gly Trp Pro Ala Gly Val Thr
            1495                1500                1505

CTG GAT ATG ATA TCG AAG CGT GTT TAC TGG GTT GAC TCT CGG TTT GAT       1843
Leu Asp Met Ile Ser Lys Arg Val Tyr Trp Val Asp Ser Arg Phe Asp
            1510                1515                1520

TAC ATT GAA ACT GTA ACT TAT GAT GGA ATT CAA AGG AAG ACT GTA GTT       1891
Tyr Ile Glu Thr Val Thr Tyr Asp Gly Ile Gln Arg Lys Thr Val Val
1525                1530                1535                1540

CAT GGA GGC TCC CTC ATT CCT CAT CCC TTT GGA GTA AGC TTA TTT GAA       1939
His Gly Gly Ser Leu Ile Pro His Pro Phe Gly Val Ser Leu Phe Glu
                1545                1550                1555

GGT CAG GTG TTC TTT ACA GAT TGG ACA AAG ATG GCC GTG CTG AAG GCA       1987
Gly Gln Val Phe Phe Thr Asp Trp Thr Lys Met Ala Val Leu Lys Ala
                1560                1565                1570

AAC AAG TTC ACA GAG ACC AAC CCA CAA GTG TAC TAC CAG GCT TCC CTG       2035
Asn Lys Phe Thr Glu Thr Asn Pro Gln Val Tyr Tyr Gln Ala Ser Leu
            1575                1580                1585

AGG CCC TAT GGA GTG ACT GTT TAC CAT TCC CTC AGA CAG CCC TAT GCT       2083
Arg Pro Tyr Gly Val Thr Val Tyr His Ser Leu Arg Gln Pro Tyr Ala
1590                1595                1600

ACC AAT CCG TGT AAA GAT AAC AAT GGG GGC TGT GAG CAG GTC TGT GTT       2131
Thr Asn Pro Cys Lys Asp Asn Asn Gly Gly Cys Glu Gln Val Cys Val
1605                1610                1615                1620

CTC AGC CAC AGA ACA GAT AAT GAT GGT TTG GGT TTC CGT TGC AAG TGC       2179
Leu Ser His Arg Thr Asp Asn Asp Gly Leu Gly Phe Arg Cys Lys Cys
```

-continued

```
              1625                1630                1635
ACA TTC GGC TTC CAA CTG GAT ACA GAT GAG CGC CAC TGC ATT GCT GTT      2227
Thr Phe Gly Phe Gln Leu Asp Thr Asp Glu Arg His Cys Ile Ala Val
            1640                1645                1650

CAG AAT TTC CTC ATT TTT TCA TCC CAA GTT GCT ATT CGT GGG ATC CCG      2275
Gln Asn Phe Leu Ile Phe Ser Ser Gln Val Ala Ile Arg Gly Ile Pro
            1655                1660                1665

TTC ACC TTG TCT ACC CAG GAA GAT GTC ATG GTT CCA GTT TCG GGG AAT      2323
Phe Thr Leu Ser Thr Gln Glu Asp Val Met Val Pro Val Ser Gly Asn
            1670                1675                1680

CCT TCT TTC TTT GTC GGG ATT GAT TTT GAC GCC CAG GAC AGC ACT ATC      2371
Pro Ser Phe Phe Val Gly Ile Asp Phe Asp Ala Gln Asp Ser Thr Ile
1685                1690                1695                1700

TTT TTT TCA GAT ATG TCA AAA CAC ATG ATT TTT AAG CAA AAG ATT GAT      2419
Phe Phe Ser Asp Met Ser Lys His Met Ile Phe Lys Gln Lys Ile Asp
            1705                1710                1715

GGC ACA GGA AGA GAA ATT CTC GCA GCT AAC AGG GTG GAA AAT GTT GAA      2467
Gly Thr Gly Arg Glu Ile Leu Ala Ala Asn Arg Val Glu Asn Val Glu
            1720                1725                1730

AGT TTG GCT TTT GAT TGG ATT TCA AAG AAT CTC TAT TGG ACA GAC TCT      2515
Ser Leu Ala Phe Asp Trp Ile Ser Lys Asn Leu Tyr Trp Thr Asp Ser
            1735                1740                1745

CAT TAC AAG AGT ATC AGT GTC ATG AGG CTA GCT GAT AAA ACG AGA CGC      2563
His Tyr Lys Ser Ile Ser Val Met Arg Leu Ala Asp Lys Thr Arg Arg
            1750                1755                1760

ACA GTA GTT CAG TAT TTA AAT AAC CCA CGG TCG GTG GTA GTT CAT CCT      2611
Thr Val Val Gln Tyr Leu Asn Asn Pro Arg Ser Val Val Val His Pro
1765                1770                1775                1780

TTT GCC GGG TAT CTA TTC TTC ACT GAT TGG TTC CGT CCT GCT AAA ATT      2659
Phe Ala Gly Tyr Leu Phe Phe Thr Asp Trp Phe Arg Pro Ala Lys Ile
            1785                1790                1795

ATG AGA GCA TGG AGT GAC GGA TCT CAC CTC TTG CCT GTA ATA AAC ACT      2707
Met Arg Ala Trp Ser Asp Gly Ser His Leu Leu Pro Val Ile Asn Thr
            1800                1805                1810

ACT CTT GGA TGG CCC AAT GGC TTG GCC ATC GAT TGG GCT GCT TCA CGA      2755
Thr Leu Gly Trp Pro Asn Gly Leu Ala Ile Asp Trp Ala Ala Ser Arg
            1815                1820                1825

TTG TAC TGG GTA GAT GCC TAT TTT GAT AAA ATT GAG CAC AGC ACC TTT      2803
Leu Tyr Trp Val Asp Ala Tyr Phe Asp Lys Ile Glu His Ser Thr Phe
            1830                1835                1840

GAT GGT TTA GAC AGA AGA AGA CTG GGC CAT ATA GAG CAG ATG ACA CAT      2851
Asp Gly Leu Asp Arg Arg Arg Leu Gly His Ile Glu Gln Met Thr His
1845                1850                1855                1860

CCG TTT GGA CTT GCC ATC TTT GGA GAG CAT TTA TTT TTT ACT GAC TGG      2899
Pro Phe Gly Leu Ala Ile Phe Gly Glu His Leu Phe Phe Thr Asp Trp
            1865                1870                1875

AGA CTG GGT GCC ATT ATT CGA GTC AGG AAA GCA GAT GGT GGA GAA ATG      2947
Arg Leu Gly Ala Ile Ile Arg Val Arg Lys Ala Asp Gly Gly Glu Met
            1880                1885                1890

ACA GTT ATC CGA AGT GGC ATT GCT TAC ATA CTG CAT TTG AAA TCG TAT      2995
Thr Val Ile Arg Ser Gly Ile Ala Tyr Ile Leu His Leu Lys Ser Tyr
            1895                1900                1905

GAT GTC AAC ATC CAG ACT GGT TCT AAC GCC TGT AAT CAA CCC ACG CAT      3043
Asp Val Asn Ile Gln Thr Gly Ser Asn Ala Cys Asn Gln Pro Thr His
            1910                1915                1920

CCT AAC GGT GAC TGC AGC CAC TTC TGC TTC CCG GTG CCA AAT TTC CAG      3091
Pro Asn Gly Asp Cys Ser His Phe Cys Phe Pro Val Pro Asn Phe Gln
1925                1930                1935                1940

CGA GTG TGT GGG TGC CCT TAT GGA ATG AGG CTG GCT TCC AAT CAC TTG      3139
```

```
Arg Val Cys Gly Cys Pro Tyr Gly Met Arg Leu Ala Ser Asn His Leu
            1945                1950                1955

ACA TGC GAG GGG GAC CCA ACC AAT GAA CCA CCC ACG GAG CAG TGT GGC       3187
Thr Cys Glu Gly Asp Pro Thr Asn Glu Pro Pro Thr Glu Gln Cys Gly
            1960                1965                1970

TTA TTT TCC TTC CCC TGT AAA AAT GGC AGA TGT GTG CCC AAT TAC TAT       3235
Leu Phe Ser Phe Pro Cys Lys Asn Gly Arg Cys Val Pro Asn Tyr Tyr
        1975                1980                1985

CTC TGT GAT GGA GTC GAT GAT TGT CAT GAT AAC AGT GAT GAG CAA CTA       3283
Leu Cys Asp Gly Val Asp Asp Cys His Asp Asn Ser Asp Glu Gln Leu
        1990                1995                2000

TGT GGC ACA CTT AAT AAT ACC TGT TCA TCT TCG GCG TTC ACC TGT GGC       3331
Cys Gly Thr Leu Asn Asn Thr Cys Ser Ser Ser Ala Phe Thr Cys Gly
2005                2010                2015                2020

CAT GGG GAG TGC ATT CCT GCA CAC TGG CGC TGT GAC AAA CGC AAC GAC       3379
His Gly Glu Cys Ile Pro Ala His Trp Arg Cys Asp Lys Arg Asn Asp
                2025                2030                2035

TGT GTG GAT GGC AGT GAT GAG CAC AAC TGC CCC ACC CAC GCA CCT GCT       3427
Cys Val Asp Gly Ser Asp Glu His Asn Cys Pro Thr His Ala Pro Ala
            2040                2045                2050

TCC TGC CTT GAC ACC CAA TAC ACC TGT GAT AAT CAC CAG TGT ATC TCA       3475
Ser Cys Leu Asp Thr Gln Tyr Thr Cys Asp Asn His Gln Cys Ile Ser
        2055                2060                2065

AAG AAC TGG GTC TGT GAC ACA GAC AAT GAT TGT GGG GAT GGA TCT GAT       3523
Lys Asn Trp Val Cys Asp Thr Asp Asn Asp Cys Gly Asp Gly Ser Asp
        2070                2075                2080

GAA AAG AAC TGC AAT TCG ACA GAG ACA TGC CAA CCT AGT CAG TTT AAT       3571
Glu Lys Asn Cys Asn Ser Thr Glu Thr Cys Gln Pro Ser Gln Phe Asn
2085                2090                2095                2100

TGC CCC AAT CAT CGA TGT ATT GAC CTA TCG TTT GTC TGT GAT GGT GAC       3619
Cys Pro Asn His Arg Cys Ile Asp Leu Ser Phe Val Cys Asp Gly Asp
                2105                2110                2115

AAG GAT TGT GTT GAT GGA TCT GAT GAG GTT GGT TGT GTA TTA AAC TGT       3667
Lys Asp Cys Val Asp Gly Ser Asp Glu Val Gly Cys Val Leu Asn Cys
            2120                2125                2130

ACT GCT TCT CAA TTC AAG TGT GCC AGT GGG GAT AAA TGT ATT GGC GTC       3715
Thr Ala Ser Gln Phe Lys Cys Ala Ser Gly Asp Lys Cys Ile Gly Val
        2135                2140                2145

ACA AAT CGT TGT GAT GGT GTT TTT GAT TGC AGT GAC AAC TCG GAT GAA       3763
Thr Asn Arg Cys Asp Gly Val Phe Asp Cys Ser Asp Asn Ser Asp Glu
        2150                2155                2160

GCG GGC TGT CCA ACC AGG CCT CCT GGT ATG TGC CAC TCA GAT GAA TTT       3811
Ala Gly Cys Pro Thr Arg Pro Pro Gly Met Cys His Ser Asp Glu Phe
2165                2170                2175                2180

CAG TGC CAA GAA GAT GGT ATC TGC ATC CCG AAC TTC TGG GAA TGT GAT       3859
Gln Cys Gln Glu Asp Gly Ile Cys Ile Pro Asn Phe Trp Glu Cys Asp
                2185                2190                2195

GGG CAT CCA GAC TGC CTC TAT GGA TCT GAT GAG CAC AAT GCC TGT GTC       3907
Gly His Pro Asp Cys Leu Tyr Gly Ser Asp Glu His Asn Ala Cys Val
            2200                2205                2210

CCC AAG ACT TGC CCT TCA TCA TAT TTC CAC TGT GAC AAC GGA AAC TGC       3955
Pro Lys Thr Cys Pro Ser Ser Tyr Phe His Cys Asp Asn Gly Asn Cys
        2215                2220                2225

ATC CAC AGG GCA TGG CTC TGT GAT CGG GAC AAT GAC TGC GGG GAT ATG       4003
Ile His Arg Ala Trp Leu Cys Asp Arg Asp Asn Asp Cys Gly Asp Met
        2230                2235                2240

AGT GAT GAG AAG GAC TGC CCT ACT CAG CCC TTT CGC TGT CCT AGT TGG       4051
Ser Asp Glu Lys Asp Cys Pro Thr Gln Pro Phe Arg Cys Pro Ser Trp
2245                2250                2255                2260
```

```
CAA TGG CAG TGT CTT GGC CAT AAC ATC TGT GTG AAT CTG AGT GTA GTG    4099
Gln Trp Gln Cys Leu Gly His Asn Ile Cys Val Asn Leu Ser Val Val
                2265                2270                2275

TGT GAT GGC ATC TTT GAC TGC CCC AAT GGG ACA GAT GAG TCC CCA CTT    4147
Cys Asp Gly Ile Phe Asp Cys Pro Asn Gly Thr Asp Glu Ser Pro Leu
                2280                2285                2290

TGC AAT GGG AAC AGC TGC TCA GAT TTC AAT GGT GGT TGT ACT CAC GAG    4195
Cys Asn Gly Asn Ser Cys Ser Asp Phe Asn Gly Gly Cys Thr His Glu
                2295                2300                2305

TGT GTT CAA GAG CCC TTT GGG GCT AAA TGC CTA TGT CCA TTG GGA TTC    4243
Cys Val Gln Glu Pro Phe Gly Ala Lys Cys Leu Cys Pro Leu Gly Phe
                2310                2315                2320

TTA CTT GCC AAT GAT TCT AAG ACC TGT GAA GAC ATA GAT GAA TGT GAT    4291
Leu Leu Ala Asn Asp Ser Lys Thr Cys Glu Asp Ile Asp Glu Cys Asp
2325                2330                2335                2340

ATT CTA GGC TCT TGT AGC CAG CAC TGT TAC AAT ATG AGA GGT TCT TTC    4339
Ile Leu Gly Ser Cys Ser Gln His Cys Tyr Asn Met Arg Gly Ser Phe
                2345                2350                2355

CGG TGC TCG TGT GAT ACA GGC TAC ATG TTA GAA AGT GAT GGG AGG ACT    4387
Arg Cys Ser Cys Asp Thr Gly Tyr Met Leu Glu Ser Asp Gly Arg Thr
                2360                2365                2370

TGC AAA GTT ACA GCA TCT GAG AGT CTG CTG TTA CTT GTG GCA AGT CAG    4435
Cys Lys Val Thr Ala Ser Glu Ser Leu Leu Leu Leu Val Ala Ser Gln
                2375                2380                2385

AAC AAA ATT ATT GCC GAC AGT GTC ACC TCC CAG GTC CAC AAT ATC TAT    4483
Asn Lys Ile Ile Ala Asp Ser Val Thr Ser Gln Val His Asn Ile Tyr
                2390                2395                2400

TCA TTG GTC GAG AAT GGT TCT TAC ATT GTA GCT GTT GAT TTT GAT TCA    4531
Ser Leu Val Glu Asn Gly Ser Tyr Ile Val Ala Val Asp Phe Asp Ser
2405                2410                2415                2420

ATT AGT GGT CGT ATC TTT TGG TCT GAT GCA ACT CAG GGT AAA ACC TGG    4579
Ile Ser Gly Arg Ile Phe Trp Ser Asp Ala Thr Gln Gly Lys Thr Trp
                2425                2430                2435

AGT GCG TTT CAA AAT GGA ACG GAC AGA AGA GTG GTA TTT GAC AGT AGC    4627
Ser Ala Phe Gln Asn Gly Thr Asp Arg Arg Val Val Phe Asp Ser Ser
                2440                2445                2450

ATC ATC TTG ACT GAA ACT ATT GCA ATA GAT TGG GTA GGT CGT AAT CTT    4675
Ile Ile Leu Thr Glu Thr Ile Ala Ile Asp Trp Val Gly Arg Asn Leu
                2455                2460                2465

TAC TGG ACA GAC TAT GCT CTG GAA ACA ATT GAA GTC TCC AAA ATT GAT    4723
Tyr Trp Thr Asp Tyr Ala Leu Glu Thr Ile Glu Val Ser Lys Ile Asp
                2470                2475                2480

GGG AGC CAC AGG ACT GTG CTG ATT AGT AAA AAC CTA ACA AAT CCA AGA    4771
Gly Ser His Arg Thr Val Leu Ile Ser Lys Asn Leu Thr Asn Pro Arg
2485                2490                2495                2500

GGA CTA GCA TTA GAT CCC AGA ATG AAT GAG CAT CTA CTG TTC TGG TCT    4819
Gly Leu Ala Leu Asp Pro Arg Met Asn Glu His Leu Leu Phe Trp Ser
                2505                2510                2515

GAC TGG GGC CAC CAC CCT CGC ATC GAG CGA GCC AGC ATG GAC GGC AGC    4867
Asp Trp Gly His His Pro Arg Ile Glu Arg Ala Ser Met Asp Gly Ser
                2520                2525                2530

ATG CGC ACT GTC ATT GTC CAG GAC AAG ATC TTC TGG CCC TGC GGC TTA    4915
Met Arg Thr Val Ile Val Gln Asp Lys Ile Phe Trp Pro Cys Gly Leu
                2535                2540                2545

ACT ATT GAC TAC CCC AAC AGA CTG CTC TAC TTC ATG GAC TCC TAT CTT    4963
Thr Ile Asp Tyr Pro Asn Arg Leu Leu Tyr Phe Met Asp Ser Tyr Leu
                2550                2555                2560

GAT TAC ATG GAC TTT TGC GAT TAT AAT GGA CAC CAT CGG AGA CAG GTG    5011
Asp Tyr Met Asp Phe Cys Asp Tyr Asn Gly His His Arg Arg Gln Val
2565                2570                2575                2580
```

-continued

```
ATA GCC AGT GAT TTG ATT ATA CGG CAC CCC TAT GCC CTA ACT CTC TTT      5059
Ile Ala Ser Asp Leu Ile Ile Arg His Pro Tyr Ala Leu Thr Leu Phe
             2585                2590                2595

GAA GAC TCT GTG TAC TGG ACT GAC CGT GCT ACT CGT CGG GTT ATG CGA      5107
Glu Asp Ser Val Tyr Trp Thr Asp Arg Ala Thr Arg Arg Val Met Arg
             2600                2605                2610

GCC AAC AAG TGG CAT GGA GGG AAC CAG TCA GTT GTA ATG TAT AAT ATT      5155
Ala Asn Lys Trp His Gly Gly Asn Gln Ser Val Val Met Tyr Asn Ile
             2615                2620                2625

CAA TGG CCC CTT GGG ATT GTT GCG GTT CAT CCT TCG AAA CAA CCA AAT      5203
Gln Trp Pro Leu Gly Ile Val Ala Val His Pro Ser Lys Gln Pro Asn
             2630                2635                2640

TCC GTG AAT CCA TGT GCC TTT TCC CGC TGC AGC CAT CTC TGC CTG CTT      5251
Ser Val Asn Pro Cys Ala Phe Ser Arg Cys Ser His Leu Cys Leu Leu
2645                2650                2655                2660

TCC TCA CAG GGG CCT CAT TTT TAC TCC TGT GTT TGT CCT TCA GGA TGG      5299
Ser Ser Gln Gly Pro His Phe Tyr Ser Cys Val Cys Pro Ser Gly Trp
             2665                2670                2675

AGT CTG TCT CCT GAT CTC CTG AAT TGC TTG AGA GAT GAT CAA CCT TTC      5347
Ser Leu Ser Pro Asp Leu Leu Asn Cys Leu Arg Asp Asp Gln Pro Phe
             2680                2685                2690

TTA ATA ACT GTA AGG CAA CAT ATA ATT TTT GGA ATC TCC CTT AAT CCT      5395
Leu Ile Thr Val Arg Gln His Ile Ile Phe Gly Ile Ser Leu Asn Pro
             2695                2700                2705

GAG GTG AAG AGC AAT GAT GCT ATG GTC CCC ATA GCA GGG ATA CAG AAT      5443
Glu Val Lys Ser Asn Asp Ala Met Val Pro Ile Ala Gly Ile Gln Asn
             2710                2715                2720

GGT TTA GAT GTT GAA TTT GAT GAT GCT GAG CAA TAC ATC TAT TGG GTT      5491
Gly Leu Asp Val Glu Phe Asp Asp Ala Glu Gln Tyr Ile Tyr Trp Val
2725                2730                2735                2740

GAA AAT CCA GGT GAA ATT CAC AGA GTG AAG ACA GAT GGC ACC AAC AGG      5539
Glu Asn Pro Gly Glu Ile His Arg Val Lys Thr Asp Gly Thr Asn Arg
             2745                2750                2755

ACA GTA TTT GCT TCT ATA TCT ATG GTG GGG CCT TCT ATG AAC CTG GCC      5587
Thr Val Phe Ala Ser Ile Ser Met Val Gly Pro Ser Met Asn Leu Ala
             2760                2765                2770

TTA GAT TGG ATT TCA AGA AAC CTT TAT TCT ACC AAT CCT AGA ACT CAG      5635
Leu Asp Trp Ile Ser Arg Asn Leu Tyr Ser Thr Asn Pro Arg Thr Gln
             2775                2780                2785

TCA ATC GAG GTT TTG ACA CTC CAC GGA GAT ATC AGA TAC AGA AAA ACA      5683
Ser Ile Glu Val Leu Thr Leu His Gly Asp Ile Arg Tyr Arg Lys Thr
             2790                2795                2800

TTG ATT GCC AAT GAT GGG ACA GCT CTT GGA GTT GGC TTT CCA ATT GGC      5731
Leu Ile Ala Asn Asp Gly Thr Ala Leu Gly Val Gly Phe Pro Ile Gly
2805                2810                2815                2820

ATA ACT GTT GAT CCT GCT CGT GGG AAG CTG TAC TGG TCA GAC CAA GGA      5779
Ile Thr Val Asp Pro Ala Arg Gly Lys Leu Tyr Trp Ser Asp Gln Gly
             2825                2830                2835

ACT GAC AGT GGG GTT CCT GCC AAG ATC GCC AGT GCT AAC ATG GAT GGC      5827
Thr Asp Ser Gly Val Pro Ala Lys Ile Ala Ser Ala Asn Met Asp Gly
             2840                2845                2850

ACA TCT GTG AAA ACT CTC TTT ACT GGG AAC CTC GAA CAC CTG GAG TGT      5875
Thr Ser Val Lys Thr Leu Phe Thr Gly Asn Leu Glu His Leu Glu Cys
             2855                2860                2865

GTC ACT CTT GAC ATC GAA GAG CAG AAA CTC TAC TGG GCA GTC ACT GGA      5923
Val Thr Leu Asp Ile Glu Glu Gln Lys Leu Tyr Trp Ala Val Thr Gly
             2870                2875                2880

AGA GGA GTG ATT GAA AGA GGA AAC GTG GAT GGA ACA GAT CGG ATG ATC      5971
Arg Gly Val Ile Glu Arg Gly Asn Val Asp Gly Thr Asp Arg Met Ile
```

```
                 2885                  2890                  2895                  2900
CTG GTA CAC CAG CTT TCC CAC CCC TGG GGA ATT GCA GTC CAT GAT TCT                              6019
Leu Val His Gln Leu Ser His Pro Trp Gly Ile Ala Val His Asp Ser
                     2905                  2910                  2915

TTC CTT TAT TAT ACT GAT GAA CAG TAT GAG GTC ATT GAA AGA GTT GAT                              6067
Phe Leu Tyr Tyr Thr Asp Glu Gln Tyr Glu Val Ile Glu Arg Val Asp
                 2920                  2925                  2930

AAG GCC ACT GGG GCC AAC AAA ATA GTC TTG AGA GAT AAT GTT CCA AAT                              6115
Lys Ala Thr Gly Ala Asn Lys Ile Val Leu Arg Asp Asn Val Pro Asn
             2935                  2940                  2945

CTG AGG GGT CTT CAA GTT TAT CAC AGA CGC AAT GCC GCC GAA TCC TCA                              6163
Leu Arg Gly Leu Gln Val Tyr His Arg Arg Asn Ala Ala Glu Ser Ser
         2950                  2955                  2960

AAT GGC TGT AGC AAC AAC ATG AAT GCC TGT CAG CAG ATT TGC CTG CCT                              6211
Asn Gly Cys Ser Asn Asn Met Asn Ala Cys Gln Gln Ile Cys Leu Pro
2965                  2970                  2975                  2980

GTA CCA GGA GGA TTG TTT TCC TGC GCC TGT GCC ACT GGA TTT AAA CTC                              6259
Val Pro Gly Gly Leu Phe Ser Cys Ala Cys Ala Thr Gly Phe Lys Leu
                 2985                  2990                  2995

AAT CCT GAT AAT CGG TCC TGC TCT CCA TAT AAC TCT TTC ATT GTT GTT                              6307
Asn Pro Asp Asn Arg Ser Cys Ser Pro Tyr Asn Ser Phe Ile Val Val
             3000                  3005                  3010

TCA ATG CTG TCT GCA ATC AGA GGC TTT AGC TTG GAA TTG TCA GAT CAT                              6355
Ser Met Leu Ser Ala Ile Arg Gly Phe Ser Leu Glu Leu Ser Asp His
         3015                  3020                  3025

TCA GAA ACC ATG GTG CCG GTG GCA GGC CAA GGA CGA AAC GCA CTG CAT                              6403
Ser Glu Thr Met Val Pro Val Ala Gly Gln Gly Arg Asn Ala Leu His
     3030                  3035                  3040

GTG GAT GTG GAT GTG TCC TCT GGC TTT ATT TAT TGG TGT GAT TTT AGC                              6451
Val Asp Val Asp Val Ser Ser Gly Phe Ile Tyr Trp Cys Asp Phe Ser
3045                  3050                  3055                  3060

AGC TCA GTG GCA TCT GAT AAT GCG ATC CGT AGA ATT AAA CCA GAT GGA                              6499
Ser Ser Val Ala Ser Asp Asn Ala Ile Arg Arg Ile Lys Pro Asp Gly
                 3065                  3070                  3075

TCT TCT CTG ATG AAC ATT GTG ACA CAT GGA ATA GGA GAA AAT GGA GTC                              6547
Ser Ser Leu Met Asn Ile Val Thr His Gly Ile Gly Glu Asn Gly Val
             3080                  3085                  3090

CGG GGT ATT GCA GTG GAT TGG GTA GCA GGA AAT CTT TAT TTC ACC AAT                              6595
Arg Gly Ile Ala Val Asp Trp Val Ala Gly Asn Leu Tyr Phe Thr Asn
         3095                  3100                  3105

GCC TTT GTT TCT GAA ACA CTG ATA GAA GTT CTG CGG ATC AAT ACT ACT                              6643
Ala Phe Val Ser Glu Thr Leu Ile Glu Val Leu Arg Ile Asn Thr Thr
     3110                  3115                  3120

TAC CGC CGT GTT CTT CTT AAA GTC ACA GTG GAC ATG CCT AGG CAT ATT                              6691
Tyr Arg Arg Val Leu Leu Lys Val Thr Val Asp Met Pro Arg His Ile
3125                  3130                  3135                  3140

GTT GTA GAT CCC AAG AAC AGA TAC CTC TTC TGG GCT GAC TAT GGG CAG                              6739
Val Val Asp Pro Lys Asn Arg Tyr Leu Phe Trp Ala Asp Tyr Gly Gln
                 3145                  3150                  3155

AGA CCA AAG ATT GAG CGT TCT TTC CTT GAC TGT ACC AAT CGA ACA GTG                              6787
Arg Pro Lys Ile Glu Arg Ser Phe Leu Asp Cys Thr Asn Arg Thr Val
             3160                  3165                  3170

CTT GTG TCA GAG GGC ATT GTC ACA CCA CGG GGC TTG GCA GTG GAC CGA                              6835
Leu Val Ser Glu Gly Ile Val Thr Pro Arg Gly Leu Ala Val Asp Arg
         3175                  3180                  3185

AGT GAT GGC TAC GTT TAT TGG GTT GAT GAT TCT TTA GAT ATA ATT GCA                              6883
Ser Asp Gly Tyr Val Tyr Trp Val Asp Asp Ser Leu Asp Ile Ile Ala
     3190                  3195                  3200

AGG ATT CGT ATC AAT GGA GAG AAC TCT GAA GTG ATT CGT TAT GGC AGT                              6931
```

```
                                                    -continued
Arg Ile Arg Ile Asn Gly Glu Asn Ser Glu Val Ile Arg Tyr Gly Ser
3205                3210                3215                3220

CGT TAC CCA ACT CCT TAT GGC ATC ACT GTT TTT GAA AAT TCT ATC ATA      6979
Arg Tyr Pro Thr Pro Tyr Gly Ile Thr Val Phe Glu Asn Ser Ile Ile
                3225                3230                3235

TGG GTA GAT AGG AAT TTG AAA AAG ATC TTC CAA GCC AGC AAG GAA CCA      7027
Trp Val Asp Arg Asn Leu Lys Lys Ile Phe Gln Ala Ser Lys Glu Pro
            3240                3245                3250

GAG AAC ACA GAG CCA CCC ACA GTG ATA AGA GAC AAT ATC AAC TGG CTA      7075
Glu Asn Thr Glu Pro Pro Thr Val Ile Arg Asp Asn Ile Asn Trp Leu
        3255                3260                3265

AGA GAT GTG ACC ATC TTT GAC AAG CAA GTC CAG CCC CGG TCA CCA GCA      7123
Arg Asp Val Thr Ile Phe Asp Lys Gln Val Gln Pro Arg Ser Pro Ala
    3270                3275                3280

GAG GTC AAC AAC AAC CCT TGC TTG GAA AAC AAT GGT GGG TGC TCT CAT      7171
Glu Val Asn Asn Asn Pro Cys Leu Glu Asn Asn Gly Gly Cys Ser His
3285                3290                3295                3300

CTC TGC TTT GCT CTG CCT GGA TTG CAC ACC CCA AAA TGT GAC TGT GCC      7219
Leu Cys Phe Ala Leu Pro Gly Leu His Thr Pro Lys Cys Asp Cys Ala
                3305                3310                3315

TTT GGG ACC CTG CAA AGT GAT GGC AAG AAT TGT GCC ATT TCA ACA GAA      7267
Phe Gly Thr Leu Gln Ser Asp Gly Lys Asn Cys Ala Ile Ser Thr Glu
            3320                3325                3330

AAT TTC CTC ATC TTT GCC TTG TCT AAT TCC TTG AGA AGC TTA CAC TTG      7315
Asn Phe Leu Ile Phe Ala Leu Ser Asn Ser Leu Arg Ser Leu His Leu
        3335                3340                3345

GAC CCT GAA AAC CAT AGC CCA CCT TTC CAA ACA ATA AAT GTG GAA AGA      7363
Asp Pro Glu Asn His Ser Pro Pro Phe Gln Thr Ile Asn Val Glu Arg
    3350                3355                3360

ACT GTC ATG TCT CTA GAC TAT GAC AGT GTA AGT GAT AGA ATC TAC TTC      7411
Thr Val Met Ser Leu Asp Tyr Asp Ser Val Ser Asp Arg Ile Tyr Phe
3365                3370                3375                3380

ACA CAA AAT TTA GCC TCT GGA GTT GGA CAG ATT TCC TAT GCC ACC CTG      7459
Thr Gln Asn Leu Ala Ser Gly Val Gly Gln Ile Ser Tyr Ala Thr Leu
                3385                3390                3395

TCT TCA GGG ATC CAT ACT CCA ACT GTC ATT GCT TCA GGT ATA GGG ACT      7507
Ser Ser Gly Ile His Thr Pro Thr Val Ile Ala Ser Gly Ile Gly Thr
            3400                3405                3410

GCT GAT GGC ATT GCC TTT GAC TGG ATT ACT AGA AGA ATT TAT TAC AGT      7555
Ala Asp Gly Ile Ala Phe Asp Trp Ile Thr Arg Arg Ile Tyr Tyr Ser
        3415                3420                3425

GAC TAC CTC AAC CAG ATG ATT AAT TCC ATG GCT GAA GAT GGG TCT AAC      7603
Asp Tyr Leu Asn Gln Met Ile Asn Ser Met Ala Glu Asp Gly Ser Asn
    3430                3435                3440

CGC ACT GTG ATA GCC CGC GTT CCA AAA CCA AGA GCA ATT GTG TTA GAT      7651
Arg Thr Val Ile Ala Arg Val Pro Lys Pro Arg Ala Ile Val Leu Asp
3445                3450                3455                3460

CCC TGC CAA GGG TAC CTG TAC TGG GCT GAC TGG GAT ACA CAT GCC AAA      7699
Pro Cys Gln Gly Tyr Leu Tyr Trp Ala Asp Trp Asp Thr His Ala Lys
                3465                3470                3475

ATC GAG AGA GCC ACA TTG GGA GGA AAC TTC CGG GTA CCC ATT GTG AAC      7747
Ile Glu Arg Ala Thr Leu Gly Gly Asn Phe Arg Val Pro Ile Val Asn
            3480                3485                3490

AGC AGT CTG GTC ATG CCC AGT GGG CTG ACT CTG GAC TAT GAA GAG GAC      7795
Ser Ser Leu Val Met Pro Ser Gly Leu Thr Leu Asp Tyr Glu Glu Asp
        3495                3500                3505

CTT CTC TAC TGG GTG GAT GCT AGT CTG CAG AGG ATT GAA CGC AGC ACT      7843
Leu Leu Tyr Trp Val Asp Ala Ser Leu Gln Arg Ile Glu Arg Ser Thr
    3510                3515                3520
```

```
                                                          -continued

CTG ACG GGC GTG GAT CGT GAA GTC ATT GTC AAT GCA GCC GTT CAT GCT          7891
Leu Thr Gly Val Asp Arg Glu Val Ile Val Asn Ala Ala Val His Ala
3525            3530                3535                3540

TTT GGC TTG ACT CTC TAT GGC CAG TAT ATT TAC TGG ACT GAC TTG TAC          7939
Phe Gly Leu Thr Leu Tyr Gly Gln Tyr Ile Tyr Trp Thr Asp Leu Tyr
                3545                3550                3555

ACA CAA AGA ATT TAC CGA GCT AAC AAA TAT GAC GGG TCA GGT CAG ATT          7987
Thr Gln Arg Ile Tyr Arg Ala Asn Lys Tyr Asp Gly Ser Gly Gln Ile
            3560                3565                3570

GCA ATG ACC ACA AAT TTG CTC TCC CAG CCC AGG GGA ATC AAC ACT GTT          8035
Ala Met Thr Thr Asn Leu Leu Ser Gln Pro Arg Gly Ile Asn Thr Val
        3575                3580                3585

GTG AAG AAC CAG AAA CAA CAG TGT AAC AAT CCT TGT GAA CAG TTT AAT          8083
Val Lys Asn Gln Lys Gln Gln Cys Asn Asn Pro Cys Glu Gln Phe Asn
    3590                3595                3600

GGG GGC TGC AGC CAT ATC TGT GCA CCA GGT CCA AAT GGT GCC GAG TGC          8131
Gly Gly Cys Ser His Ile Cys Ala Pro Gly Pro Asn Gly Ala Glu Cys
3605                3610                3615                3620

CAG TGT CCA CAT GAG GGC AAC TGG TAT TTG GCC AAC AAC AGG AAG CAC          8179
Gln Cys Pro His Glu Gly Asn Trp Tyr Leu Ala Asn Asn Arg Lys His
                3625                3630                3635

TGC ATT GTG GAC AAT GGT GAA CGA TGT GGT GCA TCT TCC TTC ACC TGC          8227
Cys Ile Val Asp Asn Gly Glu Arg Cys Gly Ala Ser Ser Phe Thr Cys
            3640                3645                3650

TCC AAT GGG CGC TGC ATC TCG GAA GAG TGG AAG TGT GAT AAT GAC AAC          8275
Ser Asn Gly Arg Cys Ile Ser Glu Glu Trp Lys Cys Asp Asn Asp Asn
        3655                3660                3665

GAC TGT GGG GAT GGC AGT GAT GAG ATG GAA AGT GTC TGT GCA CTT CAC          8323
Asp Cys Gly Asp Gly Ser Asp Glu Met Glu Ser Val Cys Ala Leu His
    3670                3675                3680

ACC TGC TCA CCG ACA GCC TTC ACC TGT GCC AAT GGG CGA TGT GTC CAA          8371
Thr Cys Ser Pro Thr Ala Phe Thr Cys Ala Asn Gly Arg Cys Val Gln
3685                3690                3695                3700

TAC TCT TAC CGC TGT GAT TAC TAC AAT GAC TGT GGT GAT GGC AGT GAT          8419
Tyr Ser Tyr Arg Cys Asp Tyr Tyr Asn Asp Cys Gly Asp Gly Ser Asp
                3705                3710                3715

GAG GCA GGG TGC CTG TTC AGG GAC TGC AAT GCC ACC ACG GAG TTT ATG          8467
Glu Ala Gly Cys Leu Phe Arg Asp Cys Asn Ala Thr Thr Glu Phe Met
            3720                3725                3730

TGC AAT AAC AGA AGG TGC ATA CCT CGT GAG TTT ATC TGC AAT GGT GTA          8515
Cys Asn Asn Arg Arg Cys Ile Pro Arg Glu Phe Ile Cys Asn Gly Val
        3735                3740                3745

GAC AAC TGC CAT GAT AAT AAC ACT TCA GAT GAG AAA AAT TGC CCT GAT          8563
Asp Asn Cys His Asp Asn Asn Thr Ser Asp Glu Lys Asn Cys Pro Asp
    3750                3755                3760

CGC ACT TGC CAG TCT GGA TAC ACA AAA TGT CAT AAT TCA AAT ATT TGT          8611
Arg Thr Cys Gln Ser Gly Tyr Thr Lys Cys His Asn Ser Asn Ile Cys
3765                3770                3775                3780

ATT CCT CGC GTT TAT TTG TGT GAC GGA GAC AAT GAC TGT GGA GAT AAC          8659
Ile Pro Arg Val Tyr Leu Cys Asp Gly Asp Asn Asp Cys Gly Asp Asn
                3785                3790                3795

AGT GAT GAA AAC CCT ACT TAT TGC ACC ACT CAC ACA TGC AGC AGC AGT          8707
Ser Asp Glu Asn Pro Thr Tyr Cys Thr Thr His Thr Cys Ser Ser Ser
            3800                3805                3810

GAG TTC CAA TGC GCA TCT GGG CGC TGT ATT CCT CAA CAT TGG TAT TGT          8755
Glu Phe Gln Cys Ala Ser Gly Arg Cys Ile Pro Gln His Trp Tyr Cys
        3815                3820                3825

GAT CAA GAA ACA GAT TGT TTT GAT GCC TCT GAT GAA CCT GCC TCT TGT          8803
Asp Gln Glu Thr Asp Cys Phe Asp Ala Ser Asp Glu Pro Ala Ser Cys
    3830                3835                3840
```

```
GGT CAC TCT GAG CGA ACA TGC CTA GCT GAT GAG TTC AAG TGT GAT GGT         8851
Gly His Ser Glu Arg Thr Cys Leu Ala Asp Glu Phe Lys Cys Asp Gly
    3845                3850                3855                3860

GGG AGG TGC ATC CCA AGC GAA TGG ATC TGT GAC GGT GAT AAT GAC TGT         8899
Gly Arg Cys Ile Pro Ser Glu Trp Ile Cys Asp Gly Asp Asn Asp Cys
                    3865                3870                3875

GGG GAT ATG AGT GAC GAG GAT AAA AGG CAC CAG TGT CAG AAT CAA AAC         8947
Gly Asp Met Ser Asp Glu Asp Lys Arg His Gln Cys Gln Asn Gln Asn
            3880                3885                3890

TGC TCG GAT TCC GAG TTT CTC TGT GTA AAT GAC AGA CCT CCG GAC AGG         8995
Cys Ser Asp Ser Glu Phe Leu Cys Val Asn Asp Arg Pro Pro Asp Arg
        3895                3900                3905

AGG TGC ATT CCC CAG TCT TGG GTC TGT GAT GGC GAT GTG GAT TGT ACT         9043
Arg Cys Ile Pro Gln Ser Trp Val Cys Asp Gly Asp Val Asp Cys Thr
    3910                3915                3920

GAC GGC TAC GAT GAG AAT CAG AAT TGC ACC AGG AGA ACT TGC TCT GAA         9091
Asp Gly Tyr Asp Glu Asn Gln Asn Cys Thr Arg Arg Thr Cys Ser Glu
3925                3930                3935                3940

AAT GAA TTC ACC TGT GGT TAC GGA CTG TGT ATC CCA AAG ATA TTC AGG         9139
Asn Glu Phe Thr Cys Gly Tyr Gly Leu Cys Ile Pro Lys Ile Phe Arg
                3945                3950                3955

TGT GAC CGG CAC AAT GAC TGT GGT GAC TAT AGC GAC GAG AGG GGC TGC         9187
Cys Asp Arg His Asn Asp Cys Gly Asp Tyr Ser Asp Glu Arg Gly Cys
            3960                3965                3970

TTA TAC CAG ACT TGC CAA CAG AAT CAG TTT ACC TGT CAG AAC GGG CGC         9235
Leu Tyr Gln Thr Cys Gln Gln Asn Gln Phe Thr Cys Gln Asn Gly Arg
        3975                3980                3985

TGC ATT AGT AAA ACC TTC GTC TGT GAT GAG GAT AAT GAC TGT GGA GAC         9283
Cys Ile Ser Lys Thr Phe Val Cys Asp Glu Asp Asn Asp Cys Gly Asp
    3990                3995                4000

GGA TCT GAT GAG CTG ATG CAC CTG TGC CAC ACC CCA GAA CCC ACG TGT         9331
Gly Ser Asp Glu Leu Met His Leu Cys His Thr Pro Glu Pro Thr Cys
4005                4010                4015                4020

CCA CCT CAC GAG TTC AAG TGT GAC AAT GGG CGC TGC ATC GAG ATG ATG         9379
Pro Pro His Glu Phe Lys Cys Asp Asn Gly Arg Cys Ile Glu Met Met
                4025                4030                4035

AAA CTC TGC AAC CAC CTA GAT GAC TGT TTG GAC AAC AGC GAT GAG AAA         9427
Lys Leu Cys Asn His Leu Asp Asp Cys Leu Asp Asn Ser Asp Glu Lys
            4040                4045                4050

GGC TGT GGC ATT AAT GAA TGC CAT GAC CCT TCA ATC AGT GGC TGC GAT         9475
Gly Cys Gly Ile Asn Glu Cys His Asp Pro Ser Ile Ser Gly Cys Asp
        4055                4060                4065

CAC AAC TGC ACA GAC ACC TTA ACC AGT TTC TAT TGT TCC TGT CGT CCT         9523
His Asn Cys Thr Asp Thr Leu Thr Ser Phe Tyr Cys Ser Cys Arg Pro
    4070                4075                4080

GGT TAC AAG CTC ATG TCT GAC AAG CGG ACT TGT GTT GAT ATT GAT GAA         9571
Gly Tyr Lys Leu Met Ser Asp Lys Arg Thr Cys Val Asp Ile Asp Glu
4085                4090                4095                4100

TGC ACA GAG ATG CCT TTT GTC TGT AGC CAG AAG TGT GAG AAT GTA ATA         9619
Cys Thr Glu Met Pro Phe Val Cys Ser Gln Lys Cys Glu Asn Val Ile
                4105                4110                4115

GGC TCC TAC ATC TGT AAG TGT GCC CCA GGC TAC CTC CGA GAA CCA GAT         9667
Gly Ser Tyr Ile Cys Lys Cys Ala Pro Gly Tyr Leu Arg Glu Pro Asp
            4120                4125                4130

GGA AAG ACC TGC CGG CAA AAC AGT AAC ATC GAA CCC TAT CTC ATT TTT         9715
Gly Lys Thr Cys Arg Gln Asn Ser Asn Ile Glu Pro Tyr Leu Ile Phe
        4135                4140                4145

AGC AAC CGT TAC TAT TTG AGA AAT TTA ACT ATA GAT GGC TAT TTT TAC         9763
Ser Asn Arg Tyr Tyr Leu Arg Asn Leu Thr Ile Asp Gly Tyr Phe Tyr
```

-continued

```
          4150                4155                4160
TCC CTC ATC TTG GAA GGA CTG GAC AAT GTT GTG GCA TTA GAT TTT GAC     9811
Ser Leu Ile Leu Glu Gly Leu Asp Asn Val Val Ala Leu Asp Phe Asp
4165                4170                4175                4180

CGA GTA GAG AAG AGA TTG TAT TGG ATT GAT ACA CAG AGG CAA GTC ATT     9859
Arg Val Glu Lys Arg Leu Tyr Trp Ile Asp Thr Gln Arg Gln Val Ile
                4185                4190                4195

GAG AGA ATG TTT CTG AAT AAG ACA AAC AAG GAG ACA ATC ATA AAC CAC     9907
Glu Arg Met Phe Leu Asn Lys Thr Asn Lys Glu Thr Ile Ile Asn His
            4200                4205                4210

AGA CTA CCA GCT GCA GAA AGT CTG GCT GTA GAC TGG GTT TCC AGA AAG     9955
Arg Leu Pro Ala Ala Glu Ser Leu Ala Val Asp Trp Val Ser Arg Lys
        4215                4220                4225

CTC TAC TGG TTG GAT GCC CGC CTG GAT GGC CTC TTT GTC TCT GAC CTC    10003
Leu Tyr Trp Leu Asp Ala Arg Leu Asp Gly Leu Phe Val Ser Asp Leu
    4230                4235                4240

AAT GGT GGA CAC CGC CGC ATG CTG GCC CAG CAC TGT GTG GAT GCC AAC    10051
Asn Gly Gly His Arg Arg Met Leu Ala Gln His Cys Val Asp Ala Asn
4245                4250                4255                4260

AAC ACC TTC TGC TTT GAT AAT CCC AGA GGA CTT GCC CTT CAC CCT CAA    10099
Asn Thr Phe Cys Phe Asp Asn Pro Arg Gly Leu Ala Leu His Pro Gln
                4265                4270                4275

TAT GGG TAC CTC TAC TGG GCA GAC TGG GGT CAC CGC GCA TAC ATT GGG    10147
Tyr Gly Tyr Leu Tyr Trp Ala Asp Trp Gly His Arg Ala Tyr Ile Gly
            4280                4285                4290

AGA GTA GGC ATG GAT GGA ACC AAC AAG TCT GTG ATA ATC TCC ACC AAG    10195
Arg Val Gly Met Asp Gly Thr Asn Lys Ser Val Ile Ile Ser Thr Lys
        4295                4300                4305

TTA GAG TGG CCT AAT GGC ATC ACC ATT GAT TAC ACC AAT GAT CTA CTC    10243
Leu Glu Trp Pro Asn Gly Ile Thr Ile Asp Tyr Thr Asn Asp Leu Leu
    4310                4315                4320

TAC TGG GCA GAT GCC CAC CTG GGT TAC ATA GAG TAC TCT GAT TTG GAG    10291
Tyr Trp Ala Asp Ala His Leu Gly Tyr Ile Glu Tyr Ser Asp Leu Glu
4325                4330                4335                4340

GGC CAC CAT CGA CAC ACG GTG TAT GAT GGG GCA CTG CCT CAC CCT TTC    10339
Gly His His Arg His Thr Val Tyr Asp Gly Ala Leu Pro His Pro Phe
                4345                4350                4355

GCT ATT ACC ATT TTT GAA GAC ACT ATT TAT TGG ACA GAT TGG AAT ACA    10387
Ala Ile Thr Ile Phe Glu Asp Thr Ile Tyr Trp Thr Asp Trp Asn Thr
            4360                4365                4370

AGG ACA GTG GAA AAG GGA AAC AAA TAT GAT GGA TCA AAT AGA CAG ACA    10435
Arg Thr Val Glu Lys Gly Asn Lys Tyr Asp Gly Ser Asn Arg Gln Thr
        4375                4380                4385

CTG GTG AAC ACA ACA CAC AGA CCA TTT GAC ATC CAT GTG TAC CAT CCA    10483
Leu Val Asn Thr Thr His Arg Pro Phe Asp Ile His Val Tyr His Pro
    4390                4395                4400

TAT AGG CAG CCC ATT GTG AGC AAT CCC TGT GGT ACC AAC AAT GGT GGC    10531
Tyr Arg Gln Pro Ile Val Ser Asn Pro Cys Gly Thr Asn Asn Gly Gly
4405                4410                4415                4420

TGT TCT CAT CTC TGC CTC ATC AAG CCA GGA GGA AAA GGG TTC ACT TGC    10579
Cys Ser His Leu Cys Leu Ile Lys Pro Gly Gly Lys Gly Phe Thr Cys
                4425                4430                4435

GAG TGT CCA GAT GAC TTC CGC ACC CTT CAA CTG AGT GGC AGC ACC TAC    10627
Glu Cys Pro Asp Asp Phe Arg Thr Leu Gln Leu Ser Gly Ser Thr Tyr
            4440                4445                4450

TGC ATG CCC ATG TGC TCC AGC ACC CAG TTC CTG TGC GCT AAC AAT GAA    10675
Cys Met Pro Met Cys Ser Ser Thr Gln Phe Leu Cys Ala Asn Asn Glu
        4455                4460                4465

AAG TGC ATT CCT ATC TGG TGG AAA TGT GAT GGA CAG AAA GAC TGC TCA    10723
```

```
                                                  -continued

Lys Cys Ile Pro Ile Trp Trp Lys Cys Asp Gly Gln Lys Asp Cys Ser
    4470            4475            4480

GAT GGC TCT GAT GAA CTG GCC CTT TGC CCG CAG CGC TTC TGC CGA CTG    10771
Asp Gly Ser Asp Glu Leu Ala Leu Cys Pro Gln Arg Phe Cys Arg Leu
4485            4490            4495            4500

GGA CAG TTC CAG TGC AGT GAC GGC AAC TGC ACC AGC CCG CAG ACT TTA    10819
Gly Gln Phe Gln Cys Ser Asp Gly Asn Cys Thr Ser Pro Gln Thr Leu
            4505            4510            4515

TGC AAT GCT CAC CAA AAT TGC CCT GAT GGG TCT GAT GAA GAC CGT CTT    10867
Cys Asn Ala His Gln Asn Cys Pro Asp Gly Ser Asp Glu Asp Arg Leu
                4520            4525            4530

CTT TGT GAG AAT CAC CAC TGT GAC TCC AAT GAA TGG CAG TGC GCC AAC    10915
Leu Cys Glu Asn His His Cys Asp Ser Asn Glu Trp Gln Cys Ala Asn
            4535            4540            4545

AAA CGT TGC ATC CCA GAA TCC TGG CAG TGT GAC ACA TTT AAC GAC TGT    10963
Lys Arg Cys Ile Pro Glu Ser Trp Gln Cys Asp Thr Phe Asn Asp Cys
    4550            4555            4560

GAG GAT AAC TCA GAT GAA GAC AGT TCC CAC TGT GCC AGC AGG ACC TGC    11011
Glu Asp Asn Ser Asp Glu Asp Ser Ser His Cys Ala Ser Arg Thr Cys
4565            4570            4575            4580

CGG CCG GGC CAG TTT CGG TGT GCT AAT GGC CGC TGC ATC CCG CAG GCC    11059
Arg Pro Gly Gln Phe Arg Cys Ala Asn Gly Arg Cys Ile Pro Gln Ala
            4585            4590            4595

TGG AAG TGT GAT GTG GAT AAT GAT TGT GGA GAC CAC TCG GAT GAG CCC    11107
Trp Lys Cys Asp Val Asp Asn Asp Cys Gly Asp His Ser Asp Glu Pro
            4600            4605            4610

ATT GAA GAA TGC ATG AGC TCT GCC CAT CTC TGT GAC AAC TTC ACA GAA    11155
Ile Glu Glu Cys Met Ser Ser Ala His Leu Cys Asp Asn Phe Thr Glu
            4615            4620            4625

TTC AGC TGC AAA ACA AAT TAC CGC TGC ATC CCA AAG TGG GCC GTG TGC    11203
Phe Ser Cys Lys Thr Asn Tyr Arg Cys Ile Pro Lys Trp Ala Val Cys
            4630            4635            4640

AAT GGT GTA GAT GAC TGC AGG GAC AAC AGT GAT GAG CAA GGC TGT GAG    11251
Asn Gly Val Asp Asp Cys Arg Asp Asn Ser Asp Glu Gln Gly Cys Glu
4645            4650            4655            4660

GAG AGG ACA TGC CAT CCT GTG GGG GAT TTC CGC TGT AAA AAT CAC CAC    11299
Glu Arg Thr Cys His Pro Val Gly Asp Phe Arg Cys Lys Asn His His
                4665            4670            4675

TGC ATC CCT CTT CGT TGG CAG TGT GAT GGG CAA AAT GAC TGT GGA GAT    11347
Cys Ile Pro Leu Arg Trp Gln Cys Asp Gly Gln Asn Asp Cys Gly Asp
            4680            4685            4690

AAC TCA GAT GAG GAA AAC TGT GCT CCC CGG GAG TGC ACA GAG AGC GAG    11395
Asn Ser Asp Glu Glu Asn Cys Ala Pro Arg Glu Cys Thr Glu Ser Glu
        4695            4700            4705

TTT CGA TGT GTC AAT CAG CAG TGC ATT CCC TCG CGA TGG ATC TGT GAC    11443
Phe Arg Cys Val Asn Gln Gln Cys Ile Pro Ser Arg Trp Ile Cys Asp
    4710            4715            4720

CAT TAC AAC GAC TGT GGG GAC AAC TCA GAT GAA CGG GAC TGT GAG ATG    11491
His Tyr Asn Asp Cys Gly Asp Asn Ser Asp Glu Arg Asp Cys Glu Met
4725            4730            4735            4740

AGG ACC TGC CAT CCT GAA TAT TTT CAG TGT ACA AGT GGA CAT TGT GTA    11539
Arg Thr Cys His Pro Glu Tyr Phe Gln Cys Thr Ser Gly His Cys Val
                4745            4750            4755

CAC AGT GAA CTG AAA TGC GAT GGA TCC GCT GAC TGT TTG GAT GCG TCT    11587
His Ser Glu Leu Lys Cys Asp Gly Ser Ala Asp Cys Leu Asp Ala Ser
            4760            4765            4770

GAT GAA GCT GAT TGT CCC ACA CGC TTT CCT GAT GGT GCA TAC TGC CAG    11635
Asp Glu Ala Asp Cys Pro Thr Arg Phe Pro Asp Gly Ala Tyr Cys Gln
                4775            4780            4785
```

```
GCT ACT ATG TTC GAA TGC AAA AAC CAT GTT TGT ATC CCG CCA TAT TGG    11683
Ala Thr Met Phe Glu Cys Lys Asn His Val Cys Ile Pro Pro Tyr Trp
    4790            4795            4800

AAA TGT GAT GGC GAT GAT GAC TGT GGC GAT GGT TCA GAT GAA GAA CTT    11731
Lys Cys Asp Gly Asp Asp Asp Cys Gly Asp Gly Ser Asp Glu Glu Leu
4805            4810            4815                    4820

CAC CTG TGC TTG GAT GTT CCC TGT AAT TCA CCA AAC CGT TTC CGG TGT    11779
His Leu Cys Leu Asp Val Pro Cys Asn Ser Pro Asn Arg Phe Arg Cys
            4825            4830            4835

GAC AAC AAT CGC TGC ATT TAT AGT CAT GAG GTG TGC AAT GGT GTG GAT    11827
Asp Asn Asn Arg Cys Ile Tyr Ser His Glu Val Cys Asn Gly Val Asp
        4840            4845            4850

GAC TGT GGA GAT GGA ACT GAT GAG ACA GAG GAG CAC TGT AGA AAA CCG    11875
Asp Cys Gly Asp Gly Thr Asp Glu Thr Glu Glu His Cys Arg Lys Pro
    4855            4860            4865

ACC CCT AAA CCT TGT ACA GAA TAT GAA TAT AAG TGT GGC AAT GGG CAT    11923
Thr Pro Lys Pro Cys Thr Glu Tyr Glu Tyr Lys Cys Gly Asn Gly His
4870            4875            4880

TGC ATT CCA CAT GAC AAT GTG TGT GAT GAT GCC GAT GAC TGT GGT GAC    11971
Cys Ile Pro His Asp Asn Val Cys Asp Asp Ala Asp Asp Cys Gly Asp
4885            4890            4895            4900

TGG TCC GAT GAA CTG GGT TGC AAT AAA GGA AAA GAA AGA ACA TGT GCT    12019
Trp Ser Asp Glu Leu Gly Cys Asn Lys Gly Lys Glu Arg Thr Cys Ala
        4905            4910            4915

GAA AAT ATA TGC GAG CAA AAT TGT ACC CAA TTA AAT GAA GGA GGA TTT    12067
Glu Asn Ile Cys Glu Gln Asn Cys Thr Gln Leu Asn Glu Gly Gly Phe
            4920            4925            4930

ATC TGC TCC TGT ACA GCT GGG TTC GAA ACC AAT GTT TTT GAC AGA ACC    12115
Ile Cys Ser Cys Thr Ala Gly Phe Glu Thr Asn Val Phe Asp Arg Thr
        4935            4940            4945

TCC TGT CTA GAT ATC AAT GAA TGT GAA CAA TTT GGG ACT TGT CCC CAG    12163
Ser Cys Leu Asp Ile Asn Glu Cys Glu Gln Phe Gly Thr Cys Pro Gln
4950            4955            4960

CAC TGC AGA AAT ACC AAA GGA AGT TAT GAG TGT GTC TGT GCT GAT GGC    12211
His Cys Arg Asn Thr Lys Gly Ser Tyr Glu Cys Val Cys Ala Asp Gly
4965            4970            4975            4980

TTC ACG TCT ATG AGT GAC CGC CCT GGA AAA CGA TGT GCA GCT GAG GGT    12259
Phe Thr Ser Met Ser Asp Arg Pro Gly Lys Arg Cys Ala Ala Glu Gly
            4985            4990            4995

AGC TCT CCT TTG TTG CTA CTG CCT GAC AAT GTC CGA ATT CGA AAA TAT    12307
Ser Ser Pro Leu Leu Leu Leu Pro Asp Asn Val Arg Ile Arg Lys Tyr
        5000            5005            5010

AAT CTC TCA TCT GAG AGG TTC TCA GAG TAT CTT CAA GAT GAG GAA TAT    12355
Asn Leu Ser Ser Glu Arg Phe Ser Glu Tyr Leu Gln Asp Glu Glu Tyr
        5015            5020            5025

ATC CAA GCT GTT GAT TAT GAT TGG GAT CCC AAG GAC ATA GGC CTC AGT    12403
Ile Gln Ala Val Asp Tyr Asp Trp Asp Pro Lys Asp Ile Gly Leu Ser
    5030            5035            5040

GTT GTG TAT TAC ACT GTG CGA GGG GAG GGC TCT AGG TTT GGT GCT ATC    12451
Val Val Tyr Tyr Thr Val Arg Gly Glu Gly Ser Arg Phe Gly Ala Ile
5045            5050            5055            5060

AAA CGT GCC TAC ATC CCC AAC TTT GAA TCC GGC CGC AAT AAT CTT GTG    12499
Lys Arg Ala Tyr Ile Pro Asn Phe Glu Ser Gly Arg Asn Asn Leu Val
            5065            5070            5075

CAG GAA GTT GAC CTG AAA CTG AAA TAC GTA ATG CAG CCA GAT GGA ATA    12547
Gln Glu Val Asp Leu Lys Leu Lys Tyr Val Met Gln Pro Asp Gly Ile
        5080            5085            5090

GCA GTG GAC TGG GTT GGA AGG CAT ATT TAC TGG TCA GAT GTC AAG AAT    12595
Ala Val Asp Trp Val Gly Arg His Ile Tyr Trp Ser Asp Val Lys Asn
    5095            5100            5105
```

```
AAA CGC ATT GAG GTG GCT AAA CTT GAT GGA AGG TAC AGA AAG TGG CTG        12643
Lys Arg Ile Glu Val Ala Lys Leu Asp Gly Arg Tyr Arg Lys Trp Leu
        5110                5115                5120

ATT TCC ACT GAC CTG GAC CAA CCA GCT GCT ATT GCT GTG AAT CCC AAA        12691
Ile Ser Thr Asp Leu Asp Gln Pro Ala Ala Ile Ala Val Asn Pro Lys
5125                5130                5135                5140

CTA GGG CTT ATG TTC TGG ACT GAC TGG GGA AAG GAA CCT AAA ATC GAG        12739
Leu Gly Leu Met Phe Trp Thr Asp Trp Gly Lys Glu Pro Lys Ile Glu
                5145                5150                5155

TCT GCC TGG ATG AAT GGA GAG GAC CGC AAC ATC CTG GTT TTC GAG GAC        12787
Ser Ala Trp Met Asn Gly Glu Asp Arg Asn Ile Leu Val Phe Glu Asp
            5160                5165                5170

CTT GGT TGG CCA ACT GGC CTT TCT ATC GAT TAT TTG AAC AAT GAC CGA        12835
Leu Gly Trp Pro Thr Gly Leu Ser Ile Asp Tyr Leu Asn Asn Asp Arg
        5175                5180                5185

ATC TAC TGG AGT GAC TTC AAG GAG GAC GTT ATT GAA ACC ATA AAA TAT        12883
Ile Tyr Trp Ser Asp Phe Lys Glu Asp Val Ile Glu Thr Ile Lys Tyr
    5190                5195                5200

GAT GGG ACT GAT AGG AGA GTC ATT GCA AAG GAA GCA ATG AAC CCT TAC        12931
Asp Gly Thr Asp Arg Arg Val Ile Ala Lys Glu Ala Met Asn Pro Tyr
5205                5210                5215                5220

AGC CTG GAC ATC TTT GAA GAC CAG TTA TAC TGG ATA TCT AAG GAA AAG        12979
Ser Leu Asp Ile Phe Glu Asp Gln Leu Tyr Trp Ile Ser Lys Glu Lys
                5225                5230                5235

GGA GAA GTA TGG AAA CAA AAT AAA TTT GGG CAA GGA AAG AAA GAG AAA        13027
Gly Glu Val Trp Lys Gln Asn Lys Phe Gly Gln Gly Lys Lys Glu Lys
            5240                5245                5250

ACG CTG GTA GTG AAC CCT TGG CTC ACT CAA GTT CGA ATC TTT CAT CAA        13075
Thr Leu Val Val Asn Pro Trp Leu Thr Gln Val Arg Ile Phe His Gln
        5255                5260                5265

CTC AGA TAC AAT AAG TCA GTG CCC AAC CTT TGC AAA CAG ATC TGC AGC        13123
Leu Arg Tyr Asn Lys Ser Val Pro Asn Leu Cys Lys Gln Ile Cys Ser
    5270                5275                5280

CAC CTC TGC CTT CTG AGA CCT GGA GGA TAC AGC TGT GCC TGT CCC CAA        13171
His Leu Cys Leu Leu Arg Pro Gly Gly Tyr Ser Cys Ala Cys Pro Gln
5285                5290                5295                5300

GGC TCC AGC TTT ATA GAG GGG AGC ACC ACT GAG TGT GAT GCA GCC ATC        13219
Gly Ser Ser Phe Ile Glu Gly Ser Thr Thr Glu Cys Asp Ala Ala Ile
                5305                5310                5315

GAA CTG CCT ATC AAC CTG CCC CCC CCA TGC AGG TGC ATG CAC GGA GGA        13267
Glu Leu Pro Ile Asn Leu Pro Pro Pro Cys Arg Cys Met His Gly Gly
            5320                5325                5330

AAT TGC TAT TTT GAT GAG ACT GAC CTC CCC AAA TGC AAG TGT CCT AGC        13315
Asn Cys Tyr Phe Asp Glu Thr Asp Leu Pro Lys Cys Lys Cys Pro Ser
        5335                5340                5345

GGC TAC ACC GGA AAA TAT TGT GAA ATG GCG TTT TCA AAA GGC ATC TCT        13363
Gly Tyr Thr Gly Lys Tyr Cys Glu Met Ala Phe Ser Lys Gly Ile Ser
    5350                5355                5360

CCA GGA ACA ACC GCA GTA GCT GTG CTG TTG ACA ATC CTC TTG ATC GTC        13411
Pro Gly Thr Thr Ala Val Ala Val Leu Leu Thr Ile Leu Leu Ile Val
5365                5370                5375                5380

GTA ATT GGA GCT CTG GCA ATT GCA GGA TTC TTC CAC TAT AGA AGG ACC        13459
Val Ile Gly Ala Leu Ala Ile Ala Gly Phe Phe His Tyr Arg Arg Thr
                5385                5390                5395

GGC TCC CTT TTG CCT GCT CTG CCC AAG CTG CCA AGC TTA AGC AGT CTC        13507
Gly Ser Leu Leu Pro Ala Leu Pro Lys Leu Pro Ser Leu Ser Ser Leu
            5400                5405                5410

GTC AAG CCC TCT GAA AAT GGG AAT GGG GTG ACC TTC AGA TCA GGG GCA        13555
Val Lys Pro Ser Glu Asn Gly Asn Gly Val Thr Phe Arg Ser Gly Ala
```

```
                5415                5420                    5425
GAT CTT AAC ATG GAT ATT GGA GTG TCT GGT TTT GGA CCT GAG ACT GCT     13603
Asp Leu Asn Met Asp Ile Gly Val Ser Gly Phe Gly Pro Glu Thr Ala
            5430                5435                5440

ATT GAC AGG TCA ATG GCA ATG AGT GAA GAC TTT GTC ATG GAA ATG GGG     13651
Ile Asp Arg Ser Met Ala Met Ser Glu Asp Phe Val Met Glu Met Gly
5445                5450                5455                5460

AAG CAG CCC ATA ATA TTT GAA AAC CCA ATG TAC TCA GCC AGA GAC AGT     13699
Lys Gln Pro Ile Ile Phe Glu Asn Pro Met Tyr Ser Ala Arg Asp Ser
                5465                5470                5475

GCT GTC AAA GTG GTT CAG CCA ATC CAG GTG ACT GTA TCT GAA AAT GTG     13747
Ala Val Lys Val Val Gln Pro Ile Gln Val Thr Val Ser Glu Asn Val
            5480                5485                5490

GAT AAT AAG AAT TAT GGA AGT CCC ATA AAC CCT TCT GAG ATA GTT CCA     13795
Asp Asn Lys Asn Tyr Gly Ser Pro Ile Asn Pro Ser Glu Ile Val Pro
        5495                5500                5505

GAG ACA AAC CCA ACT TCA CCA GCT GCT GAT GGA ACT CAG GTG ACA AAA     13843
Glu Thr Asn Pro Thr Ser Pro Ala Ala Asp Gly Thr Gln Val Thr Lys
            5510                5515                5520

TGG AAT CTC TTC AAA CGA AAA TCT AAA CAA ACT ACC AAC TTT GAA AAT     13891
Trp Asn Leu Phe Lys Arg Lys Ser Lys Gln Thr Thr Asn Phe Glu Asn
5525                5530                5535                5540

CCA ATC TAT GCA CAG ATG GAG AAC GAG CAA AAG GAA AGT GTT GCT GCG     13939
Pro Ile Tyr Ala Gln Met Glu Asn Glu Gln Lys Glu Ser Val Ala Ala
            5545                5550                5555

ACA CCA CCT CCA TCA CCT TCG CTC CCT GCT AAG CCT AAG CCT CCT TCG     13987
Thr Pro Pro Pro Ser Pro Ser Leu Pro Ala Lys Pro Lys Pro Pro Ser
                5560                5565                5570

AGA AGA GAC CCA ACT CCA ACC TAT TCT GCA ACA GAA GAC ACT TTT AAA     14035
Arg Arg Asp Pro Thr Pro Thr Tyr Ser Ala Thr Glu Asp Thr Phe Lys
            5575                5580                5585

GAC ACC GCA AAT CTT GTT AAA GAA GAC TCT GAA GTA TAG GATCAAGAAG      14084
Asp Thr Ala Asn Leu Val Lys Glu Asp Ser Glu Val  *
        5590                5595            5600

AA                                                                  14086

(2) INFORMATION FOR SEQ ID NO:84:

(i) SEQUENCE CHARACTERISTICS:
        (A) LENGTH:  4655 amino acids
        (B) TYPE: amino acid
        (D) TOPOLOGY: linear (ii) MOLECULE TYPE: protein (xi) SEQUENCE DESCRIPTION: SEQ ID NO:84:

Met Asp Arg Gly Pro Ala Ala Val Ala Cys Thr Leu Leu Ala Leu
 1               5                  10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
            35                  40                  45

Gly Thr Lys Asp Cys Ser Asp Ala Asp Glu Ile Gly Cys Ala Val
        50                  55                  60

Val Thr Cys Gln Gln Gly Tyr Phe Lys Cys Ser Glu Gly Gln Cys
 65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
```

```
                 100                 105                 110
Ile Thr Cys Ser Asn Gly Gln Cys Ile Pro Ser Glu Tyr Arg Cys Asp
                115                 120                 125

His Val Arg Asp Cys Pro Asp Gly Ala Asp Glu Asn Asp Cys Gln Tyr
130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
                180                 185                 190

Gly Glu Cys Ile Pro Arg Ala Tyr Val Cys Asp His Asp Asn Asp Cys
                195                 200                 205

Gln Asp Gly Ser Asp Glu His Ala Cys Asn Tyr Pro Thr Cys Gly Gly
                210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
                275                 280                 285

Ile Leu Asp Cys Pro Gly Arg Glu Asp Glu Asn Asn Thr Ser Thr Gly
                290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
                355                 360                 365

His Leu Cys His Cys Glu Glu Gly Tyr Ile Leu Glu Arg Gly Gln Tyr
370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
                420                 425                 430

Tyr His Leu Gln Arg Val Phe Trp Thr Asp Thr Val Gln Asn Lys Val
                435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
                500                 505                 510

Arg Gly Ile Ala Val Asp Pro Thr Val Gly Tyr Leu Phe Phe Ser Asp
                515                 520                 525
```

```
Trp Glu Ser Leu Ser Gly Glu Pro Lys Leu Glu Arg Ala Phe Met Asp
    530                 535                 540
Gly Ser Asn Arg Lys Asp Leu Val Lys Thr Lys Leu Gly Trp Pro Ala
545                 550                 555                 560
Gly Val Thr Leu Asp Met Ile Ser Lys Arg Val Tyr Trp Val Asp Ser
                565                 570                 575
Arg Phe Asp Tyr Ile Glu Thr Val Thr Tyr Asp Gly Ile Gln Arg Lys
                580                 585                 590
Thr Val Val His Gly Gly Ser Leu Ile Pro His Pro Phe Gly Val Ser
            595                 600                 605
Leu Phe Glu Gly Gln Val Phe Phe Thr Asp Trp Thr Lys Met Ala Val
    610                 615                 620
Leu Lys Ala Asn Lys Phe Thr Glu Thr Asn Pro Gln Val Tyr Tyr Gln
625                 630                 635                 640
Ala Ser Leu Arg Pro Tyr Gly Val Thr Val Tyr His Ser Leu Arg Gln
                645                 650                 655
Pro Tyr Ala Thr Asn Pro Cys Lys Asp Asn Asn Gly Gly Cys Glu Gln
                660                 665                 670
Val Cys Val Leu Ser His Arg Thr Asp Asn Asp Gly Leu Gly Phe Arg
            675                 680                 685
Cys Lys Cys Thr Phe Gly Phe Gln Leu Asp Thr Asp Glu Arg His Cys
    690                 695                 700
Ile Ala Val Gln Asn Phe Leu Ile Phe Ser Ser Gln Val Ala Ile Arg
705                 710                 715                 720
Gly Ile Pro Phe Thr Leu Ser Thr Gln Glu Asp Val Met Val Pro Val
                725                 730                 735
Ser Gly Asn Pro Ser Phe Phe Val Gly Ile Asp Phe Asp Ala Gln Asp
                740                 745                 750
Ser Thr Ile Phe Phe Ser Asp Met Ser Lys His Met Ile Phe Lys Gln
            755                 760                 765
Lys Ile Asp Gly Thr Gly Arg Glu Ile Leu Ala Ala Asn Arg Val Glu
    770                 775                 780
Asn Val Glu Ser Leu Ala Phe Asp Trp Ile Ser Lys Asn Leu Tyr Trp
785                 790                 795                 800
Thr Asp Ser His Tyr Lys Ser Ile Ser Val Met Arg Leu Ala Asp Lys
                805                 810                 815
Thr Arg Arg Thr Val Val Gln Tyr Leu Asn Asn Pro Arg Ser Val Val
                820                 825                 830
Val His Pro Phe Ala Gly Tyr Leu Phe Phe Thr Asp Trp Phe Arg Pro
            835                 840                 845
Ala Lys Ile Met Arg Ala Trp Ser Asp Gly Ser His Leu Leu Pro Val
    850                 855                 860
Ile Asn Thr Thr Leu Gly Trp Pro Asn Gly Leu Ala Ile Asp Trp Ala
865                 870                 875                 880
Ala Ser Arg Leu Tyr Trp Val Asp Ala Tyr Phe Asp Lys Ile Glu His
                885                 890                 895
Ser Thr Phe Asp Gly Leu Asp Arg Arg Arg Leu Gly His Ile Glu Gln
                900                 905                 910
Met Thr His Pro Phe Gly Leu Ala Ile Phe Gly Glu His Leu Phe Phe
            915                 920                 925
Thr Asp Trp Arg Leu Gly Ala Ile Ile Arg Val Arg Lys Ala Asp Gly
    930                 935                 940
```

-continued

```
Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
        995                1000                1005

Asn His Leu Thr Cys Glu Gly Asp Pro Thr Asn Glu Pro Pro Thr Glu
   1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ala Phe
            1060                1065                1070

Thr Cys Gly His Gly Glu Cys Ile Pro Ala His Trp Arg Cys Asp Lys
        1075                1080                1085

Arg Asn Asp Cys Val Asp Gly Ser Asp Glu His Asn Cys Pro Thr His
   1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
                1125                1130                1135

Gly Ser Asp Glu Lys Asn Cys Asn Ser Thr Glu Thr Cys Gln Pro Ser
            1140                1145                1150

Gln Phe Asn Cys Pro Asn His Arg Cys Ile Asp Leu Ser Phe Val Cys
        1155                1160                1165

Asp Gly Asp Lys Asp Cys Val Asp Gly Ser Asp Glu Val Gly Cys Val
   1170                1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
                1205                1210                1215

Ser Asp Glu Ala Gly Cys Pro Thr Arg Pro Pro Gly Met Cys His Ser
            1220                1225                1230

Asp Glu Phe Gln Cys Gln Glu Asp Gly Ile Cys Ile Pro Asn Phe Trp
        1235                1240                1245

Glu Cys Asp Gly His Pro Asp Cys Leu Tyr Gly Ser Asp Glu His Asn
   1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
                1285                1290                1295

Gly Asp Met Ser Asp Glu Lys Asp Cys Pro Thr Gln Pro Phe Arg Cys
            1300                1305                1310

Pro Ser Trp Gln Trp Gln Cys Leu Gly His Asn Ile Cys Val Asn Leu
        1315                1320                1325

Ser Val Val Cys Asp Gly Ile Phe Asp Cys Pro Asn Gly Thr Asp Glu
   1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
```

-continued

```
                 1365            1370            1375
Leu Gly Phe Leu Leu Ala Asn Asp Ser Lys Thr Cys Glu Asp Ile Asp
                1380            1385            1390
Glu Cys Asp Ile Leu Gly Ser Cys Ser Gln His Cys Tyr Asn Met Arg
    1395            1400            1405
Gly Ser Phe Arg Cys Ser Cys Asp Thr Gly Tyr Met Leu Glu Ser Asp
        1410            1415            1420
Gly Arg Thr Cys Lys Val Thr Ala Ser Glu Ser Leu Leu Leu Val
1425            1430            1435            1440
Ala Ser Gln Asn Lys Ile Ile Ala Asp Ser Val Thr Ser Gln Val His
            1445            1450            1455
Asn Ile Tyr Ser Leu Val Glu Asn Gly Ser Tyr Ile Val Ala Val Asp
        1460            1465            1470
Phe Asp Ser Ile Ser Gly Arg Ile Phe Trp Ser Asp Ala Thr Gln Gly
            1475            1480            1485
Lys Thr Trp Ser Ala Phe Gln Asn Gly Thr Asp Arg Arg Val Val Phe
        1490            1495            1500
Asp Ser Ser Ile Ile Leu Thr Glu Thr Ile Ala Ile Asp Trp Val Gly
1505            1510            1515            1520
Arg Asn Leu Tyr Trp Thr Asp Tyr Ala Leu Glu Thr Ile Glu Val Ser
            1525            1530            1535
Lys Ile Asp Gly Ser His Arg Thr Val Leu Ile Ser Lys Asn Leu Thr
        1540            1545            1550
Asn Pro Arg Gly Leu Ala Leu Asp Pro Arg Met Asn Glu His Leu Leu
        1555            1560            1565
Phe Trp Ser Asp Trp Gly His His Pro Arg Ile Glu Arg Ala Ser Met
        1570            1575            1580
Asp Gly Ser Met Arg Thr Val Ile Val Gln Asp Lys Ile Phe Trp Pro
1585            1590            1595            1600
Cys Gly Leu Thr Ile Asp Tyr Pro Asn Arg Leu Leu Tyr Phe Met Asp
            1605            1610            1615
Ser Tyr Leu Asp Tyr Met Asp Phe Cys Asp Tyr Asn Gly His His Arg
        1620            1625            1630
Arg Gln Val Ile Ala Ser Asp Leu Ile Ile Arg His Pro Tyr Ala Leu
        1635            1640            1645
Thr Leu Phe Glu Asp Ser Val Tyr Trp Thr Asp Arg Ala Thr Arg Arg
    1650            1655            1660
Val Met Arg Ala Asn Lys Trp His Gly Gly Asn Gln Ser Val Val Met
1665            1670            1675            1680
Tyr Asn Ile Gln Trp Pro Leu Gly Ile Val Ala Val His Pro Ser Lys
            1685            1690            1695
Gln Pro Asn Ser Val Asn Pro Cys Ala Phe Ser Arg Cys Ser His Leu
        1700            1705            1710
Cys Leu Leu Ser Ser Gln Gly Pro His Phe Tyr Ser Cys Val Cys Pro
        1715            1720            1725
Ser Gly Trp Ser Leu Ser Pro Asp Leu Leu Asn Cys Leu Arg Asp Asp
        1730            1735            1740
Gln Pro Phe Leu Ile Thr Val Arg Gln His Ile Ile Phe Gly Ile Ser
1745            1750            1755            1760
Leu Asn Pro Glu Val Lys Ser Asn Asp Ala Met Val Pro Ile Ala Gly
        1765            1770            1775
Ile Gln Asn Gly Leu Asp Val Glu Phe Asp Asp Ala Glu Gln Tyr Ile
        1780            1785            1790
```

```
Tyr Trp Val Glu Asn Pro Gly Glu Ile His Arg Val Lys Thr Asp Gly
        1795                1800                1805

Thr Asn Arg Thr Val Phe Ala Ser Ile Ser Met Val Gly Pro Ser Met
    1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
            1845                1850                1855

Arg Lys Thr Leu Ile Ala Asn Asp Gly Thr Ala Leu Val Gly Phe
            1860                1865                1870

Pro Ile Gly Ile Thr Val Asp Pro Ala Arg Gly Lys Leu Tyr Trp Ser
            1875                1880                1885

Asp Gln Gly Thr Asp Ser Gly Val Pro Ala Lys Ile Ala Ser Ala Asn
        1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
            1925                1930                1935

Val Thr Gly Arg Gly Val Ile Glu Arg Gly Asn Val Asp Gly Thr Asp
            1940                1945                1950

Arg Met Ile Leu Val His Gln Leu Ser His Pro Trp Gly Ile Ala Val
        1955                1960                1965

His Asp Ser Phe Leu Tyr Tyr Thr Asp Glu Gln Tyr Glu Val Ile Glu
        1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Arg Asn Ala Ala
                2005                2010                2015

Glu Ser Ser Asn Gly Cys Ser Asn Asn Met Asn Ala Cys Gln Gln Ile
            2020                2025                2030

Cys Leu Pro Val Pro Gly Gly Leu Phe Ser Cys Ala Cys Ala Thr Gly
            2035                2040                2045

Phe Lys Leu Asn Pro Asp Asn Arg Ser Cys Ser Pro Tyr Asn Ser Phe
    2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
            2100                2105                2110

Asp Phe Ser Ser Ser Val Ala Ser Asp Asn Ala Ile Arg Arg Ile Lys
        2115                2120                2125

Pro Asp Gly Ser Ser Leu Met Asn Ile Val Thr His Gly Ile Gly Glu
    2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
            2165                2170                2175

Asn Thr Thr Tyr Arg Arg Val Leu Leu Lys Val Thr Val Asp Met Pro
        2180                2185                2190

Arg His Ile Val Val Asp Pro Lys Asn Arg Tyr Leu Phe Trp Ala Asp
        2195                2200                2205
```

-continued

Tyr Gly Gln Arg Pro Lys Ile Glu Arg Ser Phe Leu Asp Cys Thr Asn
    2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Ser Leu Asp
            2245                2250                2255

Ile Ile Ala Arg Ile Arg Ile Asn Gly Glu Asn Ser Glu Val Ile Arg
        2260                2265                2270

Tyr Gly Ser Arg Tyr Pro Thr Pro Tyr Gly Ile Thr Val Phe Glu Asn
            2275                2280                2285

Ser Ile Ile Trp Val Asp Arg Asn Leu Lys Lys Ile Phe Gln Ala Ser
    2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
            2325                2330                2335

Ser Pro Ala Glu Val Asn Asn Asn Pro Cys Leu Glu Asn Asn Gly Gly
            2340                2345                2350

Cys Ser His Leu Cys Phe Ala Leu Pro Gly Leu His Thr Pro Lys Cys
            2355                2360                2365

Asp Cys Ala Phe Gly Thr Leu Gln Ser Asp Gly Lys Asn Cys Ala Ile
            2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
            2405                2410                2415

Val Glu Arg Thr Val Met Ser Leu Asp Tyr Asp Ser Val Ser Asp Arg
            2420                2425                2430

Ile Tyr Phe Thr Gln Asn Leu Ala Ser Gly Val Gly Gln Ile Ser Tyr
            2435                2440                2445

Ala Thr Leu Ser Ser Gly Ile His Thr Pro Thr Val Ile Ala Ser Gly
            2450                2455                2460

Ile Gly Thr Ala Asp Gly Ile Ala Phe Asp Trp Ile Thr Arg Arg Ile
2465                2470                2475                2480

Tyr Tyr Ser Asp Tyr Leu Asn Gln Met Ile Asn Ser Met Ala Glu Asp
            2485                2490                2495

Gly Ser Asn Arg Thr Val Ile Ala Arg Val Pro Lys Pro Arg Ala Ile
            2500                2505                2510

Val Leu Asp Pro Cys Gln Gly Tyr Leu Tyr Trp Ala Asp Trp Asp Thr
            2515                2520                2525

His Ala Lys Ile Glu Arg Ala Thr Leu Gly Gly Asn Phe Arg Val Pro
            2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
            2565                2570                2575

Arg Ser Thr Leu Thr Gly Val Asp Arg Glu Val Ile Val Asn Ala Ala
            2580                2585                2590

Val His Ala Phe Gly Leu Thr Leu Tyr Gly Gln Tyr Ile Tyr Trp Thr
            2595                2600                2605

Asp Leu Tyr Thr Gln Arg Ile Tyr Arg Ala Asn Lys Tyr Asp Gly Ser
            2610                2615                2620

Gly Gln Ile Ala Met Thr Thr Asn Leu Leu Ser Gln Pro Arg Gly Ile

```
             2625                2630                2635                2640
     Asn Thr Val Val Lys Asn Gln Lys Gln Gln Cys Asn Asn Pro Cys Glu
                     2645                2650                2655
     Gln Phe Asn Gly Gly Cys Ser His Ile Cys Ala Pro Gly Pro Asn Gly
                     2660                2665                2670
     Ala Glu Cys Gln Cys Pro His Glu Gly Asn Trp Tyr Leu Ala Asn Asn
                     2675                2680                2685
     Arg Lys His Cys Ile Val Asp Asn Gly Glu Arg Cys Gly Ala Ser Ser
                     2690                2695                2700
     Phe Thr Cys Ser Asn Gly Arg Cys Ile Ser Glu Trp Lys Cys Asp
     2705                2710                2715                2720
     Asn Asp Asn Asp Cys Gly Asp Gly Ser Asp Glu Met Glu Ser Val Cys
                     2725                2730                2735
     Ala Leu His Thr Cys Ser Pro Thr Ala Phe Thr Cys Ala Asn Gly Arg
                     2740                2745                2750
     Cys Val Gln Tyr Ser Tyr Arg Cys Asp Tyr Tyr Asn Asp Cys Gly Asp
                     2755                2760                2765
     Gly Ser Asp Glu Ala Gly Cys Leu Phe Arg Asp Cys Asn Ala Thr Thr
                     2770                2775                2780
     Glu Phe Met Cys Asn Asn Arg Arg Cys Ile Pro Arg Glu Phe Ile Cys
     2785                2790                2795                2800
     Asn Gly Val Asp Asn Cys His Asp Asn Asn Thr Ser Asp Glu Lys Asn
                     2805                2810                2815
     Cys Pro Asp Arg Thr Cys Gln Ser Gly Tyr Thr Lys Cys His Asn Ser
                     2820                2825                2830
     Asn Ile Cys Ile Pro Arg Val Tyr Leu Cys Asp Gly Asp Asn Asp Cys
                     2835                2840                2845
     Gly Asp Asn Ser Asp Glu Asn Pro Thr Tyr Cys Thr Thr His Thr Cys
                     2850                2855                2860
     Ser Ser Ser Glu Phe Gln Cys Ala Ser Gly Arg Cys Ile Pro Gln His
     2865                2870                2875                2880
     Trp Tyr Cys Asp Gln Glu Thr Asp Cys Phe Asp Ala Ser Asp Glu Pro
                     2885                2890                2895
     Ala Ser Cys Gly His Ser Glu Arg Thr Cys Leu Ala Asp Glu Phe Lys
                     2900                2905                2910
     Cys Asp Gly Gly Arg Cys Ile Pro Ser Glu Trp Ile Cys Asp Gly Asp
                     2915                2920                2925
     Asn Asp Cys Gly Asp Met Ser Asp Glu Asp Lys Arg His Gln Cys Gln
                     2930                2935                2940
     Asn Gln Asn Cys Ser Asp Ser Glu Phe Leu Cys Val Asn Asp Arg Pro
     2945                2950                2955                2960
     Pro Asp Arg Arg Cys Ile Pro Gln Ser Trp Val Cys Asp Gly Asp Val
                     2965                2970                2975
     Asp Cys Thr Asp Gly Tyr Asp Glu Asn Gln Asn Cys Thr Arg Arg Thr
                     2980                2985                2990
     Cys Ser Glu Asn Glu Phe Thr Cys Gly Tyr Gly Leu Cys Ile Pro Lys
                     2995                3000                3005
     Ile Phe Arg Cys Asp Arg His Asn Asp Cys Gly Asp Tyr Ser Asp Glu
                     3010                3015                3020
     Arg Gly Cys Leu Tyr Gln Thr Cys Gln Gln Asn Gln Phe Thr Cys Gln
     3025                3030                3035                3040
     Asn Gly Arg Cys Ile Ser Lys Thr Phe Val Cys Asp Glu Asp Asn Asp
                     3045                3050                3055
```

```
Cys Gly Asp Gly Ser Asp Glu Leu Met His Leu Cys His Thr Pro Glu
        3060                3065                3070

Pro Thr Cys Pro Pro His Glu Phe Lys Cys Asp Asn Gly Arg Cys Ile
        3075                3080                3085

Glu Met Met Lys Leu Cys Asn His Leu Asp Asp Cys Leu Asp Asn Ser
        3090                3095                3100

Asp Glu Lys Gly Cys Gly Ile Asn Glu Cys His Asp Pro Ser Ile Ser
3105                3110                3115                3120

Gly Cys Asp His Asn Cys Thr Asp Thr Leu Thr Ser Phe Tyr Cys Ser
                3125                3130                3135

Cys Arg Pro Gly Tyr Lys Leu Met Ser Asp Lys Arg Thr Cys Val Asp
        3140                3145                3150

Ile Asp Glu Cys Thr Glu Met Pro Phe Val Cys Ser Gln Lys Cys Glu
        3155                3160                3165

Asn Val Ile Gly Ser Tyr Ile Cys Lys Cys Ala Pro Gly Tyr Leu Arg
        3170                3175                3180

Glu Pro Asp Gly Lys Thr Cys Arg Gln Asn Ser Asn Ile Glu Pro Tyr
3185                3190                3195                3200

Leu Ile Phe Ser Asn Arg Tyr Tyr Leu Arg Asn Leu Thr Ile Asp Gly
                3205                3210                3215

Tyr Phe Tyr Ser Leu Ile Leu Glu Gly Leu Asp Asn Val Val Ala Leu
                3220                3225                3230

Asp Phe Asp Arg Val Glu Lys Arg Leu Tyr Trp Ile Asp Thr Gln Arg
        3235                3240                3245

Gln Val Ile Glu Arg Met Phe Leu Asn Lys Thr Asn Lys Glu Thr Ile
        3250                3255                3260

Ile Asn His Arg Leu Pro Ala Ala Glu Ser Leu Ala Val Asp Trp Val
3265                3270                3275                3280

Ser Arg Lys Leu Tyr Trp Leu Asp Ala Arg Leu Asp Gly Leu Phe Val
                3285                3290                3295

Ser Asp Leu Asn Gly Gly His Arg Arg Met Leu Ala Gln His Cys Val
                3300                3305                3310

Asp Ala Asn Asn Thr Phe Cys Phe Asp Asn Pro Arg Gly Leu Ala Leu
                3315                3320                3325

His Pro Gln Tyr Gly Tyr Leu Tyr Trp Ala Asp Trp Gly His Arg Ala
        3330                3335                3340

Tyr Ile Gly Arg Val Gly Met Asp Gly Thr Asn Lys Ser Val Ile Ile
3345                3350                3355                3360

Ser Thr Lys Leu Glu Trp Pro Asn Gly Ile Thr Ile Asp Tyr Thr Asn
                3365                3370                3375

Asp Leu Leu Tyr Trp Ala Asp Ala His Leu Gly Tyr Ile Glu Tyr Ser
                3380                3385                3390

Asp Leu Glu Gly His His Arg His Thr Val Tyr Asp Gly Ala Leu Pro
                3395                3400                3405

His Pro Phe Ala Ile Thr Ile Phe Glu Asp Thr Ile Tyr Trp Thr Asp
        3410                3415                3420

Trp Asn Thr Arg Thr Val Glu Lys Gly Asn Lys Tyr Asp Gly Ser Asn
3425                3430                3435                3440

Arg Gln Thr Leu Val Asn Thr Thr His Arg Pro Phe Asp Ile His Val
                3445                3450                3455

Tyr His Pro Tyr Arg Gln Pro Ile Val Ser Asn Pro Cys Gly Thr Asn
        3460                3465                3470
```

```
Asn Gly Gly Cys Ser His Leu Cys Leu Ile Lys Pro Gly Lys Gly
        3475                3480                3485

Phe Thr Cys Glu Cys Pro Asp Asp Phe Arg Thr Leu Gln Leu Ser Gly
    3490                3495                3500

Ser Thr Tyr Cys Met Pro Met Cys Ser Ser Thr Gln Phe Leu Cys Ala
3505                3510                3515                3520

Asn Asn Glu Lys Cys Ile Pro Ile Trp Trp Lys Cys Asp Gly Gln Lys
        3525                3530                3535

Asp Cys Ser Asp Gly Ser Asp Glu Leu Ala Leu Cys Pro Gln Arg Phe
        3540                3545                3550

Cys Arg Leu Gly Gln Phe Gln Cys Ser Asp Gly Asn Cys Thr Ser Pro
        3555                3560                3565

Gln Thr Leu Cys Asn Ala His Gln Asn Cys Pro Asp Gly Ser Asp Glu
    3570                3575                3580

Asp Arg Leu Leu Cys Glu Asn His His Cys Asp Ser Asn Glu Trp Gln
3585                3590                3595                3600

Cys Ala Asn Lys Arg Cys Ile Pro Glu Ser Trp Gln Cys Asp Thr Phe
        3605                3610                3615

Asn Asp Cys Glu Asp Asn Ser Asp Glu Asp Ser Ser His Cys Ala Ser
        3620                3625                3630

Arg Thr Cys Arg Pro Gly Gln Phe Arg Cys Ala Asn Gly Arg Cys Ile
        3635                3640                3645

Pro Gln Ala Trp Lys Cys Asp Val Asp Asn Asp Cys Gly Asp His Ser
        3650                3655                3660

Asp Glu Pro Ile Glu Glu Cys Met Ser Ser Ala His Leu Cys Asp Asn
3665                3670                3675                3680

Phe Thr Glu Phe Ser Cys Lys Thr Asn Tyr Arg Cys Ile Pro Lys Trp
        3685                3690                3695

Ala Val Cys Asn Gly Val Asp Asp Cys Arg Asp Asn Ser Asp Glu Gln
        3700                3705                3710

Gly Cys Glu Glu Arg Thr Cys His Pro Val Gly Asp Phe Arg Cys Lys
        3715                3720                3725

Asn His His Cys Ile Pro Leu Arg Trp Gln Cys Asp Gly Gln Asn Asp
    3730                3735                3740

Cys Gly Asp Asn Ser Asp Glu Glu Asn Cys Ala Pro Arg Glu Cys Thr
3745                3750                3755                3760

Glu Ser Glu Phe Arg Cys Val Asn Gln Gln Cys Ile Pro Ser Arg Trp
        3765                3770                3775

Ile Cys Asp His Tyr Asn Asp Cys Gly Asp Asn Ser Asp Glu Arg Asp
        3780                3785                3790

Cys Glu Met Arg Thr Cys His Pro Glu Tyr Phe Gln Cys Thr Ser Gly
        3795                3800                3805

His Cys Val His Ser Glu Leu Lys Cys Asp Gly Ser Ala Asp Cys Leu
    3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Cys Gly Asp Gly Ser Asp Glu
        3860                3865                3870

Glu Glu Leu His Leu Cys Leu Asp Val Pro Cys Asn Ser Pro Asn Arg
        3875                3880                3885

Phe Arg Cys Asp Asn Asn Arg Cys Ile Tyr Ser His Glu Val Cys Asn
```

-continued

```
                3890                3895                3900
Gly Val Asp Asp Cys Gly Asp Gly Thr Asp Glu Thr Glu His Cys
3905                3910                3915                3920

Arg Lys Pro Thr Pro Lys Pro Cys Thr Glu Tyr Glu Tyr Lys Cys Gly
                3925                3930                3935

Asn Gly His Cys Ile Pro His Asp Asn Val Cys Asp Asp Ala Asp Asp
                3940                3945                3950

Cys Gly Asp Trp Ser Asp Glu Leu Gly Cys Asn Lys Gly Lys Glu Arg
                3955                3960                3965

Thr Cys Ala Glu Asn Ile Cys Glu Gln Asn Cys Thr Gln Leu Asn Glu
                3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
                4005                4010                4015

Cys Pro Gln His Cys Arg Asn Thr Lys Gly Ser Tyr Glu Cys Val Cys
                4020                4025                4030

Ala Asp Gly Phe Thr Ser Met Ser Asp Arg Pro Gly Lys Arg Cys Ala
                4035                4040                4045

Ala Glu Gly Ser Ser Pro Leu Leu Leu Leu Pro Asp Asn Val Arg Ile
                4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Lys Asp Ile
                4085                4090                4095

Gly Leu Ser Val Val Tyr Tyr Thr Val Arg Gly Glu Gly Ser Arg Phe
                4100                4105                4110

Gly Ala Ile Lys Arg Ala Tyr Ile Pro Asn Phe Glu Ser Gly Arg Asn
                4115                4120                4125

Asn Leu Val Gln Glu Val Asp Leu Lys Leu Lys Tyr Val Met Gln Pro
                4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
                4165                4170                4175

Lys Trp Leu Ile Ser Thr Asp Leu Asp Gln Pro Ala Ala Ile Ala Val
                4180                4185                4190

Asn Pro Lys Leu Gly Leu Met Phe Trp Thr Asp Trp Gly Lys Glu Pro
                4195                4200                4205

Lys Ile Glu Ser Ala Trp Met Asn Gly Glu Asp Arg Asn Ile Leu Val
                4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
                4245                4250                4255

Ile Lys Tyr Asp Gly Thr Asp Arg Arg Val Ile Ala Lys Glu Ala Met
                4260                4265                4270

Asn Pro Tyr Ser Leu Asp Ile Phe Glu Asp Gln Leu Tyr Trp Ile Ser
                4275                4280                4285

Lys Glu Lys Gly Glu Val Trp Lys Gln Asn Lys Phe Gly Gln Gly Lys
                4290                4295                4300

Lys Glu Lys Thr Leu Val Val Asn Pro Trp Leu Thr Gln Val Arg Ile
4305                4310                4315                4320
```

```
Phe His Gln Leu Arg Tyr Asn Lys Ser Val Pro Asn Leu Cys Lys Gln
            4325                4330                4335

Ile Cys Ser His Leu Cys Leu Leu Arg Pro Gly Gly Tyr Ser Cys Ala
            4340                4345                4350

Cys Pro Gln Gly Ser Ser Phe Ile Glu Gly Ser Thr Thr Glu Cys Asp
            4355                4360                4365

Ala Ala Ile Glu Leu Pro Ile Asn Leu Pro Pro Cys Arg Cys Met
    4370                4375                4380

His Gly Gly Asn Cys Tyr Phe Asp Glu Thr Asp Leu Pro Lys Cys Lys
4385                4390                4395                4400

Cys Pro Ser Gly Tyr Thr Gly Lys Tyr Cys Glu Met Ala Phe Ser Lys
            4405                4410                4415

Gly Ile Ser Pro Gly Thr Thr Ala Val Ala Val Leu Leu Thr Ile Leu
            4420                4425                4430

Leu Ile Val Val Ile Gly Ala Leu Ala Ile Ala Gly Phe Phe His Tyr
            4435                4440                4445

Arg Arg Thr Gly Ser Leu Leu Pro Ala Leu Pro Lys Leu Pro Ser Leu
    4450                4455                4460

Ser Ser Leu Val Lys Pro Ser Glu Asn Gly Asn Gly Val Thr Phe Arg
4465                4470                4475                4480

Ser Gly Ala Asp Leu Asn Met Asp Ile Gly Val Ser Gly Phe Gly Pro
            4485                4490                4495

Glu Thr Ala Ile Asp Arg Ser Met Ala Met Ser Glu Asp Phe Val Met
            4500                4505                4510

Glu Met Gly Lys Gln Pro Ile Ile Phe Glu Asn Pro Met Tyr Ser Ala
            4515                4520                4525

Arg Asp Ser Ala Val Lys Val Val Gln Pro Ile Gln Val Thr Val Ser
    4530                4535                4540

Glu Asn Val Asp Asn Lys Asn Tyr Gly Ser Pro Ile Asn Pro Ser Glu
4545                4550                4555                4560

Ile Val Pro Glu Thr Asn Pro Thr Ser Pro Ala Ala Asp Gly Thr Gln
            4565                4570                4575

Val Thr Lys Trp Asn Leu Phe Lys Arg Lys Ser Lys Gln Thr Thr Asn
            4580                4585                4590

Phe Glu Asn Pro Ile Tyr Ala Gln Met Glu Asn Glu Gln Lys Glu Ser
            4595                4600                4605

Val Ala Ala Thr Pro Pro Pro Ser Pro Ser Leu Pro Ala Lys Pro Lys
    4610                4615                4620

Pro Pro Ser Arg Arg Asp Pro Thr Pro Thr Tyr Ser Ala Thr Glu Asp
4625                4630                4635                4640

Thr Phe Lys Asp Thr Ala Asn Leu Val Lys Glu Asp Ser Glu Val
            4645                4650                4655
```

(2) INFORMATION FOR SEQ ID NO:85:

(i) SEQUENCE CHARACTERISTICS:
        (A) LENGTH: 14042 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Homo sapiens
    (F) TISSUE TYPE: Placenta (ix) FEATURE:
    (A) NAME/KEY: CDS
    (B) LOCATION: 68..14035

(xi) SEQUENCE DESCRIPTION: SEQ ID NO:85:

```
CGGTGCGGTG TGCTACGCGC GCCCACCTCC CGGGGAAGGA ACGGCGAGGC CGGGGACCGT        60

CGCGGAG ATG GAT CGC GGG CCG GCA GCA GTG GCG TGC ACG CTG CTC CTG        109
        Met Asp Arg Gly Pro Ala Ala Val Ala Cys Thr Leu Leu Leu
        1               5                   10

GCT CTC GTC GCC TGC CTA GCC CCG GCC AGT GGC CAA GAA TGT GAC AGT        157
Ala Leu Val Ala Cys Leu Ala Pro Ala Ser Gly Gln Glu Cys Asp Ser
15              20                  25                  30

GCG CAT TTT CGC TGT GGA AGT GGG CAT TGC ATC CCT GCA GAC TGG AGG        205
Ala His Phe Arg Cys Gly Ser Gly His Cys Ile Pro Ala Asp Trp Arg
                35                  40                  45

TGT GAT GGG ACC AAA GAC TGT TCA GAT GAC GCG GAT GAA ATT GGC TGC        253
Cys Asp Gly Thr Lys Asp Cys Ser Asp Asp Ala Asp Glu Ile Gly Cys
            50                  55                  60

GCT GTT GTG ACC TGC CAG CAG GGC TAT TTC AAG TGC CAG AGT GAG GGA        301
Ala Val Val Thr Cys Gln Gln Gly Tyr Phe Lys Cys Gln Ser Glu Gly
65              70                  75

CAA TGC ATC CCC AGC TCC TGG GTG TGT GAC CAA GAT CAA GAC TGT GAT        349
Gln Cys Ile Pro Ser Ser Trp Val Cys Asp Gln Asp Gln Asp Cys Asp
        80                  85                  90

GAT GGC TCA GAT GAA CGT CAA GAT TGC TCA CAA AGT ACA TGC TCA AGT        397
Asp Gly Ser Asp Glu Arg Gln Asp Cys Ser Gln Ser Thr Cys Ser Ser
95                  100                 105                 110

CAT CAG ATA ACA TGC TCC AAT GGT CAG TGT ATC CCA AGT GAA TAC AGG        445
His Gln Ile Thr Cys Ser Asn Gly Gln Cys Ile Pro Ser Glu Tyr Arg
                115                 120                 125

TGC GAC CAC GTC AGA GAC TGC CCC GAT GGA GCT GAT GAG AAT GAC TGC        493
Cys Asp His Val Arg Asp Cys Pro Asp Gly Ala Asp Glu Asn Asp Cys
            130                 135                 140

CAG TAC CCA ACA TGT GAG CAG CTT ACT TGT GAC AAT GGG GCC TGC TAT        541
Gln Tyr Pro Thr Cys Glu Gln Leu Thr Cys Asp Asn Gly Ala Cys Tyr
        145                 150                 155

AAC ACC AGT CAG AAG TGT GAT TGG AAA GTT GAT TGC AGG GAC TCC TCA        589
Asn Thr Ser Gln Lys Cys Asp Trp Lys Val Asp Cys Arg Asp Ser Ser
160                 165                 170

GAT GAA ATC AAC TGC ACT GAG ATA TGC TTG CAC AAT GAG TTT TCA TGT        637
Asp Glu Ile Asn Cys Thr Glu Ile Cys Leu His Asn Glu Phe Ser Cys
175                 180                 185                 190

GGC AAT GGA GAG TGT ATC CCT CGT GCT TAT GTC TGT GAC CAT GAC AAT        685
Gly Asn Gly Glu Cys Ile Pro Arg Ala Tyr Val Cys Asp His Asp Asn
                195                 200                 205

GAT TGC CAA GAC GGC AGT GAY GAA CAT GCT TGC AAC TAT CCG ACC TGC        733
Asp Cys Gln Asp Gly Ser Asp Glu His Ala Cys Asn Tyr Pro Thr Cys
            210                 215                 220

GGT GGT TAC CAG TTC ACT TGC CCC AGT GGC CGA TGC ATT TAT CAA AAC        781
Gly Gly Tyr Gln Phe Thr Cys Pro Ser Gly Arg Cys Ile Tyr Gln Asn
        225                 230                 235

TGG GTT TGT GAT GGA GAA GAT GAC TGT AAA GAT AAT GGA GAT GAA GAT        829
Trp Val Cys Asp Gly Glu Asp Asp Cys Lys Asp Asn Gly Asp Glu Asp
240                 245                 250

GGA TGT GAA AGC GGT CCT CAT GAT GTT CAT AAA TGT TCC CCA AGA GAA        877
Gly Cys Glu Ser Gly Pro His Asp Val His Lys Cys Ser Pro Arg Glu
255                 260                 265                 270
```

```
TGG TCT TGC CCA GAG TCG GGA CGA TGC ATC TCC ATT TAT AAA GTT TGT        925
Trp Ser Cys Pro Glu Ser Gly Arg Cys Ile Ser Ile Tyr Lys Val Cys
                275                 280                 285

GAT GGG ATT TTA GAT TGC CCA GGA AGA GAA GAT GAA AAC AAC ACT AGT        973
Asp Gly Ile Leu Asp Cys Pro Gly Arg Glu Asp Glu Asn Asn Thr Ser
                290                 295                 300

ACC GGA AAA TAC TGT AGT ATG ACT CTG TGC TCT GCC TTG AAC TGC CAG       1021
Thr Gly Lys Tyr Cys Ser Met Thr Leu Cys Ser Ala Leu Asn Cys Gln
                305                 310                 315

TAC CAG TGC CAT GAG ACG CCG TAT GGA GGA GCG TGT TTT TGT CCC CCA       1069
Tyr Gln Cys His Glu Thr Pro Tyr Gly Gly Ala Cys Phe Cys Pro Pro
            320                 325                 330

GGT TAT ATC ATC AAC CAC AAT GAC AGC CGT ACC TGT GTT GAG TTT GAT       1117
Gly Tyr Ile Ile Asn His Asn Asp Ser Arg Thr Cys Val Glu Phe Asp
335                 340                 345                 350

GAT TGC CAG ATA TGG GGA ATT TGT GAC CAG AAG TGT GAA AGC CGA CCT       1165
Asp Cys Gln Ile Trp Gly Ile Cys Asp Gln Lys Cys Glu Ser Arg Pro
                355                 360                 365

GGC CGT CAC CTG TGC CAC TGT GAA GAA GGG TAT ATC TTG GAG CGT GGA       1213
Gly Arg His Leu Cys His Cys Glu Glu Gly Tyr Ile Leu Glu Arg Gly
                370                 375                 380

CAG TAT TGC AAA GCT AAT GAT TCC TTT GGC GAG GCC TCC ATT ATC TTC       1261
Gln Tyr Cys Lys Ala Asn Asp Ser Phe Gly Glu Ala Ser Ile Ile Phe
            385                 390                 395

TCC AAT GGT CGG GAT TTG TTA ATT GGT GAT ATT CAT GGA AGG AGC TTC       1309
Ser Asn Gly Arg Asp Leu Leu Ile Gly Asp Ile His Gly Arg Ser Phe
                400                 405                 410

CGG ATC CTA GTG GAG TCT CAG AAT CGT GGA GTG GCC GTG GGT GTG GCT       1357
Arg Ile Leu Val Glu Ser Gln Asn Arg Gly Val Ala Val Gly Val Ala
415                 420                 425                 430

TTC CAC TAT CAC CTG CAA AGA GTT TTT TGG ACA GAC ACC GTG CAA AAT       1405
Phe His Tyr His Leu Gln Arg Val Phe Trp Thr Asp Thr Val Gln Asn
                435                 440                 445

AAG GTT TTT TCA GTT GAC ATT AAT GGT TTA AAT ATC CAA GAG GTT CTC       1453
Lys Val Phe Ser Val Asp Ile Asn Gly Leu Asn Ile Gln Glu Val Leu
                450                 455                 460

AAT GTT TCT GTT GAA ACC CCA GAG AAC CTG GCT GTG GAC TGG GTT AAT       1501
Asn Val Ser Val Glu Thr Pro Glu Asn Leu Ala Val Asp Trp Val Asn
                465                 470                 475

AAT AAA ATC TAT CTA GTG GAA ACC AAG GTC AAC CGC ATA GAT ATG GTA       1549
Asn Lys Ile Tyr Leu Val Glu Thr Lys Val Asn Arg Ile Asp Met Val
            480                 485                 490

AAT TTG GAT GGA AGC TAT CGG GTT ACC CTT ATA ACT GAA AAC TTG GGG       1597
Asn Leu Asp Gly Ser Tyr Arg Val Thr Leu Ile Thr Glu Asn Leu Gly
495                 500                 505                 510

CAT CCT AGA GGA ATT GCC GTG GAC CCA ACT GTT GGT TAT TTA TTT TTC       1645
His Pro Arg Gly Ile Ala Val Asp Pro Thr Val Gly Tyr Leu Phe Phe
                515                 520                 525

TCA GAT TGG GAG AGC CTT TCT GGG GAA CCT AAG CTG GAA AGG GCA TTC       1693
Ser Asp Trp Glu Ser Leu Ser Gly Glu Pro Lys Leu Glu Arg Ala Phe
                530                 535                 540

ATG GAT GGC AGC AAC CGT AAA GAC TTG GTG AAA ACA AAG CTG GGA TGG       1741
Met Asp Gly Ser Asn Arg Lys Asp Leu Val Lys Thr Lys Leu Gly Trp
                545                 550                 555

CCT GCT GGG GTA ACT CTG GAT ATG ATA TCG AAG CGT GTT TAC TGG GTT       1789
Pro Ala Gly Val Thr Leu Asp Met Ile Ser Lys Arg Val Tyr Trp Val
560                 565                 570

GAC TCT CGG TTT GAT TAC ATT GAA ACT GTA ACT TAT GAT GGA ATT CAA       1837
Asp Ser Arg Phe Asp Tyr Ile Glu Thr Val Thr Tyr Asp Gly Ile Gln
```

-continued

```
         575                 580                 585                 590
AGG AAG ACT GTA GTT CAT GGA GGC TCC CTC ATT CCT CAT CCC TTT GGA       1885
Arg Lys Thr Val Val His Gly Gly Ser Leu Ile Pro His Pro Phe Gly
                    595                 600                 605

GTA AGC TTA TTT GAA GGT CAG GTG TTC TTT ACA GAT TGG ACA AAG ATG       1933
Val Ser Leu Phe Glu Gly Gln Val Phe Phe Thr Asp Trp Thr Lys Met
                610                 615                 620

GCC GTG CTG AAG GCA AAC AAG TTC ACA GAG ACC AAC CCA CAA GTG TAC       1981
Ala Val Leu Lys Ala Asn Lys Phe Thr Glu Thr Asn Pro Gln Val Tyr
            625                 630                 635

TAC CAG GCT TCC CTG AGG CCC TAT GGA GTG ACT GTT TAC CAT TCC CTC       2029
Tyr Gln Ala Ser Leu Arg Pro Tyr Gly Val Thr Val Tyr His Ser Leu
        640                 645                 650

AGA CAG CCC TAT GCT ACC AAT CCG TGT AAA GAT AAC AAT GGG GGC TGT       2077
Arg Gln Pro Tyr Ala Thr Asn Pro Cys Lys Asp Asn Asn Gly Gly Cys
655                 660                 665                 670

GAG CAG GTC TGT GTY CTC AGC CAC AGA ACA GAT AAT GAT GGT TTG GGT       2125
Glu Gln Val Cys Val Leu Ser His Arg Thr Asp Asn Asp Gly Leu Gly
                    675                 680                 685

TTC CGT TGC AAG TGC ACA TTC GGC TTC CAA CTG GAT ACA GAT GAG CGC       2173
Phe Arg Cys Lys Cys Thr Phe Gly Phe Gln Leu Asp Thr Asp Glu Arg
                690                 695                 700

CAC TGC ATT GCT GTT CAG AAT TTC CTC ATT TTT TCA TCC CAA GTT GCT       2221
His Cys Ile Ala Val Gln Asn Phe Leu Ile Phe Ser Ser Gln Val Ala
            705                 710                 715

ATT CGT GGG ATC CCG TTC ACC TTG TCT ACC CAG GAA GAT GTC ATG GTT       2269
Ile Arg Gly Ile Pro Phe Thr Leu Ser Thr Gln Glu Asp Val Met Val
        720                 725                 730

CCA GTT TCG GGG AAT CCT TCT TTC TTT GTC GGG ATT GAT TTT GAC GCC       2317
Pro Val Ser Gly Asn Pro Ser Phe Phe Val Gly Ile Asp Phe Asp Ala
735                 740                 745                 750

CAG GAC AGC ACT ATC TTT TTT TCA GAT ATG TCA AAA CAC ATG ATT TTT       2365
Gln Asp Ser Thr Ile Phe Phe Ser Asp Met Ser Lys His Met Ile Phe
                    755                 760                 765

AAG CAA AAG ATT GAT GGC ACA GGA AGA GAA ATT CTC GCA GCT AAC AGG       2413
Lys Gln Lys Ile Asp Gly Thr Gly Arg Glu Ile Leu Ala Ala Asn Arg
                770                 775                 780

GTG GAA AAT GTT GAA AGT TTG GCT TTT GAC TGG ATT TCA AAG AAT CTC       2461
Val Glu Asn Val Glu Ser Leu Ala Phe Asp Trp Ile Ser Lys Asn Leu
            785                 790                 795

TAT TGG ACA GAC TCT CAT TAC AAG AGT ATC AGT GTC ATG AGG CTA GCT       2509
Tyr Trp Thr Asp Ser His Tyr Lys Ser Ile Ser Val Met Arg Leu Ala
        800                 805                 810

GAT AAA ACG AGA CGC ACG GTA GTT CAG TAT TTA AAT AAC CCA CGG TCG       2557
Asp Lys Thr Arg Arg Thr Val Val Gln Tyr Leu Asn Asn Pro Arg Ser
815                 820                 825                 830

GTG GTA GTT CAT CCT TTT GCC GGG TAT CTA TTC TTC ACT GAT TGG TTC       2605
Val Val Val His Pro Phe Ala Gly Tyr Leu Phe Phe Thr Asp Trp Phe
                    835                 840                 845

CGT CCT GCT AAA ATT ATG AGA GCA TGG AGT GAC GGA TCT CAC CTC TTG       2653
Arg Pro Ala Lys Ile Met Arg Ala Trp Ser Asp Gly Ser His Leu Leu
                850                 855                 860

CCT GTA ATA AAC ACT ACT CTT GGA TGG CCC AAT GGC TTG GCC ATC GAT       2701
Pro Val Ile Asn Thr Thr Leu Gly Trp Pro Asn Gly Leu Ala Ile Asp
            865                 870                 875

TGG GCT GCT TCA CGA TTG TAC TGG GTA GAT GCC TAT TTT GAT AAA ATT       2749
Trp Ala Ala Ser Arg Leu Tyr Trp Val Asp Ala Tyr Phe Asp Lys Ile
        880                 885                 890

GAG CAC AGC ACC TTT GAT GGT TTA GAC AGA AGA AGA CTG GGC CAT ATA       2797
```

-continued

```
Glu His Ser Thr Phe Asp Gly Leu Asp Arg Arg Arg Leu Gly His Ile
895                 900                 905                 910

GAG CAG ATG ACA CAT CCG TTT GGA CTT GCC ATC TTT GGA GAG CAT TTA        2845
Glu Gln Met Thr His Pro Phe Gly Leu Ala Ile Phe Gly Glu His Leu
                915                 920                 925

TTT TTT ACT GAC TGG AGA CTG GGT GCC ATT ATT CGA GTC AGG AAA GCA        2893
Phe Phe Thr Asp Trp Arg Leu Gly Ala Ile Ile Arg Val Arg Lys Ala
            930                 935                 940

GAT GGT GGA GAA ATG ACA GTT ATC CGA AGT GGC ATT GCT TAC ATA CTG        2941
Asp Gly Gly Glu Met Thr Val Ile Arg Ser Gly Ile Ala Tyr Ile Leu
        945                 950                 955

CAT TTG AAA TCG TAT GAT GTC AAC ATC CAG ACT GGT TCT AAC GCC TGT        2989
His Leu Lys Ser Tyr Asp Val Asn Ile Gln Thr Gly Ser Asn Ala Cys
    960                 965                 970

AAT CAA CCC ACG CAT CCT AAC GGT GAC TGC AGC CAC TTC TGC TTC CCG        3037
Asn Gln Pro Thr His Pro Asn Gly Asp Cys Ser His Phe Cys Phe Pro
975                 980                 985                 990

GTG CCA AAT TTC CAG CGA GTG TGT GGG TGC CCT TAT GGA ATG AGG CTG        3085
Val Pro Asn Phe Gln Arg Val Cys Gly Cys Pro Tyr Gly Met Arg Leu
                995                 1000                1005

GCT TCC AAT CAC TTG ACA TGC GAG GGG GAC CCA ACA AAT GAA CCA CCC        3133
Ala Ser Asn His Leu Thr Cys Glu Gly Asp Pro Thr Asn Glu Pro Pro
            1010                1015                1020

ACG GAG CAG TGT GGC TTA TTT TCC TTC CCC TGT AAA AAT GGC AGA TGT        3181
Thr Glu Gln Cys Gly Leu Phe Ser Phe Pro Cys Lys Asn Gly Arg Cys
        1025                1030                1035

GTG CCC AAT TAC TAT CTC TGT GAT GGA GTC GAT GAT TGT CAT GAT AAC        3229
Val Pro Asn Tyr Tyr Leu Cys Asp Gly Val Asp Asp Cys His Asp Asn
    1040                1045                1050

AGT GAT GAG CAA CTA TGT GGC ACA CTT AAT AAT ACC TGT TCA TCT TCG        3277
Ser Asp Glu Gln Leu Cys Gly Thr Leu Asn Asn Thr Cys Ser Ser Ser
1055                1060                1065                1070

GCG TTC ACC TGT GGC CAT GGG GAG TGC ATT CCT GCA CAC TGG CGC TGT        3325
Ala Phe Thr Cys Gly His Gly Glu Cys Ile Pro Ala His Trp Arg Cys
                1075                1080                1085

GAC AAA CGC AAC GAC TGT GTG GAT GGC AGT GAT GAG CAC AAC TGC CCC        3373
Asp Lys Arg Asn Asp Cys Val Asp Gly Ser Asp Glu His Asn Cys Pro
            1090                1095                1100

ACC CAC GCA CCT GCT TCC TGC CTT GAC ACC CAA TAC ACC TGT GAT AAT        3421
Thr His Ala Pro Ala Ser Cys Leu Asp Thr Gln Tyr Thr Cys Asp Asn
        1105                1110                1115

CAC CAG TGT ATC TCA AAG AAC TGG GTC TGT GAC ACA GAC AAT GAT TGT        3469
His Gln Cys Ile Ser Lys Asn Trp Val Cys Asp Thr Asp Asn Asp Cys
    1120                1125                1130

GGG GAT GGA TCT GAT GAA AAG AAC TGC AAT TCG ACA GAG ACA TGC CAA        3517
Gly Asp Gly Ser Asp Glu Lys Asn Cys Asn Ser Thr Glu Thr Cys Gln
1135                1140                1145                1150

CCT AGT CAG TTT AAT TGC CCC AAT CAT CGA TGT ATT GAC CTA TCG TTT        3565
Pro Ser Gln Phe Asn Cys Pro Asn His Arg Cys Ile Asp Leu Ser Phe
                1155                1160                1165

GTC TGT GAT GGT GAC AAG GAT TGT GTT GAT GGA TCT GAT GAG GTT GGT        3613
Val Cys Asp Gly Asp Lys Asp Cys Val Asp Gly Ser Asp Glu Val Gly
            1170                1175                1180

TGT GTA TTA AAC TGT ACT GCT TCT CAA TTC AAG TGT GCC AGT GGG GAT        3661
Cys Val Leu Asn Cys Thr Ala Ser Gln Phe Lys Cys Ala Ser Gly Asp
        1185                1190                1195

AAA TGT ATT GGC GTC ACA AAT CGT TGT GAT GGT GTT TTT GAT TGC AGT        3709
Lys Cys Ile Gly Val Thr Asn Arg Cys Asp Gly Val Phe Asp Cys Ser
    1200                1205                1210
```

```
GAC AAC TCG GAT GAA GCG GGC TGT CCA ACC AGG CCT CCT GGT ATG TGC    3757
Asp Asn Ser Asp Glu Ala Gly Cys Pro Thr Arg Pro Pro Gly Met Cys
1215                1220                1225                1230

CAC TCA GAT GAA TTT CAG TGC CAA GAA GAT GGT ATC TGC ATC CCG AAC    3805
His Ser Asp Glu Phe Gln Cys Gln Glu Asp Gly Ile Cys Ile Pro Asn
            1235                1240                1245

TTC TGG GAA TGT GAT GGG CAT CCA GAC TGC CTC TAT GGA TCT GAT GAG    3853
Phe Trp Glu Cys Asp Gly His Pro Asp Cys Leu Tyr Gly Ser Asp Glu
        1250                1255                1260

CAC AAT GCC TGT GTC CCC AAG ACT TGC CCH TCA TCA TAT TTC CAC TGT    3901
His Asn Ala Cys Val Pro Lys Thr Cys Pro Ser Ser Tyr Phe His Cys
    1265                1270                1275

GAC AAC GGA AAC TGC ATC CAC AGG SCA TGG CTC TGT GAT CGG GAC AAT    3949
Asp Asn Gly Asn Cys Ile His Arg Xaa Trp Leu Cys Asp Arg Asp Asn
1280                1285                1290

GAC TGC GGG GAT ATG AGT GAT GAG AAG GAC TGC CCT ACT CAG CCC TTT    3997
Asp Cys Gly Asp Met Ser Asp Glu Lys Asp Cys Pro Thr Gln Pro Phe
1295                1300                1305                1310

CGC TGT CCT AGT TGG CAA TGG CAG TGT CTT GGC CAT AAC ATC TGT GTG    4045
Arg Cys Pro Ser Trp Gln Trp Gln Cys Leu Gly His Asn Ile Cys Val
            1315                1320                1325

AAT CTG AGT GTA GTG TGT GAT GGC ATC TTT GAC TGC CCC AAT GGG ACA    4093
Asn Leu Ser Val Val Cys Asp Gly Ile Phe Asp Cys Pro Asn Gly Thr
        1330                1335                1340

GAT GAG TCC CCA CTT TGC AAT GGG AAC AGC TGC TCA GAT TTC AAT GGT    4141
Asp Glu Ser Pro Leu Cys Asn Gly Asn Ser Cys Ser Asp Phe Asn Gly
    1345                1350                1355

GGT TGT ACT CAC GAG TGT GTT CAA GAG CCC TTT GGG GCT AAA TGC CTA    4189
Gly Cys Thr His Glu Cys Val Gln Glu Pro Phe Gly Ala Lys Cys Leu
1360                1365                1370

TGT CCA TTG GGA TTC TTA CTT GCC AAT GAT TCT AAG ACC TGT GAA GAC    4237
Cys Pro Leu Gly Phe Leu Leu Ala Asn Asp Ser Lys Thr Cys Glu Asp
1375                1380                1385                1390

ATA GAT GAA TGT GAT ATT CTA GGC TCT TGT AGC CAG CAC TGT TAC AAT    4285
Ile Asp Glu Cys Asp Ile Leu Gly Ser Cys Ser Gln His Cys Tyr Asn
            1395                1400                1405

ATG AGA GGT TCT TTC CGG TGC TCG TGT GAT ACA GGC TAC ATG TTA GAA    4333
Met Arg Gly Ser Phe Arg Cys Ser Cys Asp Thr Gly Tyr Met Leu Glu
        1410                1415                1420

AGT GAT GGG AGG ACT TGC AAA GTT ACA GCA TCT GAG AGT CTG CTG TTA    4381
Ser Asp Gly Arg Thr Cys Lys Val Thr Ala Ser Glu Ser Leu Leu Leu
    1425                1430                1435

CTT GTG GCA AGT CAG AAC AAA ATT ATT GCC GAC AGT GTC ACC TCC CAG    4429
Leu Val Ala Ser Gln Asn Lys Ile Ile Ala Asp Ser Val Thr Ser Gln
1440                1445                1450

GTC CAC AAT ATC TAT TCA TTG GTC GAG AAT GGT TCT TAC ATT GTA GCT    4477
Val His Asn Ile Tyr Ser Leu Val Glu Asn Gly Ser Tyr Ile Val Ala
1455                1460                1465                1470

GTT GAT TTT GAT TCA ATT AGT GGT CGT ATC TTT TGG TCT GAT GCA ACT    4525
Val Asp Phe Asp Ser Ile Ser Gly Arg Ile Phe Trp Ser Asp Ala Thr
            1475                1480                1485

CAG GGT AAA ACC TGG AGT GCG TTT CAA AAT GGA ACG GAC AGA AGA GTG    4573
Gln Gly Lys Thr Trp Ser Ala Phe Gln Asn Gly Thr Asp Arg Arg Val
        1490                1495                1500

GTA TTT GAC AGT AGC ATC ATC TTG ACT GAA ACT ATT GCA ATA GAT TGG    4621
Val Phe Asp Ser Ser Ile Ile Leu Thr Glu Thr Ile Ala Ile Asp Trp
    1505                1510                1515

GTA GGT CGT AAT CTT TAC TGG ACA GAC TAT GCT CTG GAA ACA ATT GAA    4669
Val Gly Arg Asn Leu Tyr Trp Thr Asp Tyr Ala Leu Glu Thr Ile Glu
1520                1525                1530
```

```
GTC TCC AAA ATT GAT GGG AGC CAC AGG ACT GTG CTG ATT AGT AAA AAC      4717
Val Ser Lys Ile Asp Gly Ser His Arg Thr Val Leu Ile Ser Lys Asn
1535                1540                1545                1550

CTA ACA AAT CCA AGA GGA CTA GCA TTA GAT CCC AGA ATG AAT GAG CAT      4765
Leu Thr Asn Pro Arg Gly Leu Ala Leu Asp Pro Arg Met Asn Glu His
                    1555                1560                1565

CTA CTG TTC TGG TCT GAC TGG GGC CAC CAC CCT CGC ATC GAG CGA GCC      4813
Leu Leu Phe Trp Ser Asp Trp Gly His His Pro Arg Ile Glu Arg Ala
            1570                1575                1580

AGC ATG GAC GGC AGC ATG CGC ACT GTC ATT GTC CAG GAC AAG ATC TTC      4861
Ser Met Asp Gly Ser Met Arg Thr Val Ile Val Gln Asp Lys Ile Phe
        1585                1590                1595

TGG CCC TGC GGC TTA ACT ATT GAC TAC CCC AAC AGA CTG CTC TAC TTC      4909
Trp Pro Cys Gly Leu Thr Ile Asp Tyr Pro Asn Arg Leu Leu Tyr Phe
    1600                1605                1610

ATG GAC TCC TAT CTT GAT TAC ATG GAC TTT TGC GAT TAT AAT GGA CAC      4957
Met Asp Ser Tyr Leu Asp Tyr Met Asp Phe Cys Asp Tyr Asn Gly His
1615                1620                1625                1630

CAT CGG AGA CAG GTG ATA GCC AGT GAT TTG ATT ATA CGG CAC CCC TAT      5005
His Arg Arg Gln Val Ile Ala Ser Asp Leu Ile Ile Arg His Pro Tyr
                    1635                1640                1645

GCC CTA ACT CTC TTT GAA GAC TCT GTG TAC TGG ACT GAC CGT GCT ACT      5053
Ala Leu Thr Leu Phe Glu Asp Ser Val Tyr Trp Thr Asp Arg Ala Thr
            1650                1655                1660

CGT CGG GTT ATG CGA GCC AAC AAG TGG CAT GGA GGG AAC CAG TCA GTT      5101
Arg Arg Val Met Arg Ala Asn Lys Trp His Gly Gly Asn Gln Ser Val
        1665                1670                1675

GTA ATG TAT AAT ATT CAA TGG CCC CTT GGG ATT GTT GCG GTT CAT CCT      5149
Val Met Tyr Asn Ile Gln Trp Pro Leu Gly Ile Val Ala Val His Pro
    1680                1685                1690

TCG AAA CAA CCA AAT TCT GTG AAT CCA TGT GCC TTT TCC CGC TGC AGC      5197
Ser Lys Gln Pro Asn Ser Val Asn Pro Cys Ala Phe Ser Arg Cys Ser
1695                1700                1705                1710

CAT CTC TGC CTG CTT TCC TCA CAG GGG CCT CAT TTT TAC TCC TGT GTT      5245
His Leu Cys Leu Leu Ser Ser Gln Gly Pro His Phe Tyr Ser Cys Val
                    1715                1720                1725

TGT CCT TCA GGA TGG AGT CTG TCT CCT GAT CTC CTG AAT TGC TTG AGA      5293
Cys Pro Ser Gly Trp Ser Leu Ser Pro Asp Leu Leu Asn Cys Leu Arg
            1730                1735                1740

GAT GAT CAA CCT TTC TTA ATA ACT GTA AGG CAA CAT ATA ATT TTT GGA      5341
Asp Asp Gln Pro Phe Leu Ile Thr Val Arg Gln His Ile Ile Phe Gly
        1745                1750                1755

ATC TCC CTT AAT CCT GAG GTG AAG AGC AAT GAT GCT ATG GTC CCC ATA      5389
Ile Ser Leu Asn Pro Glu Val Lys Ser Asn Asp Ala Met Val Pro Ile
    1760                1765                1770

GCA GGG ATA CAG AAT GGT TTA GAT GTT GAA TTT GAT GAT GCT GAG CAA      5437
Ala Gly Ile Gln Asn Gly Leu Asp Val Glu Phe Asp Asp Ala Glu Gln
1775                1780                1785                1790

TAC ATC TAT TGG GTT GAA AAT CCA GGT GAA ATT CAC AGA GTG AAG ACA      5485
Tyr Ile Tyr Trp Val Glu Asn Pro Gly Glu Ile His Arg Val Lys Thr
                    1795                1800                1805

GAT GGC ACC AAC AGG ACA GTA TTT GCT TCT ATA TCT ATG GTG GGG CCT      5533
Asp Gly Thr Asn Arg Thr Val Phe Ala Ser Ile Ser Met Val Gly Pro
            1810                1815                1820

TCT ATG AAC CTG GCC TTA GAT TGG ATT TCA AGA AAC CTT TAT TCT ACC      5581
Ser Met Asn Leu Ala Leu Asp Trp Ile Ser Arg Asn Leu Tyr Ser Thr
        1825                1830                1835

AAT CCT AGA ACT CAG TCA ATC GAG GTT TTG ACA CTC CAC GGA GAT ATC      5629
Asn Pro Arg Thr Gln Ser Ile Glu Val Leu Thr Leu His Gly Asp Ile
```

```
                                                       -continued
        1840                1845                1850

AGA TAC AGA AAA ACA TTG ATT GCC AAT GAT GGG ACA GCT CTT GGA GTT      5677
Arg Tyr Arg Lys Thr Leu Ile Ala Asn Asp Gly Thr Ala Leu Gly Val
1855                1860                1865                1870

GGC TTT CCA ATT GGC ATA ACT GTT GAT CCT GCT CGT GGG AAG CTG TAC      5725
Gly Phe Pro Ile Gly Ile Thr Val Asp Pro Ala Arg Gly Lys Leu Tyr
            1875                1880                1885

TGG TCA GAC CAA GGA ACT GAC AGT GGG GTT CCT GCC AAG ATC GCC AGT      5773
Trp Ser Asp Gln Gly Thr Asp Ser Gly Val Pro Ala Lys Ile Ala Ser
                1890                1895                1900

GCT AAC ATG GAT GGC ACA TCT GTG AAA ACT CTC TTT ACT GGG AAC CTC      5821
Ala Asn Met Asp Gly Thr Ser Val Lys Thr Leu Phe Thr Gly Asn Leu
                    1905                1910                1915

GAA CAC CTG GAG TGT GTC ACT CTT GAC ATC GAA GAG CAG AAA CTC TAC      5869
Glu His Leu Glu Cys Val Thr Leu Asp Ile Glu Glu Gln Lys Leu Tyr
        1920                1925                1930

TGG GCA GTC ACT GGA AGA GGA GTG ATT GAA AGA GGA AAC GTG GAT GGA      5917
Trp Ala Val Thr Gly Arg Gly Val Ile Glu Arg Gly Asn Val Asp Gly
1935                1940                1945                1950

ACA GAT CGG ATG ATC CTG GTA CAC CAG CTT TCC CAC CCC TGG GGA ATT      5965
Thr Asp Arg Met Ile Leu Val His Gln Leu Ser His Pro Trp Gly Ile
            1955                1960                1965

GCA GTC CAT GAT TCT TTC CTT TAT TAT ACT GAT GAA CAG TAT GAG GTC      6013
Ala Val His Asp Ser Phe Leu Tyr Tyr Thr Asp Glu Gln Tyr Glu Val
                1970                1975                1980

ATT GAA AGA GTT GAT AAG GCC ACT GGG GCC AAC AAA ATA GTC TTG AGA      6061
Ile Glu Arg Val Asp Lys Ala Thr Gly Ala Asn Lys Ile Val Leu Arg
                    1985                1990                1995

GAT AAT GTT CCA AAT CTG AGG GGT CTT CAA GTT TAT CAC AGA CGC AAT      6109
Asp Asn Val Pro Asn Leu Arg Gly Leu Gln Val Tyr His Arg Arg Asn
        2000                2005                2010

GCC GCC GAA TCC TCA AAT GGC TGT AGC AAC AAC ATG AAT GCC TGT CAG      6157
Ala Ala Glu Ser Ser Asn Gly Cys Ser Asn Asn Met Asn Ala Cys Gln
2015                2020                2025                2030

CAG ATT TGC CTG CCT GTA CCA GGA GGA TTG TTT TCC TGC GCC TGT GCC      6205
Gln Ile Cys Leu Pro Val Pro Gly Gly Leu Phe Ser Cys Ala Cys Ala
            2035                2040                2045

ACT GGA TTT AAA CTC AAT CCT GAT AAT CGG TCC TGC TCT CCA TAT AAC      6253
Thr Gly Phe Lys Leu Asn Pro Asp Asn Arg Ser Cys Ser Pro Tyr Asn
                2050                2055                2060

TCT TTC ATT GTT GTT TCA ATG CTG TCT GCA ATC AGA GGC TTT AGC TTG      6301
Ser Phe Ile Val Val Ser Met Leu Ser Ala Ile Arg Gly Phe Ser Leu
                    2065                2070                2075

GAA TTG TCA GAT CAT TCA GAA ACC ATG GTG CCG GTG GCA GGC CAA GGA      6349
Glu Leu Ser Asp His Ser Glu Thr Met Val Pro Val Ala Gly Gln Gly
        2080                2085                2090

CGA AAC GCA CTG CAT GTG GAT GTG GAT GTG TCC TCT GGC TTT ATT TAT      6397
Arg Asn Ala Leu His Val Asp Val Asp Val Ser Ser Gly Phe Ile Tyr
2095                2100                2105                2110

TGG TGT GAT TTT AGC AGC TCA GTG GCA TCT GAT AAT GCG ATC CGT AGA      6445
Trp Cys Asp Phe Ser Ser Ser Val Ala Ser Asp Asn Ala Ile Arg Arg
            2115                2120                2125

ATT AAA CCA GAT GGA TCT TCT CTG ATG AAC ATT GTG ACA CAT GGA ATA      6493
Ile Lys Pro Asp Gly Ser Ser Leu Met Asn Ile Val Thr His Gly Ile
                2130                2135                2140

GGA GAA AAT GGA GTC CGG GGT ATT GCA GTG GAT TGG GTA GCA GGA AAT      6541
Gly Glu Asn Gly Val Arg Gly Ile Ala Val Asp Trp Val Ala Gly Asn
                    2145                2150                2155

CTT TAT TTC ACC AAT GCC TTT GTT TCT GAA ACA CTG ATA GAA GTT CTG      6589
```

```
Leu Tyr Phe Thr Asn Ala Phe Val Ser Glu Thr Leu Ile Glu Val Leu
        2160                2165                2170

CGG ATC AAT ACT ACT TAC CGC CGT GTT CTT CTT AAA GTC ACA GTG GAC          6637
Arg Ile Asn Thr Thr Tyr Arg Arg Val Leu Leu Lys Val Thr Val Asp
2175                2180                2185                2190

ATG CCT AGG CAT ATT GTT GTA GAT CCC AAG AAC AGA TAC CTC TTC TGG          6685
Met Pro Arg His Ile Val Val Asp Pro Lys Asn Arg Tyr Leu Phe Trp
                2195                2200                2205

GCT GAC TAT GGG CAG AGA CCA AAG ATT GAG CGT TCT TTC CTT GAC TGT          6733
Ala Asp Tyr Gly Gln Arg Pro Lys Ile Glu Arg Ser Phe Leu Asp Cys
            2210                2215                2220

ACC AAT CGA ACA GTG CTT GTG TCA GAG GGC ATT GTC ACA CCA CGG GGC          6781
Thr Asn Arg Thr Val Leu Val Ser Glu Gly Ile Val Thr Pro Arg Gly
        2225                2230                2235

TTG GCA GTG GAC CGA AGT GAT GGC TAC GTT TAT TGG GTT GAT GAT TCT          6829
Leu Ala Val Asp Arg Ser Asp Gly Tyr Val Tyr Trp Val Asp Asp Ser
2240                2245                2250

TTA GAT ATA ATT GCA AGG ATT CGT ATC AAT GGA GAG AAC TCT GAA GTG          6877
Leu Asp Ile Ile Ala Arg Ile Arg Ile Asn Gly Glu Asn Ser Glu Val
2255                2260                2265                2270

ATT CGT TAT GGC AGT CGT TAC CCA ACT CCT TAT GGC ATC ACT GTT TTT          6925
Ile Arg Tyr Gly Ser Arg Tyr Pro Thr Pro Tyr Gly Ile Thr Val Phe
                2275                2280                2285

GAA AAT TCT ATC ATA TGG GTA GAT AGG AAT TTG AAA AAG ATC TTC CAA          6973
Glu Asn Ser Ile Ile Trp Val Asp Arg Asn Leu Lys Lys Ile Phe Gln
            2290                2295                2300

GCC AGC AAG GAA CCA GAG AAC ACA GAG CCA CCC ACA GTG ATA AGA GAC          7021
Ala Ser Lys Glu Pro Glu Asn Thr Glu Pro Pro Thr Val Ile Arg Asp
        2305                2310                2315

AAT ATC AAC TGG CTA AGA GAT GTG ACC ATC TTT GAC AAG CAA GTC CAG          7069
Asn Ile Asn Trp Leu Arg Asp Val Thr Ile Phe Asp Lys Gln Val Gln
    2320                2325                2330

CCC CGG TCA CCA GCA GAG GTC AAC AAC AAC CCT TGC TTG GAA AAC AAT          7117
Pro Arg Ser Pro Ala Glu Val Asn Asn Asn Pro Cys Leu Glu Asn Asn
2335                2340                2345                2350

GGT GGG TGC TCT CAT CTC TGC TTT GCT CTG CCT GGA TTG CAC ACC CCA          7165
Gly Gly Cys Ser His Leu Cys Phe Ala Leu Pro Gly Leu His Thr Pro
                2355                2360                2365

AAA TGT GAC TGT GCC TTT GGG ACC CTG CAA AGT GAT GGC AAG AAT TGT          7213
Lys Cys Asp Cys Ala Phe Gly Thr Leu Gln Ser Asp Gly Lys Asn Cys
            2370                2375                2380

GCC ATT TCA ACA GAA AAT TTC CTC ATC TTT GCC TTG TCT AAT TCC TTG          7261
Ala Ile Ser Thr Glu Asn Phe Leu Ile Phe Ala Leu Ser Asn Ser Leu
        2385                2390                2395

AGA AGC TTA CAC TTG GAC CCT GAA AAC CAT AGC CCA CCT TTC CAA ACA          7309
Arg Ser Leu His Leu Asp Pro Glu Asn His Ser Pro Pro Phe Gln Thr
    2400                2405                2410

ATA AAT GTG GAA AGA ACT GTC ATG TCT CTA GAC TAT GAC AGT GTA AGT          7357
Ile Asn Val Glu Arg Thr Val Met Ser Leu Asp Tyr Asp Ser Val Ser
2415                2420                2425                2430

GAT AGA ATC TAC TTC ACA CAA AAT TTA GCC TCT GGA GTT GGA CAG ATT          7405
Asp Arg Ile Tyr Phe Thr Gln Asn Leu Ala Ser Gly Val Gly Gln Ile
                2435                2440                2445

TCC TAT GCC ACC CTG TCT TCA GGG ATC CAT ACT CCA ACT GTC ATT GCT          7453
Ser Tyr Ala Thr Leu Ser Ser Gly Ile His Thr Pro Thr Val Ile Ala
            2450                2455                2460

TCA GGT ATA GGG ACT GCT GAT GGC ATT GCC TTT GAC TGG ATT ACT AGA          7501
Ser Gly Ile Gly Thr Ala Asp Gly Ile Ala Phe Asp Trp Ile Thr Arg
        2465                2470                2475
```

-continued

```
AGA ATT TAT TAC AGT GAC TAC CTC AAC CAG ATG ATT AAT TCC ATG GCT      7549
Arg Ile Tyr Tyr Ser Asp Tyr Leu Asn Gln Met Ile Asn Ser Met Ala
        2480                2485                2490

GAA GAT GGG TCT AAC CGC ACT GTG ATA GCC CGC GTT CCA AAA CCA AGA      7597
Glu Asp Gly Ser Asn Arg Thr Val Ile Ala Arg Val Pro Lys Pro Arg
2495                2500                2505                2510

GCA ATT GTG TTA GAT CCC TGC CAA GGG TAC CTG TAC TGG GCT GAC TGG      7645
Ala Ile Val Leu Asp Pro Cys Gln Gly Tyr Leu Tyr Trp Ala Asp Trp
            2515                2520                2525

GAT ACA CAT GCC AAA ATC GAG AGA GCC ACA TTG GGA GGA AAC TTC CGC      7693
Asp Thr His Ala Lys Ile Glu Arg Ala Thr Leu Gly Gly Asn Phe Arg
                2530                2535                2540

GTA CCC ATT GTG AAC AGC AGT CTG GTC ATG CCC AGT GGG CTG ACT CTG      7741
Val Pro Ile Val Asn Ser Ser Leu Val Met Pro Ser Gly Leu Thr Leu
        2545                2550                2555

GAC TAT GAA GAG GAC CTT CTC TAC TGG GTG GAT GCT AGT CTG CAG AGG      7789
Asp Tyr Glu Glu Asp Leu Leu Tyr Trp Val Asp Ala Ser Leu Gln Arg
    2560                2565                2570

ATT GAA CGC AGC ACT CTG ACG GGC GTG GAT CGT GAA GTC ATT GTC AAT      7837
Ile Glu Arg Ser Thr Leu Thr Gly Val Asp Arg Glu Val Ile Val Asn
2575                2580                2585                2590

GCA GCC GTT CAT GCT TTT GGC TTG ACT CTC TAT GGC CAG TAT ATT TAC      7885
Ala Ala Val His Ala Phe Gly Leu Thr Leu Tyr Gly Gln Tyr Ile Tyr
            2595                2600                2605

TGG ACT GAC TTG TAC ACA CAA AGA ATT TAC CGA GCT AAC AAA TAT GAC      7933
Trp Thr Asp Leu Tyr Thr Gln Arg Ile Tyr Arg Ala Asn Lys Tyr Asp
                2610                2615                2620

GGG TCA GGT CAG ATT GCA ATG ACC ACA AAT TTG CTC TCC CAG CCC AGG      7981
Gly Ser Gly Gln Ile Ala Met Thr Thr Asn Leu Leu Ser Gln Pro Arg
        2625                2630                2635

GGA ATC AAC ACT GTT GTG AAG AAC CAG AAA CAA CAG TGT AAC AAT CCT      8029
Gly Ile Asn Thr Val Val Lys Asn Gln Lys Gln Gln Cys Asn Asn Pro
    2640                2645                2650

TGT GAA CAG TTT AAT GGG GGC TGC AGC CAT ATC TGT GCA CCA GGT CCA      8077
Cys Glu Gln Phe Asn Gly Gly Cys Ser His Ile Cys Ala Pro Gly Pro
2655                2660                2665                2670

AAT GGT GCC GAG TGC CAG TGT CCA CAT GAG GGC AAC TGG TAT TTG GCC      8125
Asn Gly Ala Glu Cys Gln Cys Pro His Glu Gly Asn Trp Tyr Leu Ala
            2675                2680                2685

AAC AAC AGG AAG CAC TGC ATT GTG GAC AAT GGT GAA CGA TGT GGT GCA      8173
Asn Asn Arg Lys His Cys Ile Val Asp Asn Gly Glu Arg Cys Gly Ala
                2690                2695                2700

TCT TCC TTC ACC TGC TCC AAT GGG CGC TGC ATC TCG GAA GAG TGG AAG      8221
Ser Ser Phe Thr Cys Ser Asn Gly Arg Cys Ile Ser Glu Glu Trp Lys
        2705                2710                2715

TGT GAT AAT GAC AAC GAC TGT GGG GAT GGC AGT GAT GAG ATG GAA AGT      8269
Cys Asp Asn Asp Asn Asp Cys Gly Asp Gly Ser Asp Glu Met Glu Ser
    2720                2725                2730

GTC TGT GCA CTT CAC ACC TGC TCA CCG ACA GCC TTC ACC TGT GCC AAT      8317
Val Cys Ala Leu His Thr Cys Ser Pro Thr Ala Phe Thr Cys Ala Asn
2735                2740                2745                2750

GGG CGA TGT GTC CAA TAC TCT TAC CGC TGT GAT TAC TAC AAT GAC TGT      8365
Gly Arg Cys Val Gln Tyr Ser Tyr Arg Cys Asp Tyr Tyr Asn Asp Cys
            2755                2760                2765

GGT GAT GGC AGT GAT GAG GCA GGG TGC CTG TTC AGG GAC TGC AAT GCC      8413
Gly Asp Gly Ser Asp Glu Ala Gly Cys Leu Phe Arg Asp Cys Asn Ala
                2770                2775                2780

ACC ACG GAG TTT ATG TGC AAT AAC AGA AGG TGC ATA CCT CGT GAG TTT      8461
Thr Thr Glu Phe Met Cys Asn Asn Arg Arg Cys Ile Pro Arg Glu Phe
        2785                2790                2795
```

```
ATC TGC AAT GGT GTA GAC AAC TGC CAT GAT AAT AAC ACT TCA GAT GAG      8509
Ile Cys Asn Gly Val Asp Asn Cys His Asp Asn Asn Thr Ser Asp Glu
            2800            2805            2810

AAA AAT TGC CCT GAT CGC ACT TGC CAG TCT GGA TAC ACA AAA TGT CAT      8557
Lys Asn Cys Pro Asp Arg Thr Cys Gln Ser Gly Tyr Thr Lys Cys His
2815            2820            2825            2830

AAT TCA AAT ATT TGT ATT CCT CGC GTT TAT TTG TGT GAC GGA GAC AAT      8605
Asn Ser Asn Ile Cys Ile Pro Arg Val Tyr Leu Cys Asp Gly Asp Asn
                2835            2840            2845

GAC TGT GGA GAT AAC AGT GAT GAA AAC CCT ACT TAT TGC ACC ACT CAC      8653
Asp Cys Gly Asp Asn Ser Asp Glu Asn Pro Thr Tyr Cys Thr Thr His
            2850            2855            2860

ACG TGC AGC AGC AGT GAG TTC CAA TGC ACA TCT GGG CGC TGT ATT CCT      8701
Thr Cys Ser Ser Ser Glu Phe Gln Cys Thr Ser Gly Arg Cys Ile Pro
            2865            2870            2875

CAA CAT TGG TAT TGT GAT CAA GAA ACA GAT TGT TTT GAT GCC TCT GAT      8749
Gln His Trp Tyr Cys Asp Gln Glu Thr Asp Cys Phe Asp Ala Ser Asp
            2880            2885            2890

GAA CCT GCC TCT TGT GGT CAC TCT GAG CGA ACA TGC CTA GCT GAT GAG      8797
Glu Pro Ala Ser Cys Gly His Ser Glu Arg Thr Cys Leu Ala Asp Glu
2895            2900            2905            2910

TTC AAG TGT GAT GGT GGG AGG TGC ATC CCA AGC GAA TGG ATC TGT GAC      8845
Phe Lys Cys Asp Gly Gly Arg Cys Ile Pro Ser Glu Trp Ile Cys Asp
            2915            2920            2925

GGT GAT AAT GAC TGT GGG GAT ATG AGT GAC GAG GAT AAA AGG CAC CAG      8893
Gly Asp Asn Asp Cys Gly Asp Met Ser Asp Glu Asp Lys Arg His Gln
            2930            2935            2940

TGT CAG AAT CAA AAC TGC TCG GAT TCC GAG TTT CTC TGT GTA AAT GAC      8941
Cys Gln Asn Gln Asn Cys Ser Asp Ser Glu Phe Leu Cys Val Asn Asp
            2945            2950            2955

AGA CCT CCG GAC AGG AGG TGC ATT CCC CAG TCT TGG GTC TGT GAT GGC      8989
Arg Pro Pro Asp Arg Arg Cys Ile Pro Gln Ser Trp Val Cys Asp Gly
            2960            2965            2970

GAT GTG GAT TGT ACT GAC GGC TAC GAT GAG AAT CAG AAT TGC ACC AGG      9037
Asp Val Asp Cys Thr Asp Gly Tyr Asp Glu Asn Gln Asn Cys Thr Arg
2975            2980            2985            2990

AGA ACT TGC TCT GAA AAT GAA TTC ACC TGT GGT TAC GGA CTG TGT ATC      9085
Arg Thr Cys Ser Glu Asn Glu Phe Thr Cys Gly Tyr Gly Leu Cys Ile
            2995            3000            3005

CCA AAG ATA TTC AGG TGT GAC CGG CAC AAT GAC TGT GGT GAC TAT AGC      9133
Pro Lys Ile Phe Arg Cys Asp Arg His Asn Asp Cys Gly Asp Tyr Ser
            3010            3015            3020

GAC GAG AGG GGC TGC TTA TAC CAG ACT TGC CAA CAG AAT CAG TTT ACC      9181
Asp Glu Arg Gly Cys Leu Tyr Gln Thr Cys Gln Gln Asn Gln Phe Thr
            3025            3030            3035

TGT CAG AAC GGG CGC TGC ATT AGT AAA ACC TTC GTC TGT GAT GAG GAT      9229
Cys Gln Asn Gly Arg Cys Ile Ser Lys Thr Phe Val Cys Asp Glu Asp
            3040            3045            3050

AAT GAC TGT GGA GAC GGA TCT GAT GAG CTG ATG CAC CTG TGC CAC ACC      9277
Asn Asp Cys Gly Asp Gly Ser Asp Glu Leu Met His Leu Cys His Thr
3055            3060            3065            3070

CCA GAA CCC ACG TGT CCA CCT CAC GAG TTC AAG TGT GAC AAT GGG CGC      9325
Pro Glu Pro Thr Cys Pro Pro His Glu Phe Lys Cys Asp Asn Gly Arg
            3075            3080            3085

TGC ATC GAG ATG ATG AAA CTC TGC AAC CAC CTA GAT GAC TGT TTG GAC      9373
Cys Ile Glu Met Met Lys Leu Cys Asn His Leu Asp Asp Cys Leu Asp
            3090            3095            3100

AAC AGC GAT GAG AAA GGC TGT GGC ATT AAT GAA TGC CAT GAC CCT TCA      9421
Asn Ser Asp Glu Lys Gly Cys Gly Ile Asn Glu Cys His Asp Pro Ser
```

-continued

| | | | |
|---|---|---|---|
| ATC AGT GGC TGC GAT CAC AAC TGC ACA GAC ACC TTA ACC AGT TTC TAT | | | 9469 |
| Ile Ser Gly Cys Asp His Asn Cys Thr Asp Thr Leu Thr Ser Phe Tyr | | | |
| 3120 3125 3130 | | | |
| TGT TCC TGT CGT CCT GGT TAC AAG CTC ATG TCT GAC AAG CGG ACT TGT | | | 9517 |
| Cys Ser Cys Arg Pro Gly Tyr Lys Leu Met Ser Asp Lys Arg Thr Cys | | | |
| 3135 3140 3145 3150 | | | |
| GTT GAT ATT GAT GAA TGC ACA GAG ATG CCT TTT GTC TGT AGC CAG AAG | | | 9565 |
| Val Asp Ile Asp Glu Cys Thr Glu Met Pro Phe Val Cys Ser Gln Lys | | | |
| 3155 3160 3165 | | | |
| TGT GAG AAT GTA ATA GGC TCC TAC ATC TGT AAG TGT GCC CCA GGC TAC | | | 9613 |
| Cys Glu Asn Val Ile Gly Ser Tyr Ile Cys Lys Cys Ala Pro Gly Tyr | | | |
| 3170 3175 3180 | | | |
| CTC CGA GAA CCA GAT GGA AAG ACC TGC CGG CAA AAC AGT AAC ATC GAA | | | 9661 |
| Leu Arg Glu Pro Asp Gly Lys Thr Cys Arg Gln Asn Ser Asn Ile Glu | | | |
| 3185 3190 3195 | | | |
| CCC TAT CTC ATT TTT AGC AAC CGT TAC TAT TTG AGA AAT TTA ACT ATA | | | 9709 |
| Pro Tyr Leu Ile Phe Ser Asn Arg Tyr Tyr Leu Arg Asn Leu Thr Ile | | | |
| 3200 3205 3210 | | | |
| GAT GGC TAT TTT TAC TCC CTC ATC TTG GAA GGA CTG GAC AAT GTT GTG | | | 9757 |
| Asp Gly Tyr Phe Tyr Ser Leu Ile Leu Glu Gly Leu Asp Asn Val Val | | | |
| 3215 3220 3225 3230 | | | |
| GCA TTA GAT TTT GAC CGA GTA GAG AAG AGA TTG TAT TGG ATT GAT ACA | | | 9805 |
| Ala Leu Asp Phe Asp Arg Val Glu Lys Arg Leu Tyr Trp Ile Asp Thr | | | |
| 3235 3240 3245 | | | |
| CAG AGG CAA GTC ATT GAG AGA ATG TTT CTG AAT AAG ACA AAC AAG GAG | | | 9853 |
| Gln Arg Gln Val Ile Glu Arg Met Phe Leu Asn Lys Thr Asn Lys Glu | | | |
| 3250 3255 3260 | | | |
| ACA ATC ATA AAC CAC AGA CTA CCA GCT GCA GAA AGT CTG GCT GTA GAC | | | 9901 |
| Thr Ile Ile Asn His Arg Leu Pro Ala Ala Glu Ser Leu Ala Val Asp | | | |
| 3265 3270 3275 | | | |
| TGG GTT TCC AGA AAG CTC TAC TGG TTG GAT GCC CGC CTG GAT GGC CTC | | | 9949 |
| Trp Val Ser Arg Lys Leu Tyr Trp Leu Asp Ala Arg Leu Asp Gly Leu | | | |
| 3280 3285 3290 | | | |
| TTT GTC TCT GAC CTC AAT GGT GGA CAC CGC CGC ATG CTG GCC CAG CAC | | | 9997 |
| Phe Val Ser Asp Leu Asn Gly Gly His Arg Arg Met Leu Ala Gln His | | | |
| 3295 3300 3305 3310 | | | |
| TGT GTG GAT GCC AAC AAC ACC TTC TGC TTT GAT AAT CCC AGA GGA CTT | | | 10045 |
| Cys Val Asp Ala Asn Asn Thr Phe Cys Phe Asp Asn Pro Arg Gly Leu | | | |
| 3315 3320 3325 | | | |
| GCC CTT CAC CCT CAA TAT GGG TAC CTC TAC TGG GCA GAC TGG GGT CAC | | | 10093 |
| Ala Leu His Pro Gln Tyr Gly Tyr Leu Tyr Trp Ala Asp Trp Gly His | | | |
| 3330 3335 3340 | | | |
| CGC GCA TAC ATT GGG AGA GTA GGC ATG GAT GGA ACC AAC AAG TCT GTG | | | 10141 |
| Arg Ala Tyr Ile Gly Arg Val Gly Met Asp Gly Thr Asn Lys Ser Val | | | |
| 3345 3350 3355 | | | |
| ATA ATC TCC ACC AAG TTA GAG TGG CCT AAT GGC ATC ACC ATT GAT TAC | | | 10189 |
| Ile Ile Ser Thr Lys Leu Glu Trp Pro Asn Gly Ile Thr Ile Asp Tyr | | | |
| 3360 3365 3370 | | | |
| ACC AAT GAT CTA CTC TAC TGG GCA GAT GCC CAC CTG GGT TAC ATA GAG | | | 10237 |
| Thr Asn Asp Leu Leu Tyr Trp Ala Asp Ala His Leu Gly Tyr Ile Glu | | | |
| 3375 3380 3385 3390 | | | |
| TAC TCT GAT TTG GAG GGC CAC CAT CGA CAC ACG GTG TAT GAT GGG GCA | | | 10285 |
| Tyr Ser Asp Leu Glu Gly His His Arg His Thr Val Tyr Asp Gly Ala | | | |
| 3395 3400 3405 | | | |
| CTG CCT CAC CCT TTC GCT ATT ACC ATT TTT GAA GAC ACT ATT TAT TGG | | | 10333 |
| Leu Pro His Pro Phe Ala Ile Thr Ile Phe Glu Asp Thr Ile Tyr Trp | | | |
| 3410 3415 3420 | | | |
| ACA GAT TGG AAT ACA AGG ACA GTG GAA AAG GGA AAC AAA TAT GAT GGA | | | 10381 |

```
                                        -continued

Thr Asp Trp Asn Thr Arg Thr Val Glu Lys Gly Asn Lys Tyr Asp Gly
        3425                3430                3435

TCA AAT AGA CAG ACA CTG GTG AAC ACA ACA CAC AGA CCA TTT GAC ATC        10429
Ser Asn Arg Gln Thr Leu Val Asn Thr Thr His Arg Pro Phe Asp Ile
        3440                3445                3450

CAT GTG TAC CAT CCA TAT AGG CAG CCC ATT GTG AGC AAT CCC TGT GGT        10477
His Val Tyr His Pro Tyr Arg Gln Pro Ile Val Ser Asn Pro Cys Gly
3455                3460                3465                3470

ACC AAC AAT GGT GGC TGT TCT CAT CTC TGC CTC ATC AAG CCA GGA GGA        10525
Thr Asn Asn Gly Gly Cys Ser His Leu Cys Leu Ile Lys Pro Gly Gly
                3475                3480                3485

AAA GGG TTC ACT TGC GAG TGT CCA GAT GAC TTC CGC ACC CTT CAG CTG        10573
Lys Gly Phe Thr Cys Glu Cys Pro Asp Asp Phe Arg Thr Leu Gln Leu
                3490                3495                3500

AGT GGC AGC ACC TAC TGC ATG CCC ATG TGC TCC AGC ACC CAG TTC CTG        10621
Ser Gly Ser Thr Tyr Cys Met Pro Met Cys Ser Ser Thr Gln Phe Leu
        3505                3510                3515

TGC GCT AAC AAT GAA AAG TGC ATT CCT ATC TGG TGG AAA TGT GAT GGA        10669
Cys Ala Asn Asn Glu Lys Cys Ile Pro Ile Trp Trp Lys Cys Asp Gly
        3520                3525                3530

CAG AAA GAC TGC TCA GAT GGC TCT GAT GAA CTG GCC CTT TGC CCG CAG        10717
Gln Lys Asp Cys Ser Asp Gly Ser Asp Glu Leu Ala Leu Cys Pro Gln
3535                3540                3545                3550

CGC TTC TGC CGA CTG GGA CAG TTC CAG TGC AGT GAC GGC AAC TGC ACC        10765
Arg Phe Cys Arg Leu Gly Gln Phe Gln Cys Ser Asp Gly Asn Cys Thr
                3555                3560                3565

AGC CCG CAG ACT TTA TGC AAT GCT CAC CAA AAT TGC CCT GAT GGG TCT        10813
Ser Pro Gln Thr Leu Cys Asn Ala His Gln Asn Cys Pro Asp Gly Ser
                3570                3575                3580

GAT GAA GAC CGT CTT CTT TGT GAG AAT CAC CAC TGT GAC TCC AAT GAA        10861
Asp Glu Asp Arg Leu Leu Cys Glu Asn His His Cys Asp Ser Asn Glu
        3585                3590                3595

TGG CAG TGC GCC AAC AAA CGT TGC ATC CCA GAA TCC TGG CAG TGT GAC        10909
Trp Gln Cys Ala Asn Lys Arg Cys Ile Pro Glu Ser Trp Gln Cys Asp
        3600                3605                3610

ACA TTT AAC GAC TGT GAG GAT AAC TCA GAT GAA GAC AGT TCC CAC TGT        10957
Thr Phe Asn Asp Cys Glu Asp Asn Ser Asp Glu Asp Ser Ser His Cys
3615                3620                3625                3630

GCC AGC AGG ACC TGC CGG CCG GGC CAG TTT CGG TGT GCT AAT GGC CGC        11005
Ala Ser Arg Thr Cys Arg Pro Gly Gln Phe Arg Cys Ala Asn Gly Arg
                3635                3640                3645

TGC ATC CCG CAG GCC TGG AAG TGT GAT GTG GAT AAT GAT TGT GGA GAC        11053
Cys Ile Pro Gln Ala Trp Lys Cys Asp Val Asp Asn Asp Cys Gly Asp
                3650                3655                3660

CAC TCG GAT GAG CCC ATT GAA GAA TGC ATG AGC TCT GCC CAT CTC TGT        11101
His Ser Asp Glu Pro Ile Glu Glu Cys Met Ser Ser Ala His Leu Cys
        3665                3670                3675

GAC AAC TTC ACA GAA TTC AGC TGC AAA ACA AAT TAC CGC TGC ATC CCA        11149
Asp Asn Phe Thr Glu Phe Ser Cys Lys Thr Asn Tyr Arg Cys Ile Pro
        3680                3685                3690

AAG TGG GCC GTG TGC AAT GGT GTA GAT GAC TGC AGG GAC AAC AGT GAT        11197
Lys Trp Ala Val Cys Asn Gly Val Asp Asp Cys Arg Asp Asn Ser Asp
3695                3700                3705                3710

GAG CAA GGC TGT GAG GAG AGG ACA TGC CAT CCT GTG GGG GAT TTC CGC        11245
Glu Gln Gly Cys Glu Glu Arg Thr Cys His Pro Val Gly Asp Phe Arg
                3715                3720                3725

TGT AAA AAT CAC CAC TGC ATC CCT CTT CGT TGG CAG TGT GAT GGG CAA        11293
Cys Lys Asn His His Cys Ile Pro Leu Arg Trp Gln Cys Asp Gly Gln
                3730                3735                3740
```

```
AAT GAC TGT GGA GAT AAC TCA GAT GAG GAA AAC TGT GCT CCC CGG GAG          11341
Asn Asp Cys Gly Asp Asn Ser Asp Glu Glu Asn Cys Ala Pro Arg Glu
            3745                3750                3755

TGC ACA GAG AGC GAG TTT CGA TGT GTC AAT CAG CAG TGC ATT CCC TCG          11389
Cys Thr Glu Ser Glu Phe Arg Cys Val Asn Gln Gln Cys Ile Pro Ser
        3760                3765                3770

CGA TGG ATC TGT GAC CAT TAC AAC GAC TGT GGG GAC AAC TCA GAT GAA          11437
Arg Trp Ile Cys Asp His Tyr Asn Asp Cys Gly Asp Asn Ser Asp Glu
3775                3780                3785                3790

CGG GAC TGT GAG ATG AGG ACC TGC CAT CCT GAA TAT TTT CAG TGT ACA          11485
Arg Asp Cys Glu Met Arg Thr Cys His Pro Glu Tyr Phe Gln Cys Thr
                3795                3800                3805

AGT GGA CAT TGT GTA CAC AGT GAA CTG AAA TGC GAT GGA TCC GCT GAC          11533
Ser Gly His Cys Val His Ser Glu Leu Lys Cys Asp Gly Ser Ala Asp
            3810                3815                3820

TGT TTG GAT GCG TCT GAT GAA GCT GAT TGT CCC ACA CGC TTT CCT GAT          11581
Cys Leu Asp Ala Ser Asp Glu Ala Asp Cys Pro Thr Arg Phe Pro Asp
        3825                3830                3835

GGT GCA TAC TGC CAG GCT ACT ATG TTC GAA TGC AAA AAC CAT GTT TGT          11629
Gly Ala Tyr Cys Gln Ala Thr Met Phe Glu Cys Lys Asn His Val Cys
    3840                3845                3850

ATC CCG CCA TAT TGG AAA TGT GAT GGC GAT GAT GAC TGT GGC GAT GGT          11677
Ile Pro Pro Tyr Trp Lys Cys Asp Gly Asp Asp Asp Cys Gly Asp Gly
3855                3860                3865                3870

TCA GAT GAA GAA CTT CAC CTG TGC TTG GAT GTT CCC TGT AAT TCA CCA          11725
Ser Asp Glu Glu Leu His Leu Cys Leu Asp Val Pro Cys Asn Ser Pro
                3875                3880                3885

AAC CGT TTC CGG TGT GAC AAC AAT CGC TGC ATT TAT AGT CAT GAG GTG          11773
Asn Arg Phe Arg Cys Asp Asn Asn Arg Cys Ile Tyr Ser His Glu Val
            3890                3895                3900

TGC AAT GGT GTG GAT GAC TGT GGA GAT GGA ACT GAT GAG ACA GAG GAG          11821
Cys Asn Gly Val Asp Asp Cys Gly Asp Gly Thr Asp Glu Thr Glu Glu
        3905                3910                3915

CAC TGT AGA AAA CCG ACC CCT AAA CCT TGT ACA GAA TAT GAA TAT AAG          11869
His Cys Arg Lys Pro Thr Pro Lys Pro Cys Thr Glu Tyr Glu Tyr Lys
    3920                3925                3930

TGT GGC AAT GGG CAT TGC ATT CCA CAT GAC AAT GTG TGT GAT GAT GCC          11917
Cys Gly Asn Gly His Cys Ile Pro His Asp Asn Val Cys Asp Asp Ala
3935                3940                3945                3950

GAT GAC TGT GGT GAC TGG TCC GAT GAA CTG GGT TGC AAT AAA GGA AAA          11965
Asp Asp Cys Gly Asp Trp Ser Asp Glu Leu Gly Cys Asn Lys Gly Lys
                3955                3960                3965

GAA AGA ACA TGT GCT GAA AAT ATA TGC GAG CAA AAT TGT ACC CAA TTA          12013
Glu Arg Thr Cys Ala Glu Asn Ile Cys Glu Gln Asn Cys Thr Gln Leu
            3970                3975                3980

AAT GAA GGA GGA TTT ATC TGC TCC TGT ACA GCT GGG TTC GAA ACC AAT          12061
Asn Glu Gly Gly Phe Ile Cys Ser Cys Thr Ala Gly Phe Glu Thr Asn
        3985                3990                3995

GTT TTT GAC AGA ACC TCC TGT CTA GAT ATC AAT GAA TGT GAA CAA TTT          12109
Val Phe Asp Arg Thr Ser Cys Leu Asp Ile Asn Glu Cys Glu Gln Phe
    4000                4005                4010

GGG ACT TGT CCC CAG CAC TGC AGA AAT ACC AAA GGA AGT TAT GAG TGT          12157
Gly Thr Cys Pro Gln His Cys Arg Asn Thr Lys Gly Ser Tyr Glu Cys
4015                4020                4025                4030

GTC TGT GCT GAT GGC TTC ACG TCT ATG AGT GAC CGC CCT GGA AAA CGA          12205
Val Cys Ala Asp Gly Phe Thr Ser Met Ser Asp Arg Pro Gly Lys Arg
                4035                4040                4045

TGT GCA GCT GAG GGT AGC TCT CCT TTG TTG CTA CTG CCT GAC AAT GTC          12253
Cys Ala Ala Glu Gly Ser Ser Pro Leu Leu Leu Leu Pro Asp Asn Val
            4050                4055                4060
```

```
CGA ATT CGA AAA TAT AAT CTC TCA TCT GAG AGG TTC TCA GAG TAT CTT       12301
Arg Ile Arg Lys Tyr Asn Leu Ser Ser Glu Arg Phe Ser Glu Tyr Leu
        4065                4070                4075

CAA GAT GAG GAA TAT ATC CAA GCT GTT GAT TAT GAT TGG GAT CCC RAG       12349
Gln Asp Glu Glu Tyr Ile Gln Ala Val Asp Tyr Asp Trp Asp Pro Xaa
        4080                4085                4090

GAC ATA GGC CTC AGT GTT GTG TAT TAC ACT GTG CGA GGG GAG GGC TCT       12397
Asp Ile Gly Leu Ser Val Val Tyr Tyr Thr Val Arg Gly Glu Gly Ser
4095                4100                4105                4110

AGG TTT GGT GCT ATC AAA CGT GCC TAC ATC CCC AAC TTT GAA TCC GGC       12445
Arg Phe Gly Ala Ile Lys Arg Ala Tyr Ile Pro Asn Phe Glu Ser Gly
                4115                4120                4125

CGC AAT AAT CTT GTG CAG GAA GTT GAC CTG AAA CTG AAA TAC GTA ATG       12493
Arg Asn Asn Leu Val Gln Glu Val Asp Leu Lys Leu Lys Tyr Val Met
        4130                4135                4140

CAG CCA GAT GGA ATA GCA GTG GAC TGG GTT GGA AGG CAT ATT TAC TGG       12541
Gln Pro Asp Gly Ile Ala Val Asp Trp Val Gly Arg His Ile Tyr Trp
        4145                4150                4155

TCA GAT GTC AAG AAT AAA CGC ATT GAG GTG GCT AAA CTT GAT GGA AGG       12589
Ser Asp Val Lys Asn Lys Arg Ile Glu Val Ala Lys Leu Asp Gly Arg
        4160                4165                4170

TAC AGA AAG TGG CTG ATT TCC ACT GAC CTG GAC CAA CCA GCT GCT ATT       12637
Tyr Arg Lys Trp Leu Ile Ser Thr Asp Leu Asp Gln Pro Ala Ala Ile
4175                4180                4185                4190

GCT GTG AAT CCC AAA CTA GGG CTT ATG TTC TGG ACT GAC TGG GGA AAG       12685
Ala Val Asn Pro Lys Leu Gly Leu Met Phe Trp Thr Asp Trp Gly Lys
                4195                4200                4205

GAA CCT AAA MTC GAG TCT GCC TGG ATG AAT GGA GAG GAC CGC AAC ATC       12733
Glu Pro Lys Xaa Glu Ser Ala Trp Met Asn Gly Glu Asp Arg Asn Ile
        4210                4215                4220

CTG GTT TTC GAG GAC CTT GGT TGG CCA ACT GGC CTT TCT ATC GAT TAT       12781
Leu Val Phe Glu Asp Leu Gly Trp Pro Thr Gly Leu Ser Ile Asp Tyr
        4225                4230                4235

TTG AAC AAT GAC CGA ATC TAC TGG AGT GAC TTC AAG GAG GAC GTT ATT       12829
Leu Asn Asn Asp Arg Ile Tyr Trp Ser Asp Phe Lys Glu Asp Val Ile
        4240                4245                4250

GAA ACC ATA AAA TAT GAT GGG ACT GAT AGG AGA GTC ATT GCA AAG GAA       12877
Glu Thr Ile Lys Tyr Asp Gly Thr Asp Arg Arg Val Ile Ala Lys Glu
4255                4260                4265                4270

GCA ATG AAC CCT TAC AGC CTG GAC ATC TTT GAA GAC CAG TTA TAC TGG       12925
Ala Met Asn Pro Tyr Ser Leu Asp Ile Phe Glu Asp Gln Leu Tyr Trp
                4275                4280                4285

ATA TCT AAG GAA AAG GGA GAA GTA TGG AAA CAA AAT AAA TTT GGG CAA       12973
Ile Ser Lys Glu Lys Gly Glu Val Trp Lys Gln Asn Lys Phe Gly Gln
        4290                4295                4300

GGA AAG AAA GAG AAA ACG CTG GTA GTG AAC CCT TGG CTC ACT CAA GTT       13021
Gly Lys Lys Glu Lys Thr Leu Val Val Asn Pro Trp Leu Thr Gln Val
        4305                4310                4315

CGA ATC TTT CAT CAA CTC AGA TAC AAT AAG TCA GTG CCC AAC CTT TGC       13069
Arg Ile Phe His Gln Leu Arg Tyr Asn Lys Ser Val Pro Asn Leu Cys
        4320                4325                4330

AAA CAG ATC TGC AGC CAC CTC TGC CTT CTG AGA CCT GGA GGA TAC AGC       13117
Lys Gln Ile Cys Ser His Leu Cys Leu Leu Arg Pro Gly Gly Tyr Ser
4335                4340                4345                4350

TGT GCC TGT CCC CAA GGC TCC AGC TTT ATA GAG GGG AGC ACC ACT GAG       13165
Cys Ala Cys Pro Gln Gly Ser Ser Phe Ile Glu Gly Ser Thr Thr Glu
                4355                4360                4365

TGT GAT GCA GCC ATY GAA CTG CCT ATC AAC CTG CCC CCC CCA TGC AGG       13213
Cys Asp Ala Ala Ile Glu Leu Pro Ile Asn Leu Pro Pro Pro Cys Arg
```

|  |  |
|---|---|
| TGC ATG CAC GGA GGA AAT TGC TAT TTT GAT GAG ACT GAC CTC CCC AAA<br>Cys Met His Gly Gly Asn Cys Tyr Phe Asp Glu Thr Asp Leu Pro Lys<br>    4385        4390        4395 | 13261 |
| TGC AAG TGT CCT AGC GGC TAC ACC GGA AAA TAT TGT GAA ATG GCG TTT<br>Cys Lys Cys Pro Ser Gly Tyr Thr Gly Lys Tyr Cys Glu Met Ala Phe<br>4400        4405        4410 | 13309 |
| TCA AAA GGC ATC TCT CCA GGA ACA ACC GCA GTA GCT GTG CTG TTG ACA<br>Ser Lys Gly Ile Ser Pro Gly Thr Thr Ala Val Ala Val Leu Leu Thr<br>4415        4420        4425        4430 | 13357 |
| ATC CTC TTG ATC GTC GTA ATT GGA GCT CTG GCA ATT GCA GGA TTC TTC<br>Ile Leu Leu Ile Val Val Ile Gly Ala Leu Ala Ile Ala Gly Phe Phe<br>        4435        4440        4445 | 13405 |
| CAC TAT AGA AGG ACC GGC TCC CTT TTG CCT GCT CTG CCC AAG CTG CCA<br>His Tyr Arg Arg Thr Gly Ser Leu Leu Pro Ala Leu Pro Lys Leu Pro<br>        4450        4455        4460 | 13453 |
| AGC TTA AGC AGT CTC GTC AAG CCC TCT GAA AAT GGG AAT GGG GTG ACC<br>Ser Leu Ser Ser Leu Val Lys Pro Ser Glu Asn Gly Asn Gly Val Thr<br>        4465        4470        4475 | 13501 |
| TTC AGA TCA GGG GCA GAT CTT AAC ATG GAT ATT GGA GTG TCT GGT TTT<br>Phe Arg Ser Gly Ala Asp Leu Asn Met Asp Ile Gly Val Ser Gly Phe<br>    4480        4485        4490 | 13549 |
| GGA CCT GAG ACT GCT ATT GAC AGG TCA ATG GCA ATG AGT GAA GAC TTT<br>Gly Pro Glu Thr Ala Ile Asp Arg Ser Met Ala Met Ser Glu Asp Phe<br>4495        4500        4505        4510 | 13597 |
| GTC ATG GAA ATG GGG AAG CAG CCC ATA ATA TTT GAA AAC CCA ATG TAC<br>Val Met Glu Met Gly Lys Gln Pro Ile Ile Phe Glu Asn Pro Met Tyr<br>        4515        4520        4525 | 13645 |
| TCA GCC AGA GAC AGT GCT GTC AAA GTG GTT CAG CCA ATC CAG GTG ACT<br>Ser Ala Arg Asp Ser Ala Val Lys Val Val Gln Pro Ile Gln Val Thr<br>    4530        4535        4540 | 13693 |
| GTA TCT GAA AAT GTG GAT AAT AAG AAT TAT GGA AGT CCC ATA AAC CCT<br>Val Ser Glu Asn Val Asp Asn Lys Asn Tyr Gly Ser Pro Ile Asn Pro<br>    4545        4550        4555 | 13741 |
| TCT GAG ATA GTT CCA GAG ACA AAC CCA ACT TCA CCA GCT GCT GAT GGA<br>Ser Glu Ile Val Pro Glu Thr Asn Pro Thr Ser Pro Ala Ala Asp Gly<br>    4560        4565        4570 | 13789 |
| ACT CAG GTG ACA AAA TGG AAT CTC TTC AAA CGA AAA TCT AAA CAA ACT<br>Thr Gln Val Thr Lys Trp Asn Leu Phe Lys Arg Lys Ser Lys Gln Thr<br>4575        4580        4585        4590 | 13837 |
| ACC AAC TTT GAA AAT CCA ATC TAT GCA CAG ATG GAG AAC GAG CAA AAG<br>Thr Asn Phe Glu Asn Pro Ile Tyr Ala Gln Met Glu Asn Glu Gln Lys<br>        4595        4600        4605 | 13885 |
| GAA AGT GTT GCT GCG ACA CCA CCT CCA TCA CCT TCG CTC CCT GCT AAG<br>Glu Ser Val Ala Ala Thr Pro Pro Pro Ser Pro Ser Leu Pro Ala Lys<br>        4610        4615        4620 | 13933 |
| CCT AAG CCT CCT TCG AGA AGA GAC CCA ACT CCA ACC TAT TCT GCA ACA<br>Pro Lys Pro Pro Ser Arg Arg Asp Pro Thr Pro Thr Tyr Ser Ala Thr<br>    4625        4630        4635 | 13981 |
| GAA GAC ACT TTT AAA GAC ACC GCA AAT CTT GTT AAA GAA GAC TCT GAA<br>Glu Asp Thr Phe Lys Asp Thr Ala Asn Leu Val Lys Glu Asp Ser Glu<br>4640        4645        4650 | 14029 |
| GTA TAG CTATACC<br>Val *<br>4655 | 14042 |

(2) INFORMATION FOR SEQ ID NO:86:

(i) SEQUENCE CHARACTERISTICS:
    (A) LENGTH: 4655 amino acids

```
        (B) TYPE: amino acid
        (D) TOPOLOGY: linear (ii) MOLECULE TYPE: protein (xi) SEQUENCE DESCRIPTION: SEQ ID NO:86:

Met Asp Arg Gly Pro Ala Ala Val Ala Cys Thr Leu Leu Ala Leu
 1               5                  10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
                35                  40                      45

Gly Thr Lys Asp Cys Ser Asp Asp Ala Asp Glu Ile Gly Cys Ala Val
         50                  55                  60

Val Thr Cys Gln Gln Gly Tyr Phe Lys Cys Gln Ser Glu Gly Gln Cys
 65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
                    100                 105                 110

Ile Thr Cys Ser Asn Gly Gln Cys Ile Pro Ser Glu Tyr Arg Cys Asp
            115                 120                 125

His Val Arg Asp Cys Pro Asp Gly Ala Asp Glu Asn Asp Cys Gln Tyr
        130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
            195                 200                 205

Gln Asp Gly Ser Asp Glu His Ala Cys Asn Tyr Pro Thr Cys Gly Gly
        210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
                275                 280                 285

Ile Leu Asp Cys Pro Gly Arg Glu Asp Glu Asn Asn Thr Ser Thr Gly
290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
            340                 345                 350

Gln Ile Trp Gly Ile Cys Asp Gln Lys Cys Glu Ser Arg Pro Gly Arg
        355                 360                 365

His Leu Cys His Cys Glu Glu Gly Tyr Ile Leu Glu Arg Gly Gln Tyr
370                 375                 380
```

-continued

```
Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
            420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
            580                 585                 590

Thr Val His Gly Gly Ser Leu Ile Pro His Pro Phe Gly Val Ser
        595                 600                 605

Leu Phe Glu Gly Gln Val Phe Phe Thr Asp Trp Thr Lys Met Ala Val
610                 615                 620

Leu Lys Ala Asn Lys Phe Thr Glu Thr Asn Pro Gln Val Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
        675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
        755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
```

```
                  805                 810                 815
Thr Arg Arg Thr Val Val Gln Tyr Leu Asn Asn Pro Arg Ser Val Val
            820                 825                 830

Val His Pro Phe Ala Gly Tyr Leu Phe Thr Asp Trp Phe Arg Pro
            835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Arg Leu Gly His Ile Glu Gln
            900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
            930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
            995                 1000                1005

Asn His Leu Thr Cys Glu Gly Asp Pro Thr Asn Glu Pro Pro Thr Glu
            1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ser Ala Phe
            1060                1065                1070

Thr Cys Gly His Gly Glu Cys Ile Pro Ala His Trp Arg Cys Asp Lys
            1075                1080                1085

Arg Asn Asp Cys Val Asp Gly Ser Asp Glu His Asn Cys Pro Thr His
            1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
                1125                1130                1135

Gly Ser Asp Glu Lys Asn Cys Asn Ser Thr Glu Thr Cys Gln Pro Ser
            1140                1145                1150

Gln Phe Asn Cys Pro Asn His Arg Cys Ile Asp Leu Ser Phe Val Cys
            1155                1160                1165

Asp Gly Asp Lys Asp Cys Val Asp Gly Ser Asp Glu Val Gly Cys Val
            1170                1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
                1205                1210                1215

Ser Asp Glu Ala Gly Cys Pro Thr Arg Pro Pro Gly Met Cys His Ser
            1220                1225                1230
```

-continued

```
Asp Glu Phe Gln Cys Gln Glu Asp Gly Ile Cys Ile Pro Asn Phe Trp
        1235                1240                1245
Glu Cys Asp Gly His Pro Asp Cys Leu Tyr Gly Ser Asp Glu His Asn
        1250                1255                1260
Ala Cys Val Pro Lys Thr Cys Pro Ser Ser Tyr Phe His Cys Asp Asn
1265                1270                1275                1280
Gly Asn Cys Ile His Arg Xaa Trp Leu Cys Asp Arg Asp Asn Asp Cys
            1285                1290                1295
Gly Asp Met Ser Asp Glu Lys Asp Cys Pro Thr Gln Pro Phe Arg Cys
        1300                1305                1310
Pro Ser Trp Gln Trp Gln Cys Leu Gly His Asn Ile Cys Val Asn Leu
        1315                1320                1325
Ser Val Val Cys Asp Gly Ile Phe Asp Cys Pro Asn Gly Thr Asp Glu
        1330                1335                1340
Ser Pro Leu Cys Asn Gly Asn Ser Cys Ser Asp Phe Asn Gly Gly Cys
1345                1350                1355                1360
Thr His Glu Cys Val Gln Glu Pro Phe Gly Ala Lys Cys Leu Cys Pro
            1365                1370                1375
Leu Gly Phe Leu Leu Ala Asn Asp Ser Lys Thr Cys Glu Asp Ile Asp
        1380                1385                1390
Glu Cys Asp Ile Leu Gly Ser Cys Ser Gln His Cys Tyr Asn Met Arg
        1395                1400                1405
Gly Ser Phe Arg Cys Ser Cys Asp Thr Gly Tyr Met Leu Glu Ser Asp
        1410                1415                1420
Gly Arg Thr Cys Lys Val Thr Ala Ser Glu Ser Leu Leu Leu Leu Val
1425                1430                1435                1440
Ala Ser Gln Asn Lys Ile Ile Ala Asp Ser Val Thr Ser Gln Val His
            1445                1450                1455
Asn Ile Tyr Ser Leu Val Glu Asn Gly Ser Tyr Ile Val Ala Val Asp
            1460                1465                1470
Phe Asp Ser Ile Ser Gly Arg Ile Phe Trp Ser Asp Ala Thr Gln Gly
        1475                1480                1485
Lys Thr Trp Ser Ala Phe Gln Asn Gly Thr Asp Arg Arg Val Val Phe
        1490                1495                1500
Asp Ser Ser Ile Ile Leu Thr Glu Thr Ile Ala Ile Asp Trp Val Gly
1505                1510                1515                1520
Arg Asn Leu Tyr Trp Thr Asp Tyr Ala Leu Glu Thr Ile Glu Val Ser
            1525                1530                1535
Lys Ile Asp Gly Ser His Arg Thr Val Leu Ile Ser Lys Asn Leu Thr
        1540                1545                1550
Asn Pro Arg Gly Leu Ala Leu Asp Pro Arg Met Asn Glu His Leu Leu
        1555                1560                1565
Phe Trp Ser Asp Trp Gly His His Pro Arg Ile Glu Arg Ala Ser Met
        1570                1575                1580
Asp Gly Ser Met Arg Thr Val Ile Val Gln Asp Lys Ile Phe Trp Pro
1585                1590                1595                1600
Cys Gly Leu Thr Ile Asp Tyr Pro Asn Arg Leu Leu Tyr Phe Met Asp
            1605                1610                1615
Ser Tyr Leu Asp Tyr Met Asp Phe Cys Asp Tyr Asn Gly His His Arg
            1620                1625                1630
Arg Gln Val Ile Ala Ser Asp Leu Ile Ile Arg His Pro Tyr Ala Leu
        1635                1640                1645
```

-continued

```
Thr Leu Phe Glu Asp Ser Val Tyr Trp Thr Asp Arg Ala Thr Arg Arg
    1650                1655                1660
Val Met Arg Ala Asn Lys Trp His Gly Gly Asn Gln Ser Val Val Met
1665                1670                1675                1680
Tyr Asn Ile Gln Trp Pro Leu Gly Ile Val Ala Val His Pro Ser Lys
            1685                1690                1695
Gln Pro Asn Ser Val Asn Pro Cys Ala Phe Ser Arg Cys Ser His Leu
            1700                1705                1710
Cys Leu Leu Ser Ser Gln Gly Pro His Phe Tyr Ser Cys Val Cys Pro
            1715                1720                1725
Ser Gly Trp Ser Leu Ser Pro Asp Leu Leu Asn Cys Leu Arg Asp Asp
            1730                1735                1740
Gln Pro Phe Leu Ile Thr Val Arg Gln His Ile Ile Phe Gly Ile Ser
1745                1750                1755                1760
Leu Asn Pro Glu Val Lys Ser Asn Asp Ala Met Val Pro Ile Ala Gly
            1765                1770                1775
Ile Gln Asn Gly Leu Asp Val Glu Phe Asp Asp Ala Glu Gln Tyr Ile
            1780                1785                1790
Tyr Trp Val Glu Asn Pro Gly Glu Ile His Arg Val Lys Thr Asp Gly
            1795                1800                1805
Thr Asn Arg Thr Val Phe Ala Ser Ile Ser Met Val Gly Pro Ser Met
            1810                1815                1820
Asn Leu Ala Leu Asp Trp Ile Ser Arg Asn Leu Tyr Ser Thr Asn Pro
1825                1830                1835                1840
Arg Thr Gln Ser Ile Glu Val Leu Thr Leu His Gly Asp Ile Arg Tyr
            1845                1850                1855
Arg Lys Thr Leu Ile Ala Asn Asp Gly Thr Ala Leu Gly Val Gly Phe
            1860                1865                1870
Pro Ile Gly Ile Thr Val Asp Pro Ala Arg Gly Lys Leu Tyr Trp Ser
            1875                1880                1885
Asp Gln Gly Thr Asp Ser Gly Val Pro Ala Lys Ile Ala Ser Ala Asn
            1890                1895                1900
Met Asp Gly Thr Ser Val Lys Thr Leu Phe Thr Gly Asn Leu Glu His
1905                1910                1915                1920
Leu Glu Cys Val Thr Leu Asp Ile Glu Glu Gln Lys Leu Tyr Trp Ala
            1925                1930                1935
Val Thr Gly Arg Gly Val Ile Glu Arg Gly Asn Val Asp Gly Thr Asp
            1940                1945                1950
Arg Met Ile Leu Val His Gln Leu Ser His Pro Trp Gly Ile Ala Val
            1955                1960                1965
His Asp Ser Phe Leu Tyr Tyr Thr Asp Glu Gln Tyr Glu Val Ile Glu
            1970                1975                1980
Arg Val Asp Lys Ala Thr Gly Ala Asn Lys Ile Val Leu Arg Asp Asn
1985                1990                1995                2000
Val Pro Asn Leu Arg Gly Leu Gln Val Tyr His Arg Arg Asn Ala Ala
            2005                2010                2015
Glu Ser Ser Asn Gly Cys Ser Asn Asn Met Asn Ala Cys Gln Gln Ile
            2020                2025                2030
Cys Leu Pro Val Pro Gly Gly Leu Phe Ser Cys Ala Cys Ala Thr Gly
            2035                2040                2045
Phe Lys Leu Asn Pro Asp Asn Arg Ser Cys Ser Pro Tyr Asn Ser Phe
2050                2055                2060
Ile Val Val Ser Met Leu Ser Ala Ile Arg Gly Phe Ser Leu Glu Leu
```

-continued

```
2065                2070                2075                2080

Ser Asp His Ser Glu Thr Met Val Pro Val Ala Gly Gln Gly Arg Asn
                2085                2090                2095

Ala Leu His Val Asp Val Asp Val Ser Ser Gly Phe Ile Tyr Trp Cys
                2100                2105                2110

Asp Phe Ser Ser Ser Val Ala Ser Asp Asn Ala Ile Arg Arg Ile Lys
                2115                2120                2125

Pro Asp Gly Ser Ser Leu Met Asn Ile Val Thr His Gly Ile Gly Glu
                2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
                2165                2170                2175

Asn Thr Thr Tyr Arg Arg Val Leu Leu Lys Val Thr Val Asp Met Pro
                2180                2185                2190

Arg His Ile Val Val Asp Pro Lys Asn Arg Tyr Leu Phe Trp Ala Asp
                2195                2200                2205

Tyr Gly Gln Arg Pro Lys Ile Glu Arg Ser Phe Leu Asp Cys Thr Asn
                2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Ser Leu Asp
                2245                2250                2255

Ile Ile Ala Arg Ile Arg Ile Asn Gly Glu Asn Ser Glu Val Ile Arg
                2260                2265                2270

Tyr Gly Ser Arg Tyr Pro Thr Pro Tyr Gly Ile Thr Val Phe Glu Asn
                2275                2280                2285

Ser Ile Ile Trp Val Asp Arg Asn Leu Lys Lys Ile Phe Gln Ala Ser
                2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
                2325                2330                2335

Ser Pro Ala Glu Val Asn Asn Asn Pro Cys Leu Glu Asn Asn Gly Gly
                2340                2345                2350

Cys Ser His Leu Cys Phe Ala Leu Pro Gly Leu His Thr Pro Lys Cys
                2355                2360                2365

Asp Cys Ala Phe Gly Thr Leu Gln Ser Asp Gly Lys Asn Cys Ala Ile
                2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
                2405                2410                2415

Val Glu Arg Thr Val Met Ser Leu Asp Tyr Asp Ser Val Ser Asp Arg
                2420                2425                2430

Ile Tyr Phe Thr Gln Asn Leu Ala Ser Gly Val Gly Gln Ile Ser Tyr
                2435                2440                2445

Ala Thr Leu Ser Ser Gly Ile His Thr Pro Thr Val Ile Ala Ser Gly
                2450                2455                2460

Ile Gly Thr Ala Asp Gly Ile Ala Phe Asp Trp Ile Thr Arg Arg Ile
2465                2470                2475                2480

Tyr Tyr Ser Asp Tyr Leu Asn Gln Met Ile Asn Ser Met Ala Glu Asp
                2485                2490                2495
```

-continued

Gly Ser Asn Arg Thr Val Ile Ala Arg Val Pro Lys Pro Arg Ala Ile
            2500                2505                2510

Val Leu Asp Pro Cys Gln Gly Tyr Leu Tyr Trp Ala Asp Trp Asp Thr
        2515                2520                2525

His Ala Lys Ile Glu Arg Ala Thr Leu Gly Gly Asn Phe Arg Val Pro
        2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
            2565                2570                2575

Arg Ser Thr Leu Thr Gly Val Asp Arg Glu Val Ile Val Asn Ala Ala
            2580                2585                2590

Val His Ala Phe Gly Leu Thr Leu Tyr Gly Gln Tyr Ile Tyr Trp Thr
            2595                2600                2605

Asp Leu Tyr Thr Gln Arg Ile Tyr Arg Ala Asn Lys Tyr Asp Gly Ser
            2610                2615                2620

Gly Gln Ile Ala Met Thr Thr Asn Leu Leu Ser Gln Pro Arg Gly Ile
2625                2630                2635                2640

Asn Thr Val Val Lys Asn Gln Lys Gln Gln Cys Asn Asn Pro Cys Glu
            2645                2650                2655

Gln Phe Asn Gly Gly Cys Ser His Ile Cys Ala Pro Gly Pro Asn Gly
            2660                2665                2670

Ala Glu Cys Gln Cys Pro His Glu Gly Asn Trp Tyr Leu Ala Asn Asn
            2675                2680                2685

Arg Lys His Cys Ile Val Asp Asn Gly Glu Arg Cys Gly Ala Ser Ser
            2690                2695                2700

Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
            2725                2730                2735

Ala Leu His Thr Cys Ser Pro Thr Ala Phe Thr Cys Ala Asn Gly Arg
            2740                2745                2750

Cys Val Gln Tyr Ser Tyr Arg Cys Asp Tyr Tyr Asn Asp Cys Gly Asp
            2755                2760                2765

Gly Ser Asp Glu Ala Gly Cys Leu Phe Arg Asp Cys Asn Ala Thr Thr
            2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Asn Thr Ser Asp Glu Lys Asn
            2805                2810                2815

Cys Pro Asp Arg Thr Cys Gln Ser Gly Tyr Thr Lys Cys His Asn Ser
            2820                2825                2830

Asn Ile Cys Ile Pro Arg Val Tyr Leu Cys Asp Gly Asp Asn Asp Cys
            2835                2840                2845

Gly Asp Asn Ser Asp Glu Asn Pro Thr Tyr Cys Thr Thr His Thr Cys
            2850                2855                2860

Ser Ser Ser Glu Phe Gln Cys Thr Ser Gly Arg Cys Ile Pro Gln His
2865                2870                2875                2880

Trp Tyr Cys Asp Gln Glu Thr Asp Cys Phe Asp Ala Ser Asp Glu Pro
            2885                2890                2895

Ala Ser Cys Gly His Ser Glu Arg Thr Cys Leu Ala Asp Glu Phe Lys
            2900                2905                2910

```
Cys Asp Gly Gly Arg Cys Ile Pro Ser Glu Trp Ile Cys Asp Gly Asp
        2915                2920                2925

Asn Asp Cys Gly Asp Met Ser Asp Glu Asp Lys Arg His Gln Cys Gln
    2930                2935                2940

Asn Gln Asn Cys Ser Asp Ser Glu Phe Leu Cys Val Asn Asp Arg Pro
2945                2950                2955                2960

Pro Asp Arg Arg Cys Ile Pro Gln Ser Trp Val Cys Asp Gly Asp Val
            2965                2970                2975

Asp Cys Thr Asp Gly Tyr Asp Glu Asn Gln Asn Cys Thr Arg Arg Thr
        2980                2985                2990

Cys Ser Glu Asn Glu Phe Thr Cys Gly Tyr Gly Leu Cys Ile Pro Lys
        2995                3000                3005

Ile Phe Arg Cys Asp Arg His Asn Asp Cys Gly Asp Tyr Ser Asp Glu
        3010                3015                3020

Arg Gly Cys Leu Tyr Gln Thr Cys Gln Gln Asn Gln Phe Thr Cys Gln
3025                3030                3035                3040

Asn Gly Arg Cys Ile Ser Lys Thr Phe Val Cys Asp Glu Asp Asn Asp
            3045                3050                3055

Cys Gly Asp Gly Ser Asp Glu Leu Met His Leu Cys His Thr Pro Glu
        3060                3065                3070

Pro Thr Cys Pro Pro His Glu Phe Lys Cys Asp Asn Gly Arg Cys Ile
    3075                3080                3085

Glu Met Met Lys Leu Cys Asn His Leu Asp Asp Cys Leu Asp Asn Ser
    3090                3095                3100

Asp Glu Lys Gly Cys Gly Ile Asn Glu Cys His Asp Pro Ser Ile Ser
3105                3110                3115                3120

Gly Cys Asp His Asn Cys Thr Asp Thr Leu Thr Ser Phe Tyr Cys Ser
            3125                3130                3135

Cys Arg Pro Gly Tyr Lys Leu Met Ser Asp Lys Arg Thr Cys Val Asp
            3140                3145                3150

Ile Asp Glu Cys Thr Glu Met Pro Phe Val Cys Ser Gln Lys Cys Glu
        3155                3160                3165

Asn Val Ile Gly Ser Tyr Ile Cys Lys Cys Ala Pro Gly Tyr Leu Arg
    3170                3175                3180

Glu Pro Asp Gly Lys Thr Cys Arg Gln Asn Ser Asn Ile Glu Pro Tyr
3185                3190                3195                3200

Leu Ile Phe Ser Asn Arg Tyr Tyr Leu Arg Asn Leu Thr Ile Asp Gly
            3205                3210                3215

Tyr Phe Tyr Ser Leu Ile Leu Glu Gly Leu Asp Asn Val Val Ala Leu
            3220                3225                3230

Asp Phe Asp Arg Val Glu Lys Arg Leu Tyr Trp Ile Asp Thr Gln Arg
            3235                3240                3245

Gln Val Ile Glu Arg Met Phe Leu Asn Lys Thr Asn Lys Glu Thr Ile
    3250                3255                3260

Ile Asn His Arg Leu Pro Ala Ala Glu Ser Leu Ala Val Asp Trp Val
3265                3270                3275                3280

Ser Arg Lys Leu Tyr Trp Leu Asp Ala Arg Leu Asp Gly Leu Phe Val
            3285                3290                3295

Ser Asp Leu Asn Gly Gly His Arg Arg Met Leu Ala Gln His Cys Val
        3300                3305                3310

Asp Ala Asn Asn Thr Phe Cys Phe Asp Asn Pro Arg Gly Leu Ala Leu
        3315                3320                3325

His Pro Gln Tyr Gly Tyr Leu Tyr Trp Ala Asp Trp Gly His Arg Ala
```

-continued

```
            3330                3335                3340
Tyr Ile Gly Arg Val Gly Met Asp Gly Thr Asn Lys Ser Val Ile Ile
3345                3350                3355                3360
Ser Thr Lys Leu Glu Trp Pro Asn Gly Ile Thr Ile Asp Tyr Thr Asn
                3365                3370                3375
Asp Leu Leu Tyr Trp Ala Asp Ala His Leu Gly Tyr Ile Glu Tyr Ser
                3380                3385                3390
Asp Leu Glu Gly His His Arg His Thr Val Tyr Asp Gly Ala Leu Pro
                3395                3400                3405
His Pro Phe Ala Ile Thr Ile Phe Glu Asp Thr Ile Tyr Trp Thr Asp
                3410                3415                3420
Trp Asn Thr Arg Thr Val Glu Lys Gly Asn Lys Tyr Asp Gly Ser Asn
3425                3430                3435                3440
Arg Gln Thr Leu Val Asn Thr Thr His Arg Pro Phe Asp Ile His Val
                3445                3450                3455
Tyr His Pro Tyr Arg Gln Pro Ile Val Ser Asn Pro Cys Gly Thr Asn
                3460                3465                3470
Asn Gly Gly Cys Ser His Leu Cys Leu Ile Lys Pro Gly Gly Lys Gly
                3475                3480                3485
Phe Thr Cys Glu Cys Pro Asp Asp Phe Arg Thr Leu Gln Leu Ser Gly
                3490                3495                3500
Ser Thr Tyr Cys Met Pro Met Cys Ser Ser Thr Gln Phe Leu Cys Ala
3505                3510                3515                3520
Asn Asn Glu Lys Cys Ile Pro Ile Trp Trp Lys Cys Asp Gly Gln Lys
                3525                3530                3535
Asp Cys Ser Asp Gly Ser Asp Glu Leu Ala Leu Cys Pro Gln Arg Phe
                3540                3545                3550
Cys Arg Leu Gly Gln Phe Gln Cys Ser Asp Gly Asn Cys Thr Ser Pro
                3555                3560                3565
Gln Thr Leu Cys Asn Ala His Gln Asn Cys Pro Asp Gly Ser Asp Glu
                3570                3575                3580
Asp Arg Leu Leu Cys Glu Asn His His Cys Asp Ser Asn Glu Trp Gln
3585                3590                3595                3600
Cys Ala Asn Lys Arg Cys Ile Pro Glu Ser Trp Gln Cys Asp Thr Phe
                3605                3610                3615
Asn Asp Cys Glu Asp Asn Ser Asp Glu Asp Ser Ser His Cys Ala Ser
                3620                3625                3630
Arg Thr Cys Arg Pro Gly Gln Phe Arg Cys Ala Asn Gly Arg Cys Ile
                3635                3640                3645
Pro Gln Ala Trp Lys Cys Asp Val Asp Asn Asp Cys Gly Asp His Ser
                3650                3655                3660
Asp Glu Pro Ile Glu Glu Cys Met Ser Ser Ala His Leu Cys Asp Asn
3665                3670                3675                3680
Phe Thr Glu Phe Ser Cys Lys Thr Asn Tyr Arg Cys Ile Pro Lys Trp
                3685                3690                3695
Ala Val Cys Asn Gly Val Asp Asp Cys Arg Asp Asn Ser Asp Glu Gln
                3700                3705                3710
Gly Cys Glu Glu Arg Thr Cys His Pro Val Gly Asp Phe Arg Cys Lys
                3715                3720                3725
Asn His His Cys Ile Pro Leu Arg Trp Gln Cys Asp Gly Gln Asn Asp
                3730                3735                3740
Cys Gly Asp Asn Ser Asp Glu Glu Asn Cys Ala Pro Arg Glu Cys Thr
3745                3750                3755                3760
```

-continued

```
Glu Ser Glu Phe Arg Cys Val Asn Gln Gln Cys Ile Pro Ser Arg Trp
            3765                3770                3775

Ile Cys Asp His Tyr Asn Asp Cys Gly Asp Asn Ser Asp Glu Arg Asp
            3780                3785                3790

Cys Glu Met Arg Thr Cys His Pro Glu Tyr Phe Gln Cys Thr Ser Gly
            3795                3800                3805

His Cys Val His Ser Glu Leu Lys Cys Asp Gly Ser Ala Asp Cys Leu
            3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Cys Gly Asp Gly Ser Asp
            3860                3865                3870

Glu Glu Leu His Leu Cys Leu Asp Val Pro Cys Asn Ser Pro Asn Arg
            3875                3880                3885

Phe Arg Cys Asp Asn Asn Arg Cys Ile Tyr Ser His Glu Val Cys Asn
            3890                3895                3900

Gly Val Asp Asp Cys Gly Asp Gly Thr Asp Glu Thr Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Asp Ala Asp Asp
            3940                3945                3950

Cys Gly Asp Trp Ser Asp Glu Leu Gly Cys Asn Lys Gly Lys Glu Arg
            3955                3960                3965

Thr Cys Ala Glu Asn Ile Cys Glu Gln Asn Cys Thr Gln Leu Asn Glu
            3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
            4020                4025                4030

Ala Asp Gly Phe Thr Ser Met Ser Asp Arg Pro Gly Lys Arg Cys Ala
            4035                4040                4045

Ala Glu Gly Ser Ser Pro Leu Leu Leu Leu Pro Asp Asn Val Arg Ile
            4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Xaa Asp Ile
            4085                4090                4095

Gly Leu Ser Val Val Tyr Tyr Thr Val Arg Gly Glu Gly Ser Arg Phe
            4100                4105                4110

Gly Ala Ile Lys Arg Ala Tyr Ile Pro Asn Phe Glu Ser Gly Arg Asn
            4115                4120                4125

Asn Leu Val Gln Glu Val Asp Leu Lys Leu Lys Tyr Val Met Gln Pro
            4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
            4165                4170                4175
```

-continued

```
Lys Trp Leu Ile Ser Thr Asp Leu Asp Gln Pro Ala Ile Ala Val
            4180            4185            4190

Asn Pro Lys Leu Gly Leu Met Phe Trp Thr Asp Trp Gly Lys Glu Pro
        4195            4200            4205

Lys Xaa Glu Ser Ala Trp Met Asn Gly Glu Asp Arg Asn Ile Leu Val
        4210            4215            4220

Phe Glu Asp Leu Gly Trp Pro Thr Gly Leu Ser Ile Asp Tyr Leu Asn
4225            4230            4235            4240

Asn Asp Arg Ile Tyr Trp Ser Asp Phe Lys Glu Asp Val Ile Glu Thr
            4245            4250            4255

Ile Lys Tyr Asp Gly Thr Asp Arg Arg Val Ile Ala Lys Glu Ala Met
            4260            4265            4270

Asn Pro Tyr Ser Leu Asp Ile Phe Glu Asp Gln Leu Tyr Trp Ile Ser
            4275            4280            4285

Lys Glu Lys Gly Glu Val Trp Lys Gln Asn Lys Phe Gly Gln Gly Lys
            4290            4295            4300

Lys Glu Lys Thr Leu Val Val Asn Pro Trp Leu Thr Gln Val Arg Ile
4305            4310            4315            4320

Phe His Gln Leu Arg Tyr Asn Lys Ser Val Pro Asn Leu Cys Lys Gln
            4325            4330            4335

Ile Cys Ser His Leu Cys Leu Leu Arg Pro Gly Gly Tyr Ser Cys Ala
            4340            4345            4350

Cys Pro Gln Gly Ser Ser Phe Ile Glu Gly Ser Thr Thr Glu Cys Asp
            4355            4360            4365

Ala Ala Ile Glu Leu Pro Ile Asn Leu Pro Pro Pro Cys Arg Cys Met
            4370            4375            4380

His Gly Gly Asn Cys Tyr Phe Asp Glu Thr Asp Leu Pro Lys Cys Lys
4385            4390            4395            4400

Cys Pro Ser Gly Tyr Thr Gly Lys Tyr Cys Glu Met Ala Phe Ser Lys
            4405            4410            4415

Gly Ile Ser Pro Gly Thr Thr Ala Val Ala Val Leu Leu Thr Ile Leu
            4420            4425            4430

Leu Ile Val Val Ile Gly Ala Leu Ala Ile Ala Gly Phe Phe His Tyr
            4435            4440            4445

Arg Arg Thr Gly Ser Leu Leu Pro Ala Leu Pro Lys Leu Pro Ser Leu
            4450            4455            4460

Ser Ser Leu Val Lys Pro Ser Glu Asn Gly Asn Gly Val Thr Phe Arg
4465            4470            4475            4480

Ser Gly Ala Asp Leu Asn Met Asp Ile Gly Val Ser Gly Phe Gly Pro
            4485            4490            4495

Glu Thr Ala Ile Asp Arg Ser Met Ala Met Ser Glu Asp Phe Val Met
            4500            4505            4510

Glu Met Gly Lys Gln Pro Ile Ile Phe Glu Asn Pro Met Tyr Ser Ala
            4515            4520            4525

Arg Asp Ser Ala Val Lys Val Val Gln Pro Ile Gln Val Thr Val Ser
            4530            4535            4540

Glu Asn Val Asp Asn Lys Asn Tyr Gly Ser Pro Ile Asn Pro Ser Glu
4545            4550            4555            4560

Ile Val Pro Glu Thr Asn Pro Thr Ser Pro Ala Ala Asp Gly Thr Gln
            4565            4570            4575

Val Thr Lys Trp Asn Leu Phe Arg Lys Ser Lys Gln Thr Thr Asn
            4580            4585            4590

Phe Glu Asn Pro Ile Tyr Ala Gln Met Glu Asn Glu Gln Lys Glu Ser
```

```
              4595              4600             4605
Val Ala Ala Thr Pro Pro Ser Pro Ser Leu Pro Ala Lys Pro Lys
        4610            4615            4620

Pro Pro Ser Arg Arg Asp Pro Thr Pro Thr Tyr Ser Ala Thr Glu Asp
4625            4630            4635            4640

Thr Phe Lys Asp Thr Ala Asn Leu Val Lys Glu Asp Ser Glu Val
            4645            4650            4655
```

(2) INFORMATION FOR SEQ ID NO:87:

(i) SEQUENCE CHARACTERISTICS:
  (A) LENGTH: 14080 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Homo sapiens
  (F) TISSUE TYPE: Kidney (ix) FEATURE:
  (A) NAME/KEY: CDS
  (B) LOCATION: 105..14072

(xi) SEQUENCE DESCRIPTION: SEQ ID NO:87:

```
GCAGACCTAA AGGAGCGTTC GCTAGCAGAG GCGCTGCCGG TGCGGTGTGC TACGCGCGCC        60

CACCTCCCGG GGAAGGAACG GCGAGGCCGG GGACCGTCGC GGAG ATG GAT CGC GGG        116
                                              Met Asp Arg Gly
                                                            4660

CCG GCA GCA GTG GCG TGC ACG CTG CTC CTG GCT CTC GTC GCC TGC CTA         164
Pro Ala Ala Val Ala Cys Thr Leu Leu Leu Ala Leu Val Ala Cys Leu
            4665                4670                4675

GCG CCG GCC AGT GGC CAA GAA TGT GAC AGT GCG CAT TTT CGC TGT GGA         212
Ala Pro Ala Ser Gly Gln Glu Cys Asp Ser Ala His Phe Arg Cys Gly
            4680                4685                4690

AGT GGG CAT TGC ATC CCT GCA GAC TGG AGG TGT GAT GGG ACC AAA GAC         260
Ser Gly His Cys Ile Pro Ala Asp Trp Arg Cys Asp Gly Thr Lys Asp
        4695                4700                4705

TGT TCA GAT GAC GCG GAT GAA ATT GGC TGC GCT GTT GTG ACC TGC CAG         308
Cys Ser Asp Asp Ala Asp Glu Ile Gly Cys Ala Val Val Thr Cys Gln
        4710                4715                4720

CAG GGC TAT TTC AAG TGC CAG AGT GAG GGA CAA TGC ATC CCC AGC TCC         356
Gln Gly Tyr Phe Lys Cys Gln Ser Glu Gly Gln Cys Ile Pro Ser Ser
4725                4730                4735                4740

TGG GTG TGT GAC CAA GAT CAA GAC TGT GAT GAT GGC TCA GAT GAA CGT         404
Trp Val Cys Asp Gln Asp Gln Asp Cys Asp Asp Gly Ser Asp Glu Arg
                4745                4750                4755

CAA GAT TGC TCA CAA AGT ACA TGC TCA AGT CAT CAG ATA ACA TGC TCC         452
Gln Asp Cys Ser Gln Ser Thr Cys Ser Ser His Gln Ile Thr Cys Ser
                    4760                4765                4770

AAT GGT CAG TGT ATC CCA AGT GAA TAC AGG TGC GAC CAC GTC AGA GAC         500
Asn Gly Gln Cys Ile Pro Ser Glu Tyr Arg Cys Asp His Val Arg Asp
                4775                4780                4785

TGC CCC GAT GGA GCT GAT GAG AAT GAC TGC CAG TAC CCA ACA TGT GAG         548
Cys Pro Asp Gly Ala Asp Glu Asn Asp Cys Gln Tyr Pro Thr Cys Glu
            4790                4795                4800

CAG CTT ACT TGT GAC AAT GGG GCC TGC TAT AAC ACC AGT CAG AAG TGT         596
```

```
                                                             -continued

Gln Leu Thr Cys Asp Asn Gly Ala Cys Tyr Asn Thr Ser Gln Lys Cys
4805                4810                4815                4820

GAT TGG AAA GTT GAT TGC AGG GAC TCC TCA GAT GAA ATC AAC TGC ACT      644
Asp Trp Lys Val Asp Cys Arg Asp Ser Ser Asp Glu Ile Asn Cys Thr
                4825                4830                4835

GAG ATA TGC TTG CAC AAT GAG TTT TCA TGT GGC AAT GGA GAG TGT ATC      692
Glu Ile Cys Leu His Asn Glu Phe Ser Cys Gly Asn Gly Glu Cys Ile
            4840                4845                4850

CCT CGT GCT TAT GTC TGT GAC CAT GAC AAT GAT TGC CAA GAC GGC AGT      740
Pro Arg Ala Tyr Val Cys Asp His Asp Asn Asp Cys Gln Asp Gly Ser
            4855                4860                4865

GAT GAA CAT GCT TGC AAC TAT CCG ACC TGC GGT GGT TAC CAG TTC ACT      788
Asp Glu His Ala Cys Asn Tyr Pro Thr Cys Gly Gly Tyr Gln Phe Thr
        4870                4875                4880

TGC CCC AGT GGC CGA TGC ATT TAT CAA AAC TGG GTT TGT GAT GGA GAA      836
Cys Pro Ser Gly Arg Cys Ile Tyr Gln Asn Trp Val Cys Asp Gly Glu
4885                4890                4895                4900

GAT GAC TGT AAA GAT AAT GGA GAT GAA GAT GGA TGT GAA AGC GGT CCT      884
Asp Asp Cys Lys Asp Asn Gly Asp Glu Asp Gly Cys Glu Ser Gly Pro
                4905                4910                4915

CAT GAT GTT CAT AAA TGT TCC CCA AGA GAA TGG TCT TGC CCA GAG TCG      932
His Asp Val His Lys Cys Ser Pro Arg Glu Trp Ser Cys Pro Glu Ser
            4920                4925                4930

GGA CGA TGC ATC TCC ATT TAT AAA GTT TGT GAT GGG ATT TTA GAT TGC      980
Gly Arg Cys Ile Ser Ile Tyr Lys Val Cys Asp Gly Ile Leu Asp Cys
            4935                4940                4945

CCA GGA AGA GAA GAT GAA AAC AAC ACT AGT ACC GGA AAA TAC TGT AGT     1028
Pro Gly Arg Glu Asp Glu Asn Asn Thr Ser Thr Gly Lys Tyr Cys Ser
        4950                4955                4960

ATG ACT CTG TGC TCT GCC TTG AAC TGC CAG TAC CAG TGC CAT GAG ACG     1076
Met Thr Leu Cys Ser Ala Leu Asn Cys Gln Tyr Gln Cys His Glu Thr
4965                4970                4975                4980

CCG TAT GGA GGA GCG TGT TTT TGT CCC CCA GGT TAT ATC ATC AAC CAC     1124
Pro Tyr Gly Gly Ala Cys Phe Cys Pro Pro Gly Tyr Ile Ile Asn His
                4985                4990                4995

AAT GAC AGC CGT ACC TGT GTT GAG TTT GAT GAT TGC CAG ATA TGG GGA     1172
Asn Asp Ser Arg Thr Cys Val Glu Phe Asp Asp Cys Gln Ile Trp Gly
            5000                5005                5010

ATT TGT GAC CAG AAG TGT GAA AGC CGA CCT GGC CGT CAC CTG TGC CAC     1220
Ile Cys Asp Gln Lys Cys Glu Ser Arg Pro Gly Arg His Leu Cys His
            5015                5020                5025

TGT GAA GAA GGG TAT ATC TTG GAG CGT GGA CAG TAT TGC AAA GCT AAT     1268
Cys Glu Glu Gly Tyr Ile Leu Glu Arg Gly Gln Tyr Cys Lys Ala Asn
        5030                5035                5040

GAT TCC TTT GGC GAG GCC TCC ATT ATC TTC TCC AAT GGT CGG GAT TTG     1316
Asp Ser Phe Gly Glu Ala Ser Ile Ile Phe Ser Asn Gly Arg Asp Leu
5045                5050                5055                5060

TTA ATT GGT GAT ATT CAT GGA AGG AGC TTC CGG ATC CTA GTG GAG TCT     1364
Leu Ile Gly Asp Ile His Gly Arg Ser Phe Arg Ile Leu Val Glu Ser
                5065                5070                5075

CAG AAT CGT GGA GTG GCC GTG GGT GTG GCT TTC CAC TAT CAC CTG CAA     1412
Gln Asn Arg Gly Val Ala Val Gly Val Ala Phe His Tyr His Leu Gln
            5080                5085                5090

AGA GTT TTT TGG ACA GAC ACC GTG CAA AAT AAG GTT TTT TCA GTT GAC     1460
Arg Val Phe Trp Thr Asp Thr Val Gln Asn Lys Val Phe Ser Val Asp
            5095                5100                5105

ATT AAT GGT TTA AAT ATC CAA GAG GTT CTC AAT GTT TCT GTT GAA ACC     1508
Ile Asn Gly Leu Asn Ile Gln Glu Val Leu Asn Val Ser Val Glu Thr
        5110                5115                5120
```

```
CCA GAG AAC CTG GCT GTG GAC TGG GTT AAT AAT AAA ATC TAT CTA GTG        1556
Pro Glu Asn Leu Ala Val Asp Trp Val Asn Asn Lys Ile Tyr Leu Val
5125                5130                5135                5140

GAA ACC AAG GTC AAC CGC ATA GAT ATG GTA AAT TTG GAT GGA AGC TAT        1604
Glu Thr Lys Val Asn Arg Ile Asp Met Val Asn Leu Asp Gly Ser Tyr
                5145                5150                5155

CGG GTT ACC CTT ATA ACT GAA AAC TTG GGG CAT CCT AGA GGA ATT GCC        1652
Arg Val Thr Leu Ile Thr Glu Asn Leu Gly His Pro Arg Gly Ile Ala
            5160                5165                5170

GTG GAC CCA ACT GTT GGT TAT TTA TTT TTC TCA GAT TGG GAG AGC CTT        1700
Val Asp Pro Thr Val Gly Tyr Leu Phe Phe Ser Asp Trp Glu Ser Leu
        5175                5180                5185

TCT GGG GAA CCT AAG CTG GAA AGG GCA TTC ATG GAT GGC AGC AAC CGT        1748
Ser Gly Glu Pro Lys Leu Glu Arg Ala Phe Met Asp Gly Ser Asn Arg
    5190                5195                5200

AAA GAC TTG GTG AAA ACA AAG CTG GGA TGG CCT GCT GGG GTA ACT CTG        1796
Lys Asp Leu Val Lys Thr Lys Leu Gly Trp Pro Ala Gly Val Thr Leu
5205                5210                5215                5220

GAT ATG ATA TCG AAG CGT GTT TAC TGG GTT GAC TCT CGG TTT GAT TAC        1844
Asp Met Ile Ser Lys Arg Val Tyr Trp Val Asp Ser Arg Phe Asp Tyr
                5225                5230                5235

ATT GAA ACT GTA ACT TAT GAT GGA ATT CAA AGG AAG ACT GTA GTT CAT        1892
Ile Glu Thr Val Thr Tyr Asp Gly Ile Gln Arg Lys Thr Val Val His
            5240                5245                5250

GGA GGC TCC CTC ATT CCT CAT CCC TTT GGA GTA AGC TTA TTT GAA GGT        1940
Gly Gly Ser Leu Ile Pro His Pro Phe Gly Val Ser Leu Phe Glu Gly
        5255                5260                5265

CAG GTG TTC TTT ACA GAT TGG ACA AAG ATG GCC GTG CTG AAG GCA AAC        1988
Gln Val Phe Phe Thr Asp Trp Thr Lys Met Ala Val Leu Lys Ala Asn
    5270                5275                5280

AAG TTC ACA GAG ACC AAC CCA CAA GTG TAC TAC CAG GCT TCC CTG AGG        2036
Lys Phe Thr Glu Thr Asn Pro Gln Val Tyr Tyr Gln Ala Ser Leu Arg
5285                5290                5295                5300

CCC TAT GGA GTG ACT GTT TAC CAT TCC CTC AGA CAG CCC TAT GCT ACC        2084
Pro Tyr Gly Val Thr Val Tyr His Ser Leu Arg Gln Pro Tyr Ala Thr
                5305                5310                5315

AAT CCG TGT AAA GAT AAC AAT GGG GGC TGT GAG CAG GTC TGT GTT CTC        2132
Asn Pro Cys Lys Asp Asn Asn Gly Gly Cys Glu Gln Val Cys Val Leu
            5320                5325                5330

AGC CAC AGA ACA GAT AAT GAT GGT TTG GGT TTC CGT TGC AAG TGC ACA        2180
Ser His Arg Thr Asp Asn Asp Gly Leu Gly Phe Arg Cys Lys Cys Thr
        5335                5340                5345

TTC GGC TTC CAA CTG GAT ACA GAT GAG CGC CAC TGC ATT GCT GTT CAG        2228
Phe Gly Phe Gln Leu Asp Thr Asp Glu Arg His Cys Ile Ala Val Gln
    5350                5355                5360

AAT TTC CTC ATT TTT TCA TCC CAA GTT GCT ATT CGT GGG ATC CCG TTC        2276
Asn Phe Leu Ile Phe Ser Ser Gln Val Ala Ile Arg Gly Ile Pro Phe
5365                5370                5375                5380

ACC TTG TCT ACC CAG GAA GAT GTC ATG GTT CCA GTT TCG GGG AAT CCT        2324
Thr Leu Ser Thr Gln Glu Asp Val Met Val Pro Val Ser Gly Asn Pro
                5385                5390                5395

TCT TTC TTT GTC GGG ATT GAT TTT GAC GCC CAG GAC AGC ACT ATC TTT        2372
Ser Phe Phe Val Gly Ile Asp Phe Asp Ala Gln Asp Ser Thr Ile Phe
            5400                5405                5410

TTT TCA GAT ATG TCA AAA CAC ATG ATT TTT AAG CAA AAG ATT GAT GGC        2420
Phe Ser Asp Met Ser Lys His Met Ile Phe Lys Gln Lys Ile Asp Gly
        5415                5420                5425

ACA GGA AGA GAA ATT CTC GCA GCT AAC AGG GTG GAA AAT GTT GAA AGT        2468
Thr Gly Arg Glu Ile Leu Ala Ala Asn Arg Val Glu Asn Val Glu Ser
    5430                5435                5440
```

```
TTG GCT TTT GAT TGG ATT TCA AAG AAT CTC TAT TGG ACA GAC TCT CAT    2516
Leu Ala Phe Asp Trp Ile Ser Lys Asn Leu Tyr Trp Thr Asp Ser His
5445                5450                5455                5460

TAC AAG AGT ATC AGT GTC ATG AGG CTA GCT GAT AAA ACG AGA CGC ACA    2564
Tyr Lys Ser Ile Ser Val Met Arg Leu Ala Asp Lys Thr Arg Arg Thr
                5465                5470                5475

GTA GTT CAG TAT TTA AAT AAC CCA CGG TCG GTG GTA GTT CAT CCT TTT    2612
Val Val Gln Tyr Leu Asn Asn Pro Arg Ser Val Val His Pro Phe
            5480                5485                5490

GCC GGG TAT CTA TTC TTC ACT GAT TGG TTC CGT CCT GCT AAA ATT ATG    2660
Ala Gly Tyr Leu Phe Phe Thr Asp Trp Phe Arg Pro Ala Lys Ile Met
        5495                5500                5505

AGA GCA TGG AGT GAC GGA TCT CAC CTC TTG CCT GTA ATA AAC ACT ACT    2708
Arg Ala Trp Ser Asp Gly Ser His Leu Leu Pro Val Ile Asn Thr Thr
    5510                5515                5520

CTT GGA TGG CCC AAT GGC TTG GCC ATC GAT TGG GCT GCT TCA CGA TTG    2756
Leu Gly Trp Pro Asn Gly Leu Ala Ile Asp Trp Ala Ala Ser Arg Leu
5525                5530                5535                5540

TAC TGG GTA GAT GCC TAT TTT GAT AAA ATT GAG CAC AGC ACC TTT GAT    2804
Tyr Trp Val Asp Ala Tyr Phe Asp Lys Ile Glu His Ser Thr Phe Asp
                5545                5550                5555

GGT TTA GAC AGA AGA AGA CTG GGC CAT ATA GAG CAG ATG ACA CAT CCG    2852
Gly Leu Asp Arg Arg Arg Leu Gly His Ile Glu Gln Met Thr His Pro
            5560                5565                5570

TTT GGA CTT GCC ATC TTT GGA GAG CAT TTA TTT TTT ACT GAC TGG AGA    2900
Phe Gly Leu Ala Ile Phe Gly Glu His Leu Phe Phe Thr Asp Trp Arg
        5575                5580                5585

CTG GGT GCC ATT ATT CGA GTC AGG AAA GCA GAT GGT GGA GAA ATG ACA    2948
Leu Gly Ala Ile Ile Arg Val Arg Lys Ala Asp Gly Gly Glu Met Thr
    5590                5595                5600

GTT ATC CGA AGT GGC ATT GCT TAC ATA CTG CAT TTG AAA TCG TAT GAT    2996
Val Ile Arg Ser Gly Ile Ala Tyr Ile Leu His Leu Lys Ser Tyr Asp
5605                5610                5615                5620

GTC AAC ATC CAG ACT GGT TCT AAC GCC TGT AAT CAA CCC ACG CAT CCT    3044
Val Asn Ile Gln Thr Gly Ser Asn Ala Cys Asn Gln Pro Thr His Pro
                5625                5630                5635

AAC GGT GAC TGC AGC CAC TTC TGC TTC CCG GTG CCA AAT TTC CAG CGA    3092
Asn Gly Asp Cys Ser His Phe Cys Phe Pro Val Pro Asn Phe Gln Arg
            5640                5645                5650

GTG TGT GGG TGC CCT TAT GGA ATG AGG CTG GCT TCC AAT CAC TTG ACA    3140
Val Cys Gly Cys Pro Tyr Gly Met Arg Leu Ala Ser Asn His Leu Thr
        5655                5660                5665

TGC GAG GGG GAC CCA ACC AAT GAA CCA CCC ACG GAG CAG TGT GGC TTA    3188
Cys Glu Gly Asp Pro Thr Asn Glu Pro Pro Thr Glu Gln Cys Gly Leu
    5670                5675                5680

TTT TCC TTC CCC TGT AAA AAT GGC AGA TGT GTG CCC AAT TAC TAT CTC    3236
Phe Ser Phe Pro Cys Lys Asn Gly Arg Cys Val Pro Asn Tyr Tyr Leu
5685                5690                5695                5700

TGT GAT GGA GTC GAT GAT TGT CAT GAT AAC AGT GAT GAG CAA CTA TGT    3284
Cys Asp Gly Val Asp Asp Cys His Asp Asn Ser Asp Glu Gln Leu Cys
                5705                5710                5715

GGC ACA CTT AAT AAT ACC TGT TCA TCT TCG GCG TTC ACC TGT GGC CAT    3332
Gly Thr Leu Asn Asn Thr Cys Ser Ser Ser Ala Phe Thr Cys Gly His
            5720                5725                5730

GGG GAG TGC ATT CCT GCA CAC TGG CGC TGT GAC AAA CGC AAC GAC TGT    3380
Gly Glu Cys Ile Pro Ala His Trp Arg Cys Asp Lys Arg Asn Asp Cys
        5735                5740                5745

GTG GAT GGC AGT GAT GAG CAC AAC TGC CCC ACC CAC GCA CCT GCT TCC    3428
Val Asp Gly Ser Asp Glu His Asn Cys Pro Thr His Ala Pro Ala Ser
```

```
                  5750                5755                5760
TGC CTT GAC ACC CAA TAC ACC TGT GAT AAT CAC CAG TGT ATC TCA AAG    3476
Cys Leu Asp Thr Gln Tyr Thr Cys Asp Asn His Gln Cys Ile Ser Lys
5765                5770                5775                5780

AAC TGG GTC TGT GAC ACA GAC AAT GAT TGT GGG GAT GGA TCT GAT GAA    3524
Asn Trp Val Cys Asp Thr Asp Asn Asp Cys Gly Asp Gly Ser Asp Glu
                    5785                5790                5795

AAG AAC TGC AAT TCG ACA GAG ACA TGC CAA CCT AGT CAG TTT AAT TGC    3572
Lys Asn Cys Asn Ser Thr Glu Thr Cys Gln Pro Ser Gln Phe Asn Cys
                5800                5805                5810

CCC AAT CAT CGA TGT ATT GAC CTA TCG TTT GTC TGT GAT GGT GAC AAG    3620
Pro Asn His Arg Cys Ile Asp Leu Ser Phe Val Cys Asp Gly Asp Lys
            5815                5820                5825

GAT TGT GTT GAT GGA TCT GAT GAG GTT GGT TGT GTA TTA AAC TGT ACT    3668
Asp Cys Val Asp Gly Ser Asp Glu Val Gly Cys Val Leu Asn Cys Thr
        5830                5835                5840

GCT TCT CAA TTC AAG TGT GCC AGT GGG GAT AAA TGT ATT GGC GTC ACA    3716
Ala Ser Gln Phe Lys Cys Ala Ser Gly Asp Lys Cys Ile Gly Val Thr
5845                5850                5855                5860

AAT CGT TGT GAT GGT GTT TTT GAT TGC AGT GAC AAC TCG GAT GAA GCG    3764
Asn Arg Cys Asp Gly Val Phe Asp Cys Ser Asp Asn Ser Asp Glu Ala
                    5865                5870                5875

GGC TGT CCA ACC AGG CCT CCT GGT ATG TGC CAC TCA GAT GAA TTT CAG    3812
Gly Cys Pro Thr Arg Pro Pro Gly Met Cys His Ser Asp Glu Phe Gln
                5880                5885                5890

TGC CAA GAA GAT GGT ATC TGC ATC CCG AAC TTC TGG GAA TGT GAT GGG    3860
Cys Gln Glu Asp Gly Ile Cys Ile Pro Asn Phe Trp Glu Cys Asp Gly
            5895                5900                5905

CAT CCA GAC TGC CTC TAT GGA TCT GAT GAG CAC AAT GCC TGT GTC CCC    3908
His Pro Asp Cys Leu Tyr Gly Ser Asp Glu His Asn Ala Cys Val Pro
        5910                5915                5920

AAG ACT TGC CCT TCA TCA TAT TTC CAC TGT GAC AAC GGA AAC TGC ATC    3956
Lys Thr Cys Pro Ser Ser Tyr Phe His Cys Asp Asn Gly Asn Cys Ile
5925                5930                5935                5940

CAC AGG GCA TGG CTC TGT GAT CGG GAC AAT GAC TGC GGG GAT ATG AGT    4004
His Arg Ala Trp Leu Cys Asp Arg Asp Asn Asp Cys Gly Asp Met Ser
                    5945                5950                5955

GAT GAG AAG GAC TGC CCT ACT CAG CCC TTT CGC TGT CCT AGT TGG CAA    4052
Asp Glu Lys Asp Cys Pro Thr Gln Pro Phe Arg Cys Pro Ser Trp Gln
                5960                5965                5970

TGG CAG TGT CTT GGC CAT AAC ATC TGT GTG AAT CTG AGT GTA GTG TGT    4100
Trp Gln Cys Leu Gly His Asn Ile Cys Val Asn Leu Ser Val Val Cys
            5975                5980                5985

GAT GGC ATC TTT GAC TGC CCC AAT GGG ACA GAT GAG TCC CCA CTT TGC    4148
Asp Gly Ile Phe Asp Cys Pro Asn Gly Thr Asp Glu Ser Pro Leu Cys
        5990                5995                6000

AAT GGG AAC AGC TGC TCA GAT TTC AAT GGT GGT TGT ACT CAC GAG TGT    4196
Asn Gly Asn Ser Cys Ser Asp Phe Asn Gly Gly Cys Thr His Glu Cys
6005                6010                6015                6020

GTT CAA GAG CCC TTT GGG GCT AAA TGC CTA TGT CCA TTG GGA TTC TTA    4244
Val Gln Glu Pro Phe Gly Ala Lys Cys Leu Cys Pro Leu Gly Phe Leu
                    6025                6030                6035

CTT GCC AAT GAT TCT AAG ACC TGT GAA GAC ATA GAT GAA TGT GAT ATT    4292
Leu Ala Asn Asp Ser Lys Thr Cys Glu Asp Ile Asp Glu Cys Asp Ile
                6040                6045                6050

CTA GGC TCT TGT AGC CAG CAC TGT TAC AAT ATG AGA GGT CTT TTC CGG    4340
Leu Gly Ser Cys Ser Gln His Cys Tyr Asn Met Arg Gly Ser Phe Arg
            6055                6060                6065

TGC TCG TGT GAT ACA GGC TAC ATG TTA GAA AGT GAT GGG AGG ACT TGC    4388
```

```
Cys Ser Cys Asp Thr Gly Tyr Met Leu Glu Ser Asp Gly Arg Thr Cys
    6070            6075                6080

AAA GTT ACA GCA TCT GAG AGT CTG CTG TTA CTT GTG GCA AGT CAG AAC          4436
Lys Val Thr Ala Ser Glu Ser Leu Leu Leu Leu Val Ala Ser Gln Asn
6085            6090                6095                6100

AAA ATT ATT GCC GAC AGT GTC ACC TCC CAG GTC CAC AAT ATC TAT TCA          4484
Lys Ile Ile Ala Asp Ser Val Thr Ser Gln Val His Asn Ile Tyr Ser
            6105                6110                6115

TTG GTC GAG AAT GGT TCT TAC ATT GTA GCT GTT GAT TTT GAT TCA ATT          4532
Leu Val Glu Asn Gly Ser Tyr Ile Val Ala Val Asp Phe Asp Ser Ile
                6120                6125                6130

AGT GGT CGT ATC TTT TGG TCT GAT GCA ACT CAG GGT AAA ACC TGG AGT          4580
Ser Gly Arg Ile Phe Trp Ser Asp Ala Thr Gln Gly Lys Thr Trp Ser
            6135                6140                6145

GCG TTT CAA AAT GGA ACG GAC AGA AGA GTG GTA TTT GAC AGT AGC ATC          4628
Ala Phe Gln Asn Gly Thr Asp Arg Arg Val Val Phe Asp Ser Ser Ile
6150                6155                6160

ATC TTG ACT GAA ACT ATT GCA ATA GAT TGG GTA GGT CGT AAT CTT TAC          4676
Ile Leu Thr Glu Thr Ile Ala Ile Asp Trp Val Gly Arg Asn Leu Tyr
6165                6170                6175                6180

TGG ACA GAC TAT GCT CTG GAA ACA ATT GAA GTC TCC AAA ATT GAT GGG          4724
Trp Thr Asp Tyr Ala Leu Glu Thr Ile Glu Val Ser Lys Ile Asp Gly
                6185                6190                6195

AGC CAC AGG ACT GTG CTG ATT AGT AAA AAC CTA ACA AAT CCA AGA GGA          4772
Ser His Arg Thr Val Leu Ile Ser Lys Asn Leu Thr Asn Pro Arg Gly
            6200                6205                6210

CTA GCA TTA GAT CCC AGA ATG AAT GAG CAT CTA CTG TTC TGG TCT GAC          4820
Leu Ala Leu Asp Pro Arg Met Asn Glu His Leu Leu Phe Trp Ser Asp
            6215                6220                6225

TGG GGC CAC CAC CCT CGC ATC GAG CGA GCC AGC ATG GAC GGC AGC ATG          4868
Trp Gly His His Pro Arg Ile Glu Arg Ala Ser Met Asp Gly Ser Met
    6230                6235                6240

CGC ACT GTC ATT GTC CAG GAC AAG ATC TTC TGG CCC TGC GGC TTA ACT          4916
Arg Thr Val Ile Val Gln Asp Lys Ile Phe Trp Pro Cys Gly Leu Thr
6245                6250                6255                6260

ATT GAC TAC CCC AAC AGA CTG CTC TAC TTC ATG GAC TCC TAT CTT GAT          4964
Ile Asp Tyr Pro Asn Arg Leu Leu Tyr Phe Met Asp Ser Tyr Leu Asp
                6265                6270                6275

TAC ATG GAC TTT TGC GAT TAT AAT GGA CAC CAT CGG AGA CAG GTG ATA          5012
Tyr Met Asp Phe Cys Asp Tyr Asn Gly His His Arg Arg Gln Val Ile
            6280                6285                6290

GCC AGT GAT TTG ATT ATA CGG CAC CCC TAT GCC CTA ACT CTC TTT GAA          5060
Ala Ser Asp Leu Ile Ile Arg His Pro Tyr Ala Leu Thr Leu Phe Glu
            6295                6300                6305

GAC TCT GTG TAC TGG ACT GAC CGT GCT ACT CGT CGG GTT ATG CGA GCC          5108
Asp Ser Val Tyr Trp Thr Asp Arg Ala Thr Arg Arg Val Met Arg Ala
            6310                6315                6320

AAC AAG TGG CAT GGA GGG AAC CAG TCA GTT GTA ATG TAT AAT ATT CAA          5156
Asn Lys Trp His Gly Gly Asn Gln Ser Val Val Met Tyr Asn Ile Gln
6325                6330                6335                6340

TGG CCC CTT GGG ATT GTT GCG GTT CAT CCT TCG AAA CAA CCA AAT TCC          5204
Trp Pro Leu Gly Ile Val Ala Val His Pro Ser Lys Gln Pro Asn Ser
                6345                6350                6355

GTG AAT CCA TGT GCC TTT TCC CGC TGC AGC CAT CTC TGC CTG CTT TCC          5252
Val Asn Pro Cys Ala Phe Ser Arg Cys Ser His Leu Cys Leu Leu Ser
            6360                6365                6370

TCA CAG GGG CCT CAT TTT TAC TCC TGT GTT TGT CCT TCA GGA TGG AGT          5300
Ser Gln Gly Pro His Phe Tyr Ser Cys Val Cys Pro Ser Gly Trp Ser
            6375                6380                6385
```

```
CTG TCT CCT GAT CTC CTG AAT TGC TTG AGA GAT GAT CAA CCT TTC TTA      5348
Leu Ser Pro Asp Leu Leu Asn Cys Leu Arg Asp Asp Gln Pro Phe Leu
        6390            6395            6400

ATA ACT GTA AGG CAA CAT ATA ATT TTT GGA ATC TCC CTT AAT CCT GAG      5396
Ile Thr Val Arg Gln His Ile Ile Phe Gly Ile Ser Leu Asn Pro Glu
6405            6410            6415            6420

GTG AAG AGC AAT GAT GCT ATG GTC CCC ATA GCA GGG ATA CAG AAT GGT      5444
Val Lys Ser Asn Asp Ala Met Val Pro Ile Ala Gly Ile Gln Asn Gly
            6425            6430            6435

TTA GAT GTT GAA TTT GAT GAT GCT GAG CAA TAC ATC TAT TGG GTT GAA      5492
Leu Asp Val Glu Phe Asp Asp Ala Glu Gln Tyr Ile Tyr Trp Val Glu
        6440            6445            6450

AAT CCA GGT GAA ATT CAC AGA GTG AAG ACA GAT GGC ACC AAC AGG ACA      5540
Asn Pro Gly Glu Ile His Arg Val Lys Thr Asp Gly Thr Asn Arg Thr
            6455            6460            6465

GTA TTT GCT TCT ATA TCT ATG GTG GGG CCT TCT ATG AAC CTG GCC TTA      5588
Val Phe Ala Ser Ile Ser Met Val Gly Pro Ser Met Asn Leu Ala Leu
        6470            6475            6480

GAT TGG ATT TCA AGA AAC CTT TAT TCT ACC AAT CCT AGA ACT CAG TCA      5636
Asp Trp Ile Ser Arg Asn Leu Tyr Ser Thr Asn Pro Arg Thr Gln Ser
6485            6490            6495            6500

ATC GAG GTT TTG ACA CTC CAC GGA GAT ATC AGA TAC AGA AAA ACA TTG      5684
Ile Glu Val Leu Thr Leu His Gly Asp Ile Arg Tyr Arg Lys Thr Leu
            6505            6510            6515

ATT GCC AAT GAT GGG ACA GCT CTT GGA GTT GGC TTT CCA ATT GGC ATA      5732
Ile Ala Asn Asp Gly Thr Ala Leu Gly Val Gly Phe Pro Ile Gly Ile
        6520            6525            6530

ACT GTT GAT CCT GCT CGT GGG AAG CTG TAC TGG TCA GAC CAA GGA ACT      5780
Thr Val Asp Pro Ala Arg Gly Lys Leu Tyr Trp Ser Asp Gln Gly Thr
            6535            6540            6545

GAC AGT GGG GTT CCT GCC AAG ATC GCC AGT GCT AAC ATG GAT GGC ACA      5828
Asp Ser Gly Val Pro Ala Lys Ile Ala Ser Ala Asn Met Asp Gly Thr
6550            6555            6560

TCT GTG AAA ACT CTC TTT ACT GGG AAC CTC GAA CAC CTG GAG TGT GTC      5876
Ser Val Lys Thr Leu Phe Thr Gly Asn Leu Glu His Leu Glu Cys Val
6565            6570            6575            6580

ACT CTT GAC ATC GAA GAG CAG AAA CTC TAC TGG GCA GTC ACT GGA AGA      5924
Thr Leu Asp Ile Glu Glu Gln Lys Leu Tyr Trp Ala Val Thr Gly Arg
            6585            6590            6595

GGA GTG ATT GAA AGA GGA AAC GTG GAT GGA ACA GAT CGG ATG ATC CTG      5972
Gly Val Ile Glu Arg Gly Asn Val Asp Gly Thr Asp Arg Met Ile Leu
        6600            6605            6610

GTA CAC CAG CTT TCC CAC CCC TGG GGA ATT GCA GTC CAT GAT TCT TTC      6020
Val His Gln Leu Ser His Pro Trp Gly Ile Ala Val His Asp Ser Phe
            6615            6620            6625

CTT TAT TAT ACT GAT GAA CAG TAT GAG GTC ATT GAA AGA GTT GAT AAG      6068
Leu Tyr Tyr Thr Asp Glu Gln Tyr Glu Val Ile Glu Arg Val Asp Lys
        6630            6635            6640

GCC ACT GGG GCC AAC AAA ATA GTC TTG AGA GAT AAT GTT CCA AAT CTG      6116
Ala Thr Gly Ala Asn Lys Ile Val Leu Arg Asp Asn Val Pro Asn Leu
6645            6650            6655            6660

AGG GGT CTT CAA GTT TAT CAC AGA CGC AAT GCC GCC GAA TCC TCA AAT      6164
Arg Gly Leu Gln Val Tyr His Arg Arg Asn Ala Ala Glu Ser Ser Asn
            6665            6670            6675

GGC TGT AGC AAC AAC ATG AAT GCC TGT CAG CAG ATT TGC CTG CCT GTA      6212
Gly Cys Ser Asn Asn Met Asn Ala Cys Gln Gln Ile Cys Leu Pro Val
        6680            6685            6690

CCA GGA GGA TTG TTT TCC TGC GCC TGT GCC ACT GGA TTT AAA CTC AAT      6260
Pro Gly Gly Leu Phe Ser Cys Ala Cys Ala Thr Gly Phe Lys Leu Asn
            6695            6700            6705
```

| | |
|---|---|
| CCT GAT AAT CGG TCC TGC TCT CCA TAT AAC TCT TTC ATT GTT GTT TCA<br>Pro Asp Asn Arg Ser Cys Ser Pro Tyr Asn Ser Phe Ile Val Val Ser<br>     6710                          6715                         6720 | 6308 |
| ATG CTG TCT GCA ATC AGA GGC TTT AGC TTG GAA TTG TCA GAT CAT TCA<br>Met Leu Ser Ala Ile Arg Gly Phe Ser Leu Glu Leu Ser Asp His Ser<br>6725                        6730                        6735                       6740 | 6356 |
| GAA ACC ATG GTG CCG GTG GCA GGC CAA GGA CGA AAC GCA CTG CAT GTG<br>Glu Thr Met Val Pro Val Ala Gly Gln Gly Arg Asn Ala Leu His Val<br>                         6745                         6750                       6755 | 6404 |
| GAT GTG GAT GTG TCC TCT GGC TTT ATT TAT TGG TGT GAT TTT AGC AGC<br>Asp Val Asp Val Ser Ser Gly Phe Ile Tyr Trp Cys Asp Phe Ser Ser<br>               6760                         6765                       6770 | 6452 |
| TCA GTG GCA TCT GAT AAT GCG ATC CGT AGA ATT AAA CCA GAT GGA TCT<br>Ser Val Ala Ser Asp Asn Ala Ile Arg Arg Ile Lys Pro Asp Gly Ser<br>     6775                          6780                        6785 | 6500 |
| TCT CTG ATG AAC ATT GTG ACA CAT GGA ATA GGA GAA AAT GGA GTC CGG<br>Ser Leu Met Asn Ile Val Thr His Gly Ile Gly Glu Asn Gly Val Arg<br>                         6790                         6795                       6800 | 6548 |
| GGT ATT GCA GTG GAT TGG GTA GCA GGA AAT CTT TAT TTC ACC AAT GCC<br>Gly Ile Ala Val Asp Trp Val Ala Gly Asn Leu Tyr Phe Thr Asn Ala<br>6805                        6810                        6815                       6820 | 6596 |
| TTT GTT TCT GAA ACA CTG ATA GAA GTT CTG CGG ATC AAT ACT ACT TAC<br>Phe Val Ser Glu Thr Leu Ile Glu Val Leu Arg Ile Asn Thr Thr Tyr<br>                         6825                         6830                       6835 | 6644 |
| CGC CGT GTT CTT CTT AAA GTC ACA GTG GAC ATG CCT AGG CAT ATT GTT<br>Arg Arg Val Leu Leu Lys Val Thr Val Asp Met Pro Arg His Ile Val<br>               6840                         6845                       6850 | 6692 |
| GTA GAT CCC AAG AAC AGA TAC CTC TTC TGG GCT GAC TAT GGG CAG AGA<br>Val Asp Pro Lys Asn Arg Tyr Leu Phe Trp Ala Asp Tyr Gly Gln Arg<br>     6855                          6860                        6865 | 6740 |
| CCA AAG ATT GAG CGT TCT TTC CTT GAC TGT ACC AAT CGA ACA GTG CTT<br>Pro Lys Ile Glu Arg Ser Phe Leu Asp Cys Thr Asn Arg Thr Val Leu<br>            6870                          6875                       6880 | 6788 |
| GTG TCA GAG GGC ATT GTC ACA CCA CGG GGC TTG GCA GTG GAC CGA AGT<br>Val Ser Glu Gly Ile Val Thr Pro Arg Gly Leu Ala Val Asp Arg Ser<br>6885                        6890                        6895                       6900 | 6836 |
| GAT GGC TAC GTT TAT TGG GTT GAT GAT TCT TTA GAT ATA ATT GCA AGG<br>Asp Gly Tyr Val Tyr Trp Val Asp Asp Ser Leu Asp Ile Ile Ala Arg<br>               6905                         6910                       6915 | 6884 |
| ATT CGT ATC AAT GGA GAG AAC TCT GAA GTG ATT CGT TAT GGC AGT CGT<br>Ile Arg Ile Asn Gly Glu Asn Ser Glu Val Ile Arg Tyr Gly Ser Arg<br>                         6920                         6925                       6930 | 6932 |
| TAC CCA ACT CCT TAT GGC ATC ACT GTT TTT GAA AAT TCT ATC ATA TGG<br>Tyr Pro Thr Pro Tyr Gly Ile Thr Val Phe Glu Asn Ser Ile Ile Trp<br>            6935                          6940                       6945 | 6980 |
| GTA GAT AGG AAT TTG AAA AAG ATC TTC CAA GCC AGC AAG GAA CCA GAG<br>Val Asp Arg Asn Leu Lys Lys Ile Phe Gln Ala Ser Lys Glu Pro Glu<br>               6950                         6955                       6960 | 7028 |
| AAC ACA GAG CCA CCC ACA GTG ATA AGA GAC AAT ATC AAC TGG CTA AGA<br>Asn Thr Glu Pro Pro Thr Val Ile Arg Asp Asn Ile Asn Trp Leu Arg<br>6965                        6970                        6975                       6980 | 7076 |
| GAT GTG ACC ATC TTT GAC AAG CAA GTC CAG CCC CGG TCA CCA GCA GAG<br>Asp Val Thr Ile Phe Asp Lys Gln Val Gln Pro Arg Ser Pro Ala Glu<br>                         6985                         6990                       6995 | 7124 |
| GTC AAC AAC AAC CCT TGC TTG GAA AAC AAT GGT GGG TGC TCT CAT CTC<br>Val Asn Asn Asn Pro Cys Leu Glu Asn Asn Gly Gly Cys Ser His Leu<br>                       7000                         7005                       7010 | 7172 |
| TGC TTT GCT CTG CCT GGA TTG CAC ACC CCA AAA TGT GAC TGT GCC TTT<br>Cys Phe Ala Leu Pro Gly Leu His Thr Pro Lys Cys Asp Cys Ala Phe | 7220 |

```
              7015                7020                7025
GGG ACC CTG CAA AGT GAT GGC AAG AAT TGT GCC ATT TCA ACA GAA AAT      7268
Gly Thr Leu Gln Ser Asp Gly Lys Asn Cys Ala Ile Ser Thr Glu Asn
            7030                7035            7040

TTC CTC ATC TTT GCC TTG TCT AAT TCC TTG AGA AGC TTA CAC TTG GAC      7316
Phe Leu Ile Phe Ala Leu Ser Asn Ser Leu Arg Ser Leu His Leu Asp
7045            7050                7055                7060

CCT GAA AAC CAT AGC CCA CCT TTC CAA ACA ATA AAT GTG GAA AGA ACT      7364
Pro Glu Asn His Ser Pro Pro Phe Gln Thr Ile Asn Val Glu Arg Thr
                7065                7070                7075

GTC ATG TCT CTA GAC TAT GAC AGT GTA AGT GAT AGA ATC TAC TTC ACA      7412
Val Met Ser Leu Asp Tyr Asp Ser Val Ser Asp Arg Ile Tyr Phe Thr
            7080                7085                7090

CAA AAT TTA GCC TCT GGA GTT GGA CAG ATT TCC TAT GCC ACC CTG TCT      7460
Gln Asn Leu Ala Ser Gly Val Gly Gln Ile Ser Tyr Ala Thr Leu Ser
                7095                7100                7105

TCA GGG ATC CAT ACT CCA ACT GTC ATT GCT TCA GGT ATA GGG ACT GCT      7508
Ser Gly Ile His Thr Pro Thr Val Ile Ala Ser Gly Ile Gly Thr Ala
            7110                7115                7120

GAT GGC ATT GCC TTT GAC TGG ATT ACT AGA AGA ATT TAT TAC AGT GAC      7556
Asp Gly Ile Ala Phe Asp Trp Ile Thr Arg Arg Ile Tyr Tyr Ser Asp
7125            7130                7135                7140

TAC CTC AAC CAG ATG ATT AAT TCC ATG GCT GAA GAT GGG TCT AAC CGC      7604
Tyr Leu Asn Gln Met Ile Asn Ser Met Ala Glu Asp Gly Ser Asn Arg
                7145                7150                7155

ACT GTG ATA GCC CGC GTT CCA AAA CCA AGA GCA ATT GTG TTA GAT CCC      7652
Thr Val Ile Ala Arg Val Pro Lys Pro Arg Ala Ile Val Leu Asp Pro
            7160                7165                7170

TGC CAA GGG TAC CTG TAC TGG GCT GAC TGG GAT ACA CAT GCC AAA ATC      7700
Cys Gln Gly Tyr Leu Tyr Trp Ala Asp Trp Asp Thr His Ala Lys Ile
                7175                7180                7185

GAG AGA GCC ACA TTG GGA GGA AAC TTC CGG GTA CCC ATT GTG AAC AGC      7748
Glu Arg Ala Thr Leu Gly Gly Asn Phe Arg Val Pro Ile Val Asn Ser
            7190                7195                7200

AGT CTG GTC ATG CCC AGT GGG CTG ACT CTG GAC TAT GAA GAG GAC CTT      7796
Ser Leu Val Met Pro Ser Gly Leu Thr Leu Asp Tyr Glu Glu Asp Leu
7205            7210                7215                7220

CTC TAC TGG GTG GAT GCT AGT CTG CAG AGG ATT GAA CGC AGC ACT CTG      7844
Leu Tyr Trp Val Asp Ala Ser Leu Gln Arg Ile Glu Arg Ser Thr Leu
                7225                7230                7235

ACG GGC GTG GAT CGT GAA GTC ATT GTC AAT GCA GCC GTT CAT GCT TTT      7892
Thr Gly Val Asp Arg Glu Val Ile Val Asn Ala Ala Val His Ala Phe
            7240                7245                7250

GGC TTG ACT CTC TAT GGC CAG TAT ATT TAC TGG ACT GAC TTG TAC ACA      7940
Gly Leu Thr Leu Tyr Gly Gln Tyr Ile Tyr Trp Thr Asp Leu Tyr Thr
            7255                7260                7265

CAA AGA ATT TAC CGA GCT AAC AAA TAT GAC GGG TCA GGT CAG ATT GCA      7988
Gln Arg Ile Tyr Arg Ala Asn Lys Tyr Asp Gly Ser Gly Gln Ile Ala
            7270                7275                7280

ATG ACC ACA AAT TTG CTC TCC CAG CCC AGG GGA ATC AAC ACT GTT GTG      8036
Met Thr Thr Asn Leu Leu Ser Gln Pro Arg Gly Ile Asn Thr Val Val
7285            7290                7295                7300

AAG AAC CAG AAA CAA CAG TGT AAC AAT CCT TGT GAA CAG TTT AAT GGG      8084
Lys Asn Gln Lys Gln Gln Cys Asn Asn Pro Cys Glu Gln Phe Asn Gly
                7305                7310                7315

GGC TGC AGC CAT ATC TGT GCA CCA GGT CCA AAT GGT GCC GAG TGC CAG      8132
Gly Cys Ser His Ile Cys Ala Pro Gly Pro Asn Gly Ala Glu Cys Gln
            7320                7325                7330

TGT CCA CAT GAG GGC AAC TGG TAT TTG GCC AAC AAC AGG AAG CAC TGC      8180
```

```
Cys Pro His Glu Gly Asn Trp Tyr Leu Ala Asn Asn Arg Lys His Cys
        7335                7340                7345

ATT GTG GAC AAT GGT GAA CGA TGT GGT GCA TCT TCC TTC ACC TGC TCC    8228
Ile Val Asp Asn Gly Glu Arg Cys Gly Ala Ser Ser Phe Thr Cys Ser
        7350                7355                7360

AAT GGG CGC TGC ATC TCG GAA GAG TGG AAG TGT GAT AAT GAC AAC GAC    8276
Asn Gly Arg Cys Ile Ser Glu Glu Trp Lys Cys Asp Asn Asp Asn Asp
7365                7370                7375                7380

TGT GGG GAT GGC AGT GAT GAG ATG GAA AGT GTC TGT GCA CTT CAC ACC    8324
Cys Gly Asp Gly Ser Asp Glu Met Glu Ser Val Cys Ala Leu His Thr
                7385                7390                7395

TGC TCA CCG ACA GCC TTC ACC TGT GCC AAT GGG CGA TGT GTC CAA TAC    8372
Cys Ser Pro Thr Ala Phe Thr Cys Ala Asn Gly Arg Cys Val Gln Tyr
            7400                7405                7410

TCT TAC CGC TGT GAT TAC TAC AAT GAC TGT GGT GAT GGC AGT GAT GAG    8420
Ser Tyr Arg Cys Asp Tyr Tyr Asn Asp Cys Gly Asp Gly Ser Asp Glu
        7415                7420                7425

GCA GGG TGC CTG TTC AGG GAC TGC AAT GCC ACC ACG GAG TTT ATG TGC    8468
Ala Gly Cys Leu Phe Arg Asp Cys Asn Ala Thr Thr Glu Phe Met Cys
    7430                7435                7440

AAT AAC AGA AGG TGC ATA CCT CGT GAG TTT ATC TGC AAT GGT GTA GAC    8516
Asn Asn Arg Arg Cys Ile Pro Arg Glu Phe Ile Cys Asn Gly Val Asp
7445                7450                7455                7460

AAC TGC CAT GAT AAT AAC ACT TCA GAT GAG AAA AAT TGC CCT GAT CGC    8564
Asn Cys His Asp Asn Asn Thr Ser Asp Glu Lys Asn Cys Pro Asp Arg
                7465                7470                7475

ACT TGC CAG TCT GGA TAC ACA AAA TGT CAT AAT TCA AAT ATT TGT ATT    8612
Thr Cys Gln Ser Gly Tyr Thr Lys Cys His Asn Ser Asn Ile Cys Ile
            7480                7485                7490

CCT CGC GTT TAT TTG TGT GAC GGA GAC AAT GAC TGT GGA GAT AAC AGT    8660
Pro Arg Val Tyr Leu Cys Asp Gly Asp Asn Asp Cys Gly Asp Asn Ser
        7495                7500                7505

GAT GAA AAC CCT ACT TAT TGC ACC ACT CAC ACA TGC AGC AGC AGT GAG    8708
Asp Glu Asn Pro Thr Tyr Cys Thr Thr His Thr Cys Ser Ser Ser Glu
    7510                7515                7520

TTC CAA TGC GCA TCT GGG CGC TGT ATT CCT CAA CAT TGG TAT TGT GAT    8756
Phe Gln Cys Ala Ser Gly Arg Cys Ile Pro Gln His Trp Tyr Cys Asp
7525                7530                7535                7540

CAA GAA ACA GAT TGT TTT GAT GCC TCT GAT GAA CCT GCC TCT TGT GGT    8804
Gln Glu Thr Asp Cys Phe Asp Ala Ser Asp Glu Pro Ala Ser Cys Gly
                7545                7550                7555

CAC TCT GAG CGA ACA TGC CTA GCT GAT GAG TTC AAG TGT GAT GGT GGG    8852
His Ser Glu Arg Thr Cys Leu Ala Asp Glu Phe Lys Cys Asp Gly Gly
            7560                7565                7570

AGG TGC ATC CCA AGC GAA TGG ATC TGT GAC GGT GAT AAT GAC TGT GGG    8900
Arg Cys Ile Pro Ser Glu Trp Ile Cys Asp Gly Asp Asn Asp Cys Gly
        7575                7580                7585

GAT ATG AGT GAC GAG GAT AAA AGG CAC CAG TGT CAG AAT CAA AAC TGC    8948
Asp Met Ser Asp Glu Asp Lys Arg His Gln Cys Gln Asn Gln Asn Cys
    7590                7595                7600

TCG GAT TCC GAG TTT CTC TGT GTA AAT GAC AGA CCT CCG GAC AGG AGG    8996
Ser Asp Ser Glu Phe Leu Cys Val Asn Asp Arg Pro Pro Asp Arg Arg
7605                7610                7615                7620

TGC ATT CCC CAG TCT TGG GTC TGT GAT GGC GAT GTG GAT TGT ACT GAC    9044
Cys Ile Pro Gln Ser Trp Val Cys Asp Gly Asp Val Asp Cys Thr Asp
                7625                7630                7635

GGC TAC GAT GAG AAT CAG AAT TGC ACC AGG AGA ACT TGC TCT GAA AAT    9092
Gly Tyr Asp Glu Asn Gln Asn Cys Thr Arg Arg Thr Cys Ser Glu Asn
            7640                7645                7650
```

```
                                                            -continued

GAA TTC ACC TGT GGT TAC GGA CTG TGT ATC CCA AAG ATA TTC AGG TGT      9140
Glu Phe Thr Cys Gly Tyr Gly Leu Cys Ile Pro Lys Ile Phe Arg Cys
        7655                7660                7665

GAC CGG CAC AAT GAC TGT GGT GAC TAT AGC GAC GAG AGG GGC TGC TTA      9188
Asp Arg His Asn Asp Cys Gly Asp Tyr Ser Asp Glu Arg Gly Cys Leu
        7670                7675                7680

TAC CAG ACT TGC CAA CAG AAT CAG TTT ACC TGT CAG AAC GGG CGC TGC      9236
Tyr Gln Thr Cys Gln Gln Asn Gln Phe Thr Cys Gln Asn Gly Arg Cys
7685                7690                7695                7700

ATT AGT AAA ACC TTC GTC TGT GAT GAG GAT AAT GAC TGT GGA GAC GGA      9284
Ile Ser Lys Thr Phe Val Cys Asp Glu Asp Asn Asp Cys Gly Asp Gly
        7705                7710                7715

TCT GAT GAG CTG ATG CAC CTG TGC CAC ACC CCA GAA CCC ACG TGT CCA      9332
Ser Asp Glu Leu Met His Leu Cys His Thr Pro Glu Pro Thr Cys Pro
        7720                7725                7730

CCT CAC GAG TTC AAG TGT GAC AAT GGG CGC TGC ATC GAG ATG ATG AAA      9380
Pro His Glu Phe Lys Cys Asp Asn Gly Arg Cys Ile Glu Met Met Lys
        7735                7740                7745

CTC TGC AAC CAC CTA GAT GAC TGT TTG GAC AAC AGC GAT GAG AAA GGC      9428
Leu Cys Asn His Leu Asp Asp Cys Leu Asp Asn Ser Asp Glu Lys Gly
        7750                7755                7760

TGT GGC ATT AAT GAA TGC CAT GAC CCT TCA ATC AGT GGC TGC GAT CAC      9476
Cys Gly Ile Asn Glu Cys His Asp Pro Ser Ile Ser Gly Cys Asp His
7765                7770                7775                7780

AAC TGC ACA GAC ACC TTA ACC AGT TTC TAT TGT TCC TGT CGT CCT GGT      9524
Asn Cys Thr Asp Thr Leu Thr Ser Phe Tyr Cys Ser Cys Arg Pro Gly
        7785                7790                7795

TAC AAG CTC ATG TCT GAC AAG CGG ACT TGT GTT GAT ATT GAT GAA TGC      9572
Tyr Lys Leu Met Ser Asp Lys Arg Thr Cys Val Asp Ile Asp Glu Cys
        7800                7805                7810

ACA GAG ATG CCT TTT GTC TGT AGC CAG AAG TGT GAG AAT GTA ATA GGC      9620
Thr Glu Met Pro Phe Val Cys Ser Gln Lys Cys Glu Asn Val Ile Gly
        7815                7820                7825

TCC TAC ATC TGT AAG TGT GCC CCA GGC TAC CTC CGA GAA CCA GAT GGA      9668
Ser Tyr Ile Cys Lys Cys Ala Pro Gly Tyr Leu Arg Glu Pro Asp Gly
        7830                7835                7840

AAG ACC TGC CGG CAA AAC AGT AAC ATC GAA CCC TAT CTC ATT TTT AGC      9716
Lys Thr Cys Arg Gln Asn Ser Asn Ile Glu Pro Tyr Leu Ile Phe Ser
7845                7850                7855                7860

AAC CGT TAC TAT TTG AGA AAT TTA ACT ATA GAT GGC TAT TTT TAC TCC      9764
Asn Arg Tyr Tyr Leu Arg Asn Leu Thr Ile Asp Gly Tyr Phe Tyr Ser
        7865                7870                7875

CTC ATC TTG GAA GGA CTG GAC AAT GTT GTG GCA TTA GAT TTT GAC CGA      9812
Leu Ile Leu Glu Gly Leu Asp Asn Val Val Ala Leu Asp Phe Asp Arg
        7880                7885                7890

GTA GAG AAG AGA TTG TAT TGG ATT GAT ACA CAG AGG CAA GTC ATT GAG      9860
Val Glu Lys Arg Leu Tyr Trp Ile Asp Thr Gln Arg Gln Val Ile Glu
        7895                7900                7905

AGA ATG TTT CTG AAT AAG ACA AAC AAG GAG ACA ATC ATA AAC CAC AGA      9908
Arg Met Phe Leu Asn Lys Thr Asn Lys Glu Thr Ile Ile Asn His Arg
        7910                7915                7920

CTA CCA GCT GCA GAA AGT CTG GCT GTA GAC TGG GTT TCC AGA AAG CTC      9956
Leu Pro Ala Ala Glu Ser Leu Ala Val Asp Trp Val Ser Arg Lys Leu
7925                7930                7935                7940

TAC TGG TTG GAT GCC CGC CTG GAT GGC CTC TTT GTC TCT GAC CTC AAT     10004
Tyr Trp Leu Asp Ala Arg Leu Asp Gly Leu Phe Val Ser Asp Leu Asn
        7945                7950                7955

GGT GGA CAC CGC CGC ATG CTG GCC CAG CAC TGT GTG GAT GCC AAC AAC     10052
Gly Gly His Arg Arg Met Leu Ala Gln His Cys Val Asp Ala Asn Asn
        7960                7965                7970
```

| | | | | | | | | | | | | | | |
|---|---|---|---|---|---|---|---|---|---|---|---|---|---|---|
| ACC | TTC | TGC | TTT | GAT | AAT | CCC | AGA | GGA | CTT | GCC | CTT | CAC | CCT | CAA | TAT | 10100 |
| Thr | Phe | Cys | Phe | Asp | Asn | Pro | Arg | Gly | Leu | Ala | Leu | His | Pro | Gln | Tyr |
| | | 7975 | | | | 7980 | | | | 7985 | | | |

| GGT | TAC | CTC | TAC | TGG | GCA | GAC | TGG | GGT | CAC | CGC | GCA | TAC | ATT | GGG | AGA | 10148 |
| Gly | Tyr | Leu | Tyr | Trp | Ala | Asp | Trp | Gly | His | Arg | Ala | Tyr | Ile | Gly | Arg |
| | | 7990 | | | | 7995 | | | | 8000 | | | |

| GTA | GGC | ATG | GAT | GGA | ACC | AAC | AAG | TCT | GTG | ATA | ATC | TCC | ACC | AAG | TTA | 10196 |
| Val | Gly | Met | Asp | Gly | Thr | Asn | Lys | Ser | Val | Ile | Ile | Ser | Thr | Lys | Leu |
| 8005 | | | | 8010 | | | | 8015 | | | | 8020 |

| GAG | TGG | CCT | AAT | GGC | ATC | ACC | ATT | GAT | TAC | ACC | AAT | GAT | CTA | CTC | TAC | 10244 |
| Glu | Trp | Pro | Asn | Gly | Ile | Thr | Ile | Asp | Tyr | Thr | Asn | Asp | Leu | Leu | Tyr |
| | | 8025 | | | | 8030 | | | | 8035 | | | |

| TGG | GCA | GAT | GCC | CAC | CTG | GGT | TAC | ATA | GAG | TAC | TCT | GAT | TTG | GAG | GGC | 10292 |
| Trp | Ala | Asp | Ala | His | Leu | Gly | Tyr | Ile | Glu | Tyr | Ser | Asp | Leu | Glu | Gly |
| | | 8040 | | | | 8045 | | | | 8050 | | | |

| CAC | CAT | CGA | CAC | ACG | GTG | TAT | GAT | GGG | GCA | CTG | CCT | CAC | CCT | TTC | GCT | 10340 |
| His | His | Arg | His | Thr | Val | Tyr | Asp | Gly | Ala | Leu | Pro | His | Pro | Phe | Ala |
| | | 8055 | | | | 8060 | | | | 8065 | | | |

| ATT | ACC | ATT | TTT | GAA | GAC | ACT | ATT | TAT | TGG | ACA | GAT | TGG | AAT | ACA | AGG | 10388 |
| Ile | Thr | Ile | Phe | Glu | Asp | Thr | Ile | Tyr | Trp | Thr | Asp | Trp | Asn | Thr | Arg |
| | | 8070 | | | | 8075 | | | | 8080 | | | |

| ACA | GTG | GAA | AAG | GGA | AAC | AAA | TAT | GAT | GGA | TCA | AAT | AGA | CAG | ACA | CTG | 10436 |
| Thr | Val | Glu | Lys | Gly | Asn | Lys | Tyr | Asp | Gly | Ser | Asn | Arg | Gln | Thr | Leu |
| 8085 | | | | 8090 | | | | 8095 | | | | 8100 |

| GTG | AAC | ACA | ACA | CAC | AGA | CCA | TTT | GAC | ATC | CAT | GTG | TAC | CAT | CCA | TAT | 10484 |
| Val | Asn | Thr | Thr | His | Arg | Pro | Phe | Asp | Ile | His | Val | Tyr | His | Pro | Tyr |
| | | 8105 | | | | 8110 | | | | 8115 | | | |

| AGG | CAG | CCC | ATT | GTG | AGC | AAT | CCC | TGT | GGT | ACC | AAC | AAT | GGT | GGC | TGT | 10532 |
| Arg | Gln | Pro | Ile | Val | Ser | Asn | Pro | Cys | Gly | Thr | Asn | Asn | Gly | Gly | Cys |
| | | 8120 | | | | 8125 | | | | 8130 | | | |

| TCT | CAT | CTC | TGC | CTC | ATC | AAG | CCA | GGA | GGA | AAA | GGG | TTC | ACT | TGC | GAG | 10580 |
| Ser | His | Leu | Cys | Leu | Ile | Lys | Pro | Gly | Gly | Lys | Gly | Phe | Thr | Cys | Glu |
| | | 8135 | | | | 8140 | | | | 8145 | | | |

| TGT | CCA | GAT | GAC | TTC | CGC | ACC | CTT | CAA | CTG | AGT | GGC | AGC | ACC | TAC | TGC | 10628 |
| Cys | Pro | Asp | Asp | Phe | Arg | Thr | Leu | Gln | Leu | Ser | Gly | Ser | Thr | Tyr | Cys |
| | | 8150 | | | | 8155 | | | | 8160 | | | |

| ATG | CCC | ATG | TGC | TCC | AGC | ACC | CAG | TTC | CTG | TGC | GCT | AAC | AAT | GAA | AAG | 10676 |
| Met | Pro | Met | Cys | Ser | Ser | Thr | Gln | Phe | Leu | Cys | Ala | Asn | Asn | Glu | Lys |
| 8165 | | | | 8170 | | | | 8175 | | | | 8180 |

| TGC | ATT | CCT | ATC | TGG | TGG | AAA | TGT | GAT | GGA | CAG | AAA | GAC | TGC | TCA | GAT | 10724 |
| Cys | Ile | Pro | Ile | Trp | Trp | Lys | Cys | Asp | Gly | Gln | Lys | Asp | Cys | Ser | Asp |
| | | 8185 | | | | 8190 | | | | 8195 | | | |

| GGC | TCT | GAT | GAA | CTG | GCC | CTT | TGC | CCG | CAG | CGC | TTC | TGC | CGA | CTG | GGA | 10772 |
| Gly | Ser | Asp | Glu | Leu | Ala | Leu | Cys | Pro | Gln | Arg | Phe | Cys | Arg | Leu | Gly |
| | | 8200 | | | | 8205 | | | | 8210 | | | |

| CAG | TTC | CAG | TGC | AGT | GAC | GGC | AAC | TGC | ACC | AGC | CCG | CAG | ACT | TTA | TGC | 10820 |
| Gln | Phe | Gln | Cys | Ser | Asp | Gly | Asn | Cys | Thr | Ser | Pro | Gln | Thr | Leu | Cys |
| | | 8215 | | | | 8220 | | | | 8225 | | | |

| AAT | GCT | CAC | CAA | AAT | TGC | CCT | GAT | GGG | TCT | GAT | GAA | GAC | CGT | CTT | CTT | 10868 |
| Asn | Ala | His | Gln | Asn | Cys | Pro | Asp | Gly | Ser | Asp | Glu | Asp | Arg | Leu | Leu |
| | | 8230 | | | | 8235 | | | | 8240 | | | |

| TGT | GAG | AAT | CAC | CAC | TGT | GAC | TCC | AAT | GAA | TGG | CAG | TGC | GCC | AAC | AAA | 10916 |
| Cys | Glu | Asn | His | His | Cys | Asp | Ser | Asn | Glu | Trp | Gln | Cys | Ala | Asn | Lys |
| 8245 | | | | 8250 | | | | 8255 | | | | 8260 |

| CGT | TGC | ATC | CCA | GAA | TCC | TGG | CAG | TGT | GAC | ACA | TTT | AAC | GAC | TGT | GAG | 10964 |
| Arg | Cys | Ile | Pro | Glu | Ser | Trp | Gln | Cys | Asp | Thr | Phe | Asn | Asp | Cys | Glu |
| | | 8265 | | | | 8270 | | | | 8275 | | | |

| GAT | AAC | TCA | GAT | GAA | GAC | AGT | TCC | CAC | TGT | GCC | AGC | AGG | ACC | TGC | CGG | 11012 |
| Asp | Asn | Ser | Asp | Glu | Asp | Ser | Ser | His | Cys | Ala | Ser | Arg | Thr | Cys | Arg |

-continued

```
           8280                 8285                 8290

CCG GGC CAG TTT CGG TGT GCT AAT GGC CGC TGC ATC CCG CAG GCC TGG    11060
Pro Gly Gln Phe Arg Cys Ala Asn Gly Arg Cys Ile Pro Gln Ala Trp
        8295                 8300                 8305

AAG TGT GAT GTG GAT AAT GAT TGT GGA GAC CAC TCG GAT GAG CCC ATT    11108
Lys Cys Asp Val Asp Asn Asp Cys Gly Asp His Ser Asp Glu Pro Ile
            8310                 8315                 8320

GAA GAA TGC ATG AGC TCT GCC CAT CTC TGT GAC AAC TTC ACA GAA TTC    11156
Glu Glu Cys Met Ser Ser Ala His Leu Cys Asp Asn Phe Thr Glu Phe
8325                 8330                 8335                 8340

AGC TGC AAA ACA AAT TAC CGC TGC ATC CCA AAG TGG GCC GTG TGC AAT    11204
Ser Cys Lys Thr Asn Tyr Arg Cys Ile Pro Lys Trp Ala Val Cys Asn
        8345                 8350                 8355

GGT GTA GAT GAC TGC AGG GAC AAC AGT GAT GAG CAA GGC TGT GAG GAG    11252
Gly Val Asp Asp Cys Arg Asp Asn Ser Asp Glu Gln Gly Cys Glu Glu
            8360                 8365                 8370

AGG ACA TGC CAT CCT GTG GGG GAT TTC CGC TGT AAA AAT CAC CAC TGC    11300
Arg Thr Cys His Pro Val Gly Asp Phe Arg Cys Lys Asn His His Cys
        8375                 8380                 8385

ATC CCT CTT CGT TGG CAG TGT GAT GGG CAA AAT GAC TGT GGA GAT AAC    11348
Ile Pro Leu Arg Trp Gln Cys Asp Gly Gln Asn Asp Cys Gly Asp Asn
        8390                 8395                 8400

TCA GAT GAG GAA AAC TGT GCT CCC CGG GAG TGC ACA GAG AGC GAG TTT    11396
Ser Asp Glu Glu Asn Cys Ala Pro Arg Glu Cys Thr Glu Ser Glu Phe
8405                 8410                 8415                 8420

CGA TGT GTC AAT CAG CAG TGC ATT CCC TCG CGA TGG ATC TGT GAC CAT    11444
Arg Cys Val Asn Gln Gln Cys Ile Pro Ser Arg Trp Ile Cys Asp His
            8425                 8430                 8435

TAC AAC GAC TGT GGG GAC AAC TCA GAT GAA CGG GAC TGT GAG ATG AGG    11492
Tyr Asn Asp Cys Gly Asp Asn Ser Asp Glu Arg Asp Cys Glu Met Arg
        8440                 8445                 8450

ACC TGC CAT CCT GAA TAT TTT CAG TGT ACA AGT GGA CAT TGT GTA CAC    11540
Thr Cys His Pro Glu Tyr Phe Gln Cys Thr Ser Gly His Cys Val His
            8455                 8460                 8465

AGT GAA CTG AAA TGC GAT GGA TCC GCT GAC TGT TTG GAT GCG TCT GAT    11588
Ser Glu Leu Lys Cys Asp Gly Ser Ala Asp Cys Leu Asp Ala Ser Asp
        8470                 8475                 8480

GAA GCT GAT TGT CCC ACA CGC TTT CCT GAT GGT GCA TAC TGC CAG GCT    11636
Glu Ala Asp Cys Pro Thr Arg Phe Pro Asp Gly Ala Tyr Cys Gln Ala
8485                 8490                 8495                 8500

ACT ATG TTC GAA TGC AAA AAC CAT GTT TGT ATC CCG CCA TAT TGG AAA    11684
Thr Met Phe Glu Cys Lys Asn His Val Cys Ile Pro Pro Tyr Trp Lys
            8505                 8510                 8515

TGT GAT GGC GAT GAT GAC TGT GGC GAT GGT TCA GAT GAA GAA CTT CAC    11732
Cys Asp Gly Asp Asp Asp Cys Gly Asp Gly Ser Asp Glu Glu Leu His
            8520                 8525                 8530

CTG TGC TTG GAT GTT CCC TGT AAT TCA CCA AAC CGT TTC CGG TGT GAC    11780
Leu Cys Leu Asp Val Pro Cys Asn Ser Pro Asn Arg Phe Arg Cys Asp
        8535                 8540                 8545

AAC AAT CGC TGC ATT TAT AGT CAT GAG GTG TGC AAT GGT GTG GAT GAC    11828
Asn Asn Arg Cys Ile Tyr Ser His Glu Val Cys Asn Gly Val Asp Asp
        8550                 8555                 8560

TGT GGA GAT GGA ACT GAT GAG ACA GAG GAG CAC TGT AGA AAA CCG ACC    11876
Cys Gly Asp Gly Thr Asp Glu Thr Glu Glu His Cys Arg Lys Pro Thr
8565                 8570                 8575                 8580

CCT AAA CCT TGT ACA GAA TAT GAA TAT AAG TGT GGC AAT GGG CAT TGC    11924
Pro Lys Pro Cys Thr Glu Tyr Glu Tyr Lys Cys Gly Asn Gly His Cys
        8585                 8590                 8595

ATT CCA CAT GAC AAT GTG TGT GAT GAT GCC GAT GAC TGT GGT GAC TGG    11972
```

```
Ile Pro His Asp Asn Val Cys Asp Asp Ala Asp Cys Gly Asp Trp
        8600                8605                8610

TCC GAT GAA CTG GGT TGC AAT AAA GGA AAA GAA AGA ACA TGT GCT GAA    12020
Ser Asp Glu Leu Gly Cys Asn Lys Gly Lys Glu Arg Thr Cys Ala Glu
        8615                8620                8625

AAT ATA TGC GAG CAA AAT TGT ACC CAA TTA AAT GAA GGA GGA TTT ATC    12068
Asn Ile Cys Glu Gln Asn Cys Thr Gln Leu Asn Glu Gly Gly Phe Ile
        8630                8635                8640

TGC TCC TGT ACA GCT GGG TTC GAA ACC AAT GTT TTT GAC AGA ACC TCC    12116
Cys Ser Cys Thr Ala Gly Phe Glu Thr Asn Val Phe Asp Arg Thr Ser
8645                8650                8655                8660

TGT CTA GAT ATC AAT GAA TGT GAA CAA TTT GGG ACT TGT CCC CAG CAC    12164
Cys Leu Asp Ile Asn Glu Cys Glu Gln Phe Gly Thr Cys Pro Gln His
                8665                8670                8675

TGC AGA AAT ACC AAA GGA AGT TAT GAG TGT GTC TGT GCT GAT GGC TTC    12212
Cys Arg Asn Thr Lys Gly Ser Tyr Glu Cys Val Cys Ala Asp Gly Phe
        8680                8685                8690

ACG TCT ATG AGT GAC CGC CCT GGA AAA CGA TGT GCA GCT GAG GGT AGC    12260
Thr Ser Met Ser Asp Arg Pro Gly Lys Arg Cys Ala Ala Glu Gly Ser
        8695                8700                8705

TCT CCT TTG TTG CTA CTG CCT GAC AAT GTC CGA ATT CGA AAA TAT AAT    12308
Ser Pro Leu Leu Leu Leu Pro Asp Asn Val Arg Ile Arg Lys Tyr Asn
        8710                8715                8720

CTC TCA TCT GAG AGG TTC TCA GAG TAT CTT CAA GAT GAG GAA TAT ATC    12356
Leu Ser Ser Glu Arg Phe Ser Glu Tyr Leu Gln Asp Glu Glu Tyr Ile
8725                8730                8735                8740

CAA GCT GTT GAT TAT GAT TGG GAT CCC GAG GAC ATA GGC CTC AGT GTT    12404
Gln Ala Val Asp Tyr Asp Trp Asp Pro Glu Asp Ile Gly Leu Ser Val
                8745                8750                8755

GTG TAT TAC ACT GTG CGA GGG GAG GGC TCT AGG TTT GGT GCT ATC AAA    12452
Val Tyr Tyr Thr Val Arg Gly Glu Gly Ser Arg Phe Gly Ala Ile Lys
        8760                8765                8770

CGT GCC TAC ATC CCC AAC TTT GAA TCC GGC CGC AAT AAT CTT GTG CAG    12500
Arg Ala Tyr Ile Pro Asn Phe Glu Ser Gly Arg Asn Asn Leu Val Gln
        8775                8780                8785

GAA GTT GAC CTG AAA CTG AAA TAC GTA ATG CAG CCA GAT GGA ATA GCA    12548
Glu Val Asp Leu Lys Leu Lys Tyr Val Met Gln Pro Asp Gly Ile Ala
        8790                8795                8800

GTG GAC TGG GTT GGA AGG CAT ATT TAC TGG TCA GAT GTC AAG AAT AAA    12596
Val Asp Trp Val Gly Arg His Ile Tyr Trp Ser Asp Val Lys Asn Lys
8805                8810                8815                8820

CGC ATT GAG GTG GCT AAA CTT GAT GGA AGG TAC AGA AAG TGG CTG ATT    12644
Arg Ile Glu Val Ala Lys Leu Asp Gly Arg Tyr Arg Lys Trp Leu Ile
                8825                8830                8835

TCC ACT GAC CTG GAC CAA CCA GCT GCT ATT GCT GTG AAT CCC AAA CTA    12692
Ser Thr Asp Leu Asp Gln Pro Ala Ala Ile Ala Val Asn Pro Lys Leu
        8840                8845                8850

GGG CTT ATG TTC TGG ACT GAC TGG GGA AAG GAA CCT AAA MTC GAG TCT    12740
Gly Leu Met Phe Trp Thr Asp Trp Gly Lys Glu Pro Lys Xaa Glu Ser
        8855                8860                8865

GCC TGG ATG AAT GGA GAG GAC CGC AAC ATC CTG GTT TTC GAG GAC CTT    12788
Ala Trp Met Asn Gly Glu Asp Arg Asn Ile Leu Val Phe Glu Asp Leu
        8870                8875                8880

GGT TGG CCA ACT GGC CTT TCT ATC GAT TAT TTG AAC AAT GAC CGA ATC    12836
Gly Trp Pro Thr Gly Leu Ser Ile Asp Tyr Leu Asn Asn Asp Arg Ile
8885                8890                8895                8900

TAC TGG AGT GAC TTC AAG GAG GAC GTT ATT GAA ACC ATA AAA TAT GAT    12884
Tyr Trp Ser Asp Phe Lys Glu Asp Val Ile Glu Thr Ile Lys Tyr Asp
                8905                8910                8915
```

-continued

| | |
|---|---|
| GGG ACT GAT AGG AGA GTC ATT GCA AAG GAA GCA ATG AAC CCT TAC AGC<br>Gly Thr Asp Arg Arg Val Ile Ala Lys Glu Ala Met Asn Pro Tyr Ser<br>              8920                        8925                       8930 | 12932 |
| CTG GAC ATC TTT GAA GAC CAG TTA TAC TGG ATA TCT AAG GAA AAG GGA<br>Leu Asp Ile Phe Glu Asp Gln Leu Tyr Trp Ile Ser Lys Glu Lys Gly<br>              8935                        8940                       8945 | 12980 |
| GAA GTA TGG AAA CAA AAT AAA TTT GGG CAA GGA AAG AAA GAG AAA ACG<br>Glu Val Trp Lys Gln Asn Lys Phe Gly Gln Gly Lys Lys Glu Lys Thr<br>              8950                        8955                       8960 | 13028 |
| CTG GTA GTG AAC CCT TGG CTC ACT CAA GTT CGA ATC TTT CAT CAA CTC<br>Leu Val Val Asn Pro Trp Leu Thr Gln Val Arg Ile Phe His Gln Leu<br>8965                       8970                       8975                       8980 | 13076 |
| AGA TAC AAT AAG TCA GTG CCC AAC CTT TGC AAA CAG ATC TGC AGC CAC<br>Arg Tyr Asn Lys Ser Val Pro Asn Leu Cys Lys Gln Ile Cys Ser His<br>              8985                        8990                       8995 | 13124 |
| CTC TGC CTT CTG AGA CCT GGA GGA TAC AGC TGT GCC TGT CCC CAA GGC<br>Leu Cys Leu Leu Arg Pro Gly Gly Tyr Ser Cys Ala Cys Pro Gln Gly<br>              9000                        9005                       9010 | 13172 |
| TCC AGC TTT ATA GAG GGG AGC ACC ACT GAG TGT GAT GCA GCC ATC GAA<br>Ser Ser Phe Ile Glu Gly Ser Thr Thr Glu Cys Asp Ala Ala Ile Glu<br>              9015                        9020                       9025 | 13220 |
| CTG CCT ATC AAC CTG CCC CCC CCA TGC AGG TGC ATG CAC GGA GGA AAT<br>Leu Pro Ile Asn Leu Pro Pro Pro Cys Arg Cys Met His Gly Gly Asn<br>              9030                        9035                       9040 | 13268 |
| TGC TAT TTT GAT GAG ACT GAC CTC CCC AAA TGC AAG TGT CCT AGC GGC<br>Cys Tyr Phe Asp Glu Thr Asp Leu Pro Lys Cys Lys Cys Pro Ser Gly<br>9045                       9050                       9055                       9060 | 13316 |
| TAC ACC GGA AAA TAT TGT GAA ATG GCG TTT TCA AAA GGC ATC TCT CCA<br>Tyr Thr Gly Lys Tyr Cys Glu Met Ala Phe Ser Lys Gly Ile Ser Pro<br>              9065                        9070                       9075 | 13364 |
| GGA ACA ACC GCA GTA GCT GTG CTG TTG ACA ATC CTC TTG ATC GTC GTA<br>Gly Thr Thr Ala Val Ala Val Leu Leu Thr Ile Leu Leu Ile Val Val<br>              9080                        9085                       9090 | 13412 |
| ATT GGA GCT CTG GCA ATT GCA GGA TTC TTC CAC TAT AGA AGG ACC GGC<br>Ile Gly Ala Leu Ala Ile Ala Gly Phe Phe His Tyr Arg Arg Thr Gly<br>              9095                        9100                       9105 | 13460 |
| TCC CTT TTG CCT GCT CTG CCC AAG CTG CCA AGC TTA AGC AGT CTC GTC<br>Ser Leu Leu Pro Ala Leu Pro Lys Leu Pro Ser Leu Ser Ser Leu Val<br>              9110                        9115                       9120 | 13508 |
| AAG CCC TCT GAA AAT GGG AAT GGG GTG ACC TTC AGA TCA GGG GCA GAT<br>Lys Pro Ser Glu Asn Gly Asn Gly Val Thr Phe Arg Ser Gly Ala Asp<br>9125                       9130                       9135                       9140 | 13556 |
| CTT AAC ATG GAT ATT GGA GTG TCT GGT TTT GGA CCT GAG ACT GCT ATT<br>Leu Asn Met Asp Ile Gly Val Ser Gly Phe Gly Pro Glu Thr Ala Ile<br>              9145                        9150                       9155 | 13604 |
| GAC AGG TCA ATG GCA ATG AGT GAA GAC TTT GTC ATG GAA ATG GGG AAG<br>Asp Arg Ser Met Ala Met Ser Glu Asp Phe Val Met Glu Met Gly Lys<br>              9160                        9165                       9170 | 13652 |
| CAG CCC ATA ATA TTT GAA AAC CCA ATG TAC TCA GCC AGA GAC AGT GCT<br>Gln Pro Ile Ile Phe Glu Asn Pro Met Tyr Ser Ala Arg Asp Ser Ala<br>              9175                        9180                       9185 | 13700 |
| GTC AAA GTG GTT CAG CCA ATC CAG GTG ACT GTA TCT GAA AAT GTG GAT<br>Val Lys Val Val Gln Pro Ile Gln Val Thr Val Ser Glu Asn Val Asp<br>              9190                        9195                       9200 | 13748 |
| AAT AAG AAT TAT GGA AGT CCC ATA AAC CCT TCT GAG ATA GTT CCA GAG<br>Asn Lys Asn Tyr Gly Ser Pro Ile Asn Pro Ser Glu Ile Val Pro Glu<br>9205                       9210                       9215                       9220 | 13796 |
| ACA AAC CCA ACT TCA CCA GCT GCT GAT GGA ACT CAG GTG ACA AAA TGG<br>Thr Asn Pro Thr Ser Pro Ala Ala Asp Gly Thr Gln Val Thr Lys Trp<br>              9225                        9230                       9235 | 13844 |

```
AAT CTC TTC AAA CGA AAA TCT AAA CAA ACT ACC AAC TTT GAA AAT CCA      13892
Asn Leu Phe Lys Arg Lys Ser Lys Gln Thr Thr Asn Phe Glu Asn Pro
        9240                9245                9250

ATC TAT GCA CAG ATG GAG AAC GAG CAA AAG GAA AGT GTT GCT GCG ACA      13940
Ile Tyr Ala Gln Met Glu Asn Glu Gln Lys Glu Ser Val Ala Ala Thr
        9255                9260                9265

CCA CCT CCA TCA CCT TCG CTC CCT GCT AAG CCT AAG CCT CCT TCG AGA      13988
Pro Pro Pro Ser Pro Ser Leu Pro Ala Lys Pro Lys Pro Pro Ser Arg
        9270                9275                9280

AGA GAC CCA ACT CCA ACC TAT TCT GCA ACA GAA GAC ACT TTT AAA GAC      14036
Arg Asp Pro Thr Pro Thr Tyr Ser Ala Thr Glu Asp Thr Phe Lys Asp
9285                9290                9295                9300

ACC GCA AAT CTT GTT AAA GAA GAC TCT GAA GTA TAG CTATACCA             14080
Thr Ala Asn Leu Val Lys Glu Asp Ser Glu Val  *
                9305                9310
```

(2) INFORMATION FOR SEQ ID NO:88:

(i) SEQUENCE CHARACTERISTICS:
        (A) LENGTH: 4655 amino acids
        (B) TYPE: amino acid
        (D) TOPOLOGY: linear (ii) MOLECULE TYPE: protein (xi) SEQUENCE DESCRIPTION: SEQ ID NO:88:

```
Met Asp Arg Gly Pro Ala Ala Val Ala Cys Thr Leu Leu Ala Leu
 1               5                  10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
            35                  40                  45

Gly Thr Lys Asp Cys Ser Asp Ala Asp Glu Ile Gly Cys Ala Val
    50                  55                  60

Val Thr Cys Gln Gln Gly Tyr Phe Lys Cys Gln Ser Glu Gly Gln Cys
 65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
            100                 105                 110

Ile Thr Cys Ser Asn Gly Gln Cys Ile Pro Ser Glu Tyr Arg Cys Asp
            115                 120                 125

His Val Arg Asp Cys Pro Asp Gly Ala Asp Glu Asn Asp Cys Gln Tyr
    130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
            195                 200                 205

Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
```

-continued

```
                245                 250                 255
Glu Ser Gly Pro His Asp Val His Lys Cys Ser Pro Arg Glu Trp Ser
                260                 265                 270
Cys Pro Glu Ser Gly Arg Cys Ile Ser Ile Tyr Lys Val Cys Asp Gly
            275                 280                 285
Ile Leu Asp Cys Pro Gly Arg Glu Asp Glu Asn Asn Thr Ser Thr Gly
        290                 295                 300
Lys Tyr Cys Ser Met Thr Leu Cys Ser Ala Leu Asn Cys Gln Tyr Gln
305                 310                 315                 320
Cys His Glu Thr Pro Tyr Gly Gly Ala Cys Phe Cys Pro Pro Gly Tyr
                325                 330                 335
Ile Ile Asn His Asn Asp Ser Arg Thr Cys Val Glu Phe Asp Asp Cys
            340                 345                 350
Gln Ile Trp Gly Ile Cys Asp Gln Lys Cys Glu Ser Arg Pro Gly Arg
        355                 360                 365
His Leu Cys His Cys Glu Glu Gly Tyr Ile Leu Glu Arg Gly Gln Tyr
        370                 375                 380
Cys Lys Ala Asn Asp Ser Phe Gly Glu Ala Ser Ile Ile Phe Ser Asn
385                 390                 395                 400
Gly Arg Asp Leu Leu Ile Gly Asp Ile His Gly Arg Ser Phe Arg Ile
                405                 410                 415
Leu Val Glu Ser Gln Asn Arg Gly Val Ala Val Gly Val Ala Phe His
            420                 425                 430
Tyr His Leu Gln Arg Val Phe Trp Thr Asp Thr Val Gln Asn Lys Val
        435                 440                 445
Phe Ser Val Asp Ile Asn Gly Leu Asn Ile Gln Glu Val Leu Asn Val
    450                 455                 460
Ser Val Glu Thr Pro Glu Asn Leu Ala Val Asp Trp Val Asn Asn Lys
465                 470                 475                 480
Ile Tyr Leu Val Glu Thr Lys Val Asn Arg Ile Asp Met Val Asn Leu
                485                 490                 495
Asp Gly Ser Tyr Arg Val Thr Leu Ile Thr Glu Asn Leu Gly His Pro
            500                 505                 510
Arg Gly Ile Ala Val Asp Pro Thr Val Gly Tyr Leu Phe Phe Ser Asp
        515                 520                 525
Trp Glu Ser Leu Ser Gly Glu Pro Lys Leu Glu Arg Ala Phe Met Asp
    530                 535                 540
Gly Ser Asn Arg Lys Asp Leu Val Lys Thr Lys Leu Gly Trp Pro Ala
545                 550                 555                 560
Gly Val Thr Leu Asp Met Ile Ser Lys Arg Val Tyr Trp Val Asp Ser
                565                 570                 575
Arg Phe Asp Tyr Ile Glu Thr Val Thr Tyr Asp Gly Ile Gln Arg Lys
            580                 585                 590
Thr Val Val His Gly Gly Ser Leu Ile Pro His Pro Phe Gly Val Ser
        595                 600                 605
Leu Phe Glu Gly Gln Val Phe Phe Thr Asp Trp Thr Lys Met Ala Val
    610                 615                 620
Leu Lys Ala Asn Lys Phe Thr Glu Thr Asn Pro Gln Val Tyr Tyr Gln
625                 630                 635                 640
Ala Ser Leu Arg Pro Tyr Gly Val Thr Val Tyr His Ser Leu Arg Gln
                645                 650                 655
Pro Tyr Ala Thr Asn Pro Cys Lys Asp Asn Asn Gly Gly Cys Glu Gln
            660                 665                 670
```

```
Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
            690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750

Ser Thr Ile Phe Phe Ser Asp Met Ser Lys His Met Ile Phe Lys Gln
            755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
            820                 825                 830

Val His Pro Phe Ala Gly Tyr Leu Phe Phe Thr Asp Trp Phe Arg Pro
            835                 840                 845

Ala Lys Ile Met Arg Ala Trp Ser Asp Gly Ser His Leu Leu Pro Val
            850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Leu Gly His Ile Glu Gln
            900                 905                 910

Met Thr His Pro Phe Gly Leu Ala Ile Phe Gly Glu His Leu Phe Phe
            915                 920                 925

Thr Asp Trp Arg Leu Gly Ala Ile Ile Arg Val Arg Lys Ala Asp Gly
930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
            995                 1000                1005

Asn His Leu Thr Cys Glu Gly Asp Pro Thr Asn Glu Pro Pro Thr Glu
        1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ala Phe
            1060                1065                1070

Thr Cys Gly His Gly Glu Cys Ile Pro Ala His Trp Arg Cys Asp Lys
            1075                1080                1085
```

-continued

```
Arg Asn Asp Cys Val Asp Gly Ser Asp Glu His Asn Cys Pro Thr His
    1090                1095                1100
Ala Pro Ala Ser Cys Leu Asp Thr Gln Tyr Thr Cys Asp Asn His Gln
1105            1110                1115                1120
Cys Ile Ser Lys Asn Trp Val Cys Asp Thr Asp Asn Asp Cys Gly Asp
                1125                1130                1135
Gly Ser Asp Glu Lys Asn Cys Asn Ser Thr Glu Thr Cys Gln Pro Ser
            1140                1145                1150
Gln Phe Asn Cys Pro Asn His Arg Cys Ile Asp Leu Ser Phe Val Cys
        1155                1160                1165
Asp Gly Asp Lys Asp Cys Val Asp Gly Ser Asp Glu Val Gly Cys Val
    1170                1175                1180
Leu Asn Cys Thr Ala Ser Gln Phe Lys Cys Ala Ser Gly Asp Lys Cys
1185            1190                1195                1200
Ile Gly Val Thr Asn Arg Cys Asp Gly Val Phe Asp Cys Ser Asp Asn
                1205                1210                1215
Ser Asp Glu Ala Gly Cys Pro Thr Arg Pro Pro Gly Met Cys His Ser
            1220                1225                1230
Asp Glu Phe Gln Cys Gln Glu Asp Gly Ile Cys Ile Pro Asn Phe Trp
        1235                1240                1245
Glu Cys Asp Gly His Pro Asp Cys Leu Tyr Gly Ser Asp Glu His Asn
        1250                1255                1260
Ala Cys Val Pro Lys Thr Cys Pro Ser Ser Tyr Phe His Cys Asp Asn
1265            1270                1275                1280
Gly Asn Cys Ile His Arg Ala Trp Leu Cys Asp Arg Asp Asn Asp Cys
                1285                1290                1295
Gly Asp Met Ser Asp Glu Lys Asp Cys Pro Thr Gln Pro Phe Arg Cys
            1300                1305                1310
Pro Ser Trp Gln Trp Gln Cys Leu Gly His Asn Ile Cys Val Asn Leu
        1315                1320                1325
Ser Val Val Cys Asp Gly Ile Phe Asp Cys Pro Asn Gly Thr Asp Glu
    1330                1335                1340
Ser Pro Leu Cys Asn Gly Asn Ser Cys Ser Asp Phe Asn Gly Gly Cys
1345            1350                1355                1360
Thr His Glu Cys Val Gln Glu Pro Phe Gly Ala Lys Cys Leu Cys Pro
                1365                1370                1375
Leu Gly Phe Leu Leu Ala Asn Asp Ser Lys Thr Cys Glu Asp Ile Asp
            1380                1385                1390
Glu Cys Asp Ile Leu Gly Ser Cys Ser Gln His Cys Tyr Asn Met Arg
        1395                1400                1405
Gly Ser Phe Arg Cys Ser Cys Asp Thr Gly Tyr Met Leu Glu Ser Asp
    1410                1415                1420
Gly Arg Thr Cys Lys Val Thr Ala Ser Glu Ser Leu Leu Leu Val
1425            1430                1435                1440
Ala Ser Gln Asn Lys Ile Ile Ala Asp Ser Val Thr Ser Gln Val His
                1445                1450                1455
Asn Ile Tyr Ser Leu Val Glu Asn Gly Ser Tyr Ile Val Ala Val Asp
            1460                1465                1470
Phe Asp Ser Ile Ser Gly Arg Ile Phe Trp Ser Asp Ala Thr Gln Gly
        1475                1480                1485
Lys Thr Trp Ser Ala Phe Gln Asn Gly Thr Asp Arg Arg Val Val Phe
    1490                1495                1500
Asp Ser Ser Ile Ile Leu Thr Glu Thr Ile Ala Ile Asp Trp Val Gly
```

```
1505                1510                1515                1520
Arg Asn Leu Tyr Trp Thr Asp Tyr Ala Leu Glu Thr Ile Glu Val Ser
            1525                1530                1535
Lys Ile Asp Gly Ser His Arg Thr Val Leu Ile Ser Lys Asn Leu Thr
        1540                1545                1550
Asn Pro Arg Gly Leu Ala Leu Asp Pro Arg Met Asn Glu His Leu Leu
        1555                1560                1565
Phe Trp Ser Asp Trp Gly His His Pro Arg Ile Glu Arg Ala Ser Met
    1570                1575                1580
Asp Gly Ser Met Arg Thr Val Ile Val Gln Asp Lys Ile Phe Trp Pro
1585                1590                1595                1600
Cys Gly Leu Thr Ile Asp Tyr Pro Asn Arg Leu Leu Tyr Phe Met Asp
            1605                1610                1615
Ser Tyr Leu Asp Tyr Met Asp Phe Cys Asp Tyr Asn Gly His His Arg
        1620                1625                1630
Arg Gln Val Ile Ala Ser Asp Leu Ile Ile Arg His Pro Tyr Ala Leu
        1635                1640                1645
Thr Leu Phe Glu Asp Ser Val Tyr Trp Thr Asp Arg Ala Thr Arg Arg
    1650                1655                1660
Val Met Arg Ala Asn Lys Trp His Gly Gly Asn Gln Ser Val Val Met
1665                1670                1675                1680
Tyr Asn Ile Gln Trp Pro Leu Gly Ile Val Ala Val His Pro Ser Lys
            1685                1690                1695
Gln Pro Asn Ser Val Asn Pro Cys Ala Phe Ser Arg Cys Ser His Leu
        1700                1705                1710
Cys Leu Leu Ser Ser Gln Gly Pro His Phe Tyr Ser Cys Val Cys Pro
        1715                1720                1725
Ser Gly Trp Ser Leu Ser Pro Asp Leu Leu Asn Cys Leu Arg Asp Asp
    1730                1735                1740
Gln Pro Phe Leu Ile Thr Val Arg Gln His Ile Ile Phe Gly Ile Ser
1745                1750                1755                1760
Leu Asn Pro Glu Val Lys Ser Asn Asp Ala Met Val Pro Ile Ala Gly
            1765                1770                1775
Ile Gln Asn Gly Leu Asp Val Glu Phe Asp Asp Ala Glu Gln Tyr Ile
        1780                1785                1790
Tyr Trp Val Glu Asn Pro Gly Glu Ile His Arg Val Lys Thr Asp Gly
        1795                1800                1805
Thr Asn Arg Thr Val Phe Ala Ser Ile Ser Met Val Gly Pro Ser Met
        1810                1815                1820
Asn Leu Ala Leu Asp Trp Ile Ser Arg Asn Leu Tyr Ser Thr Asn Pro
1825                1830                1835                1840
Arg Thr Gln Ser Ile Glu Val Leu Thr Leu His Gly Asp Ile Arg Tyr
            1845                1850                1855
Arg Lys Thr Leu Ile Ala Asn Asp Gly Thr Ala Leu Gly Val Gly Phe
        1860                1865                1870
Pro Ile Gly Ile Thr Val Asp Pro Ala Arg Gly Lys Leu Tyr Trp Ser
        1875                1880                1885
Asp Gln Gly Thr Asp Ser Gly Val Pro Ala Lys Ile Ala Ser Ala Asn
        1890                1895                1900
Met Asp Gly Thr Ser Val Lys Thr Leu Phe Thr Gly Asn Leu Glu His
1905                1910                1915                1920
Leu Glu Cys Val Thr Leu Asp Ile Glu Glu Gln Lys Leu Tyr Trp Ala
            1925                1930                1935
```

-continued

Val Thr Gly Arg Gly Val Ile Glu Arg Gly Asn Val Asp Gly Thr Asp
            1940                1945                1950

Arg Met Ile Leu Val His Gln Leu Ser His Pro Trp Gly Ile Ala Val
            1955                1960                1965

His Asp Ser Phe Leu Tyr Tyr Thr Asp Glu Gln Tyr Glu Val Ile Glu
            1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Asn Ala Ala
            2005                2010                2015

Glu Ser Ser Asn Gly Cys Ser Asn Met Asn Ala Cys Gln Gln Ile
            2020                2025                2030

Cys Leu Pro Val Pro Gly Gly Leu Phe Ser Cys Ala Cys Ala Thr Gly
            2035                2040                2045

Phe Lys Leu Asn Pro Asp Asn Arg Ser Cys Ser Pro Tyr Asn Ser Phe
            2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
            2085                2090                2095

Ala Leu His Val Asp Val Asp Val Ser Ser Gly Phe Ile Tyr Trp Cys
            2100                2105                2110

Asp Phe Ser Ser Ser Val Ala Ser Asp Asn Ala Ile Arg Arg Ile Lys
            2115                2120                2125

Pro Asp Gly Ser Ser Leu Met Asn Ile Val Thr His Gly Ile Gly Glu
            2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
            2165                2170                2175

Asn Thr Thr Tyr Arg Arg Val Leu Leu Lys Val Thr Val Asp Met Pro
            2180                2185                2190

Arg His Ile Val Val Asp Pro Lys Asn Arg Tyr Leu Phe Trp Ala Asp
            2195                2200                2205

Tyr Gly Gln Arg Pro Lys Ile Glu Arg Ser Phe Leu Asp Cys Thr Asn
            2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Asp Ser Leu Asp
            2245                2250                2255

Ile Ile Ala Arg Ile Arg Ile Asn Gly Glu Asn Ser Glu Val Ile Arg
            2260                2265                2270

Tyr Gly Ser Arg Tyr Pro Thr Pro Tyr Gly Ile Thr Val Phe Glu Asn
            2275                2280                2285

Ser Ile Ile Trp Val Asp Arg Asn Leu Lys Lys Ile Phe Gln Ala Ser
            2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
            2325                2330                2335

Ser Pro Ala Glu Val Asn Asn Asn Pro Cys Leu Glu Asn Asn Gly Gly
            2340                2345                2350

-continued

```
Cys Ser His Leu Cys Phe Ala Leu Pro Gly Leu His Thr Pro Lys Cys
        2355                2360                2365
Asp Cys Ala Phe Gly Thr Leu Gln Ser Asp Gly Lys Asn Cys Ala Ile
2370                2375                2380
Ser Thr Glu Asn Phe Leu Ile Phe Ala Leu Ser Asn Ser Leu Arg Ser
2385                2390                2395                2400
Leu His Leu Asp Pro Glu Asn His Ser Pro Pro Phe Gln Thr Ile Asn
        2405                2410                2415
Val Glu Arg Thr Val Met Ser Leu Asp Tyr Asp Ser Val Ser Asp Arg
        2420                2425                2430
Ile Tyr Phe Thr Gln Asn Leu Ala Ser Gly Val Gly Gln Ile Ser Tyr
        2435                2440                2445
Ala Thr Leu Ser Ser Gly Ile His Thr Pro Thr Val Ile Ala Ser Gly
        2450                2455                2460
Ile Gly Thr Ala Asp Gly Ile Ala Phe Asp Trp Ile Thr Arg Arg Ile
2465                2470                2475                2480
Tyr Tyr Ser Asp Tyr Leu Asn Gln Met Ile Asn Ser Met Ala Glu Asp
        2485                2490                2495
Gly Ser Asn Arg Thr Val Ile Ala Arg Val Pro Lys Pro Arg Ala Ile
        2500                2505                2510
Val Leu Asp Pro Cys Gln Gly Tyr Leu Tyr Trp Ala Asp Trp Asp Thr
        2515                2520                2525
His Ala Lys Ile Glu Arg Ala Thr Leu Gly Gly Asn Phe Arg Val Pro
        2530                2535                2540
Ile Val Asn Ser Ser Leu Val Met Pro Ser Gly Leu Thr Leu Asp Tyr
2545                2550                2555                2560
Glu Glu Asp Leu Leu Tyr Trp Val Asp Ala Ser Leu Gln Arg Ile Glu
        2565                2570                2575
Arg Ser Thr Leu Thr Gly Val Asp Arg Glu Val Ile Val Asn Ala Ala
        2580                2585                2590
Val His Ala Phe Gly Leu Thr Leu Tyr Gly Gln Tyr Ile Tyr Trp Thr
        2595                2600                2605
Asp Leu Tyr Thr Gln Arg Ile Tyr Arg Ala Asn Lys Tyr Asp Gly Ser
2610                2615                2620
Gly Gln Ile Ala Met Thr Thr Asn Leu Leu Ser Gln Pro Arg Gly Ile
2625                2630                2635                2640
Asn Thr Val Val Lys Asn Gln Lys Gln Cys Asn Asn Pro Cys Glu
        2645                2650                2655
Gln Phe Asn Gly Gly Cys Ser His Ile Cys Ala Pro Gly Pro Asn Gly
        2660                2665                2670
Ala Glu Cys Gln Cys Pro His Glu Gly Asn Trp Tyr Leu Ala Asn Asn
        2675                2680                2685
Arg Lys His Cys Ile Val Asp Asn Gly Glu Arg Cys Gly Ala Ser Ser
        2690                2695                2700
Phe Thr Cys Ser Asn Gly Arg Cys Ile Ser Glu Glu Trp Lys Cys Asp
2705                2710                2715                2720
Asn Asp Asn Asp Cys Gly Asp Gly Ser Asp Glu Met Glu Ser Val Cys
        2725                2730                2735
Ala Leu His Thr Cys Ser Pro Thr Ala Phe Thr Cys Ala Asn Gly Arg
        2740                2745                2750
Cys Val Gln Tyr Ser Tyr Arg Cys Asp Tyr Tyr Asn Asp Cys Gly Asp
        2755                2760                2765
Gly Ser Asp Glu Ala Gly Cys Leu Phe Arg Asp Cys Asn Ala Thr Thr
```

-continued

```
        2770            2775            2780

Glu Phe Met Cys Asn Asn Arg Arg Cys Ile Pro Arg Glu Phe Ile Cys
2785            2790            2795            2800

Asn Gly Val Asp Asn Cys His Asp Asn Asn Thr Ser Asp Glu Lys Asn
            2805            2810            2815

Cys Pro Asp Arg Thr Cys Gln Ser Gly Tyr Thr Lys Cys His Asn Ser
        2820            2825            2830

Asn Ile Cys Ile Pro Arg Val Tyr Leu Cys Asp Gly Asp Asn Asp Cys
        2835            2840            2845

Gly Asp Asn Ser Asp Glu Asn Pro Thr Tyr Cys Thr Thr His Thr Cys
        2850            2855            2860

Ser Ser Ser Glu Phe Gln Cys Ala Ser Gly Arg Cys Ile Pro Gln His
2865            2870            2875            2880

Trp Tyr Cys Asp Gln Glu Thr Asp Cys Phe Asp Ala Ser Asp Glu Pro
            2885            2890            2895

Ala Ser Cys Gly His Ser Glu Arg Thr Cys Leu Ala Asp Glu Phe Lys
        2900            2905            2910

Cys Asp Gly Gly Arg Cys Ile Pro Ser Glu Trp Ile Cys Asp Gly Asp
        2915            2920            2925

Asn Asp Cys Gly Asp Met Ser Asp Glu Asp Lys Arg His Gln Cys Gln
        2930            2935            2940

Asn Gln Asn Cys Ser Asp Ser Glu Phe Leu Cys Val Asn Asp Arg Pro
2945            2950            2955            2960

Pro Asp Arg Arg Cys Ile Pro Gln Ser Trp Val Cys Asp Gly Asp Val
            2965            2970            2975

Asp Cys Thr Asp Gly Tyr Asp Glu Asn Gln Asn Cys Thr Arg Arg Thr
        2980            2985            2990

Cys Ser Glu Asn Glu Phe Thr Cys Gly Tyr Gly Leu Cys Ile Pro Lys
        2995            3000            3005

Ile Phe Arg Cys Asp Arg His Asn Asp Cys Gly Asp Tyr Ser Asp Glu
        3010            3015            3020

Arg Gly Cys Leu Tyr Gln Thr Cys Gln Gln Asn Gln Phe Thr Cys Gln
3025            3030            3035            3040

Asn Gly Arg Cys Ile Ser Lys Thr Phe Val Cys Asp Glu Asp Asn Asp
            3045            3050            3055

Cys Gly Asp Gly Ser Asp Glu Leu Met His Leu Cys His Thr Pro Glu
        3060            3065            3070

Pro Thr Cys Pro Pro His Glu Phe Lys Cys Asp Asn Gly Arg Cys Ile
        3075            3080            3085

Glu Met Met Lys Leu Cys Asn His Leu Asp Asp Cys Leu Asp Asn Ser
        3090            3095            3100

Asp Glu Lys Gly Cys Gly Ile Asn Glu Cys His Asp Pro Ser Ile Ser
3105            3110            3115            3120

Gly Cys Asp His Asn Cys Thr Asp Thr Leu Thr Ser Phe Tyr Cys Ser
            3125            3130            3135

Cys Arg Pro Gly Tyr Lys Leu Met Ser Asp Lys Arg Thr Cys Val Asp
        3140            3145            3150

Ile Asp Glu Cys Thr Glu Met Pro Phe Val Cys Ser Gln Lys Cys Glu
        3155            3160            3165

Asn Val Ile Gly Ser Tyr Ile Cys Lys Cys Ala Pro Gly Tyr Leu Arg
        3170            3175            3180

Glu Pro Asp Gly Lys Thr Cys Arg Gln Asn Ser Asn Ile Glu Pro Tyr
3185            3190            3195            3200
```

-continued

```
Leu Ile Phe Ser Asn Arg Tyr Tyr Leu Arg Asn Leu Thr Ile Asp Gly
              3205                3210                3215
Tyr Phe Tyr Ser Leu Ile Leu Glu Gly Leu Asp Asn Val Val Ala Leu
              3220                3225                3230
Asp Phe Asp Arg Val Glu Lys Arg Leu Tyr Trp Ile Asp Thr Gln Arg
              3235                3240                3245
Gln Val Ile Glu Arg Met Phe Leu Asn Lys Thr Asn Lys Glu Thr Ile
3250                3255                3260
Ile Asn His Arg Leu Pro Ala Glu Ser Leu Ala Val Asp Trp Val
3265                3270                3275                3280
Ser Arg Lys Leu Tyr Trp Leu Asp Ala Arg Leu Asp Gly Leu Phe Val
              3285                3290                3295
Ser Asp Leu Asn Gly His Arg Arg Met Leu Ala Gln His Cys Val
              3300                3305                3310
Asp Ala Asn Asn Thr Phe Cys Phe Asp Asn Pro Arg Gly Leu Ala Leu
              3315                3320                3325
His Pro Gln Tyr Gly Tyr Leu Tyr Trp Ala Asp Trp Gly His Arg Ala
              3330                3335                3340
Tyr Ile Gly Arg Val Gly Met Asp Gly Thr Asn Lys Ser Val Ile Ile
3345                3350                3355                3360
Ser Thr Lys Leu Glu Trp Pro Asn Gly Ile Thr Ile Asp Tyr Thr Asn
              3365                3370                3375
Asp Leu Leu Tyr Trp Ala Asp Ala His Leu Gly Tyr Ile Glu Tyr Ser
              3380                3385                3390
Asp Leu Glu Gly His His Arg His Thr Val Tyr Asp Gly Ala Leu Pro
              3395                3400                3405
His Pro Phe Ala Ile Thr Ile Phe Glu Asp Thr Ile Tyr Trp Thr Asp
              3410                3415                3420
Trp Asn Thr Arg Thr Val Glu Lys Gly Asn Lys Tyr Asp Gly Ser Asn
3425                3430                3435                3440
Arg Gln Thr Leu Val Asn Thr Thr His Arg Pro Phe Asp Ile His Val
              3445                3450                3455
Tyr His Pro Tyr Arg Gln Pro Ile Val Ser Asn Pro Cys Gly Thr Asn
              3460                3465                3470
Asn Gly Gly Cys Ser His Leu Cys Leu Ile Lys Pro Gly Gly Lys Gly
              3475                3480                3485
Phe Thr Cys Glu Cys Pro Asp Asp Phe Arg Thr Leu Gln Leu Ser Gly
              3490                3495                3500
Ser Thr Tyr Cys Met Pro Met Cys Ser Ser Thr Gln Phe Leu Cys Ala
3505                3510                3515                3520
Asn Asn Glu Lys Cys Ile Pro Ile Trp Trp Lys Cys Asp Gly Gln Lys
              3525                3530                3535
Asp Cys Ser Asp Gly Ser Asp Glu Leu Ala Leu Cys Pro Gln Arg Phe
              3540                3545                3550
Cys Arg Leu Gly Gln Phe Gln Cys Ser Asp Gly Asn Cys Thr Ser Pro
              3555                3560                3565
Gln Thr Leu Cys Asn Ala His Gln Asn Cys Pro Asp Gly Ser Asp Glu
              3570                3575                3580
Asp Arg Leu Leu Cys Glu Asn His His Cys Asp Ser Asn Glu Trp Gln
3585                3590                3595                3600
Cys Ala Asn Lys Arg Cys Ile Pro Glu Ser Trp Gln Cys Asp Thr Phe
              3605                3610                3615
```

-continued

```
Asn Asp Cys Glu Asp Asn Ser Asp Glu Asp Ser Ser His Cys Ala Ser
            3620                3625                3630

Arg Thr Cys Arg Pro Gly Gln Phe Arg Cys Ala Asn Gly Arg Cys Ile
        3635                3640                3645

Pro Gln Ala Trp Lys Cys Asp Val Asp Asn Asp Cys Gly Asp His Ser
    3650                3655                3660

Asp Glu Pro Ile Glu Cys Met Ser Ser Ala His Leu Cys Asp Asn
3665                3670                3675                3680

Phe Thr Glu Phe Ser Cys Lys Thr Asn Tyr Arg Cys Ile Pro Lys Trp
            3685                3690                3695

Ala Val Cys Asn Gly Val Asp Asp Cys Arg Asp Asn Ser Asp Glu Gln
        3700                3705                3710

Gly Cys Glu Glu Arg Thr Cys His Pro Val Gly Asp Phe Arg Cys Lys
        3715                3720                3725

Asn His His Cys Ile Pro Leu Arg Trp Gln Cys Asp Gly Gln Asn Asp
    3730                3735                3740

Cys Gly Asp Asn Ser Asp Glu Glu Asn Cys Ala Pro Arg Glu Cys Thr
3745                3750                3755                3760

Glu Ser Glu Phe Arg Cys Val Asn Gln Gln Cys Ile Pro Ser Arg Trp
            3765                3770                3775

Ile Cys Asp His Tyr Asn Asp Cys Gly Asp Asn Ser Asp Glu Arg Asp
        3780                3785                3790

Cys Glu Met Arg Thr Cys His Pro Glu Tyr Phe Gln Cys Thr Ser Gly
        3795                3800                3805

His Cys Val His Ser Glu Leu Lys Cys Asp Gly Ser Ala Asp Cys Leu
    3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Asp Cys Gly Asp Gly Ser Asp
        3860                3865                3870

Glu Glu Leu His Leu Cys Leu Asp Val Pro Cys Asn Ser Pro Asn Arg
    3875                3880                3885

Phe Arg Cys Asp Asn Asn Arg Cys Ile Tyr Ser His Glu Val Cys Asn
        3890                3895                3900

Gly Val Asp Asp Cys Gly Asp Gly Thr Asp Glu Thr Glu Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Asp Ala Asp Asp
        3940                3945                3950

Cys Gly Asp Trp Ser Asp Glu Leu Gly Cys Asn Lys Gly Lys Glu Arg
    3955                3960                3965

Thr Cys Ala Glu Asn Ile Cys Glu Gln Asn Cys Thr Gln Leu Asn Glu
    3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
        4020                4025                4030

Ala Asp Gly Phe Thr Ser Met Ser Asp Arg Pro Gly Lys Arg Cys Ala
```

-continued

```
                4035              4040              4045
Ala Glu Gly Ser Ser Pro Leu Leu Leu Pro Asp Asn Val Arg Ile
4050                4055              4060

Arg Lys Tyr Asn Leu Ser Ser Glu Arg Phe Ser Glu Tyr Leu Gln Asp
4065                4070              4075              4080

Glu Glu Tyr Ile Gln Ala Val Asp Tyr Asp Trp Asp Pro Glu Asp Ile
                4085              4090              4095

Gly Leu Ser Val Val Tyr Tyr Thr Val Arg Gly Glu Gly Ser Arg Phe
                4100              4105              4110

Gly Ala Ile Lys Arg Ala Tyr Ile Pro Asn Phe Glu Ser Gly Arg Asn
                4115              4120              4125

Asn Leu Val Gln Glu Val Asp Leu Lys Leu Lys Tyr Val Met Gln Pro
                4130              4135              4140

Asp Gly Ile Ala Val Asp Trp Val Gly Arg His Ile Tyr Trp Ser Asp
4145                4150              4155              4160

Val Lys Asn Lys Arg Ile Glu Val Ala Lys Leu Asp Gly Arg Tyr Arg
                4165              4170              4175

Lys Trp Leu Ile Ser Thr Asp Leu Asp Gln Pro Ala Ala Ile Ala Val
                4180              4185              4190

Asn Pro Lys Leu Gly Leu Met Phe Trp Thr Asp Trp Gly Lys Glu Pro
                4195              4200              4205

Lys Xaa Glu Ser Ala Trp Met Asn Gly Glu Asp Arg Asn Ile Leu Val
                4210              4215              4220

Phe Glu Asp Leu Gly Trp Pro Thr Gly Leu Ser Ile Asp Tyr Leu Asn
4225                4230              4235              4240

Asn Asp Arg Ile Tyr Trp Ser Asp Phe Lys Glu Asp Val Ile Glu Thr
                4245              4250              4255

Ile Lys Tyr Asp Gly Thr Asp Arg Arg Val Ile Ala Lys Glu Ala Met
                4260              4265              4270

Asn Pro Tyr Ser Leu Asp Ile Phe Glu Asp Gln Leu Tyr Trp Ile Ser
                4275              4280              4285

Lys Glu Lys Gly Glu Val Trp Lys Gln Asn Lys Phe Gly Gln Gly Lys
                4290              4295              4300

Lys Glu Lys Thr Leu Val Val Asn Pro Trp Leu Thr Gln Val Arg Ile
4305                4310              4315              4320

Phe His Gln Leu Arg Tyr Asn Lys Ser Val Pro Asn Leu Cys Lys Gln
                4325              4330              4335

Ile Cys Ser His Leu Cys Leu Leu Arg Pro Gly Gly Tyr Ser Cys Ala
                4340              4345              4350

Cys Pro Gln Gly Ser Ser Phe Ile Glu Gly Ser Thr Thr Glu Cys Asp
                4355              4360              4365

Ala Ala Ile Glu Leu Pro Ile Asn Leu Pro Pro Cys Arg Cys Met
                4370              4375              4380

His Gly Gly Asn Cys Tyr Phe Asp Glu Thr Asp Leu Pro Lys Cys Lys
4385                4390              4395              4400

Cys Pro Ser Gly Tyr Thr Gly Lys Tyr Cys Glu Met Ala Phe Ser Lys
                4405              4410              4415

Gly Ile Ser Pro Gly Thr Thr Ala Val Ala Val Leu Leu Thr Ile Leu
                4420              4425              4430

Leu Ile Val Val Ile Gly Ala Leu Ala Ile Ala Gly Phe Phe His Tyr
                4435              4440              4445

Arg Arg Thr Gly Ser Leu Leu Pro Ala Leu Pro Lys Leu Pro Ser Leu
                4450              4455              4460
```

```
Ser Ser Leu Val Lys Pro Ser Glu Asn Gly Asn Gly Val Thr Phe Arg
4465            4470            4475            4480

Ser Gly Ala Asp Leu Asn Met Asp Ile Gly Val Ser Gly Phe Gly Pro
            4485            4490            4495

Glu Thr Ala Ile Asp Arg Ser Met Ala Met Ser Glu Asp Phe Val Met
        4500            4505            4510

Glu Met Gly Lys Gln Pro Ile Ile Phe Glu Asn Pro Met Tyr Ser Ala
    4515            4520            4525

Arg Asp Ser Ala Lys Val Val Gln Pro Ile Gln Val Thr Val Ser
    4530            4535            4540

Glu Asn Val Asp Asn Lys Asn Tyr Gly Ser Pro Ile Asn Pro Ser Glu
4545            4550            4555            4560

Ile Val Pro Glu Thr Asn Pro Thr Ser Pro Ala Ala Asp Gly Thr Gln
            4565            4570            4575

Val Thr Lys Trp Asn Leu Phe Lys Arg Lys Ser Lys Gln Thr Thr Asn
            4580            4585            4590

Phe Glu Asn Pro Ile Tyr Ala Gln Met Glu Asn Glu Gln Lys Glu Ser
        4595            4600            4605

Val Ala Ala Thr Pro Pro Pro Ser Pro Ser Leu Pro Ala Lys Pro Lys
    4610            4615            4620

Pro Pro Ser Arg Arg Asp Pro Thr Pro Thr Tyr Ser Ala Thr Glu Asp
4625            4630            4635            4640

Thr Phe Lys Asp Thr Ala Asn Leu Val Lys Glu Asp Ser Glu Val
            4645            4650            4655

(2) INFORMATION FOR SEQ ID NO:89:

(i) SEQUENCE CHARACTERISTICS:
        (A) LENGTH: 14044 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (F) TISSUE TYPE: Parathyroid (ix) FEATURE:
        (A) NAME/KEY: CDS
        (B) LOCATION: 65..14032

(xi) SEQUENCE DESCRIPTION: SEQ ID NO:89:

TGCGGTGTGC TACGCGCGCC CACCTCCCGG GGAAGGAACG GCGAGGCCGG GGACCGTCGC      60

GGAG ATG GAT CGC GGG CCG GCA GCA GTG GCG TGC ACG CTG CTC CTG GCT     109
     Met Asp Arg Gly Pro Ala Ala Val Ala Cys Thr Leu Leu Leu Ala
         4660            4665            4670

CTC GTC GCC TGC CTA GCC CCG GCC AGT GGC CAA GAA TGT GAC AGT GCG      157
Leu Val Ala Cys Leu Ala Pro Ala Ser Gly Gln Glu Cys Asp Ser Ala
            4675            4680            4685

CAT TTT CGC TGT GGA AGT GGG CAT TGC ATC CCT GCA GAC TGG AGG TGT      205
His Phe Arg Cys Gly Ser Gly His Cys Ile Pro Ala Asp Trp Arg Cys
        4690            4695            4700

GAT GGG ACC AAA GAC TGT TCA GAT GAC GCG GAT GAA ATT GGC TGC GCT      253
Asp Gly Thr Lys Asp Cys Ser Asp Asp Ala Asp Glu Ile Gly Cys Ala
    4705            4710            4715
```

-continued

```
GTT GTG ACC TGC CAG CAG GGC TAT TTC AAG TGC CAG AGT GAG GGA CAA       301
Val Val Thr Cys Gln Gln Gly Tyr Phe Lys Cys Gln Ser Glu Gly Gln
4720            4725                4730                4735

TGC ATC CCC AGC TCC TGG GTG TGT GAC CAA GAT CAA GAC TGT GAT GAT       349
Cys Ile Pro Ser Ser Trp Val Cys Asp Gln Asp Gln Asp Cys Asp Asp
                4740                4745                4750

GGC TCA GAT GAA CGT CAA GAT TGC TCA CAA AGT ACA TGC TCA AGT CAT       397
Gly Ser Asp Glu Arg Gln Asp Cys Ser Gln Ser Thr Cys Ser Ser His
            4755                4760                4765

CAG ATA ACA TGC TCC AAT GGT CAG TGT ATC CCA AGT GAA TAC AGG TGC       445
Gln Ile Thr Cys Ser Asn Gly Gln Cys Ile Pro Ser Glu Tyr Arg Cys
        4770                4775                4780

GAC CAC GTC AGA GAC TGC CCC GAT GGA GCT GAT GAG AAT GAC TGC CAG       493
Asp His Val Arg Asp Cys Pro Asp Gly Ala Asp Glu Asn Asp Cys Gln
    4785                4790                4795

TAC CCA ACA TGT GAG CAG CTT ACT TGT GAC AAT GGG GCC TGC TAT AAC       541
Tyr Pro Thr Cys Glu Gln Leu Thr Cys Asp Asn Gly Ala Cys Tyr Asn
4800            4805                4810                4815

ACC AGT CAG AAG TGT GAT TGG AAA GTT GAT TGC AGG GAC TCC TCA GAT       589
Thr Ser Gln Lys Cys Asp Trp Lys Val Asp Cys Arg Asp Ser Ser Asp
                4820                4825                4830

GAA ATC AAC TGC ACT GAG ATA TGC TTG CAC AAT GAG TTT TCA TGT GGC       637
Glu Ile Asn Cys Thr Glu Ile Cys Leu His Asn Glu Phe Ser Cys Gly
            4835                4840                4845

AAT GGA GAG TGT ATC CCT CGT GCT TAT GTC TGT GAC CAT GAC AAT GAT       685
Asn Gly Glu Cys Ile Pro Arg Ala Tyr Val Cys Asp His Asp Asn Asp
        4850                4855                4860

TGC CAA GAC GGC AGT GAC GAA CAT GCT TGC AAC TAT CCG ACC TGC GGT       733
Cys Gln Asp Gly Ser Asp Glu His Ala Cys Asn Tyr Pro Thr Cys Gly
    4865                4870                4875

GGT TAC CAG TTC ACT TGC CCC AGT GGC CGA TGC ATT TAT CAA AAC TGG       781
Gly Tyr Gln Phe Thr Cys Pro Ser Gly Arg Cys Ile Tyr Gln Asn Trp
4880            4885                4890                4895

GTT TGT GAT GGA GAA GAT GAC TGT AAA GAT AAT GGA GAT GAA GAT GGA       829
Val Cys Asp Gly Glu Asp Asp Cys Lys Asp Asn Gly Asp Glu Asp Gly
                4900                4905                4910

TGT GAA AGC GGT CCT CAT GAT GTT CAT AAA TGT TCC CCA AGA GAA TGG       877
Cys Glu Ser Gly Pro His Asp Val His Lys Cys Ser Pro Arg Glu Trp
            4915                4920                4925

TCT TGC CCA GAG TCG GGA CGA TGC ATC TCC ATT TAT AAA GTT TGT GAT       925
Ser Cys Pro Glu Ser Gly Arg Cys Ile Ser Ile Tyr Lys Val Cys Asp
        4930                4935                4940

GGG ATT TTA GAT TGC CCA GGA AGA GAA GAT GAA AAC AAC ACT AGT ACC       973
Gly Ile Leu Asp Cys Pro Gly Arg Glu Asp Glu Asn Asn Thr Ser Thr
    4945                4950                4955

GGA AAA TAC TGT AGT ATG ACT CTG TGC TCT GCC TTG AAC TGC CAG TAC      1021
Gly Lys Tyr Cys Ser Met Thr Leu Cys Ser Ala Leu Asn Cys Gln Tyr
4960            4965                4970                4975

CAG TGC CAT GAG ACG CCG TAT GGA GGA GCG TGT TTT TGT CCC CCA GGT      1069
Gln Cys His Glu Thr Pro Tyr Gly Gly Ala Cys Phe Cys Pro Pro Gly
                4980                4985                4990

TAT ATC ATC AAC CAC AAT GAC AGC CGT ACC TGT GTT GAG TTT GAT GAT      1117
Tyr Ile Ile Asn His Asn Asp Ser Arg Thr Cys Val Glu Phe Asp Asp
            4995                5000                5005

TGC CAG ATA TGG GGA ATT TGT GAC CAG AAG TGT GAA AGC CGA CCT GGC      1165
Cys Gln Ile Trp Gly Ile Cys Asp Gln Lys Cys Glu Ser Arg Pro Gly
        5010                5015                5020

CGT CAC CTG TGC CAC TGT GAA GAA GGG TAT ATC TTG GAG CGT GGA CAG      1213
Arg His Leu Cys His Cys Glu Glu Gly Tyr Ile Leu Glu Arg Gly Gln
```

```
                    5025                5030                5035
TAT TGC AAA GCT AAT GAT TCC TTT GGC GAG GCC TCC ATT ATC TTC TCC    1261
Tyr Cys Lys Ala Asn Asp Ser Phe Gly Glu Ala Ser Ile Ile Phe Ser
5040                5045                5050                5055

AAT GGT CGG GAT TTG TTA ATT GGT GAT ATT CAT GGA AGG AGC TTC CGG    1309
Asn Gly Arg Asp Leu Leu Ile Gly Asp Ile His Gly Arg Ser Phe Arg
                    5060                5065                5070

ATC CTA GTG GAG TCT CAG AAT CGT GGA GTG GCC GTG GGT GTG GCT TTC    1357
Ile Leu Val Glu Ser Gln Asn Arg Gly Val Ala Val Gly Val Ala Phe
            5075                5080                5085

CAC TAT CAC CTG CAA AGA GTT TTT TGG ACA GAC ACC GTG CAA AAT AAG    1405
His Tyr His Leu Gln Arg Val Phe Trp Thr Asp Thr Val Gln Asn Lys
        5090                5095                5100

GTT TTT TCA GTT GAC ATT AAT GGT TTA AAT ATC CAA GAG GTT CTC AAT    1453
Val Phe Ser Val Asp Ile Asn Gly Leu Asn Ile Gln Glu Val Leu Asn
    5105                5110                5115

GTT TCT GTT GAA ACC CCA GAG AAC CTG GCT GTG GAC TGG GTT AAT AAT    1501
Val Ser Val Glu Thr Pro Glu Asn Leu Ala Val Asp Trp Val Asn Asn
5120                5125                5130                5135

AAA ATC TAT CTA GTG GAA ACC AAG GTC AAC CGC ATA GAT ATG GTA AAT    1549
Lys Ile Tyr Leu Val Glu Thr Lys Val Asn Arg Ile Asp Met Val Asn
                5140                5145                5150

TTG GAT GGA AGC TAT CGG GTT ACC CTT ATA ACT GAA AAC TTG GGG CAT    1597
Leu Asp Gly Ser Tyr Arg Val Thr Leu Ile Thr Glu Asn Leu Gly His
            5155                5160                5165

CCT AGA GGA ATT GCC GTG GAC CCA ACT GTT GGT TAT TTA TTT TTC TCA    1645
Pro Arg Gly Ile Ala Val Asp Pro Thr Val Gly Tyr Leu Phe Phe Ser
        5170                5175                5180

GAT TGG GAG AGC CTT TCT GGG GAA CCT AAG CTG GAA AGG GCA TTC ATG    1693
Asp Trp Glu Ser Leu Ser Gly Glu Pro Lys Leu Glu Arg Ala Phe Met
    5185                5190                5195

GAT GGC AGC AAC CGT AAA GAC TTG GTG AAA ACA AAG CTG GGA TGG CCT    1741
Asp Gly Ser Asn Arg Lys Asp Leu Val Lys Thr Lys Leu Gly Trp Pro
5200                5205                5210                5215

GCT GGG GTA ACT CTG GAT ATG ATA TCG AAG CGT GTT TAC TGG GTT GAC    1789
Ala Gly Val Thr Leu Asp Met Ile Ser Lys Arg Val Tyr Trp Val Asp
                5220                5225                5230

TCT CGG TTT GAT TAC ATT GAA ACT GTA ACT TAT GAT GGA ATT CAA AGG    1837
Ser Arg Phe Asp Tyr Ile Glu Thr Val Thr Tyr Asp Gly Ile Gln Arg
            5235                5240                5245

AAG ACT GTA GTT CAT GGA GGC TCC CTC ATT CCT CAT CCC TTT GGA GTA    1885
Lys Thr Val Val His Gly Gly Ser Leu Ile Pro His Pro Phe Gly Val
        5250                5255                5260

AGC TTA TTT GAA GGT CAG GTG TTC TTT ACA GAT TGG ACA AAG ATG GCC    1933
Ser Leu Phe Glu Gly Gln Val Phe Phe Thr Asp Trp Thr Lys Met Ala
    5265                5270                5275

GTG CTG AAG GCA AAC AAG TTC ACA GAG ACC AAC CCA CAA GTG TAC TAC    1981
Val Leu Lys Ala Asn Lys Phe Thr Glu Thr Asn Pro Gln Val Tyr Tyr
5280                5285                5290                5295

CAG GCT TCC CTG AGG CCC TAT GGA GTG ACT GTT TAC CAT TCC CTC AGA    2029
Gln Ala Ser Leu Arg Pro Tyr Gly Val Thr Val Tyr His Ser Leu Arg
                5300                5305                5310

CAG CCC TAT GCT ACC AAT CCG TGT AAA GAT AAC AAT GGG GGC TGT GAG    2077
Gln Pro Tyr Ala Thr Asn Pro Cys Lys Asp Asn Asn Gly Gly Cys Glu
            5315                5320                5325

CAG GTC TGT GTY CTC AGC CAC AGA ACA GAT AAT GAT GGT TTG GGT TTC    2125
Gln Val Cys Val Leu Ser His Arg Thr Asp Asn Asp Gly Leu Gly Phe
        5330                5335                5340

CGT TGC AAG TGC ACA TTC GGC TTC CAA CTG GAT ACA GAT GAG CGC CAC    2173
```

```
Arg Cys Lys Cys Thr Phe Gly Phe Gln Leu Asp Thr Asp Glu Arg His
    5345                5350                5355

TGC ATT GCT GTT CAG AAT TTC CTC ATT TTT TCA TCC CAA GTT GCT ATT       2221
Cys Ile Ala Val Gln Asn Phe Leu Ile Phe Ser Ser Gln Val Ala Ile
5360            5365                5370                5375

CGT GGG ATC CCG TTC ACC TTG TCT ACC CAG GAA GAT GTC ATG GTT CCA       2269
Arg Gly Ile Pro Phe Thr Leu Ser Thr Gln Glu Asp Val Met Val Pro
                5380                5385                5390

GTT TCG GGG AAT CCT TCT TTC TTT GTC GGG ATT GAT TTT GAC GCC CAG       2317
Val Ser Gly Asn Pro Ser Phe Phe Val Gly Ile Asp Phe Asp Ala Gln
            5395                5400                5405

GAC AGC ACT ATC TTT TTT TCA GAT ATG TCA AAA CAC ATG ATT TTT AAG       2365
Asp Ser Thr Ile Phe Phe Ser Asp Met Ser Lys His Met Ile Phe Lys
        5410                5415                5420

CAA AAG ATT GAT GGC ACA GGA AGA GAA ATT CTC GCA GCT AAC AGG GTG       2413
Gln Lys Ile Asp Gly Thr Gly Arg Glu Ile Leu Ala Ala Asn Arg Val
    5425                5430                5435

GAA AAT GTT GAA AGT TTG GCT TTT GAT TGG ATT TCA AAG AAT CTC TAT       2461
Glu Asn Val Glu Ser Leu Ala Phe Asp Trp Ile Ser Lys Asn Leu Tyr
5440            5445                5450                5455

TGG ACA GAC TCT CAT TAC AAG AGT ATC AGT GTC ATG AGG CTA GCT GAT       2509
Trp Thr Asp Ser His Tyr Lys Ser Ile Ser Val Met Arg Leu Ala Asp
                5460                5465                5470

AAA ACG AGA CGC ACG GTA GTT CAG TAT TTA AAT AAC CCA CGG TCG GTG       2557
Lys Thr Arg Arg Thr Val Val Gln Tyr Leu Asn Asn Pro Arg Ser Val
            5475                5480                5485

GTA GTT CAT CCT TTT GCC GGG TAT CTA TTC TTC ACT GAT TGG TTC CGT       2605
Val Val His Pro Phe Ala Gly Tyr Leu Phe Phe Thr Asp Trp Phe Arg
        5490                5495                5500

CCT GCT AAA ATT ATG AGA GCA TGG AGT GAC GGA TCT CAC CTC TTG CCT       2653
Pro Ala Lys Ile Met Arg Ala Trp Ser Asp Gly Ser His Leu Leu Pro
    5505                5510                5515

GTA ATA AAC ACT ACT CTT GGA TGG CCC AAT GGC TTG GCC ATC GAT TGG       2701
Val Ile Asn Thr Thr Leu Gly Trp Pro Asn Gly Leu Ala Ile Asp Trp
5520            5525                5530                5535

GCT GCT TCA CGA TTG TAC TGG GTA GAT GCC TAT TTT GAT AAA ATT GAG       2749
Ala Ala Ser Arg Leu Tyr Trp Val Asp Ala Tyr Phe Asp Lys Ile Glu
                5540                5545                5550

CAC AGC ACC TTT GAT GGT TTA GAC AGA AGA AGA CTG GGC CAT ATA GAG       2797
His Ser Thr Phe Asp Gly Leu Asp Arg Arg Arg Leu Gly His Ile Glu
            5555                5560                5565

CAG ATG ACA CAT CCG TTT GGA CTT GCC ATC TTT GGA GAG CAT TTA TTT       2845
Gln Met Thr His Pro Phe Gly Leu Ala Ile Phe Gly Glu His Leu Phe
        5570                5575                5580

TTT ACT GAC TGG AGA CTG GGT GCC ATT ATT CGA GTC AGG AAA GCA GAT       2893
Phe Thr Asp Trp Arg Leu Gly Ala Ile Ile Arg Val Arg Lys Ala Asp
    5585                5590                5595

GGT GGA GAA ATG ACA GTT ATC CGA AGT GGC ATT GCT TAC ATA CTG CAT       2941
Gly Gly Glu Met Thr Val Ile Arg Ser Gly Ile Ala Tyr Ile Leu His
5600            5605                5610                5615

TTG AAA TCG TAT GAT GTC AAC ATC CAG ACT GGT TCT AAC GCC TGT AAT       2989
Leu Lys Ser Tyr Asp Val Asn Ile Gln Thr Gly Ser Asn Ala Cys Asn
                5620                5625                5630

CAA CCC ACG CAT CCT AAC GGT GAC TGC AGC CAC TTC TGC TTC CCG GTG       3037
Gln Pro Thr His Pro Asn Gly Asp Cys Ser His Phe Cys Phe Pro Val
            5635                5640                5645

CCA AAT TTC CAG CGA GTG TGT GGG TGC CCT TAT GGA ATG AGG CTG GCT       3085
Pro Asn Phe Gln Arg Val Cys Gly Cys Pro Tyr Gly Met Arg Leu Ala
        5650                5655                5660
```

```
TCC AAT CAC TTG ACA TGC GAG GGG GAC CCA ACM AAT GAA CCA CCC ACG    3133
Ser Asn His Leu Thr Cys Glu Gly Asp Pro Thr Asn Glu Pro Pro Thr
            5665                    5670                5675

GAG CAG TGT GGC TTA TTT TCC TTC CCC TGT AAA AAT GGC AGA TGT GTG    3181
Glu Gln Cys Gly Leu Phe Ser Phe Pro Cys Lys Asn Gly Arg Cys Val
5680                    5685                5690                5695

CCC AAT TAC TAT CTC TGT GAT GGA GTC GAT GAT TGT CAT GAT AAC AGT    3229
Pro Asn Tyr Tyr Leu Cys Asp Gly Val Asp Asp Cys His Asp Asn Ser
                5700                5705                5710

GAT GAG CAA CTA TGT GGC ACA CTT AAT AAT ACC TGT TCA TCT TCG GCG    3277
Asp Glu Gln Leu Cys Gly Thr Leu Asn Asn Thr Cys Ser Ser Ser Ala
            5715                    5720                5725

TTC ACC TGT GGC CAT GGG GAG TGC ATT CCT GCA CAC TGG CGC TGT GAC    3325
Phe Thr Cys Gly His Gly Glu Cys Ile Pro Ala His Trp Arg Cys Asp
        5730                    5735                5740

AAA CGC AAC GAC TGT GTG GAT GGC AGT GAT GAG CAC AAC TGC CCC ACC    3373
Lys Arg Asn Asp Cys Val Asp Gly Ser Asp Glu His Asn Cys Pro Thr
    5745                    5750                5755

CAC GCA CCT GCT TCC TGC CTT GAC ACC CAA TAC ACC TGT GAT AAT CAC    3421
His Ala Pro Ala Ser Cys Leu Asp Thr Gln Tyr Thr Cys Asp Asn His
5760                    5765                5770                5775

CAG TGT ATC TCA AAG AAC TGG GTC TGT GAC ACA GAC AAT GAT TGT GGG    3469
Gln Cys Ile Ser Lys Asn Trp Val Cys Asp Thr Asp Asn Asp Cys Gly
                5780                5785                5790

GAT GGA TCT GAT GAA AAG AAC TGC AAT TCG ACA GAG ACA TGC CAA CCT    3517
Asp Gly Ser Asp Glu Lys Asn Cys Asn Ser Thr Glu Thr Cys Gln Pro
            5795                    5800                5805

AGT CAG TTT AAT TGC CCC AAT CAT CGA TGT ATT GAC CTA TCG TTT GTC    3565
Ser Gln Phe Asn Cys Pro Asn His Arg Cys Ile Asp Leu Ser Phe Val
        5810                    5815                5820

TGT GAT GGT GAC AAG GAT TGT GTT GAT GGA TCT GAT GAG GTT GGT TGT    3613
Cys Asp Gly Asp Lys Asp Cys Val Asp Gly Ser Asp Glu Val Gly Cys
    5825                    5830                5835

GTA TTA AAC TGT ACT GCT TCT CAA TTC AAG TGT GCC AGT GGG GAT AAA    3661
Val Leu Asn Cys Thr Ala Ser Gln Phe Lys Cys Ala Ser Gly Asp Lys
5840                    5845                5850                5855

TGT ATT GGC GTC ACA AAT CGT TGT GAT GGT GTT TTT GAT TGC AGT GAC    3709
Cys Ile Gly Val Thr Asn Arg Cys Asp Gly Val Phe Asp Cys Ser Asp
                5860                5865                5870

AAC TCG GAT GAA GCG GGC TGT CCA ACC AGG CCT CCT GGT ATG TGC CAC    3757
Asn Ser Asp Glu Ala Gly Cys Pro Thr Arg Pro Pro Gly Met Cys His
            5875                    5880                5885

TCA GAT GAA TTT CAG TGC CAA GAA GAT GGT ATC TGC ATC CCG AAC TTC    3805
Ser Asp Glu Phe Gln Cys Gln Glu Asp Gly Ile Cys Ile Pro Asn Phe
        5890                    5895                5900

TGG GAA TGT GAT GGG CAT CCA GAC TGC CTC TAT GGA TCT GAT GAG CAC    3853
Trp Glu Cys Asp Gly His Pro Asp Cys Leu Tyr Gly Ser Asp Glu His
    5905                    5910                5915

AAT GCC TGT GTC CCC AAG ACT TGC CCT TCA TCA TAT TTC CAC TGT GAC    3901
Asn Ala Cys Val Pro Lys Thr Cys Pro Ser Ser Tyr Phe His Cys Asp
5920                    5925                5930                5935

AAC GGA AAC TGC ATC CAC AGG GCA TGG CTC TGT GAT CGG GAC AAT GAC    3949
Asn Gly Asn Cys Ile His Arg Ala Trp Leu Cys Asp Arg Asp Asn Asp
                5940                5945                5950

TGC GGG GAT ATG AGT GAT GAG AAG GAC TGC CCT ACT CAG CCC TTT CGC    3997
Cys Gly Asp Met Ser Asp Glu Lys Asp Cys Pro Thr Gln Pro Phe Arg
            5955                    5960                5965

TGT CCT AGT TGG CAA TGG CAG TGT CTT GGC CAT AAC ATC TGT GTG AAT    4045
Cys Pro Ser Trp Gln Trp Gln Cys Leu Gly His Asn Ile Cys Val Asn
        5970                    5975                5980
```

```
CTG AGT GTA GTG TGT GAT GGC ATC TTT GAC TGC CCC AAT GGG ACA GAT    4093
Leu Ser Val Val Cys Asp Gly Ile Phe Asp Cys Pro Asn Gly Thr Asp
        5985                5990                5995

GAG TCC CCA CTT TGC AAT GGG AAC AGC TGC TCA GAT TTC AAT GGT GGT    4141
Glu Ser Pro Leu Cys Asn Gly Asn Ser Cys Ser Asp Phe Asn Gly Gly
6000                6005                6010                6015

TGT ACT CAC GAG TGT GTT CAA GAG CCC TTT GGG GCT AAA TGC CTA TGT    4189
Cys Thr His Glu Cys Val Gln Glu Pro Phe Gly Ala Lys Cys Leu Cys
        6020                6025                6030

CCA TTG GGA TTC TTA CTT GCC AAT GAT TCT AAG ACC TGT GAA GAC ATA    4237
Pro Leu Gly Phe Leu Leu Ala Asn Asp Ser Lys Thr Cys Glu Asp Ile
        6035                6040                6045

GAT GAA TGT GAT ATT CTA GGC TCT TGT AGC CAG CAC TGT TAC AAT ATG    4285
Asp Glu Cys Asp Ile Leu Gly Ser Cys Ser Gln His Cys Tyr Asn Met
        6050                6055                6060

AGA GGT TCT TTC CGG TGC TCG TGT GAT ACA GGC TAC ATG TTA GAA AGT    4333
Arg Gly Ser Phe Arg Cys Ser Cys Asp Thr Gly Tyr Met Leu Glu Ser
        6065                6070                6075

GAT GGG AGG ACT TGC AAA GTT ACA GCA TCT GAG AGT CTG CTG TTA CTT    4381
Asp Gly Arg Thr Cys Lys Val Thr Ala Ser Glu Ser Leu Leu Leu Leu
6080                6085                6090                6095

GTG GCA AGT CAG AAC AAA ATT ATT GCC GAC AGT GTC ACC TCC CAG GTC    4429
Val Ala Ser Gln Asn Lys Ile Ile Ala Asp Ser Val Thr Ser Gln Val
        6100                6105                6110

CAC AAT ATC TAT TCA TTG GTC GAG AAT GGT TCT TAC ATT GTA GCT GTT    4477
His Asn Ile Tyr Ser Leu Val Glu Asn Gly Ser Tyr Ile Val Ala Val
        6115                6120                6125

GAT TTT GAT TCA ATT AGT GGT CGT ATC TTT TGG TCT GAT GCA ACT CAG    4525
Asp Phe Asp Ser Ile Ser Gly Arg Ile Phe Trp Ser Asp Ala Thr Gln
        6130                6135                6140

GGT AAA ACC TGG AGT GCG TTT CAA AAT GGA ACG GAC AGA AGA GTG GTA    4573
Gly Lys Thr Trp Ser Ala Phe Gln Asn Gly Thr Asp Arg Arg Val Val
        6145                6150                6155

TTT GAC AGT AGC ATC ATC TTG ACT GAA ACT ATT GCA ATA GAT TGG GTA    4621
Phe Asp Ser Ser Ile Ile Leu Thr Glu Thr Ile Ala Ile Asp Trp Val
6160                6165                6170                6175

GGT CGT AAT CTT TAC TGG ACA GAC TAT GCT CTG GAA ACA ATT GAA GTC    4669
Gly Arg Asn Leu Tyr Trp Thr Asp Tyr Ala Leu Glu Thr Ile Glu Val
        6180                6185                6190

TCC AAA ATT GAT GGG AGC CAC AGG ACT GTG CTG ATT AGT AAA AAC CTA    4717
Ser Lys Ile Asp Gly Ser His Arg Thr Val Leu Ile Ser Lys Asn Leu
        6195                6200                6205

ACA AAT CCA AGA GGA CTA GCA TTA GAT CCC AGA ATG AAT GAG CAT CTA    4765
Thr Asn Pro Arg Gly Leu Ala Leu Asp Pro Arg Met Asn Glu His Leu
        6210                6215                6220

CTG TTC TGG TCT GAC TGG GGC CAC CAC CCT CGC ATC GAG CGA GCC AGC    4813
Leu Phe Trp Ser Asp Trp Gly His His Pro Arg Ile Glu Arg Ala Ser
        6225                6230                6235

ATG GAC GGC AGC ATG CGC ACT GTC ATT GTC CAG GAC AAG ATC TTC TGG    4861
Met Asp Gly Ser Met Arg Thr Val Ile Val Gln Asp Lys Ile Phe Trp
6240                6245                6250                6255

CCC TGC GGC TTA ACT ATT GAC TAC CCC AAC AGA CTG CTC TAC TTC ATG    4909
Pro Cys Gly Leu Thr Ile Asp Tyr Pro Asn Arg Leu Leu Tyr Phe Met
        6260                6265                6270

GAC TCC TAT CTT GAT TAC ATG GAC TTT TGT GAT TAT AAT GGA CAC CAT    4957
Asp Ser Tyr Leu Asp Tyr Met Asp Phe Cys Asp Tyr Asn Gly His His
        6275                6280                6285

CGG AGA CAG GTG ATA GCC AGT GAT TTG ATT ATA CGG CAC CCC TAT GCC    5005
Arg Arg Gln Val Ile Ala Ser Asp Leu Ile Ile Arg His Pro Tyr Ala
```

```
            6290                6295                6300
CTA ACT CTC TTT GAA GAC TCT GTG TAC TGG ACT GAC CGT GCT ACT CGT         5053
Leu Thr Leu Phe Glu Asp Ser Val Tyr Trp Thr Asp Arg Ala Thr Arg
        6305                6310                6315

CGG GTT ATG CGA GCC AAC AAG TGG CAT GGA GGG AAC CAG TCA GTT GTA         5101
Arg Val Met Arg Ala Asn Lys Trp His Gly Gly Asn Gln Ser Val Val
6320                6325                6330                6335

ATG TAT AAT ATT CAA TGG CCC CTT GGG ATT GTT GCG GTT CAT CCT TCG         5149
Met Tyr Asn Ile Gln Trp Pro Leu Gly Ile Val Ala Val His Pro Ser
                6340                6345                6350

AAA CAA CCA AAT TCC GTG AAT CCA TGT GCC TTT TCC CGC TGC AGC CAT         5197
Lys Gln Pro Asn Ser Val Asn Pro Cys Ala Phe Ser Arg Cys Ser His
            6355                6360                6365

CTC TGC CTG CTT TCC TCA CAG GGG CCT CAT TTT TAC TCC TGT GTT TGT         5245
Leu Cys Leu Leu Ser Ser Gln Gly Pro His Phe Tyr Ser Cys Val Cys
        6370                6375                6380

CCT TCA GGA TGG AGT CTG TCT CCT GAT CTC CTG AAT TGC TTG AGA GAT         5293
Pro Ser Gly Trp Ser Leu Ser Pro Asp Leu Leu Asn Cys Leu Arg Asp
    6385                6390                6395

GAT CAA CCT TTC TTA ATA ACT GTA AGG CAA CAT ATA ATT TTT GGA ATC         5341
Asp Gln Pro Phe Leu Ile Thr Val Arg Gln His Ile Ile Phe Gly Ile
6400                6405                6410                6415

TCC CTT AAT CCT GAG GTG AAG AGC AAT GAT GCT ATG GTC CCC ATA GCA         5389
Ser Leu Asn Pro Glu Val Lys Ser Asn Asp Ala Met Val Pro Ile Ala
                6420                6425                6430

GGG ATA CAG AAT GGT TTA GAT GTT GAA TTT GAT GAT GCT GAG CAA TAC         5437
Gly Ile Gln Asn Gly Leu Asp Val Glu Phe Asp Asp Ala Glu Gln Tyr
            6435                6440                6445

ATC TAT TGG GTT GAA AAT CCA GGT GAA ATT CAC AGA GTG AAG ACA GAT         5485
Ile Tyr Trp Val Glu Asn Pro Gly Glu Ile His Arg Val Lys Thr Asp
        6450                6455                6460

GGC ACC AAC AGG ACA GTA TTT GCT TCT ATA TCT ATG GTG GGG CCT TCT         5533
Gly Thr Asn Arg Thr Val Phe Ala Ser Ile Ser Met Val Gly Pro Ser
    6465                6470                6475

ATG AAC CTG GCC TTA GAT TGG ATT TCA AGA AAC CTT TAT TCT ACC AAT         5581
Met Asn Leu Ala Leu Asp Trp Ile Ser Arg Asn Leu Tyr Ser Thr Asn
6480                6485                6490                6495

CCT AGA ACT CAG TCA ATC GAG GTT TTG ACA CTC CAC GGA GAT ATC AGA         5629
Pro Arg Thr Gln Ser Ile Glu Val Leu Thr Leu His Gly Asp Ile Arg
                6500                6505                6510

TAC AGA AAA ACA TTG ATT GCC AAT GAT GGG ACA GCT CTT GGA GTT GGC         5677
Tyr Arg Lys Thr Leu Ile Ala Asn Asp Gly Thr Ala Leu Gly Val Gly
            6515                6520                6525

TTT CCA ATT GGC ATA ACT GTT GAT CCT GCT CGT GGG AAG CTG TAC TGG         5725
Phe Pro Ile Gly Ile Thr Val Asp Pro Ala Arg Gly Lys Leu Tyr Trp
        6530                6535                6540

TCA GAC CAA GGA ACT GAC AGT GGG GTT CCT GCC AAG ATC GCC AGT GCT         5773
Ser Asp Gln Gly Thr Asp Ser Gly Val Pro Ala Lys Ile Ala Ser Ala
    6545                6550                6555

AAC ATG GAT GGC ACA TCT GTG AAA ACT CTC TTT ACT GGG AAC CTC GAA         5821
Asn Met Asp Gly Thr Ser Val Lys Thr Leu Phe Thr Gly Asn Leu Glu
6560                6565                6570                6575

CAC CTG GAG TGT GTC ACT CTT GAC ATC GAA GAG CAG AAA CTC TAC TGG         5869
His Leu Glu Cys Val Thr Leu Asp Ile Glu Glu Gln Lys Leu Tyr Trp
                6580                6585                6590

GCA GTC ACT GGA AGA GGA GTG ATT GAA AGA GGA AAC GTG GAT GGA ACA         5917
Ala Val Thr Gly Arg Gly Val Ile Glu Arg Gly Asn Val Asp Gly Thr
            6595                6600                6605

GAT CGA ATG ATC CTG GTA CAC CAG CTT TCC CAC CCC TGG GGA ATT GCA         5965
```

```
                    -continued

Asp Arg Met Ile Leu Val His Gln Leu Ser His Pro Trp Gly Ile Ala
        6610                6615                6620

GTC CAT GAT TCT TTC CTT TAT TAT ACT GAT GAA CAG TAT GAG GTC ATT    6013
Val His Asp Ser Phe Leu Tyr Tyr Thr Asp Glu Gln Tyr Glu Val Ile
        6625                6630                6635

GAA AGA GTT GAT AAG GCC ACT GGG GCC AAC AAA ATA GTC TTG AGA GAT    6061
Glu Arg Val Asp Lys Ala Thr Gly Ala Asn Lys Ile Val Leu Arg Asp
6640                6645                6650                6655

AAT GTT CCA AAT CTG AGG GGT CTT CAA GTT TAT CAC AGA CGC AAT GCC    6109
Asn Val Pro Asn Leu Arg Gly Leu Gln Val Tyr His Arg Arg Asn Ala
                6660                6665                6670

GCC GAA TCC TCA AAT GGC TGT AGC AAC AAC ATG AAT GCC TGT CAG CAG    6157
Ala Glu Ser Ser Asn Gly Cys Ser Asn Asn Met Asn Ala Cys Gln Gln
                    6675                6680                6685

ATT TGC CTG CCT GTA CCA GGA GGA TTG TTT TCC TGC GCC TGT GCC ACT    6205
Ile Cys Leu Pro Val Pro Gly Gly Leu Phe Ser Cys Ala Cys Ala Thr
                6690                6695                6700

GGA TTT AAA CTC AAT CCT GAT AAT CGG TCC TGC TCT CCA TAT AAC TCT    6253
Gly Phe Lys Leu Asn Pro Asp Asn Arg Ser Cys Ser Pro Tyr Asn Ser
        6705                6710                6715

TTC ATT GTT GTT TCA ATG CTG TCT GCA ATC AGA GGC TTT AGC TTG GAA    6301
Phe Ile Val Val Ser Met Leu Ser Ala Ile Arg Gly Phe Ser Leu Glu
6720                6725                6730                6735

TTG TCA GAT CAT TCA GAA ACC ATG GTG CCG GTG GCA GGC CAA GGA CGA    6349
Leu Ser Asp His Ser Glu Thr Met Val Pro Val Ala Gly Gln Gly Arg
                6740                6745                6750

AAC GCA CTG CAT GTG GAT GTG GAT GTG TCC TCT GGC TTT ATT TAT TGG    6397
Asn Ala Leu His Val Asp Val Asp Val Ser Ser Gly Phe Ile Tyr Trp
                6755                6760                6765

TGT GAT TTT AGC AGC TCA GTG GCA TCT GAT AAT GCG ATC CGT AGA ATT    6445
Cys Asp Phe Ser Ser Ser Val Ala Ser Asp Asn Ala Ile Arg Arg Ile
            6770                6775                6780

AAA CCA GAT GGA TCT TCT CTG ATG AAC ATT GTG ACA CAT GGA ATA GGA    6493
Lys Pro Asp Gly Ser Ser Leu Met Asn Ile Val Thr His Gly Ile Gly
            6785                6790                6795

GAA AAT GGA GTC CGG GGT ATT GCA GTG GAT TGG GTA GCA GGA AAT CTT    6541
Glu Asn Gly Val Arg Gly Ile Ala Val Asp Trp Val Ala Gly Asn Leu
6800                6805                6810                6815

TAT TTC ACC AAT GCC TTT GTT TCT GAA ACA CTG ATA GAA GTT CTG CGG    6589
Tyr Phe Thr Asn Ala Phe Val Ser Glu Thr Leu Ile Glu Val Leu Arg
                6820                6825                6830

ATC AAT ACT ACT TAC CGC CGT GTT CTT CTT AAA GTC ACA GTG GAC ATG    6637
Ile Asn Thr Thr Tyr Arg Arg Val Leu Leu Lys Val Thr Val Asp Met
                6835                6840                6845

CCT AGG CAT ATT GTT GTA GAT CCC AAG AAC AGA TAC CTC TTC TGG GCT    6685
Pro Arg His Ile Val Val Asp Pro Lys Asn Arg Tyr Leu Phe Trp Ala
            6850                6855                6860

GAC TAT GGG CAG AGA CCA AAG ATT GAG CGT TCT TTC CTT GAC TGT ACC    6733
Asp Tyr Gly Gln Arg Pro Lys Ile Glu Arg Ser Phe Leu Asp Cys Thr
        6865                6870                6875

AAT CGA ACA GTG CTT GTG TCA GAG GGC ATT GTC ACA CCA CGG GGC TTG    6781
Asn Arg Thr Val Leu Val Ser Glu Gly Ile Val Thr Pro Arg Gly Leu
6880                6885                6890                6895

GCA GTG GAC CGA AGT GAT GGC TAC GTT TAT TGG GTT GAT GAT TCT TTA    6829
Ala Val Asp Arg Ser Asp Gly Tyr Val Tyr Trp Val Asp Asp Ser Leu
                6900                6905                6910

GAT ATA ATT GCA AGG ATT CGT ATC AAT GGA GAG AAC TCT GAA GTG ATT    6877
Asp Ile Ile Ala Arg Ile Arg Ile Asn Gly Glu Asn Ser Glu Val Ile
        6915                6920                6925
```

```
CGT TAT GGC AGT CGT TAC CCA ACT CCT TAT GGC ATC ACT GTT TTT GAA         6925
Arg Tyr Gly Ser Arg Tyr Pro Thr Pro Tyr Gly Ile Thr Val Phe Glu
            6930                6935                6940

AAT TCT ATC ATA TGG GTA GAT AGG AAT TTG AAA AAG ATC TTC CAA GCC         6973
Asn Ser Ile Ile Trp Val Asp Arg Asn Leu Lys Lys Ile Phe Gln Ala
            6945                6950                6955

AGC AAG GAA CCA GAG AAC ACA GAG CCA CCC ACA GTG ATA AGA GAC AAT         7021
Ser Lys Glu Pro Glu Asn Thr Glu Pro Pro Thr Val Ile Arg Asp Asn
6960                6965                6970                6975

ATC AAC TGG CTA AGA GAT GTG ACC ATC TTT GAC AAG CAA GTC CAG CCC         7069
Ile Asn Trp Leu Arg Asp Val Thr Ile Phe Asp Lys Gln Val Gln Pro
            6980                6985                6990

CGG TCA CCA GCA GAG GTC AAC AAC AAC CCT TGC TTG GAA AAC AAT GGT         7117
Arg Ser Pro Ala Glu Val Asn Asn Asn Pro Cys Leu Glu Asn Asn Gly
            6995                7000                7005

GGG TGC TCT CAT CTC TGC TTT GCT CTG CCT GGA TTG CAC ACC CCA AAA         7165
Gly Cys Ser His Leu Cys Phe Ala Leu Pro Gly Leu His Thr Pro Lys
            7010                7015                7020

TGT GAC TGT GCC TTT GGG ACC CTG CAA AGT GAT GGC AAG AAT TGT GCC         7213
Cys Asp Cys Ala Phe Gly Thr Leu Gln Ser Asp Gly Lys Asn Cys Ala
7025                7030                7035

ATT TCA ACA GAA AAT TTC CTC ATC TTT GCC TTG TCT AAT TCC TTG AGA         7261
Ile Ser Thr Glu Asn Phe Leu Ile Phe Ala Leu Ser Asn Ser Leu Arg
7040                7045                7050                7055

AGC TTA CAC TTG GAC CCT GAA AAC CAT AGC CCA CCT TTC CAA ACA ATA         7309
Ser Leu His Leu Asp Pro Glu Asn His Ser Pro Pro Phe Gln Thr Ile
            7060                7065                7070

AAT GTG GAA AGA ACT GTC ATG TCT CTA GAC TAT GAC AGT GTA AGT GAT         7357
Asn Val Glu Arg Thr Val Met Ser Leu Asp Tyr Asp Ser Val Ser Asp
            7075                7080                7085

AGA ATC TAC TTC ACA CAA AAT TTA GCC TCT GGA GTT GGA CAG ATT TCC         7405
Arg Ile Tyr Phe Thr Gln Asn Leu Ala Ser Gly Val Gly Gln Ile Ser
            7090                7095                7100

TAT GCC ACC CTG TCT TCA GGG ATC CAT ACT CCA ACT GTC ATT GCT TCA         7453
Tyr Ala Thr Leu Ser Ser Gly Ile His Thr Pro Thr Val Ile Ala Ser
            7105                7110                7115

GGT ATA GGG ACT GCT GAT GGC ATT GCC TTT GAC TGG ATT ACT AGA AGA         7501
Gly Ile Gly Thr Ala Asp Gly Ile Ala Phe Asp Trp Ile Thr Arg Arg
7120                7125                7130                7135

ATT TAT TAC AGT GAC TAC CTC AAC CAG ATG ATT AAT TCC ATG GCT GAA         7549
Ile Tyr Tyr Ser Asp Tyr Leu Asn Gln Met Ile Asn Ser Met Ala Glu
            7140                7145                7150

GAT GGG TCT AAC CGC ACT GTG ATA GCC CGC GTT CCA AAA CCA AGA GCA         7597
Asp Gly Ser Asn Arg Thr Val Ile Ala Arg Val Pro Lys Pro Arg Ala
            7155                7160                7165

ATT GTG TTA GAT CCC TGC CAA GGG TAC CTG TAC TGG GCT GAC TGG GAT         7645
Ile Val Leu Asp Pro Cys Gln Gly Tyr Leu Tyr Trp Ala Asp Trp Asp
            7170                7175                7180

ACA CAT GCC AAA ATC GAG AGA GCC ACA TTG GGA GGA AAC TTC CGC GTA         7693
Thr His Ala Lys Ile Glu Arg Ala Thr Leu Gly Gly Asn Phe Arg Val
            7185                7190                7195

CCC ATT GTG AAC AGC AGT CTG GTC ATG CCC AGT GGG CTG ACT CTG GAC         7741
Pro Ile Val Asn Ser Ser Leu Val Met Pro Ser Gly Leu Thr Leu Asp
7200                7205                7210                7215

TAT GAA GAG GAC CTT CTC TAC TGG GTG GAT GCT AGT CTG CAG AGG ATT         7789
Tyr Glu Glu Asp Leu Leu Tyr Trp Val Asp Ala Ser Leu Gln Arg Ile
            7220                7225                7230

GAA CGC AGC ACT CTG ACG GGC GTG GAT CGT GAA GTC ATT GTC AAT GCA         7837
Glu Arg Ser Thr Leu Thr Gly Val Asp Arg Glu Val Ile Val Asn Ala
            7235                7240                7245
```

-continued

```
GCC GTT CAT GCT TTT GGC TTG ACT CTC TAT GGC CAG TAT ATT TAC TGG        7885
Ala Val His Ala Phe Gly Leu Thr Leu Tyr Gly Gln Tyr Ile Tyr Trp
            7250                7255                7260

ACT GAC TTG TAC ACA CAA AGA ATT TAC CGA GCT AAC AAA TAT GAC GGG        7933
Thr Asp Leu Tyr Thr Gln Arg Ile Tyr Arg Ala Asn Lys Tyr Asp Gly
            7265                7270                7275

TCA GGT CAG ATT GCA ATG ACC ACA AAT TTG CTC TCC CAG CCC AGG GGA        7981
Ser Gly Gln Ile Ala Met Thr Thr Asn Leu Leu Ser Gln Pro Arg Gly
7280                7285                7290                7295

ATC AAC ACT GTT GTG AAG AAC CAG AAA CAA CAG TGT AAC AAT CCT TGT        8029
Ile Asn Thr Val Val Lys Asn Gln Lys Gln Gln Cys Asn Asn Pro Cys
            7300                7305                7310

GAA CAG TTT AAT GGG GGC TGC AGC CAT ATC TGT GCA CCA GGT CCA AAT        8077
Glu Gln Phe Asn Gly Gly Cys Ser His Ile Cys Ala Pro Gly Pro Asn
            7315                7320                7325

GGT GCC GAG TGC CAG TGT CCA CAT GAG GGC AAC TGG TAT TTG GCC AAC        8125
Gly Ala Glu Cys Gln Cys Pro His Glu Gly Asn Trp Tyr Leu Ala Asn
            7330                7335                7340

AAC AGG AAG CAC TGC ATT GTG GAC AAT GGT GAA CGA TGT GGT GCA TCT        8173
Asn Arg Lys His Cys Ile Val Asp Asn Gly Glu Arg Cys Gly Ala Ser
            7345                7350                7355

TCC TTC ACC TGC TCC AAT GGG CGC TGC ATC TCG GAA GAG TGG AAG TGT        8221
Ser Phe Thr Cys Ser Asn Gly Arg Cys Ile Ser Glu Glu Trp Lys Cys
7360                7365                7370                7375

GAT AAT GAC AAC GAC TGT GGG GAT GGC AGT GAT GAG ATG GAA AGT GTC        8269
Asp Asn Asp Asn Asp Cys Gly Asp Gly Ser Asp Glu Met Glu Ser Val
            7380                7385                7390

TGT GCA CTT CAC ACC TGC TCA CCG ACA GCC TTC ACC TGT GCC AAT GGG        8317
Cys Ala Leu His Thr Cys Ser Pro Thr Ala Phe Thr Cys Ala Asn Gly
            7395                7400                7405

CGA TGT GTC CAA TAC TCT TAC CGC TGT GAT TAC TAC AAT GAC TGT GGT        8365
Arg Cys Val Gln Tyr Ser Tyr Arg Cys Asp Tyr Tyr Asn Asp Cys Gly
            7410                7415                7420

GAT GGC AGT GAT GAG GCA GGG TGC CTG TTC AGG GAC TGC AAT GCC ACC        8413
Asp Gly Ser Asp Glu Ala Gly Cys Leu Phe Arg Asp Cys Asn Ala Thr
            7425                7430                7435

ACG GAG TTT ATG TGC AAT AAC AGA AGG TGC ATA CCT CGT GAG TTT ATC        8461
Thr Glu Phe Met Cys Asn Asn Arg Arg Cys Ile Pro Arg Glu Phe Ile
7440                7445                7450                7455

TGC AAT GGT GTA GAC AAC TGC CAT GAT AAT AAC ACT TCA GAT GAG AAA        8509
Cys Asn Gly Val Asp Asn Cys His Asp Asn Asn Thr Ser Asp Glu Lys
            7460                7465                7470

AAT TGC CCT GAT CGC ACT TGC CAG TCT GGA TAC ACA AAA TGT CAT AAT        8557
Asn Cys Pro Asp Arg Thr Cys Gln Ser Gly Tyr Thr Lys Cys His Asn
            7475                7480                7485

TCA AAT ATT TGT ATT CCT CGC GTT TAT TTG TGT GAC GGA GAC AAT GAC        8605
Ser Asn Ile Cys Ile Pro Arg Val Tyr Leu Cys Asp Gly Asp Asn Asp
            7490                7495                7500

TGT GGA GAT AAC AGT GAT GAA AAC CCT ACT TAT TGC ACC ACT CAC ACG        8653
Cys Gly Asp Asn Ser Asp Glu Asn Pro Thr Tyr Cys Thr Thr His Thr
            7505                7510                7515

TGC AGC AGC AGT GAG TTC CAA TGC GCA TCT GGG CGC TGT ATT CCT CAA        8701
Cys Ser Ser Ser Glu Phe Gln Cys Ala Ser Gly Arg Cys Ile Pro Gln
7520                7525                7530                7535

CAT TGG TAT TGT GAT CAA GAA ACA GAT TGT TTT GAT GCC TCT GAT GAA        8749
His Trp Tyr Cys Asp Gln Glu Thr Asp Cys Phe Asp Ala Ser Asp Glu
            7540                7545                7550

CCT GCC TCT TGT GGT CAC TCT GAG CGA ACA TGC CTA GCT GAT GAG TTC        8797
Pro Ala Ser Cys Gly His Ser Glu Arg Thr Cys Leu Ala Asp Glu Phe
```

```
              7555            7560            7565
AAG TGT GAT GGT GGG AGG TGC ATC CCA AGC GAA TGG ATC TGT GAC GGT   8845
Lys Cys Asp Gly Gly Arg Cys Ile Pro Ser Glu Trp Ile Cys Asp Gly
            7570            7575            7580

GAT AAT GAC TGT GGG GAT ATG AGT GAC GAG GAT AAA AGG CAC CAG TGT   8893
Asp Asn Asp Cys Gly Asp Met Ser Asp Glu Asp Lys Arg His Gln Cys
            7585            7590            7595

CAG AAT CAA AAC TGC TCG GAT TCC GAG TTT CTC TGT GTA AAT GAC AGA   8941
Gln Asn Gln Asn Cys Ser Asp Ser Glu Phe Leu Cys Val Asn Asp Arg
7600            7605            7610            7615

CCT CCG GAC AGG AGG TGC ATT CCC CAG TCT TGG GTC TGT GAT GGC GAT   8989
Pro Pro Asp Arg Arg Cys Ile Pro Gln Ser Trp Val Cys Asp Gly Asp
            7620            7625            7630

GTG GAT TGT ACT GAC GGC TAC GAT GAG AAT CAG AAT TGC ACC AGG AGA   9037
Val Asp Cys Thr Asp Gly Tyr Asp Glu Asn Gln Asn Cys Thr Arg Arg
            7635            7640            7645

ACT TGC TCT GAA AAT GAA TTC ACC TGT GGT TAC GGA CTG TGT ATC CCA   9085
Thr Cys Ser Glu Asn Glu Phe Thr Cys Gly Tyr Gly Leu Cys Ile Pro
            7650            7655            7660

AAG ATA TTC AGG TGT GAC CGG CAC AAT GAC TGT GGT GAC TAT AGC GAC   9133
Lys Ile Phe Arg Cys Asp Arg His Asn Asp Cys Gly Asp Tyr Ser Asp
            7665            7670            7675

GAG AGG GGC TGC TTA TAC CAG ACT TGC CAA CAG AAT CAG TTT ACC TGT   9181
Glu Arg Gly Cys Leu Tyr Gln Thr Cys Gln Gln Asn Gln Phe Thr Cys
7680            7685            7690            7695

CAG AAC GGG CGC TGC ATT AGT AAA ACC TTC GTC TGT GAT GAG GAT AAT   9229
Gln Asn Gly Arg Cys Ile Ser Lys Thr Phe Val Cys Asp Glu Asp Asn
            7700            7705            7710

GAC TGT GGA GAC GGA TCT GAT GAG CTG ATG CAC CTG TGC CAC ACC CCA   9277
Asp Cys Gly Asp Gly Ser Asp Glu Leu Met His Leu Cys His Thr Pro
            7715            7720            7725

GAA CCC ACG TGT CCA CCT CAC GAG TTC AAG TGT GAC AAT GGG CGC TGC   9325
Glu Pro Thr Cys Pro Pro His Glu Phe Lys Cys Asp Asn Gly Arg Cys
            7730            7735            7740

ATC GAG ATG ATG AAA CTC TGC AAC CAC CTA GAT GAC TGT TTG GAC AAC   9373
Ile Glu Met Met Lys Leu Cys Asn His Leu Asp Asp Cys Leu Asp Asn
            7745            7750            7755

AGC GAT GAG AAA GGC TGT GGC ATT AAT GAA TGC CAT GAC CCT TCA ATC   9421
Ser Asp Glu Lys Gly Cys Gly Ile Asn Glu Cys His Asp Pro Ser Ile
7760            7765            7770            7775

AGT GGC TGC GAT CAC AAC TGC ACA GAC ACC TTA ACC AGT TTC TAT TGT   9469
Ser Gly Cys Asp His Asn Cys Thr Asp Thr Leu Thr Ser Phe Tyr Cys
            7780            7785            7790

TCC TGT CGT CCT GGT TAC AAG CTC ATG TCT GAC AAG CGG ACT TGT GTT   9517
Ser Cys Arg Pro Gly Tyr Lys Leu Met Ser Asp Lys Arg Thr Cys Val
            7795            7800            7805

GAT ATT GAT GAA TGC ACA GAG ATG CCT TTT GTC TGT AGC CAG AAG TGT   9565
Asp Ile Asp Glu Cys Thr Glu Met Pro Phe Val Cys Ser Gln Lys Cys
            7810            7815            7820

GAG AAT GTA ATA GGC TCC TAC ATC TGT AAG TGT GCC CCA GGC TAC CTC   9613
Glu Asn Val Ile Gly Ser Tyr Ile Cys Lys Cys Ala Pro Gly Tyr Leu
            7825            7830            7835

CGA GAA CCA GAT GGA AAG ACC TGC CGG CAA AAC AGT AAC ATC GAA CCC   9661
Arg Glu Pro Asp Gly Lys Thr Cys Arg Gln Asn Ser Asn Ile Glu Pro
7840            7845            7850            7855

TAT CTC ATT TTT AGC AAC CGT TAC TAT TTG AGA AAT TTA ACT ATA GAT   9709
Tyr Leu Ile Phe Ser Asn Arg Tyr Tyr Leu Arg Asn Leu Thr Ile Asp
            7860            7865            7870

GGC TAT TTT TAC TCC CTC ATC TTG GAA GGA CTG GAC AAT GTT GTG GCA   9757
```

-continued

```
Gly Tyr Phe Tyr Ser Leu Ile Leu Glu Gly Leu Asp Asn Val Val Ala
        7875                7880                7885

TTA GAT TTT GAC CGA GTA GAG AAG AGA TTG TAT TGG ATT GAT ACA CAG        9805
Leu Asp Phe Asp Arg Val Glu Lys Arg Leu Tyr Trp Ile Asp Thr Gln
        7890                7895                7900

AGG CAA GTC ATT GAG AGA ATG TTT CTG AAT AAG ACA AAC AAG GAG ACA        9853
Arg Gln Val Ile Glu Arg Met Phe Leu Asn Lys Thr Asn Lys Glu Thr
        7905                7910                7915

ATC ATA AAC CAC AGA CTA CCA GCT GCA GAA AGT CTG GCT GTA GAC TGG        9901
Ile Ile Asn His Arg Leu Pro Ala Ala Glu Ser Leu Ala Val Asp Trp
7920            7925                7930                7935

GTT TCC AGA AAG CTC TAC TGG TTG GAT GCC CGC CTG GAT GGC CTC TTT        9949
Val Ser Arg Lys Leu Tyr Trp Leu Asp Ala Arg Leu Asp Gly Leu Phe
            7940                7945                7950

GTC TCT GAC CTC AAT GGT GGA CAC CGC CGC ATG CTG GCC CAG CAC TGT        9997
Val Ser Asp Leu Asn Gly Gly His Arg Arg Met Leu Ala Gln His Cys
            7955                7960                7965

GTG GAT GCC AAC AAC ACC TTC TGC TTT GAT AAT CCC AGA GGA CTT GCC       10045
Val Asp Ala Asn Asn Thr Phe Cys Phe Asp Asn Pro Arg Gly Leu Ala
            7970                7975                7980

CTT CAC CCT CAA TAT GGG TAC CTC TAC TGG GCA GAC TGG GGT CAC CGC       10093
Leu His Pro Gln Tyr Gly Tyr Leu Tyr Trp Ala Asp Trp Gly His Arg
            7985                7990                7995

GCA TAC ATT GGG AGA GTA GGC ATG GAT GGA ACC AAC AAG TCT GTG ATA       10141
Ala Tyr Ile Gly Arg Val Gly Met Asp Gly Thr Asn Lys Ser Val Ile
8000                8005                8010                8015

ATC TCC ACC AAG TTA GAG TGG CCT AAT GGC ATC ACC ATT GAT TAC ACC       10189
Ile Ser Thr Lys Leu Glu Trp Pro Asn Gly Ile Thr Ile Asp Tyr Thr
            8020                8025                8030

AAT GAT CTA CTC TAC TGG GCA GAT GCC CAC CTG GGT TAC ATA GAG TAC       10237
Asn Asp Leu Leu Tyr Trp Ala Asp Ala His Leu Gly Tyr Ile Glu Tyr
            8035                8040                8045

TCT GAT TTG GAG GGC CAC CAT CGA CAC ACG GTG TAT GAT GGG GCA CTG       10285
Ser Asp Leu Glu Gly His His Arg His Thr Val Tyr Asp Gly Ala Leu
            8050                8055                8060

CCT CAC CCT TTC GCT ATT ACC ATT TTT GAA GAC ACT ATT TAT TGG ACA       10333
Pro His Pro Phe Ala Ile Thr Ile Phe Glu Asp Thr Ile Tyr Trp Thr
        8065                8070                8075

GAT TGG AAT ACA AGG ACA GTG GAA AAG GGA AAC AAA TAT GAT GGA TCA       10381
Asp Trp Asn Thr Arg Thr Val Glu Lys Gly Asn Lys Tyr Asp Gly Ser
8080            8085                8090                8095

AAT AGA CAG ACA CTG GTG AAC ACA ACA CAC AGA CCA TTT GAC ATC CAT       10429
Asn Arg Gln Thr Leu Val Asn Thr Thr His Arg Pro Phe Asp Ile His
            8100                8105                8110

GTG TAC CAT CCA TAT AGG CAG CCC ATT GTG AGC AAT CCC TGT GGT ACC       10477
Val Tyr His Pro Tyr Arg Gln Pro Ile Val Ser Asn Pro Cys Gly Thr
            8115                8120                8125

AAC AAT GGT GGC TGT TCT CAT CTC TGC CTC ATC AAG CCA GGA GGA AAA       10525
Asn Asn Gly Gly Cys Ser His Leu Cys Leu Ile Lys Pro Gly Gly Lys
            8130                8135                8140

GGG TTC ACT TGC GAG TGT CCA GAT GAC TTC CGC ACC CTT CAA CTG AGT       10573
Gly Phe Thr Cys Glu Cys Pro Asp Asp Phe Arg Thr Leu Gln Leu Ser
            8145                8150                8155

GGC AGC ACC TAC TGC ATG CCC ATG TGC TCC AGC ACC CAG TTC CTG TGC       10621
Gly Ser Thr Tyr Cys Met Pro Met Cys Ser Ser Thr Gln Phe Leu Cys
8160                8165                8170                8175

GCT AAC AAT GAA AAG TGC ATT CCT ATC TGG TGG AAA TGT GAT GGA CAG       10669
Ala Asn Asn Glu Lys Cys Ile Pro Ile Trp Trp Lys Cys Asp Gly Gln
            8180                8185                8190
```

```
AAA GAC TGC TCA GAT GGC TCT GAT GAA CTG GCC CTT TGC CCG CAG CGC         10717
Lys Asp Cys Ser Asp Gly Ser Asp Glu Leu Ala Leu Cys Pro Gln Arg
            8195                8200                8205

TTC TGC CGA CTG GGA CAG TTC CAG TGC AGT GAC GGC AAC TGC ACC AGC         10765
Phe Cys Arg Leu Gly Gln Phe Gln Cys Ser Asp Gly Asn Cys Thr Ser
            8210                8215                8220

CCG CAG ACT TTA TGC AAT GCT CAC CAA AAT TGC CCT GAT GGG TCT GAT         10813
Pro Gln Thr Leu Cys Asn Ala His Gln Asn Cys Pro Asp Gly Ser Asp
            8225                8230                8235

GAA GAC CGT CTT CTT TGT GAG AAT CAC CAC TGT GAC TCC AAT GAA TGG         10861
Glu Asp Arg Leu Leu Cys Glu Asn His His Cys Asp Ser Asn Glu Trp
8240            8245                8250                8255

CAG TGC GCC AAC AAA CGT TGC ATC CCA GAA TCC TGG CAG TGT GAC ACA         10909
Gln Cys Ala Asn Lys Arg Cys Ile Pro Glu Ser Trp Gln Cys Asp Thr
                8260                8265                8270

TTT AAC GAC TGT GAG GAT AAC TCA GAT GAA GAC AGT TCC CAC TGT GCC         10957
Phe Asn Asp Cys Glu Asp Asn Ser Asp Glu Asp Ser Ser His Cys Ala
                8275                8280                8285

AGC AGG ACC TGC CGG CCG GGC CAG TTT CGG TGT GCT AAT GGC CGC TGC         11005
Ser Arg Thr Cys Arg Pro Gly Gln Phe Arg Cys Ala Asn Gly Arg Cys
                8290                8295                8300

ATC CCG CAG GCC TGG AAG TGT GAT GTG GAT AAT GAT TGT GGA GAC CAC         11053
Ile Pro Gln Ala Trp Lys Cys Asp Val Asp Asn Asp Cys Gly Asp His
                8305                8310                8315

TCG GAT GAG CCC ATT GAA GAA TGC ATG AGC TCT GCC CAT CTC TGT GAC         11101
Ser Asp Glu Pro Ile Glu Glu Cys Met Ser Ser Ala His Leu Cys Asp
8320            8325                8330                8335

AAC TTC ACA GAA TTC AGC TGC AAA ACA AAT TAC CGC TGC ATC CCA AAG         11149
Asn Phe Thr Glu Phe Ser Cys Lys Thr Asn Tyr Arg Cys Ile Pro Lys
                8340                8345                8350

TGG GCC GTG TGC AAT GGT GTA GAT GAC TGC AGG GAC AAC AGT GAT GAG         11197
Trp Ala Val Cys Asn Gly Val Asp Asp Cys Arg Asp Asn Ser Asp Glu
                8355                8360                8365

CAA GGC TGT GAG GAG AGG ACA TGC CAT CCT GTG GGG GAT TTC CGC TGT         11245
Gln Gly Cys Glu Glu Arg Thr Cys His Pro Val Gly Asp Phe Arg Cys
                8370                8375                8380

AAA AAT CAC CAC TGC ATC CCT CTT CGT TGG CAG TGT GAT GGG CAA AAT         11293
Lys Asn His His Cys Ile Pro Leu Arg Trp Gln Cys Asp Gly Gln Asn
            8385                8390                8395

GAC TGT GGA GAT AAC TCA GAT GAG GAA AAC TGT GCT CCC CGG GAG TGC         11341
Asp Cys Gly Asp Asn Ser Asp Glu Glu Asn Cys Ala Pro Arg Glu Cys
8400            8405                8410                8415

ACA GAG AGC GAG TTT CGA TGT GTC AAT CAG CAG TGC ATT CCC TCG CGA         11389
Thr Glu Ser Glu Phe Arg Cys Val Asn Gln Gln Cys Ile Pro Ser Arg
                8420                8425                8430

TGG ATC TGT GAC CAT TAC AAC GAC TGT GGG GAC AAC TCA GAT GAA CGG         11437
Trp Ile Cys Asp His Tyr Asn Asp Cys Gly Asp Asn Ser Asp Glu Arg
            8435                8440                8445

GAC TGT GAG ATG AGG ACC TGC CAT CCT GAA TAT TTT CAG TGT ACA AGT         11485
Asp Cys Glu Met Arg Thr Cys His Pro Glu Tyr Phe Gln Cys Thr Ser
                8450                8455                8460

GGA CAT TGT GTA CAC AGT GAA CTG AAA TGC GAT GGA TCC GCT GAC TGT         11533
Gly His Cys Val His Ser Glu Leu Lys Cys Asp Gly Ser Ala Asp Cys
        8465                8470                8475

TTG GAT GCG TCT GAT GAA GCT GAT TGT CCC ACA CGC TTT CCT GAT GGT         11581
Leu Asp Ala Ser Asp Glu Ala Asp Cys Pro Thr Arg Phe Pro Asp Gly
8480                8485                8490                8495

GCA TAC TGC CAG GCT ACT ATG TTC GAA TGC AAA AAC CAT GTT TGT ATC         11629
Ala Tyr Cys Gln Ala Thr Met Phe Glu Cys Lys Asn His Val Cys Ile
                8500                8505                8510
```

```
CCG CCA TAT TGG AAA TGT GAT GGC GAT GAT GAC TGT GGC GAT GGT TCA        11677
Pro Pro Tyr Trp Lys Cys Asp Gly Asp Asp Asp Cys Gly Asp Gly Ser
            8515                    8520                    8525

GAT GAA GAA CTT CAC CTG TGC TTG GAT GTT CCC TGT AAT TCA CCA AAC        11725
Asp Glu Glu Leu His Leu Cys Leu Asp Val Pro Cys Asn Ser Pro Asn
            8530                    8535                    8540

CGT TTC CGG TGT GAC AAC AAT CGC TGC ATT TAT AGT CAT GAG GTG TGC        11773
Arg Phe Arg Cys Asp Asn Asn Arg Cys Ile Tyr Ser His Glu Val Cys
            8545                    8550                    8555

AAT GGT GTG GAT GAC TGT GGA GAT GGA ACT GAT GAG ACA GAG GAG CAC        11821
Asn Gly Val Asp Asp Cys Gly Asp Gly Thr Asp Glu Thr Glu Glu His
8560                    8565                    8570                8575

TGT AGA AAA CCG ACC CCT AAA CCT TGT ACA GAA TAT GAA TAT AAG TGT        11869
Cys Arg Lys Pro Thr Pro Lys Pro Cys Thr Glu Tyr Glu Tyr Lys Cys
            8580                    8585                    8590

GGC AAT GGG CAT TGC ATT CCA CAT GAC AAT GTG TGT GAT GAT GCC GAT        11917
Gly Asn Gly His Cys Ile Pro His Asp Asn Val Cys Asp Asp Ala Asp
            8595                    8600                    8605

GAC TGT GGT GAC TGG TCC GAT GAA CTG GGT TGC AAT AAA GGA AAA GAA        11965
Asp Cys Gly Asp Trp Ser Asp Glu Leu Gly Cys Asn Lys Gly Lys Glu
            8610                    8615                    8620

AGA ACA TGT GCT GAA AAT ATA TGC GAG CAA AAT TGT ACC CAA TTA AAT        12013
Arg Thr Cys Ala Glu Asn Ile Cys Glu Gln Asn Cys Thr Gln Leu Asn
            8625                    8630                    8635

GAA GGA GGA TTT ATC TGC TCC TGT ACA GCT GGG TTC GAA ACC AAT GTT        12061
Glu Gly Gly Phe Ile Cys Ser Cys Thr Ala Gly Phe Glu Thr Asn Val
8640                    8645                    8650                8655

TTT GAC AGA ACC TCC TGT CTA GAT ATC AAT GAA TGT GAA CAA TTT GGG        12109
Phe Asp Arg Thr Ser Cys Leu Asp Ile Asn Glu Cys Glu Gln Phe Gly
            8660                    8665                    8670

ACT TGT CCC CAG CAC TGC AGA AAT ACC AAA GGA AGT TAT GAG TGT GTC        12157
Thr Cys Pro Gln His Cys Arg Asn Thr Lys Gly Ser Tyr Glu Cys Val
            8675                    8680                    8685

TGT GCT GAT GGC TTC ACG TCT ATG AGT GAC CGC CCT GGA AAA CGA TGT        12205
Cys Ala Asp Gly Phe Thr Ser Met Ser Asp Arg Pro Gly Lys Arg Cys
            8690                    8695                    8700

GCA GCT GAG GGT AGC TCT CCT TTG TTG CTA CTG CCT GAC AAT GTC CGA        12253
Ala Ala Glu Gly Ser Ser Pro Leu Leu Leu Leu Pro Asp Asn Val Arg
            8705                    8710                    8715

ATT CGA AAA TAT AAT CTC TCA TCT GAG AGG TTC TCA GAG TAT CTT CAA        12301
Ile Arg Lys Tyr Asn Leu Ser Ser Glu Arg Phe Ser Glu Tyr Leu Gln
8720                    8725                    8730                8735

GAT GAG GAA TAT ATC CAA GCT GTT GAT TAT GAT TGG GAT CCC GAG GAC        12349
Asp Glu Glu Tyr Ile Gln Ala Val Asp Tyr Asp Trp Asp Pro Glu Asp
            8740                    8745                    8750

ATA GGC CTC AGT GTT GTG TAT TAC ACT GTG CGA GGG GAG GGC TCT AGG        12397
Ile Gly Leu Ser Val Val Tyr Tyr Thr Val Arg Gly Glu Gly Ser Arg
            8755                    8760                    8765

TTT GGT GCT ATC AAA CGT GCC TAC ATC CCC AAC TTT GAA TCC GGC CGC        12445
Phe Gly Ala Ile Lys Arg Ala Tyr Ile Pro Asn Phe Glu Ser Gly Arg
            8770                    8775                    8780

AAT AAT CTT GTG CAG GAA GTT GAC CTG AAA CTG AAA TAC GTA ATG CAG        12493
Asn Asn Leu Val Gln Glu Val Asp Leu Lys Leu Lys Tyr Val Met Gln
            8785                    8790                    8795

CCA GAT GGA ATA GCA GTG GAC TGG GTT GGA AGG CAT ATT TAC TGG TCA        12541
Pro Asp Gly Ile Ala Val Asp Trp Val Gly Arg His Ile Tyr Trp Ser
8800                    8805                    8810                8815

GAT GTC AAG AAT AAA CGC ATT GAG GTG GCT AAA CTT GAT GGA AGG TAC        12589
Asp Val Lys Asn Lys Arg Ile Glu Val Ala Lys Leu Asp Gly Arg Tyr
```

```
                8820              8825              8830
AGA AAG TGG CTG ATT TCC ACT GAC CTG GAC CAA CCA GCT GCT ATT GCT    12637
Arg Lys Trp Leu Ile Ser Thr Asp Leu Asp Gln Pro Ala Ala Ile Ala
            8835              8840              8845

GTG AAT CCC AAA CTA GGG CTT ATG TTC TGG ACT GAC TGG GGA AAG GAA    12685
Val Asn Pro Lys Leu Gly Leu Met Phe Trp Thr Asp Trp Gly Lys Glu
        8850              8855              8860

CCT AAA CTC GAG TCT GCC TGG ATG AAT GGA GAG GAC CGC AAC ATC CTG    12733
Pro Lys Leu Glu Ser Ala Trp Met Asn Gly Glu Asp Arg Asn Ile Leu
        8865              8870              8875

GTT TTC GAG GAC CTT GGT TGG CCA ACT GGC CTT TCT ATC GAT TAT TTG    12781
Val Phe Glu Asp Leu Gly Trp Pro Thr Gly Leu Ser Ile Asp Tyr Leu
8880              8885              8890              8895

AAC AAT GAC CGA ATC TAC TGG AGT GAC TTC AAG GAG GAC GTT ATT GAA    12829
Asn Asn Asp Arg Ile Tyr Trp Ser Asp Phe Lys Glu Asp Val Ile Glu
                8900              8905              8910

ACC ATA AAA TAT GAT GGG ACT GAT AGG AGA GTC ATT GCA AAG GAA GCA    12877
Thr Ile Lys Tyr Asp Gly Thr Asp Arg Arg Val Ile Ala Lys Glu Ala
            8915              8920              8925

ATG AAC CCT TAC AGC CTG GAC ATC TTT GAA GAC CAG TTA TAC TGG ATA    12925
Met Asn Pro Tyr Ser Leu Asp Ile Phe Glu Asp Gln Leu Tyr Trp Ile
        8930              8935              8940

TCT AAG GAA AAG GGA GAA GTA TGG AAA CAA AAT AAA TTT GGG CAA GGA    12973
Ser Lys Glu Lys Gly Glu Val Trp Lys Gln Asn Lys Phe Gly Gln Gly
    8945              8950              8955

AAG AAA GAG AAA ACG CTG GTA GTG AAC CCT TGG CTC ACT CAA GTT CGA    13021
Lys Lys Glu Lys Thr Leu Val Val Asn Pro Trp Leu Thr Gln Val Arg
8960              8965              8970              8975

ATC TTT CAT CAA CTC AGA TAC AAT AAG TCA GTG CCC AAC CTT TGC AAA    13069
Ile Phe His Gln Leu Arg Tyr Asn Lys Ser Val Pro Asn Leu Cys Lys
            8980              8985              8990

CAG ATC TGC AGC CAC CTC TGC CTT CTG AGA CCT GGA GGA TAC AGC TGT    13117
Gln Ile Cys Ser His Leu Cys Leu Leu Arg Pro Gly Gly Tyr Ser Cys
        8995              9000              9005

GCC TGT CCC CAA GGC TCC AGC TTT ATA GAG GGG AGC ACC ACT GAG TGT    13165
Ala Cys Pro Gln Gly Ser Ser Phe Ile Glu Gly Ser Thr Thr Glu Cys
        9010              9015              9020

GAT GCA GCC ATT GAA CTG CCT ATC AAC CTG CCC CCC CCA TGC AGG TGC    13213
Asp Ala Ala Ile Glu Leu Pro Ile Asn Leu Pro Pro Pro Cys Arg Cys
        9025              9030              9035

ATG CAC GGA GGA AAT TGC TAT TTT GAT GAG ACT GAC CTC CCC AAA TGC    13261
Met His Gly Gly Asn Cys Tyr Phe Asp Glu Thr Asp Leu Pro Lys Cys
9040              9045              9050              9055

AAG TGT CCT AGC GGC TAC ACC GGA AAA TAT TGT GAA ATG GCG TTT TCA    13309
Lys Cys Pro Ser Gly Tyr Thr Gly Lys Tyr Cys Glu Met Ala Phe Ser
            9060              9065              9070

AAA GGC ATC TCT CCA GGA ACA ACC GCA GTA GCT GTG CTG TTG ACA ATC    13357
Lys Gly Ile Ser Pro Gly Thr Thr Ala Val Ala Val Leu Leu Thr Ile
        9075              9080              9085

CTC TTG ATC GTC GTA ATT GGA GCT CTG GCA ATT GCA GGA TTC TTC CAC    13405
Leu Leu Ile Val Val Ile Gly Ala Leu Ala Ile Ala Gly Phe Phe His
        9090              9095              9100

TAT AGA AGG ACC GGC TCC CTT TTG CCT GCT CTG CCC AAG CTG CCA AGC    13453
Tyr Arg Arg Thr Gly Ser Leu Leu Pro Ala Leu Pro Lys Leu Pro Ser
        9105              9110              9115

TTA AGC AGT CTC GTC AAG CCC TCT GAA AAT GGG AAT GGG GTG ACC TTC    13501
Leu Ser Ser Leu Val Lys Pro Ser Glu Asn Gly Asn Gly Val Thr Phe
9120              9125              9130              9135

AGA TCA GGG GCA GAT CTT AAC ATG GAT ATT GGA GTG TCT GGT TTT GGA    13549
```

```
Arg Ser Gly Ala Asp Leu Asn Met Asp Ile Gly Val Ser Gly Phe Gly
            9140                9145                9150

CCT GAG ACT GCT ATT GAC AGG TCA ATG GCA ATG AGT GAA GAC TTT GTC     13597
Pro Glu Thr Ala Ile Asp Arg Ser Met Ala Met Ser Glu Asp Phe Val
            9155                9160                9165

ATG GAA ATG GGG AAG CAG CCC ATA ATA TTT GAA AAC CCA ATG TAC TCA     13645
Met Glu Met Gly Lys Gln Pro Ile Ile Phe Glu Asn Pro Met Tyr Ser
            9170                9175                9180

GCC AGA GAC AGT GCT GTC AAA GTG GTT CAG CCA ATC CAG GTG ACT GTA     13693
Ala Arg Asp Ser Ala Val Lys Val Val Gln Pro Ile Gln Val Thr Val
            9185                9190                9195

TCT GAA AAT GTG GAT AAT AAG AAT TAT GGA AGT CCC ATA AAC CCT TCT     13741
Ser Glu Asn Val Asp Asn Lys Asn Tyr Gly Ser Pro Ile Asn Pro Ser
9200                9205                9210                9215

GAG ATA GTT CCA GAG ACA AAC CCA ACT TCA CCA GCT GCT GAT GGA ACT     13789
Glu Ile Val Pro Glu Thr Asn Pro Thr Ser Pro Ala Ala Asp Gly Thr
            9220                9225                9230

CAG GTG ACA AAA TGG AAT CTC TTC AAA CGA AAA TCT AAA CAA ACT ACC     13837
Gln Val Thr Lys Trp Asn Leu Phe Lys Arg Lys Ser Lys Gln Thr Thr
            9235                9240                9245

AAC TTT GAA AAT CCA ATC TAT GCA CAG ATG GAG AAC GAG CAA AAG GAA     13885
Asn Phe Glu Asn Pro Ile Tyr Ala Gln Met Glu Asn Glu Gln Lys Glu
            9250                9255                9260

AGT GTT GCT GCG ACA CCA CCT CCA TCA CCT TCG CTC CCT GCT AAG CCT     13933
Ser Val Ala Ala Thr Pro Pro Pro Ser Pro Ser Leu Pro Ala Lys Pro
            9265                9270                9275

AAG CCT CCT TCG AGA AGA GAC CCA ACT CCA ACC TAT TCT GCA ACA GAA     13981
Lys Pro Pro Ser Arg Arg Asp Pro Thr Pro Thr Tyr Ser Ala Thr Glu
9280                9285                9290                9295

GAC ACT TTT AAA GAC ACC GCA AAT CTT GTT AAA GAA GAC TCT GAA GTA     14029
Asp Thr Phe Lys Asp Thr Ala Asn Leu Val Lys Glu Asp Ser Glu Val
            9300                9305                9310

TAG CTATACCAGC TA                                                    14044
 *

(2) INFORMATION FOR SEQ ID NO:90:

(i) SEQUENCE CHARACTERISTICS:
        (A) LENGTH: 4655 amino acids
        (B) TYPE: amino acid
        (D) TOPOLOGY: linear (ii) MOLECULE TYPE: protein (xi) SEQUENCE DESCRIPTION: SEQ ID NO:90:

Met Asp Arg Gly Pro Ala Ala Val Ala Cys Thr Leu Leu Ala Leu
 1               5                  10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
            35                  40                  45

Gly Thr Lys Asp Cys Ser Asp Ala Asp Glu Ile Gly Cys Ala Val
            50                  55                  60

Val Thr Cys Gln Gln Gly Tyr Phe Lys Cys Gln Ser Glu Gly Gln Cys
65                  70                  75                  80

Ile Pro Ser Ser Trp Val Cys Asp Gln Asp Gln Asp Cys Asp Asp Gly
                85                  90                  95

Ser Asp Glu Arg Gln Asp Cys Ser Gln Ser Thr Cys Ser Ser His Gln
            100                 105                 110
```

-continued

```
Ile Thr Cys Ser Asn Gly Gln Cys Ile Pro Ser Glu Tyr Arg Cys Asp
        115                 120                 125

His Val Arg Asp Cys Pro Asp Gly Ala Asp Glu Asn Asp Cys Gln Tyr
    130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
        195                 200                 205

Gln Asp Gly Ser Asp Glu His Ala Cys Asn Tyr Pro Thr Cys Gly Gly
210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
            260                 265                 270

Cys Pro Glu Ser Gly Arg Cys Ile Ser Ile Tyr Lys Val Cys Asp Gly
        275                 280                 285

Ile Leu Asp Cys Pro Gly Arg Glu Asp Glu Asn Asn Thr Ser Thr Gly
290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
            340                 345                 350

Gln Ile Trp Gly Ile Cys Asp Gln Lys Cys Glu Ser Arg Pro Gly Arg
        355                 360                 365

His Leu Cys His Cys Glu Glu Gly Tyr Ile Leu Glu Arg Gly Gln Tyr
370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
            420                 425                 430

Tyr His Leu Gln Arg Val Phe Trp Thr Asp Thr Val Gln Asn Lys Val
        435                 440                 445

Phe Ser Val Asp Ile Asn Gly Leu Asn Ile Gln Glu Val Leu Asn Val
450                 455                 460

Ser Val Glu Thr Pro Glu Asn Leu Ala Val Asp Trp Val Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
        515                 520                 525

Trp Glu Ser Leu Ser Gly Glu Pro Lys Leu Glu Arg Ala Phe Met Asp
```

-continued

```
            530                 535                 540
Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
                580                 585                 590

Thr Val His Gly Gly Ser Leu Ile Pro His Pro Phe Gly Val Ser
                595                 600                 605

Leu Phe Glu Gly Gln Val Phe Phe Thr Asp Trp Thr Lys Met Ala Val
            610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Gly Gly Cys Glu Gln
                660                 665                 670

Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
                740                 745                 750

Ser Thr Ile Phe Phe Ser Asp Met Ser Lys His Met Ile Phe Lys Gln
                755                 760                 765

Lys Ile Asp Gly Thr Gly Arg Glu Ile Leu Ala Ala Asn Arg Val Glu
770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
                820                 825                 830

Val His Pro Phe Ala Gly Tyr Leu Phe Phe Thr Asp Trp Phe Arg Pro
            835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Leu Gly His Ile Glu Gln
                900                 905                 910

Met Thr His Pro Phe Gly Leu Ala Ile Phe Gly Glu His Leu Phe Phe
                915                 920                 925

Thr Asp Trp Arg Leu Gly Ala Ile Ile Arg Val Arg Lys Ala Asp Gly
                930                 935                 940

Gly Glu Met Thr Val Ile Arg Ser Gly Ile Ala Tyr Ile Leu His Leu
945                 950                 955                 960
```

-continued

```
Lys Ser Tyr Asp Val Asn Ile Gln Thr Gly Ser Asn Ala Cys Asn Gln
            965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
            995                1000                1005

Asn His Leu Thr Cys Glu Gly Asp Pro Thr Asn Glu Pro Pro Thr Glu
           1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
           1045                1050                1055

Glu Gln Leu Cys Gly Thr Leu Asn Asn Thr Cys Ser Ser Ser Ala Phe
           1060                1065                1070

Thr Cys Gly His Gly Glu Cys Ile Pro Ala His Trp Arg Cys Asp Lys
           1075                1080                1085

Arg Asn Asp Cys Val Asp Gly Ser Asp Glu His Asn Cys Pro Thr His
           1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
           1125                1130                1135

Gly Ser Asp Glu Lys Asn Cys Asn Ser Thr Glu Thr Cys Gln Pro Ser
           1140                1145                1150

Gln Phe Asn Cys Pro Asn His Arg Cys Ile Asp Leu Ser Phe Val Cys
           1155                1160                1165

Asp Gly Asp Lys Asp Cys Val Asp Gly Ser Asp Glu Val Gly Cys Val
           1170                1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
           1205                1210                1215

Ser Asp Glu Ala Gly Cys Pro Thr Arg Pro Pro Gly Met Cys His Ser
           1220                1225                1230

Asp Glu Phe Gln Cys Gln Glu Asp Gly Ile Cys Ile Pro Asn Phe Trp
           1235                1240                1245

Glu Cys Asp Gly His Pro Asp Cys Leu Tyr Gly Ser Asp Glu His Asn
           1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
           1285                1290                1295

Gly Asp Met Ser Asp Glu Lys Asp Cys Pro Thr Gln Pro Phe Arg Cys
           1300                1305                1310

Pro Ser Trp Gln Trp Gln Cys Leu Gly His Asn Ile Cys Val Asn Leu
           1315                1320                1325

Ser Val Val Cys Asp Gly Ile Phe Asp Cys Pro Asn Gly Thr Asp Glu
           1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
           1365                1370                1375
```

-continued

```
Leu Gly Phe Leu Leu Ala Asn Asp Ser Lys Thr Cys Glu Asp Ile Asp
            1380                1385                1390

Glu Cys Asp Ile Leu Gly Ser Cys Ser Gln His Cys Tyr Asn Met Arg
            1395                1400                1405

Gly Ser Phe Arg Cys Ser Cys Asp Thr Gly Tyr Met Leu Glu Ser Asp
            1410                1415                1420

Gly Arg Thr Cys Lys Val Thr Ala Ser Glu Ser Leu Leu Leu Leu Val
1425                1430                1435                1440

Ala Ser Gln Asn Lys Ile Ile Ala Asp Ser Val Thr Ser Gln Val His
            1445                1450                1455

Asn Ile Tyr Ser Leu Val Glu Asn Gly Ser Tyr Ile Val Ala Val Asp
            1460                1465                1470

Phe Asp Ser Ile Ser Gly Arg Ile Phe Trp Ser Asp Ala Thr Gln Gly
            1475                1480                1485

Lys Thr Trp Ser Ala Phe Gln Asn Gly Thr Asp Arg Arg Val Val Phe
            1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
            1525                1530                1535

Lys Ile Asp Gly Ser His Arg Thr Val Leu Ile Ser Lys Asn Leu Thr
            1540                1545                1550

Asn Pro Arg Gly Leu Ala Leu Asp Pro Arg Met Asn Glu His Leu Leu
            1555                1560                1565

Phe Trp Ser Asp Trp Gly His His Pro Arg Ile Glu Arg Ala Ser Met
            1570                1575                1580

Asp Gly Ser Met Arg Thr Val Ile Val Gln Asp Lys Ile Phe Trp Pro
1585                1590                1595                1600

Cys Gly Leu Thr Ile Asp Tyr Pro Asn Arg Leu Leu Tyr Phe Met Asp
            1605                1610                1615

Ser Tyr Leu Asp Tyr Met Asp Phe Cys Asp Tyr Asn Gly His His Arg
            1620                1625                1630

Arg Gln Val Ile Ala Ser Asp Leu Ile Ile Arg His Pro Tyr Ala Leu
            1635                1640                1645

Thr Leu Phe Glu Asp Ser Val Tyr Trp Thr Asp Arg Ala Thr Arg Arg
            1650                1655                1660

Val Met Arg Ala Asn Lys Trp His Gly Gly Asn Gln Ser Val Val Met
1665                1670                1675                1680

Tyr Asn Ile Gln Trp Pro Leu Gly Ile Val Ala Val His Pro Ser Lys
            1685                1690                1695

Gln Pro Asn Ser Val Asn Pro Cys Ala Phe Ser Arg Cys Ser His Leu
            1700                1705                1710

Cys Leu Leu Ser Ser Gln Gly Pro His Phe Tyr Ser Cys Val Cys Pro
            1715                1720                1725

Ser Gly Trp Ser Leu Ser Pro Asp Leu Leu Asn Cys Leu Arg Asp Asp
            1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
            1765                1770                1775

Ile Gln Asn Gly Leu Asp Val Glu Phe Asp Asp Ala Glu Gln Tyr Ile
            1780                1785                1790

Tyr Trp Val Glu Asn Pro Gly Glu Ile His Arg Val Lys Thr Asp Gly
```

-continued

```
              1795                1800                1805
Thr Asn Arg Thr Val Phe Ala Ser Ile Ser Met Val Gly Pro Ser Met
           1810                1815                1820
Asn Leu Ala Leu Asp Trp Ile Ser Arg Asn Leu Tyr Ser Thr Asn Pro
1825                1830                1835                1840
Arg Thr Gln Ser Ile Glu Val Leu Thr Leu His Gly Asp Ile Arg Tyr
               1845                1850                1855
Arg Lys Thr Leu Ile Ala Asn Asp Gly Thr Ala Leu Gly Val Gly Phe
           1860                1865                1870
Pro Ile Gly Ile Thr Val Asp Pro Ala Arg Gly Lys Leu Tyr Trp Ser
           1875                1880                1885
Asp Gln Gly Thr Asp Ser Gly Val Pro Ala Lys Ile Ala Ser Ala Asn
       1890                1895                1900
Met Asp Gly Thr Ser Val Lys Thr Leu Phe Thr Gly Asn Leu Glu His
1905                1910                1915                1920
Leu Glu Cys Val Thr Leu Asp Ile Glu Glu Gln Lys Leu Tyr Trp Ala
               1925                1930                1935
Val Thr Gly Arg Gly Val Ile Glu Arg Gly Asn Val Asp Gly Thr Asp
           1940                1945                1950
Arg Met Ile Leu Val His Gln Leu Ser His Pro Trp Gly Ile Ala Val
           1955                1960                1965
His Asp Ser Phe Leu Tyr Tyr Thr Asp Glu Gln Tyr Glu Val Ile Glu
           1970                1975                1980
Arg Val Asp Lys Ala Thr Gly Ala Asn Lys Ile Val Leu Arg Asp Asn
1985                1990                1995                2000
Val Pro Asn Leu Arg Gly Leu Gln Val Tyr His Arg Arg Asn Ala Ala
               2005                2010                2015
Glu Ser Ser Asn Gly Cys Ser Asn Asn Met Asn Ala Cys Gln Gln Ile
               2020                2025                2030
Cys Leu Pro Val Pro Gly Gly Leu Phe Ser Cys Ala Cys Ala Thr Gly
           2035                2040                2045
Phe Lys Leu Asn Pro Asp Asn Arg Ser Cys Ser Pro Tyr Asn Ser Phe
           2050                2055                2060
Ile Val Val Ser Met Leu Ser Ala Ile Arg Gly Phe Ser Leu Glu Leu
2065                2070                2075                2080
Ser Asp His Ser Glu Thr Met Val Pro Val Ala Gly Gln Gly Arg Asn
               2085                2090                2095
Ala Leu His Val Asp Val Asp Val Ser Ser Gly Phe Ile Tyr Trp Cys
               2100                2105                2110
Asp Phe Ser Ser Val Ala Ser Asp Asn Ala Ile Arg Arg Ile Lys
           2115                2120                2125
Pro Asp Gly Ser Ser Leu Met Asn Ile Val Thr His Gly Ile Gly Glu
           2130                2135                2140
Asn Gly Val Arg Gly Ile Ala Val Asp Trp Val Ala Gly Asn Leu Tyr
2145                2150                2155                2160
Phe Thr Asn Ala Phe Val Ser Glu Thr Leu Ile Glu Val Leu Arg Ile
               2165                2170                2175
Asn Thr Thr Tyr Arg Arg Val Leu Leu Lys Val Thr Val Asp Met Pro
           2180                2185                2190
Arg His Ile Val Val Asp Pro Lys Asn Arg Tyr Leu Phe Trp Ala Asp
           2195                2200                2205
Tyr Gly Gln Arg Pro Lys Ile Glu Arg Ser Phe Leu Asp Cys Thr Asn
           2210                2215                2220
```

-continued

```
Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Asp Ser Leu Asp
                2245                2250                2255

Ile Ile Ala Arg Ile Arg Ile Asn Gly Glu Asn Ser Glu Val Ile Arg
            2260                2265                2270

Tyr Gly Ser Arg Tyr Pro Thr Pro Tyr Gly Ile Thr Val Phe Glu Asn
        2275                2280                2285

Ser Ile Ile Trp Val Asp Arg Asn Leu Lys Lys Ile Phe Gln Ala Ser
    2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
                2325                2330                2335

Ser Pro Ala Glu Val Asn Asn Pro Cys Leu Glu Asn Asn Gly Gly
            2340                2345                2350

Cys Ser His Leu Cys Phe Ala Leu Pro Gly Leu His Thr Pro Lys Cys
        2355                2360                2365

Asp Cys Ala Phe Gly Thr Leu Gln Ser Asp Gly Lys Asn Cys Ala Ile
    2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
                2405                2410                2415

Val Glu Arg Thr Val Met Ser Leu Asp Tyr Asp Ser Val Ser Asp Arg
            2420                2425                2430

Ile Tyr Phe Thr Gln Asn Leu Ala Ser Gly Val Gly Gln Ile Ser Tyr
        2435                2440                2445

Ala Thr Leu Ser Ser Gly Ile His Thr Pro Thr Val Ile Ala Ser Gly
    2450                2455                2460

Ile Gly Thr Ala Asp Gly Ile Ala Phe Asp Trp Ile Thr Arg Arg Ile
2465                2470                2475                2480

Tyr Tyr Ser Asp Tyr Leu Asn Gln Met Ile Asn Ser Met Ala Glu Asp
                2485                2490                2495

Gly Ser Asn Arg Thr Val Ile Ala Arg Val Pro Lys Pro Arg Ala Ile
            2500                2505                2510

Val Leu Asp Pro Cys Gln Gly Tyr Leu Tyr Trp Ala Asp Trp Asp Thr
        2515                2520                2525

His Ala Lys Ile Glu Arg Ala Thr Leu Gly Gly Asn Phe Arg Val Pro
    2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
                2565                2570                2575

Arg Ser Thr Leu Thr Gly Val Asp Arg Glu Val Ile Val Asn Ala Ala
            2580                2585                2590

Val His Ala Phe Gly Leu Thr Leu Tyr Gly Gln Tyr Ile Tyr Trp Thr
        2595                2600                2605

Asp Leu Tyr Thr Gln Arg Ile Tyr Arg Ala Asn Lys Tyr Asp Gly Ser
    2610                2615                2620

Gly Gln Ile Ala Met Thr Thr Asn Leu Leu Ser Gln Pro Arg Gly Ile
2625                2630                2635                2640
```

-continued

```
Asn Thr Val Val Lys Asn Gln Lys Gln Gln Cys Asn Asn Pro Cys Glu
                2645                2650                2655

Gln Phe Asn Gly Gly Cys Ser His Ile Cys Ala Pro Gly Pro Asn Gly
                2660                2665                2670

Ala Glu Cys Gln Cys Pro His Glu Gly Asn Trp Tyr Leu Ala Asn Asn
                2675                2680                2685

Arg Lys His Cys Ile Val Asp Asn Gly Glu Arg Cys Gly Ala Ser Ser
                2690                2695                2700

Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
                2725                2730                2735

Ala Leu His Thr Cys Ser Pro Thr Ala Phe Thr Cys Ala Asn Gly Arg
                2740                2745                2750

Cys Val Gln Tyr Ser Tyr Arg Cys Asp Tyr Tyr Asn Asp Cys Gly Asp
                2755                2760                2765

Gly Ser Asp Glu Ala Gly Cys Leu Phe Arg Asp Cys Asn Ala Thr Thr
                2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Thr Ser Asp Glu Lys Asn
                2805                2810                2815

Cys Pro Asp Arg Thr Cys Gln Ser Gly Tyr Thr Lys Cys His Asn Ser
                2820                2825                2830

Asn Ile Cys Ile Pro Arg Val Tyr Leu Cys Asp Gly Asp Asn Asp Cys
                2835                2840                2845

Gly Asp Asn Ser Asp Glu Asn Pro Thr Tyr Cys Thr Thr His Thr Cys
                2850                2855                2860

Ser Ser Ser Glu Phe Gln Cys Ala Ser Gly Arg Cys Ile Pro Gln His
2865                2870                2875                2880

Trp Tyr Cys Asp Gln Glu Thr Asp Cys Phe Asp Ala Ser Asp Glu Pro
                2885                2890                2895

Ala Ser Cys Gly His Ser Glu Arg Thr Cys Leu Ala Asp Glu Phe Lys
                2900                2905                2910

Cys Asp Gly Gly Arg Cys Ile Pro Ser Glu Trp Ile Cys Asp Gly Asp
                2915                2920                2925

Asn Asp Cys Gly Asp Met Ser Asp Glu Asp Lys Arg His Gln Cys Gln
                2930                2935                2940

Asn Gln Asn Cys Ser Asp Ser Glu Phe Leu Cys Val Asn Asp Arg Pro
2945                2950                2955                2960

Pro Asp Arg Arg Cys Ile Pro Gln Ser Trp Val Cys Asp Gly Asp Val
                2965                2970                2975

Asp Cys Thr Asp Gly Tyr Asp Glu Asn Gln Asn Cys Thr Arg Arg Thr
                2980                2985                2990

Cys Ser Glu Asn Glu Phe Thr Cys Gly Tyr Gly Leu Cys Ile Pro Lys
                2995                3000                3005

Ile Phe Arg Cys Asp Arg His Asn Asp Cys Gly Asp Tyr Ser Asp Glu
                3010                3015                3020

Arg Gly Cys Leu Tyr Gln Thr Cys Gln Gln Asn Gln Phe Thr Cys Gln
3025                3030                3035                3040

Asn Gly Arg Cys Ile Ser Lys Thr Phe Val Cys Asp Glu Asp Asn Asp
                3045                3050                3055

Cys Gly Asp Gly Ser Asp Glu Leu Met His Leu Cys His Thr Pro Glu
```

-continued

```
             3060              3065              3070
Pro Thr Cys Pro Pro His Glu Phe Lys Cys Asp Asn Gly Arg Cys Ile
        3075              3080              3085
Glu Met Met Lys Leu Cys Asn His Leu Asp Asp Cys Leu Asp Asn Ser
        3090              3095              3100
Asp Glu Lys Gly Cys Gly Ile Asn Glu Cys His Asp Pro Ser Ile Ser
3105              3110              3115              3120
Gly Cys Asp His Asn Cys Thr Asp Thr Leu Thr Ser Phe Tyr Cys Ser
             3125              3130              3135
Cys Arg Pro Gly Tyr Lys Leu Met Ser Asp Lys Arg Thr Cys Val Asp
             3140              3145              3150
Ile Asp Glu Cys Thr Glu Met Pro Phe Val Cys Ser Gln Lys Cys Glu
        3155              3160              3165
Asn Val Ile Gly Ser Tyr Ile Cys Lys Cys Ala Pro Gly Tyr Leu Arg
        3170              3175              3180
Glu Pro Asp Gly Lys Thr Cys Arg Gln Asn Ser Asn Ile Glu Pro Tyr
3185              3190              3195              3200
Leu Ile Phe Ser Asn Arg Tyr Tyr Leu Arg Asn Leu Thr Ile Asp Gly
             3205              3210              3215
Tyr Phe Tyr Ser Leu Ile Leu Glu Gly Leu Asp Asn Val Val Ala Leu
             3220              3225              3230
Asp Phe Asp Arg Val Glu Lys Arg Leu Tyr Trp Ile Asp Thr Gln Arg
             3235              3240              3245
Gln Val Ile Glu Arg Met Phe Leu Asn Lys Thr Asn Lys Glu Thr Ile
        3250              3255              3260
Ile Asn His Arg Leu Pro Ala Ala Glu Ser Leu Ala Val Asp Trp Val
3265              3270              3275              3280
Ser Arg Lys Leu Tyr Trp Leu Asp Ala Arg Leu Asp Gly Leu Phe Val
             3285              3290              3295
Ser Asp Leu Asn Gly Gly His Arg Arg Met Leu Ala Gln His Cys Val
             3300              3305              3310
Asp Ala Asn Asn Thr Phe Cys Phe Asp Asn Pro Arg Gly Leu Ala Leu
             3315              3320              3325
His Pro Gln Tyr Gly Tyr Leu Tyr Trp Ala Asp Trp Gly His Arg Ala
             3330              3335              3340
Tyr Ile Gly Arg Val Gly Met Asp Gly Thr Asn Lys Ser Val Ile Ile
3345              3350              3355              3360
Ser Thr Lys Leu Glu Trp Pro Asn Gly Ile Thr Ile Asp Tyr Thr Asn
             3365              3370              3375
Asp Leu Leu Tyr Trp Ala Asp Ala His Leu Gly Tyr Ile Glu Tyr Ser
             3380              3385              3390
Asp Leu Glu Gly His His Arg His Thr Val Tyr Asp Gly Ala Leu Pro
             3395              3400              3405
His Pro Phe Ala Ile Thr Ile Phe Glu Asp Thr Ile Tyr Trp Thr Asp
             3410              3415              3420
Trp Asn Thr Arg Thr Val Glu Lys Gly Asn Lys Tyr Asp Gly Ser Asn
3425              3430              3435              3440
Arg Gln Thr Leu Val Asn Thr Thr His Arg Pro Phe Asp Ile His Val
             3445              3450              3455
Tyr His Pro Tyr Arg Gln Pro Ile Val Ser Asn Pro Cys Gly Thr Asn
             3460              3465              3470
Asn Gly Gly Cys Ser His Leu Cys Leu Ile Lys Pro Gly Gly Lys Gly
             3475              3480              3485
```

```
Phe Thr Cys Glu Cys Pro Asp Asp Phe Arg Thr Leu Gln Leu Ser Gly
    3490                3495                3500
Ser Thr Tyr Cys Met Pro Met Cys Ser Ser Thr Gln Phe Leu Cys Ala
3505                3510                3515                3520
Asn Asn Glu Lys Cys Ile Pro Ile Trp Trp Lys Cys Asp Gly Gln Lys
            3525                3530                3535
Asp Cys Ser Asp Gly Ser Asp Glu Leu Ala Leu Cys Pro Gln Arg Phe
            3540                3545                3550
Cys Arg Leu Gly Gln Phe Gln Cys Ser Asp Gly Asn Cys Thr Ser Pro
            3555                3560                3565
Gln Thr Leu Cys Asn Ala His Gln Asn Cys Pro Asp Gly Ser Asp Glu
    3570                3575                3580
Asp Arg Leu Leu Cys Glu Asn His His Cys Asp Ser Asn Glu Trp Gln
3585                3590                3595                3600
Cys Ala Asn Lys Arg Cys Ile Pro Glu Ser Trp Gln Cys Asp Thr Phe
            3605                3610                3615
Asn Asp Cys Glu Asp Asn Ser Asp Glu Asp Ser Ser His Cys Ala Ser
            3620                3625                3630
Arg Thr Cys Arg Pro Gly Gln Phe Arg Cys Ala Asn Gly Arg Cys Ile
            3635                3640                3645
Pro Gln Ala Trp Lys Cys Asp Val Asp Asn Asp Cys Gly Asp His Ser
    3650                3655                3660
Asp Glu Pro Ile Glu Glu Cys Met Ser Ser Ala His Leu Cys Asp Asn
3665                3670                3675                3680
Phe Thr Glu Phe Ser Cys Lys Thr Asn Tyr Arg Cys Ile Pro Lys Trp
            3685                3690                3695
Ala Val Cys Asn Gly Val Asp Asp Cys Arg Asp Asn Ser Asp Glu Gln
            3700                3705                3710
Gly Cys Glu Glu Arg Thr Cys His Pro Val Gly Asp Phe Arg Cys Lys
            3715                3720                3725
Asn His His Cys Ile Pro Leu Arg Trp Gln Cys Asp Gly Gln Asn Asp
    3730                3735                3740
Cys Gly Asp Asn Ser Asp Glu Glu Asn Cys Ala Pro Arg Glu Cys Thr
3745                3750                3755                3760
Glu Ser Glu Phe Arg Cys Val Asn Gln Gln Cys Ile Pro Ser Arg Trp
            3765                3770                3775
Ile Cys Asp His Tyr Asn Asp Cys Gly Asp Asn Ser Asp Glu Arg Asp
            3780                3785                3790
Cys Glu Met Arg Thr Cys His Pro Glu Tyr Phe Gln Cys Thr Ser Gly
            3795                3800                3805
His Cys Val His Ser Glu Leu Lys Cys Asp Gly Ser Ala Asp Cys Leu
    3810                3815                3820
Asp Ala Ser Asp Glu Ala Asp Cys Pro Thr Arg Phe Pro Asp Gly Ala
3825                3830                3835                3840
Tyr Cys Gln Ala Thr Met Phe Gly Cys Lys Asn His Val Cys Ile Pro
            3845                3850                3855
Pro Tyr Trp Lys Cys Asp Gly Asp Asp Asp Cys Gly Asp Gly Ser Asp
            3860                3865                3870
Glu Glu Leu His Leu Cys Leu Asp Val Pro Cys Asn Ser Pro Asn Arg
            3875                3880                3885
Phe Arg Cys Asp Asn Asn Arg Cys Ile Tyr Ser His Glu Val Cys Asn
    3890                3895                3900
```

-continued

```
Gly Val Asp Asp Cys Gly Asp Gly Thr Asp Glu Thr Glu Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Ala Asp Asp
            3940                3945                3950

Cys Gly Asp Trp Ser Asp Glu Leu Gly Cys Asn Lys Gly Lys Glu Arg
            3955                3960                3965

Thr Cys Ala Glu Asn Ile Cys Glu Gln Asn Cys Thr Gln Leu Asn Glu
3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
            4020                4025                4030

Ala Asp Gly Phe Thr Ser Met Ser Asp Arg Pro Gly Lys Arg Cys Ala
            4035                4040                4045

Ala Glu Gly Ser Ser Pro Leu Leu Leu Leu Pro Asp Asn Val Arg Ile
    4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Glu Asp Ile
            4085                4090                4095

Gly Leu Ser Val Val Tyr Tyr Thr Val Arg Gly Glu Gly Ser Arg Phe
            4100                4105                4110

Gly Ala Ile Lys Arg Ala Tyr Ile Pro Asn Phe Glu Ser Gly Arg Asn
            4115                4120                4125

Asn Leu Val Gln Glu Val Asp Leu Lys Leu Lys Tyr Val Met Gln Pro
            4130                4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
            4165                4170                4175

Lys Trp Leu Ile Ser Thr Asp Leu Asp Gln Pro Ala Ala Ile Ala Val
            4180                4185                4190

Asn Pro Lys Leu Gly Leu Met Phe Trp Thr Asp Trp Gly Lys Glu Pro
            4195                4200                4205

Lys Leu Glu Ser Ala Trp Met Asn Gly Glu Asp Arg Asn Ile Leu Val
            4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
            4245                4250                4255

Ile Lys Tyr Asp Gly Thr Asp Arg Arg Val Ile Ala Lys Glu Ala Met
            4260                4265                4270

Asn Pro Tyr Ser Leu Asp Ile Phe Glu Asp Gln Leu Tyr Trp Ile Ser
            4275                4280                4285

Lys Glu Lys Gly Glu Val Trp Lys Gln Asn Lys Phe Gly Gln Gly Lys
            4290                4295                4300

Lys Glu Lys Thr Leu Val Val Asn Pro Trp Leu Thr Gln Val Arg Ile
4305                4310                4315                4320

Phe His Gln Leu Arg Tyr Asn Lys Ser Val Pro Asn Leu Cys Lys Gln
```

```
                        4325                4330                4335
Ile Cys Ser His Leu Cys Leu Leu Arg Pro Gly Gly Tyr Ser Cys Ala
                4340                4345                4350
Cys Pro Gln Gly Ser Ser Phe Ile Glu Gly Ser Thr Thr Glu Cys Asp
                4355                4360            4365
Ala Ala Ile Glu Leu Pro Ile Asn Leu Pro Pro Cys Arg Cys Met
4370                4375                4380
His Gly Gly Asn Cys Tyr Phe Asp Glu Thr Asp Leu Pro Lys Cys Lys
4385                4390                4395                4400
Cys Pro Ser Gly Tyr Thr Gly Lys Tyr Cys Glu Met Ala Phe Ser Lys
                4405                4410                4415
Gly Ile Ser Pro Gly Thr Thr Ala Val Ala Val Leu Leu Thr Ile Leu
                4420                4425                4430
Leu Ile Val Val Ile Gly Ala Leu Ala Ile Ala Gly Phe Phe His Tyr
                4435                4440                4445
Arg Arg Thr Gly Ser Leu Leu Pro Ala Leu Pro Lys Leu Pro Ser Leu
        4450                4455                4460
Ser Ser Leu Val Lys Pro Ser Glu Asn Gly Asn Gly Val Thr Phe Arg
4465                4470                4475                4480
Ser Gly Ala Asp Leu Asn Met Asp Ile Gly Val Ser Gly Phe Gly Pro
                4485                4490                4495
Glu Thr Ala Ile Asp Arg Ser Met Ala Met Ser Glu Asp Phe Val Met
                4500                4505                4510
Glu Met Gly Lys Gln Pro Ile Ile Phe Glu Asn Pro Met Tyr Ser Ala
                4515                4520                4525
Arg Asp Ser Ala Val Lys Val Val Gln Pro Ile Gln Val Thr Val Ser
                4530                4535                4540
Glu Asn Val Asp Asn Lys Asn Tyr Gly Ser Pro Ile Asn Pro Ser Glu
4545                4550                4555                4560
Ile Val Pro Glu Thr Asn Pro Thr Ser Pro Ala Ala Asp Gly Thr Gln
                4565                4570                4575
Val Thr Lys Trp Asn Leu Phe Lys Arg Lys Ser Lys Gln Thr Thr Asn
                4580                4585                4590
Phe Glu Asn Pro Ile Tyr Ala Gln Met Glu Asn Glu Gln Lys Glu Ser
                4595                4600                4605
Val Ala Ala Thr Pro Pro Pro Ser Pro Ser Leu Pro Ala Lys Pro Lys
4610                4615                4620
Pro Pro Ser Arg Arg Asp Pro Thr Pro Thr Tyr Ser Ala Thr Glu Asp
4625                4630                4635                4640
Thr Phe Lys Asp Thr Ala Asn Leu Val Lys Glu Asp Ser Glu Val
                4645                4650                4655
```

(2) INFORMATION FOR SEQ ID NO:91:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:91:

```
GCAGACCTAA AGGAGCGTT                                                    19
```

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:92:

```
CCCGACCATT GGAGAAGATA                                                   20
```

(2) INFORMATION FOR SEQ ID NO:93:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:93:

```
GCCAGTACCA GTGCCATGA                                                    19
```

(2) INFORMATION FOR SEQ ID NO:94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:94:

```
CCTCATGACA CTGATACTCT T                                                 21
```

(2) INFORMATION FOR SEQ ID NO:95:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:95:

```
GGCTGTGAGC AGGTCTGT                                                     18
```

(2) INFORMATION FOR SEQ ID NO:96:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:96:

CGACCACTAA TTGAATCAAA ATC          23

(2) INFORMATION FOR SEQ ID NO:97:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:97:

CGGTGCTCGT GTGATACAG          19

(2) INFORMATION FOR SEQ ID NO:98:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:98:

ATCCACATCC ACATGCAG          18

(2) INFORMATION FOR SEQ ID NO:99:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:99:

CCTCAAATGG CTGTAGCAAC AA          22

(2) INFORMATION FOR SEQ ID NO:100:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:100:

CTGCTGCTGC ACGTGTGA                                                 18

(2) INFORMATION FOR SEQ ID NO:101:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:101:

CCAGTCTGGA TACACAAAAT GT                                            22

(2) INFORMATION FOR SEQ ID NO:102:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:102:

GGCGCACTGC CATTC                                                    15

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:103:

CTCAGATGGC TCTGATGAAC T                                             21

(2) INFORMATION FOR SEQ ID NO:104:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:104:

GCGTTTTCTC TTTCTTTCCT T                                              21

(2) INFORMATION FOR SEQ ID NO:105:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:105:

GAGAGTCATT GCAAAGGAAG CA                                             22

(2) INFORMATION FOR SEQ ID NO:106:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:106:

AATATATGTG CAAAAGTGTG TTT                                            23

METHODS USING HUMAN CALCIUM SENSOR PROTEIN, FRAGMENTS THEREOF AND DNA ENCODING SAME

This application is a continuation-in-part of PCT/US95/15203 filed on Nov. 22, 1995, which is a continuation-in-part of Ser. No. 08/487,314 filed Jun. 7,1995, which is a continuation-in-part of Ser. No. 08/344,836 filed Nov. 23, 1994, now abandoned, which is a continuation-in-part of PCT/SE94/00483 filed May 24,1994.

BACKGROUND OF THE INVENTION

The present invention relates to a cDNA clone encoding a human calcium sensor protein of parathyroid, placental, and kidney tubule cells.

In WO 88/03271 there is described monoclonal antiparathyroid antibodies identifying a parathyroid cell membrane-bound calcium receptor or sensor, crucially involved in calcium regulation of the parathyroid hormone (PTH) release (1,2). The receptor function is essential for maintenance of normal plasma calcium concentrations, and reduced receptor expression within proliferating parathyroid cells of patients with hyperparathyroidism (HPT) results in calcium insensitivity of the PTH secretion and variably severe hypercalcemia (3–6). Reactivity with the antiparathyroid antibodies was also demonstrated for proximal kidney tubule cells and cytotrophoblast cells of the human placenta, and the cytotrophoblasts were demonstrated to exhibit an almost parathyroid-identical regulation of cytoplasmic calcium [$Ca^{2+}i$] (7,8). The antibody-reactive structure was found to exert calcium sensing function also in the cytotrophoblasts, and as these cells constitute part of the syncytium, the calcium sensor was suggested to be actively involved in the calcium homeostasis of the fetus (7,8). It was proposed that the antibody-reactive structure of the proximal kidney tubule cells exerts a similar calcium sensing function, and that the calcium sensor, thus, plays a more universal role in calcium regulation via different organ systems (1,7,9,10).

On HPT patients with hypercalcemia, surgery is performed to remove one or more of the parathyroid glands. It would be greatly desirable to have alternatives to this surgical procedure as HPT has proven to be a very common disorder and surgery is a relatively costly procedure and sometimes even entails some risks for the patients.

The calcium sensor/receptor has been revealed as a 500 kDa single chain glycoprotein (7). However, the amino acid sequence as well as the corresponding DNA sequences thereof are hitherto unknown.

SUMMARY OF THE INVENTION

Therefore, an object of the present invention was to provide sufficient structural data of the calcium sensor/receptor to enable complete characterization thereof.

In one embodiment, the present invention provides complete amino acid sequence of the human calcium sensor protein of parathyroid, placental and kidney tubule cells.

In another embodiment the invention provides nucleic acid sequence encoding the human calcium sensor and nucleic acid probes for identifying other novel calcium sensor proteins.

Another object is to use said structural data to design novel treatment methods as well as compounds and compositions for treating calcium related disorders.

In other embodiments, the present invention provides identification of peptide regions within the calcium sensor protein cytoplasmic domain which are homologous to SH2 and SH3 binding motifs involved in signal transduction pathways.

Two important human diseases associated with perturbations of the calcium ion homeostasis are hyperthyroidism and osteoporosis. Thus, in one embodiment cells expressing the calcium sensor protein or a fragment thereof or comprising the cDNA encoding the calcium sensor protein of the present invention may be utilized in an assay to identify molecules which block or enhance the activity of the calcium sensor protein, including signal transduction pathways associated with the activity of the sensor. These molecules will be useful in the treatment of mammalian pathological conditions associated with perturbations in the levels of PTH, vitamins D3 production, estrogen, osteoclast activity or osteoblast activity (therefore, bone resorption and/or formation), calcium secretion and calcium ion homeostasis.

The present invention describes the isolation and characterization of cDNA clones encoding the calcium sensor/receptor in human placenta and Northern blots verifying the presence of the corresponding mRNA within the parathyroid and kidney. Close sequence similarity between the calcium sensor and a rat *Heymann nephritis* antigen, gp330 (11, 67), suggests that the common calcium sensor of the placenta, the parathyroid and kidney tubule is related to this antigen, represents the human homologue of gp330, and belongs to a family of large glycoproteins with receptor function and calcium binding ability. Therefore, a further object of this invention is to provide diagnostic assays and therapeutic methods based on human gp330.

The invention provides a method of identifying agonists and/or antagonists of human calcium sensor protein activity comprising contacting potential agonists or antagonists with said calcium sensor protein or a biologically active sequence analog thereof and determining the ability of said potential agonists or antagonists to block or enhance the activity of said calcium sensor protein or biologically active sequence analog thereof.

The present invention further provides a method of identifying agonists and/or antagonists of human calcium sensor protein activity comprising:

a) expressing a cDNA encoding a human calcium sensor protein or a biologically active sequence analog thereof in a host cell;

b) contacting potential agonists or antagonists with said host cell; and c) determining the ability of said agonists or antagonists to block or enhance the activity of said calcium sensor protein or fragment thereof.

BRIEF DESCRIPTION OF THE DRAWINGS

FIG. 3. Partial nucleotide sequence (SEQ ID No. 3) and deduced amino acid sequence (SEQ ID No. 4) of the-cDNA clone, pCAS-2, encoding part of the calcium-sensor protein. Portions of the deduced amino acid sequence identical to the peptides 292 and 293 are underlined.

FIG. 4. Alignment of the amino acid sequence of the calcium-sensor protein (SEQ ID No. 4) to corresponding portions of the Heymann antigen (HEYMANN, SEQ ID No. 5), low density lipoprotein receptor (LDL-RC, SEQ ID No. 6), and LDL related receptor protein (LDLRRP, SEQ ID No. 7). Stars denote residues identical between the calcium sensor protein and any of the other sequences. X denotes a position in the Heymann antigen sequence where identity has not been published.

FIGS. 6A–6E. Complete nucleotide (SEQ ID No. 11) and amino acid (SEQ ID No. 12) sequence of the human calcium sensor 2.8 kb cDNA clone. The transmembrane domain of the sensor is shown in bold type. The three SH3 binding regions are underlined or overlined and the SH2 binding region is shown in strikethru.

FIG. 7. Amino acid sequence of the calcium sensor cytoplasmic domain (SEQ ID No. 13) and comparison of the three calcium sensor SH3 binding regions (SEQ ID Nos. 14–16) to known SH3 binding motifs (SEQ ID Nos. 20–37).

FIG. 9. Comparison of the calcium sensor SH2 binding region (SEQ ID No. 19) with amino acid sequence requirements necessary for interaction with the SH2 region of the p85 regulatory subunit of PI3K (SEQ ID Nos. 38–78).

FIG. 12. Comparison of the same region within different CAS cDNA sequences revealing amino acid sequence differences.

DETAILED DESCRIPTION OF PREFERRED EMBODIMENTS

Figures 1, 2:
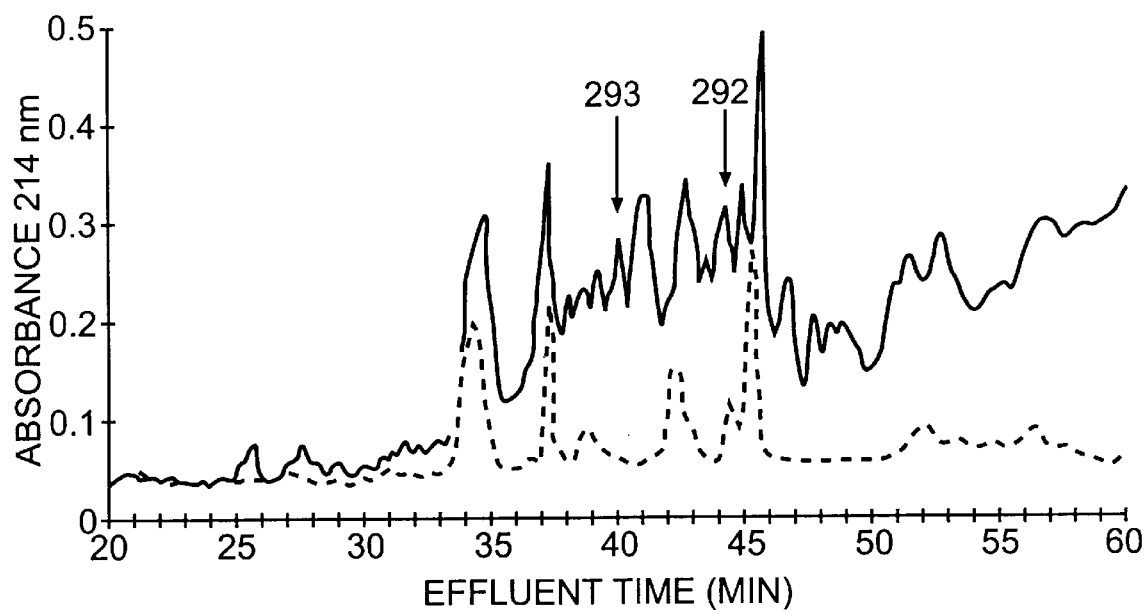
FIG. 1. Isolation by HPLC of peptides obtained after digestion of the calcium sensor protein with Lys-C endoprotease (solid line). Dashed line represents the chromatography of an identical reaction where the calcium-sensor was omitted. The flow rate was kept at 100 µl/min. Two peptide fractions which gave easily interpretable sequences are denoted by arrows.
FIG. 2. Sequences of two Lys-C peptides (SEQ ID Nos. 1 and 2) isolated by HPLC of the calcium-sensor protein.

Unless indicated otherwise herein, the following terms have the indicated meanings.

The term "polypeptide" means a linear array of amino acids connected one to the other by peptide bonds between the α-amino and carboxy groups of adjacent amino acids.

"Substantially purified" is used herein to mean "substantially homogeneous", which is defined as a material which is substantially free of compounds normally associated with it in its natural state (e.g., other proteins or peptides, carbohydrates, lipids). "Substantially purified" is not meant to exclude artificial or synthetic mixtures with other compounds. The term is also not meant to exclude the presence of impurities which do not interfere with biological activity, and which may be present, for example, due to incomplete purification or compounding with a pharmaceutically acceptable preparation.

The term "biologically active polypeptide" means the naturally occurring polypeptide per se as well as biologically active analogues thereof, including synthetically produced polypeptides and analogues thereof, as well as natural and pharmaceutically acceptable salts and pharmaceutically acceptable derivatives thereof. The term "biologically active polypeptide" also encompasses biologically active fragments thereof, as well as "biologically active sequence analogues" thereof. Different forms of the peptide may exist. These variations may be characterized by difference in the nucleotide sequence of the structural gene coding for proteins of identical biological function.

The term "biologically active sequence analogue" includes nonnaturally occurring analogues having single or multiple amino acid substitutions, deletions, additions, or replacements. All such allelic variations, modifications, and analogues resulting in derivatives which retain one or more of the native biologically active properties are included within the scope of this invention.

In this application, nucleotides are indicated by their bases using the following standard one-letter abbreviations:

| | |
|---|---|
| Guanine | G |
| Adenine | A |
| Thymine | T |
| Cytosine | C |
| Unknown | N |

In this application, amino acid residues are indicated using the following standard one-letter abbreviations:

| | |
|---|---|
| Alanine | A |
| Cysteine | C |
| Aspartic Acid | D |
| Glutamic Acid | E |
| Phenylalanine | F |
| Glycine | G |
| Histidine | H |
| Isoleucine | I |
| Lysine | K |
| Leucine | L |
| Methionine | M |
| Asparagine | N |
| Proline | P |
| Glutamine | Q |
| Arginine | R |
| Serine | S |
| Threonine | T |
| Valine | V |
| Tryptophan | W |
| Tyrosine | Y |
| Unknown | X |

The term "amino acid" as used herein is meant to denote the above recited natural amino acids and functional equivalents thereof.

This invention provides isolated nucleic acid molecules encoding a common calcium sensor protein of parathyroid, placental and kidney tubule cells and comprising a coding sequence selected from the group consisting of SEQ ID No. 3, SEQ ID No. 11, SEQ ID No. 83, SEQ ID No. 85, SEQ ID No. 87, and SEQ ID No. 89.

Furthermore, this invention provides a vector comprising an isolated nucleic acid molecule encoding the calcium sensor protein or a fragment thereof which encodes functional regions of the sensor.

Moreover, the invention provides a method of preparing calcium sensor protein which comprises inserting a nuleic acid encoding the calcium sensor or a fragment thereof in a suitable vector, inserting the resulting vector in a suitable host cell, recovering the calcium sensor protein produced by the resulting cell, and purifying the calcium sensor protein so recovered. This method for preparing a calcium sensor protein or fragment thereof uses recombinant DNA technology methods which are well known in the art. Alternatively, the calcium sensor protein or a fragment thereof may be prepared using standard solid phase methodology of peptide synthesis.

The present invention also provides antisense nucleic acids which can be used to down regulate or block the expression of the calcium sensor protein either in vitro, ex vivo or in vivo. The down regulation of gene expression can be made at both translational or transcriptional levels. Antisense nucleic acids of the invention are more preferentially RNA fragments capable of specifically hybridizing with all or part of the sequence selected from the group consisting of SEQ ID No. 3, SEQ ID No. 11, SEQ ID No. 83, SEQ ID No. 85, SEQ ID No. 87, and SEQ ID No. 89 or the corresponding messenger RNA. These antisense can be synthetic oligonucleotides prepared based on the sequence selected from the group consisting of SEQ ID No. 3, SEQ ID No. 11, SEQ ID No. 83, SEQ ID No. 85, SEQ ID No. 87, and SEQ ID No. 89, optionally modified to improve their stability of selectivity, as disclosed for instance in EP 92574. They can also be DNA sequences whose expression in the cell produces RNA complementary to all or part of the calcium The biologically active calcium sensor protein of the present invention has been isolated as described. It can also be prepared by chemical synthesis in a recombinant DNA biosystem. Biologically active fragments of the calcium sensor protein can also be prepared using synthetic or recombinant technologies which are known in the art.

Cleavage and sequence determination of isolated peptides. Cleavage of the 500 kDa protein with endoprotease Lys C from *Achromobacter lyticus* generated peptides, which were subjected to separation on a Brownlee microbore $C_4$ column (2.2×30 30 mm), equilibrated in 5% acetonitrile in 0.02% trifluoroacetic acid. A linear gradient of 5 to 60% acetonitrile in 0.02% trifluoroacetic acid was employed for peptide elution, monitored at 214 nm using Waters 990 diod-array detector (Millipore Corporation, Millford, Mass.). Amino terminal sequences of the 35 peptides were determined in an ABI 470A gas-phase sequenator, equipped with an ABI 120A PTH-amino acid chromatograph (Applied Biosystems, Foster City, Calif., USA).

Oligonucleotide synthesis. Oligonucleotides were synthesized 40 using an ABI 381 oligonucleotide synthesizer (Applied Biosystems). The following oligonucleotide mixture was utilized as a probe for screening of the placental cDNA library:

```
CCA ATA IAG CTG ATC CTC AAA GAT ATC IAG IGA ATA IGG ATT CAT IGC   (SEQ ID No. 8)
    G       G       G       G           G       G

The following two oligonucleotides were synthesized for use in
PCR reactions:
GCG GAATTC GTA ATG CAA CCA GAC GG                                  (SEQ ID No. 9)
           C       G   C   T
           G           G
           T           T ATA GGATCC TG ATC CTC AAA AAT ATC                                  (SEQ ID No. 10)
              G   T   G   G   G
                          T
``` sensor protein mRNA. These antisenses can be prepared by expression of all or part of the sequence selected from the group consisting of SEQ ID No. 3, SEQ ID No. 11, SEQ ID No. 83, SEQ ID No. 85, SEQ ID No. 87, and SEQ ID No. 89 in the opposite orientation (EP 140 308).

Material and Methods

Tissue specimens. Samples of human parathyroid glands were obtained at surgery of patients with primary HPT. Other human tissue specimens (kidney, epididymis, liver, pancreas, adrenal gland, small gut, spleen, lung and striated muscle) were sampled from organs removed at surgery. Human placental tissue was collected in conjunction with uncomplicated pregnancies at full term. All specimens were immediately quick-frozen in isopentane and stored at −70° C.

Isolation of the calcium sensor protein from human placenta. The 500 kDa calcium sensor protein was isolated and purified, from altogether 25 human placentas, by immunosorbent and ion exchange chromatographies, following a previously described protocol (7). The procedure utilizes two different monoclonal antiparathyroid antibodies (1,7), E11 and G11, known to bind different epitopes of the calcium sensing protein; E11 has displayed no functional effect, while G11 efficiently blocks calcium regulation in both parathyroid and placental cells (1,7). After purification, the calcium sensor protein preparation was subjected to gel chromatography on a Zorbax GF25 gel column (9.2×250 mm), prior to enzymatic digestion.

The first nine nucleotides contain an EcoR I and a BamH I site, respectively, and the remaining nucleotides correspond to amino acid residues 1 to 6 of peptides 293 and to residues 8 to 13 of peptide 292.

Screening of a placental cDNA library with a mixed 30 oligonucleotide probe. A placental λ gt 11 cDNA library (Clontech, Calif., USA) was plated out to a density of approximately $2 \times 10^5$ plaques within a 20×25 cm agar plate. Replicate filters (Hybond-N+, Amersham) of ten plates were prehybridized in 5×SSPE (SSPE; 120 mM NaCl, 8 mM $NaH_2PO_4$, 0.8 mM EDTA, pH 7.4), 5×Denhart's solution (12), 0.5% SDS, 20 μg/ml single stranded salmon sperm DNA (Sigma Chemical Co., S:t Louis, Ohio). The mixed oligonucleotide probe, endlabeled with γ-[$^{32}$p]-ATP and polynucleotide kinase (Amersham), was added to the hybridization mixture ($30 \times 10^6$ cpm in 50 ml), and hybridization was carried out over night at 42° C. The filter was washed twice in 2×SSPE and once in 0.1×SSPE, exposed to an autoradiography screen and analysed by a phosphorimager (Molecular Dynamics, Image Count S.W, Sun Valley Calif.).

PCR reaction. Part of the λ gt 11 cDNA clone CAS-1 was amplified by PCR using two degenerated probes corresponding to portions of peptides 292 and 293. The following conditions were used: 170 ng template DNA, 1 pmol of each oligonucleotide mixture as primers, dNTP 3 mM, Taq-polymerase 0.75 u. The reaction was carried out in 20 μl of 10 mM Tris-HCl, pH 8.0, 1.5 mM $MgCl_2$, 50 mM KCl in a Perkin-Elmer 9600 PCR-machine (Perkin-Elmer, Norwalk, USA). Two cycles of denaturation at 94° C. for 2 min. annealing at 47° C. for 1 min and extension at 72° C. for 1 min 30 sec were followed by 33 cycles of 94° C. for 1 min. 54° C. for 45 sec. 72° C. for 1 min and a final extension at 72° C. for 10 min.

Screening of a placental cDNA library with a PCR-fragment as probe. A placental λ ZAP-II cDNA library, was screened with the PCR-fragment from the cDNA clone CAS-1 labeled by random priming as the probe. The screening was carried out as above. $2 \times 10^6$ plaques distributed on ten 20×25 cm agar plates were screened.

Nucleotide sequence determination. The insert of the phage clone CAS-2 was released from the phage vector in the Bluescript+ vector using a helper phage (Stratagene, La Jolla, Calif.). Nucleotide sequence reactions were carried out according to the cycle sequencing procedure, utilizing a kit from Applied Biosystems. Sequences were analyzed in an ABI 373 A DNA sequenator using the Data Collection Program VIII software (Applied Biosystems). Completion of the CAS-2 2.8 kb cDNA sequence was accomplished by the dideoxynucleotide chain-termination method with Sequenase (United States Biochemical) and is shown in FIG. 6 (SEQ ID No. 11). Multiple sequencing analyses were performed on both strands of CAS-2 to confirm the sequence. Amino acid sequence deduced from the cDNA sequence was analyzed by a Macvector DNA/RNA software analysis package (Macintosh).

Reverse transcriptase PCR amplification and standard 32p-labeled probe screening of human lambda kidney cDNA libraries were used to complete the cloning of the CAS cDNA (SEQ ID No. 83).

Full-length human placental (SEQ ID No. 85), kidney (SEQ ID No. 87) and parathyroid (SEQ ID No. 89) CAS cDNA sequences were obtained from PCR amplified human placental, kidney and parathyroid cDNA libraries as follows. Specifically primed first-strand cDNA was prepared using oligonucleotide primers designed off SEQ ID No. 83, total RNA RNAzol B method (Tel-Test), and a cDNA synthesis kit (Promega). The following primers with indicated sequence positions were used in the reactions:

| | | | |
|---|---|---|---|
| F1s | GCAGACCTAAAGGAGCGTT | 1 | SEQ ID No.91 |
| G7as | CCCGACCATTGGAGAAGATA | 1311 | SEQ ID No.92 |
| G20s | GCCAGTACCAGTGCCATGA | 1054 | SEQ ID No.93 |
| G29as | CCTCATGACACTGATACTCTT | 2540 | SEQ ID No.94 |
| G26s | GGCTGTGAGCAGGTCTGT | 2109 | SEQ ID No.95 |
| G16as | CGACCACTAATTGAATCAAAATC | 4540 | SEQ ID No.96 |
| G16s | CGGTGCTCGTGTGATACAG | 4338 | SEQ ID No.97 |
| E2as | ATCCACATCCACATGCAG | 6413 | SEQ ID No.98 |
| E4s | CCTCAAATGGCTGTAGCAACAA | 6157 | SEQ ID NO.99 |
| B9as | CTGCTGCTGCACGTGTGA | 8704 | SEQ ID No.100 |
| B5s | CCAGTCTGGATACACAAAATGT | 8570 | SEQ ID No.101 |
| 23.5 | GGCGCACTGCCATTC | 10,910 | SEQ ID No.102 |
| G19s | CTCAGATGGCTCTGATGAACT | 10,718 | SEQ ID No.103 |
| G36as | GCGTTTTCTCTTTCTTTCCTT | 13,026 | SEQ ID No.104 |

-continued

| | | | |
|---|---|---|---|
| G35s | GAGAGTCATTGCAAAGGAAGCA | 12,893 | SEQ ID No.105 |
| G31as | AATATATGTGCAAAAGTGTGTTT | 14,120 | SEQ ID No.106 |

Four separate reverse trancriptase (RT) reactions were performed using the following primers:

| | | |
|---|---|---|
| RT reaction 1 | (RT1) | primer G29as |
| RT reaction 1 | (RT2) | primer E2as |
| RT reaction 1 | (RT3) | primer 23.5 |
| RT reaction 1 | (RT4) | primer G31as |

The following primers were used for PCR with listed RT reaction:

| primer | RT reaction |
|---|---|
| F1s/G7as | RT1 |
| G20s/G29as | RT1 |
| G26s/G16as | RT2 |
| G16s/E2as | RT2 |
| E4s/B9as | RT3 |
| B5s/23.5 | RT3 |
| G19s/G36as | RT4 |
| G35s/G31as | RT4 |

PCR amplification of first-strand cDNA was performed in a Perkin-Elmer 9600 Thermal Cycler using the following program: 1 cycle of denaturation at 94° C. for 2 min., followed by 40 cycles of denaturation at 94° C. for 15 sec., annealing at 51° C. for 10 sec., and extension at 72° C. for 3 min., after which, the products of the reactions were separated by electrophoresis and gel purified (QIAGEN). PCR reagents were purchased from Perkin- Elmer and used according to manufacturer's suggestions. PCR fragments were then nucleotide sequenced using a dideoxynucleotide chain-termination method (Perkin-Elmer Prism Dye Deoxy Terminator Cycle Sequencing Kit), and an ABI 373 automated DNA sequencer (Applied Biosystems). PCR fragments from four separate reactions were sequenced on both strands to confirm sequence data. Computer generated DNA sequence analysis was performed using Auto-Assembler and Factura (Applied Biosystems), and MacVector and AssemblyLIGN (Eastman Kodak Company) software programs.

Database search. The EMBL-31 database in the Intelligenetics format (Intelligenetics Rel.5.4), was searched for sequence similarities to the placental cDNA sequence using the FAST DB algorithm (13).

Immunostaining and Northern blot. Immunohistochemical studies were performed on acetone-fixed, 6 pm thick frozen sections, utilizing the monoclonal antiparathyroid antibodies E11 and G11, at concentrations of 5 µg/ml, together with a mouse peroxidase antiperoxidase technique on human placental, parathyroid, kidney, and epididymis specimens as well as on the other human tissues—see above (1,7). Monoclonal antibodies to collagen-type II were used as negative controls (14).

Total RNA was extracted from tissue samples by the acid phenol/chloroform method. For Northern blot analysis approximately 10 µg of total RNA was electrophoresed in a 1.5%/37% agarose/formaldehyde gel, blotted onto nylon membranes (Qiabrane, Diagen GmbH, Dusseldorf, Germany) and probed with the 2.3 kb clone (see results) labeled by the random priming method. Hybridizations were performed at 42° C. for 18–24 h in 50% formamide, 4×saline sodium citrate (SSC; 300 mM NaCl, 30 mM Na-citrate, pH 7.0), 2×Denhart's solution, 10% dextran sulfate (Kabi-Pharmacia, Uppsala, Sweden) and 100 µg/ml salmon sperm DNA. Filters were washed at a final stringency of 1×SSC/0.1% SDS for 30 sin at 42° C., and exposed within a phosphorimager as above.

CAS Peptide Binding Analysis: A peptide corresponding to one putative CAS SH3 binding region (ATPPPSPSLPAKPKPPSRR) (SEQ ID No. 18) was synthesized on an ABI model 430A synthesizer using FastMoctm chemistry. The peptide was HPLC purified and analyzed by mass spectroscopy. 5 mg of the peptide was coupled to 500 ul of Amino Link (Pierce) agarose as described by the supplier. Efficiency of coupling was checked by RP-HPLC of peptide solution before and after coupling and spectrophotometrically at a wavelength of 220 nm. Both methods indicated a coupling efficiency of >70%. The coupled peptide was reacted with 5 ug aliquots of various GST-SH3 fusion proteins at room temperature for 1 hour before the resin was washed extensively with TTBS. The resin was boiled in SDS loading dye and electrophoresed on an SDS-PAGE gel. Binding ability of the various SH3 proteins for the peptide was judged by the relative intensity of the Coomassie blue-stainable bands on the SDS gel. GST protein alone was used alone as a control.

Expression and Purification of GST-SH3 fusion Proteins: Various GST-SH3-containing fusion clones were kind gifts from Dr. I. Gout, Ludwig Inst. for Cancer Research, London, UK. The fusion 25 proteins were all produced by inducing their expression in XL1-blue *E. coli* using 1 mM IPTG. Cells containing the fusion proteins were sonicated in PBS containing 10 mM EDTA and 1% Triton-X 100. After pelleting cell debris, the cleared lysate was applied to a glutathione-Sepharose column (Pharmacia), and the bound fusion protein was eluted with 10 mM reduced glutathione in 50 mM Tris pH 8.0. These purified fusion proteins were then dialyzed extensively against PBS before being used in all subsequent experiments. Protein was quantified by measuring the absorbance at 280 nm followed by characterization by SDS polyacrylamide gel electrophoresis.

RESULTS

Isolation of the calcium sensor protein, peptide cleavage and sequence determination.

The calcium sensor protein was purified from placental tissue by means of Pectin chromatography, immunosorbent chromatography utilizing the immobilized monoclonal anti-parathyroid antibodies, and finally ion exchange chromatography (1,7). The same antibodies were used in a sandwich ELISA to monitor the purification (7). In order to avoid contamination with low molecular peptides, the whole final preparation, consisting of 200 µg of the 500 kDa protein chain (7), was made 6 M with regard to guanidine-HCl and applied to a gel chromatography column, equilibrated with 2 M guanidine-HCl, 0.1 M Tris-Cl, pH 8.5. The column was eluted with the same buffer. Virtually all protein material emerged close to the void volume at the expected position for a protein with a molecular mass of 500 kDa. Separate fractions containing this material were combined and endoproteinase Lys C (1 µg) was added. The digestion was allowed to proceed over night at 37° C. The fragmented protein was reduced by incubation with 0.1% β-mercaptoethanol at 37° C. for 30 min and subsequently alkylated with 4-vinyl pyridine (0.3%) at room temperature for 2 h. The peptide mixture was then applied to a reversed phase $C_4$ column equilibrated in 5% acetonitrile in 0.2% trifluoroacetic acid. Peptides were eluted by a linear gradient of 5–60% acetonitrile in 0.02% trifluoracetic acid (FIG. 1).

Due to the large number of peptides, the elution pattern was complex. Several peptide fractions were sequenced in a gas phase sequenator and easily interpretable sequences were obtained for two fractions (FIG. 2, SEQ ID Nos. 1 and 2).

Isolation of a cDNA clone encoding the 500 kDa calcium sensor.

An oligonucleotide mixture (48 bp) was constructed to encode amino acid residues 2 to 17 of the sequenced peptide 292. To reduce the complexity of the oligonucleotide mixture, five inosine bases were inserted at degenerated positions where no guidance could be obtained from the codon usage in humans. At nine positions, where two bases were possible, one of the bases was suggested with a likelihood exceeding 70% from codon usage, and was therefore used in the oligonucleotide mixture.

The mixed oligonucleotide was radioactively labelled and used as a probe to screen a human placental λ gt 11 cDNA library. Approximately 2×10$^6$ plaques were screened and a single positive clone, CAS-1, was found. The insert of this clone was estimated to 2.3 kb, by restriction mapping. To obtain a recognizable sequence of the clone in a rapid way, an attempt was made to PCR amplify part of the sequence using degenerated oliogonucleotides corresponding to part of peptides 292 and 293 as primers. A distinct DNA fragment of approximately 430 bp was obtained assuming that the peptide 292 is located carboxy-terminal to peptide 293. The fragment was partially sequenced using the oligonucleotide mixture corresponding to peptide 293 as the primer. In one reading frame from the obtained sequence, the sequence VGRHI could be deduced, in excellent agreement with the carboxyterminal 5 amino residues of peptide 293. To obtain a clone with a larger insert a human placental λ ZAP-II cDNA library reported to contain clones with large inserts was screened with the PCR fragment as the probe. From 2×10$^6$ plaques a single clone, CAS-2, was found. The insert of this clone, estimated to 2.8 kb, was released in the Bluescript + vector, using a helper phage. Part of the insert of this clone, pCAS-2, was sequenced using synthetic oligonucleotides as primers (FIG. 3, SEQ ID No. 3). An open reading frame was found containing both peptide 292 and 293. There was perfect agreement between the peptide sequences and the predicted amino acid sequence (SEQ ID No. 4) from the cDNA clone. The complete sequence of the 2.8 kb CAS-2 is shown in FIG. 6 (SEQ ID No. 11).

The CAS-2 sequence was extended using standard methodology. Reverse transcriptase PCR amplification and standard $^{32}$P-labeled probe screening of human lambda kidney cDNA libraries were used to complete the cloning of the CAS cDNA (SEQ ID No. 83). Probe fragments were designed off appropriate clones, starting with clone pCAS-2 (FIG. 11), to allow isolation of overlapping but 5'-extended clones from these libraries. This cDNA walking procedure was used for the isolation of all cDNA clones except clones pMeg2, pHP1C8, pHP1B1, and pM4B1. These clones were isolated from human kidney cDNA libraries using rat gp330 PCR amplified probe fragments (nts. 148–1249, 2892–3873, 4553–5693, and 5868–6968) obtained with rat cDNA prepared from rat kidney total RNA. Three small cloning gaps (aa 564–997, 1622–1836, and 2212–2312;) were completed by direct PCR amplification through these regions using specific human gp330 oligonucleotide primers and cDNA prepared from human kidney total RNA (CAS-1750, -1210, and -700).

Figure 11:
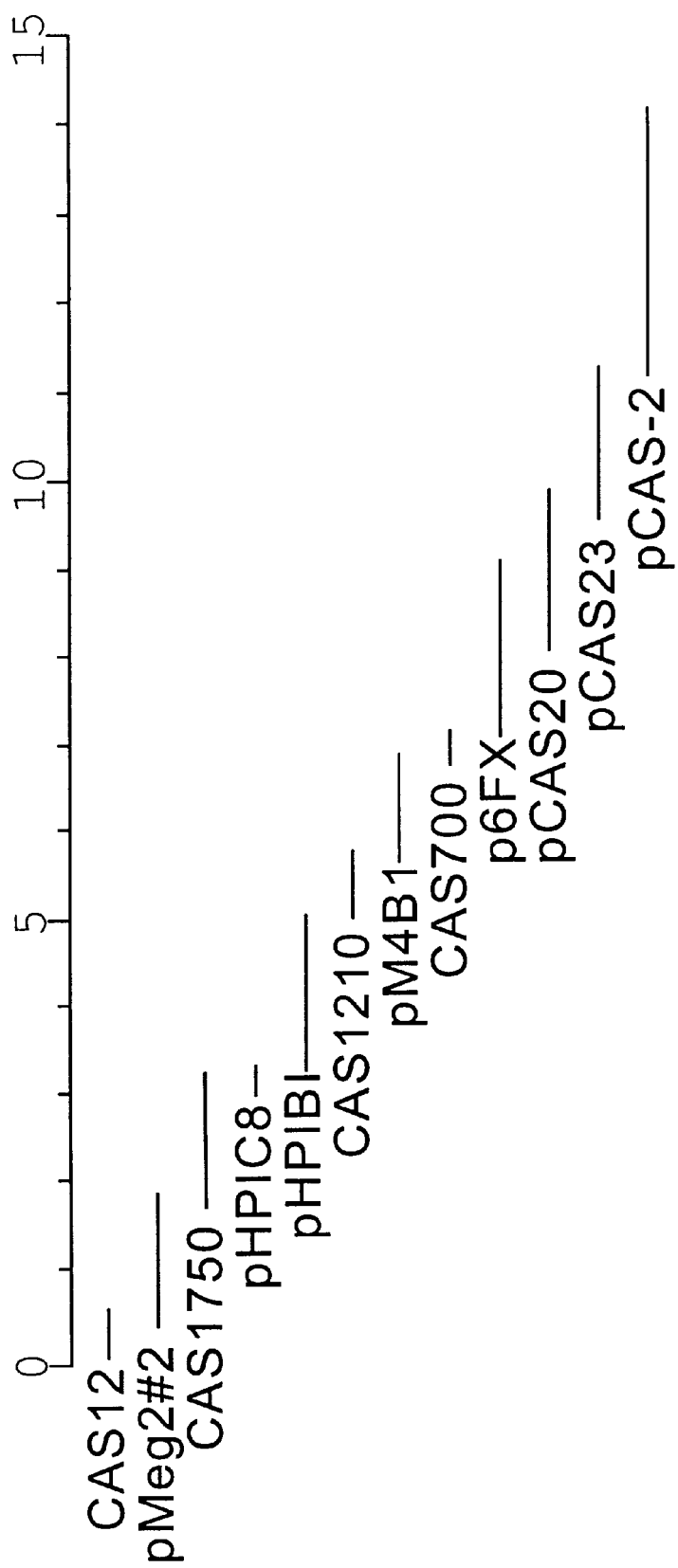
FIG. 11. Strategy for extending CAS sequence from pCAS-2.

An extended calcium sensor sequence is shown in SEQ ID No. 17. A complete human calcium sensor sequence in shown in SEQ ID Nos. 83 and 84. Based on the above cloning procedure amino acids 1–3711 of SEQ ID No. 84 were determined from human kidney cDNA whereas amino acids 3712–4655 were identified from the CAS-2 placental cDNA clone (FIG. 11).

Full-length human placental (SEQ ID Nos. 85 and 86), kidney (SEQ ID Nos. 87 and 88) and parathyroid (SEQ ID Nos. 89 and 90) CAS cDNA and amino acid sequences have been determined by sequencing PCR fragments from specifically primed first-strand human placental, kidney and parathyroid cDNA, prepared using oligonucleotide primers designed off SEQ ID No. 83, total RNA RNAzol B method, and a cDNA synthesis kit as described in Material and Methods.

Comparison of all CAS sequences obtained so far reveals only four potential differences throughout the complete amino acid sequence: $Ala^{287}$ to Ala/Pro, $Ala^{2872}$ to Thr, $Lys^{4094}$ to Lys/Glu, and $Ile^{4210}$ to Ile/Leu (FIG. 12). The ambiguous positions and the minor amino acid differences are most likely associated with normal ethnic and/or allelic variation differences being reflected in the cDNA sources used in constructing the cDNA libraries.

The 500 kDa placental calcium sensor belongs to the LDL-receptor superfamily.

Figure 10:
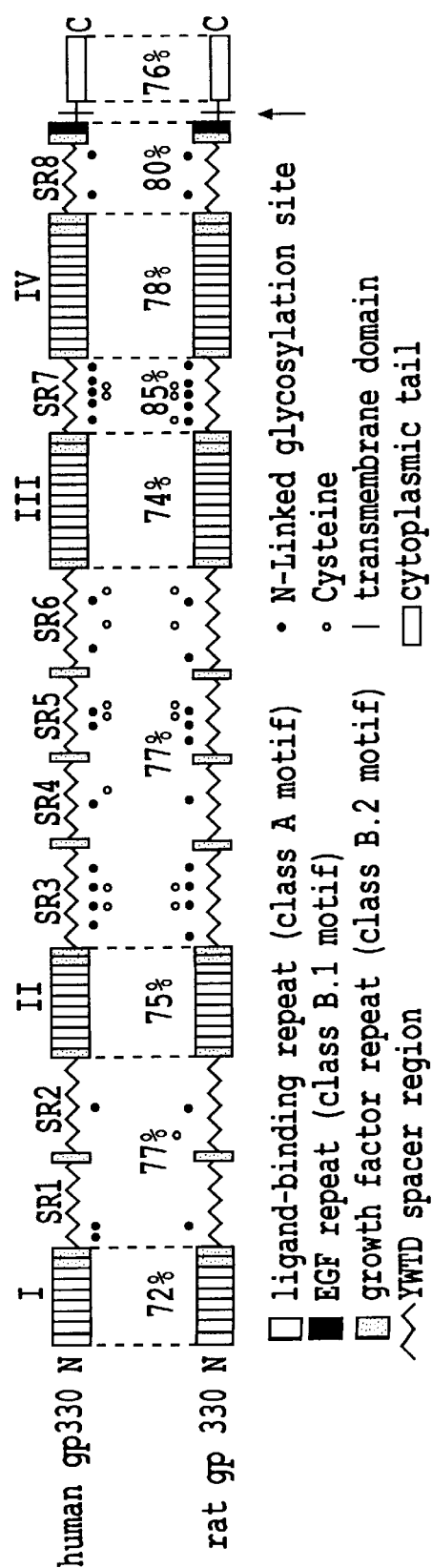
FIG. 10. Structure of human gp330, including the EGF repeat, growth factor repeats and YWTD spacer regions. N depicts the amino terminus of the protein and C the carboxyl-terminus. The arrow indicates the location of the transmembrane region.

A search in a database with the predicted amino acid sequence from FIG. 3 (SEQ ID No 3) revealed that the placental 500 kDa protein is homologous to receptors belonging to the LDL-receptor superfamily. The highest similarity was found with the rat Heymann nephritis antigen (11, 67). FIG. 4 shows an alignment of placental 500 kDa protein sequence to the sequence of the Heymann antigen (SEQ ID No. 5) as well as to two other members of the same protein superfamily, the LDL-receptor (SEQ ID No. 6) and the LDLreceptor-related protein (identical to the $\alpha_2$-acroglobulin receptor, (11,15,16), SEQ ID No. 7). The sequence identity between the placental calcium-sensor and the Heymann antigen gp330 was estimated to be 82% in the region of comparison (236 amino acid residues). A complete sequence of the human calcium sensor protein is shown in SEQ ID No. 83. Overall, the identity between rat gp330 and the human homolog is 77%. The structure of human gp330 is shown in FIG. 10. The protein is 4655 amino acids in length and comprises an N-terminal signal peptide of 25 amino acids, a 4398 amino acid extracellular domain, a transmembrane region of 23 amino acids and a C-terminal domain of 209 amino acids. As shown in FIG. 10, the structure of human gp330 closely correlates with that of the rat homolog (FIG. 3 of ref. 67).

Immunohistochemistry and Northern blot.

The close similarity between the placental 500 kDa calcium-sensor protein and the rat Heymann nephritis antigen prompted the expanded immunohistochemical investigation of the present study. The antiparathyroid antibodies (E11 and G11) were found to stain not only parathyroid, placental and proximal kidney tubule cells but also epididymal cells, as previously demonstrated for antibodies reactive with the Heymann antigen (17–20).

Figure 5:
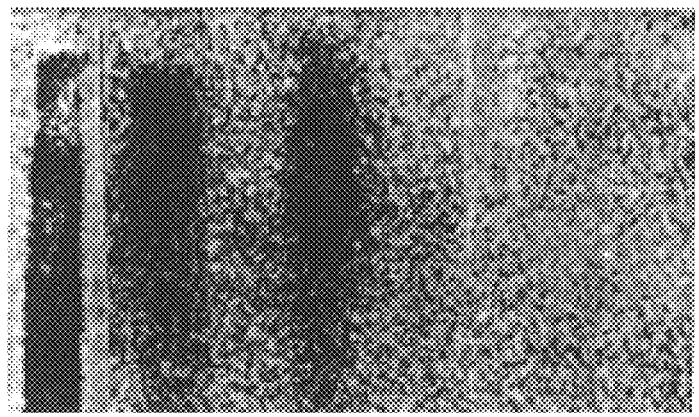
FIG. 5. Northern blot analysis of total RNA from parathyroid adenoma (1), kidney (2), liver (3), placenta (4), pancreas (5), adrenal gland (6), small gut (7). Filters were hybridized with the 2.8 kb pCAS-2 insert probe, and reactions visualized by a phosphorimager. Locations of 28S and 18S ribosomal RNA are indicated.

Northern blot analysis of total RNA (approximately 10 μg/lane) from human kidney, placenta and parathyroid glands with the identified 2.8 kb clone as the probe, revealed one major hybridizing RNA species of approximately 15,000 bases in all these tissues (FIG. 5). Human liver, pancreas, adrenal gland, and small gut (FIG. 5) as well as spleen, lung and striated muscle (not shown) lacked hybridizing species.

Identification of SH2 and SH3 binding regions in the cytoplasmic domain of the calcium sensor:

Src-homology regions 2 and 3 (SH2 and SH3) are conserved sequence motifs consisting of approximately 100 and 60 amino acid residues, respectively, and are found in many eukaryotic proteins with diverse function (42–44). SH3 domains have been identified in several cytoskeleton-associated proteins, such as p80/p85, myosinlb, spectrin, neutrophil NADPH oxidase-associated proteins p47 and p67, and in several yeast proteins important for morphogenesis (i.e., Bemlp and ABP-1), mating (FUS1) or for regulation of ras activity (cdc25 and ste6 (for review see Mussachio et al. (45)). The observation that many SH3-containing proteins are cytoskeleton-associated led to the suggestion that SH3 domains play a role in multimeric protein complex formation at or near cytoplasmic membranes. Some proteins that contain both SH2 and SH3 domains perform the function of adaptor molecules by joining activated receptor tyrosine kinases with p21 ras guanine nucleotide-releasing protein (GNRP). For example, Grb2 and its homologues bind to phosphotyrosine on activated membrane-anchored receptor tyrosine kinases through their SH2 domain and to SOS through their amino-and carboxyterminal SH3 domains (46–50). These processes lead to translocation of SOS to the plasma membrane where ras proteins are interacted with and consequently activated. Thus, SH2/SH3-containing and SH2/SH3-binding proteins are involved in a highly conserved signal transduction pathways from activated receptors.

Figure 8:
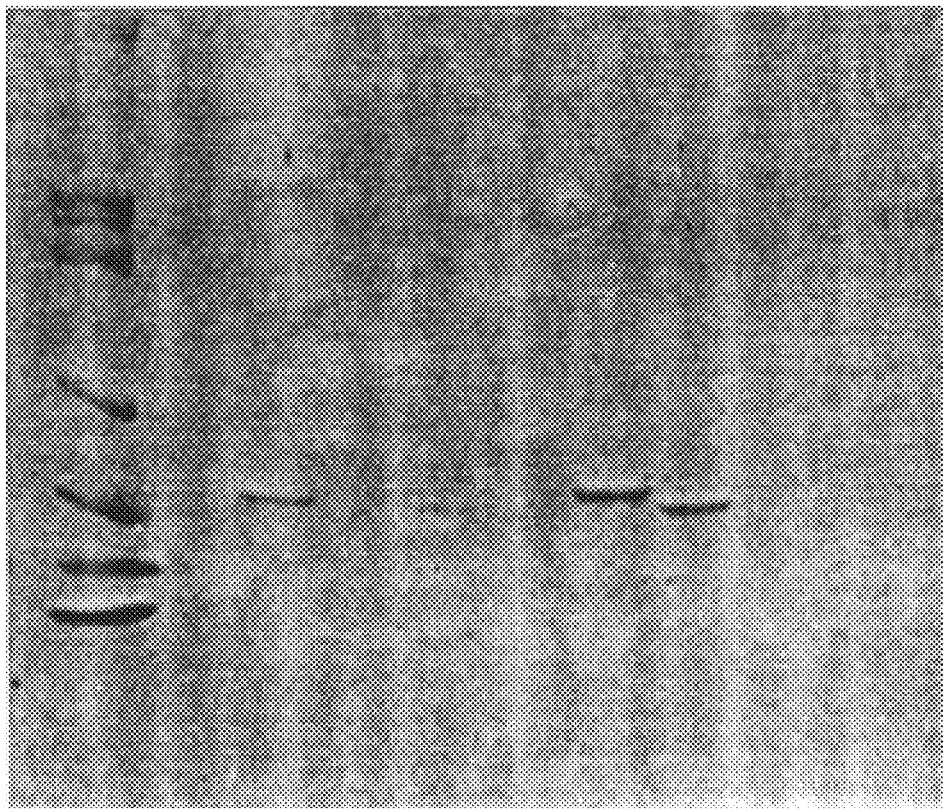
FIG. 8. Comparison of relative binding strengths between a calcium sensor SH3 binding region and various GST fusion proteins comprising an SH3 domain.

Complete nucleic acid sequencing and translation of the 2.8 kb human cDNA clone CAS-2 (FIG. 6) (SEQ ID Nos. 11 and 12) demonstrate the existence of at least three potential SH3 binding regions denoted as CAS-PEP1 (SEQ ID No. 14), CAS-PEP2 (SEQ ID No. 15), and CAS-PEP3 (SEQ ID No. 16) (FIG. 7). All three of these CAS-2 cytoplasmic peptide regions have the required consensus sequence of a SH3-binding region, which is shown together with the CAS peptides in FIG. 7 (53). Further support that the cytoplasmic domain of CAS-2 binds SH3 regions is shown in the evidence in FIG. 8. A region of the CAS-2 cytoplasmic domain (ATPPPSPSLPAKPKPPSRR) (SEQ ID No. 18) that included CAS-PEP1 (PSLPAKP, FIG. 7) was synthesized. The peptide was incubated with various purified GST-SH3 fusion proteins and the relative binding strengths of the fusion proteins was assayed by SDS-PAGE (FIG. 8). The data clearly indicate that several of the SH3-region containing proteins had an affinity for the peptide containing CAS-PEP1, with the following relative order of decreasing affinities: LANE 6: SH3-PI3K (SH3 of p85 subunit of phosphoinositol-3 kinase, (54,55))>LANE 7: SH3-PLC-gamma, (phospholipase-C gamma, (56))>LANE 2: SH3-FYN (src-family soluble tyrosine kinase, (57),>LANE 4: SH3-GRB2, (growth factor receptor binding protein N-terminal SH3) and LANE 5 (C-terminal SH3 of GRB2) (58,59).

Significantly, all of the positive reacting SH3-containing proteins shown in FIG. 8 are intimately associated with signal transduction and stimulation of cell growth (54–59). PI3K contains two SH2 regions and one SH3 region. PI3K is relatively new to the family of signal transducing molecules, but appears to be involved with insulin signaling through the glucose transporter, and is believed to associate directly with the ras protein. PLC-gamma is a well known signaling molecule also containing two SH2 regions and one SH3 region, and is known to hydrolyze membrane lipids to other powerful downstream signaling molecules (eg. IP3 and diacylglycerol) when stimulated by ligand activated growth factor receptors. FYN is a highly characterized member of the src-family of soluble tyrosine kinases known to be intimately associated with cell growth and differentiation. FYN contains one SH2 and one SH3 region, is also known to be stimulated by ligand activated growth factor receptors. GRB2 contains two SH3 regions and one SH2 region, and is known as an adaptor molecule in that it has no known intrinsic enzymatic capabilities. GRB2 molecules are also stimulated by ligand activated growth factor receptors. It is also worth noting that SH3-GAP (GTP-ase activating protein, LANE 3, (60, 61)), and SH3-NCF (neutrophil cytotoxic factor-type 1, LANE 8, or -type 2, lane 9, (62, 63)) had little or no affinity for the peptide containing CAS-PEP1. This evidence supports the specificity of the interaction between the CAS-PEP1 and various SH3 domains. In addition, CAS-PEP1 does not bind a control GST fusion protein as shown in lane 1 of FIG. 8.

The cytoplasmic domain of CAS-2 also comprises a p85-SH2 binding region. Though different SH2 containing proteins all require phosphorylated tyrosine residues for an interaction, it is well established that the amino acid residues surrounding the tyrosine residue dictate the specificity and strength of the interaction (64). FIG. 9 defines those amino acid sequence requirements that are necessary for interaction with the SH2 region of the p85 regulatory subunit of PI3K. The evidence clearly shows that for a binding interaction to take place with the SH2 region of p85, the tyrosine residue must be included in the amino acid sequence motif YXXM (where "X" can be any amino acid), and must have an acidic amino acid residue (D or E) approximately 3–5 residues in either direction of the YXXM motif. This exact amino acid sequence requirement exists in the cytoplasmic domain of CAS-2 (FENPIYAQMENE) (SEQ ID No. 19), and is underlined in the CAS-2 cytoplasmic sequences at the top of FIG. 9.

Altogether, the evidence demonstrates that the cytoplasmic domain of the calcium sensor protein of the invention contains three consensus SH3 binding regions and one potential SH2 recognition region of the type recognized by the SH2 region of p85 and supports an involvment of SH2 and SH3 mediated signal transduction for biological activity of the calcium sensor protein, possibly through PI3K. The potential interaction of PI3K with the calcium sensor protein is even more interesting in light of recent evidence linking the CAS-2 protein to calcium sensing in human parathyroid tissue, given that calcium sensing appears to involve G-protein activation, PKC activation, and inositol phosphate generation, all of which are activities that can be associated with PI3K signal transduction cascades. Therefore, these regions provide useful tools in assays for the identification of compounds that either stimulate or inhibit the signal transduction pathways used by the calcium sensor protein. Using assay techniques known to those skilled in the art, agonists or antagonists which mimic or inhibit the activity of the calcium sensor protein SH2/SH3 regions will be useful for the treatment of diseases that are intimately associated with the sensor, such as primary hyperparathyroidism (HPT) (52) and osteoporosis.

The relation of the calcium sensor protein to the LDL-receptor superfamily of proteins was noted above. All of the members of the LDL-receptor superfamily are "scavenger" proteins. None of these scavenger proteins have recognized signal transduction regions, and specifically, none of these scavenger proteins contain SH regions. Therefore it was entirely unexpected to identify SH2 and SH3 binding regions active in signal transduction in the calcium sensor protein. The occurrence of these regions is a further indication that the calcium sensor protein is not a scavenger protein, even though it has regions of homology with the LDL-receptor superfamily of scavenger proteins.

Rat Heymann nephritis antigen, gp330, belongs to the LDL receptor superfamily of large, multifunctional glycoproteins (68, 69, 70). Identification of the calcium sensor protein as the human homolog of rat gp330 enables new diagnostic and therapeutic agents for human disease.

Examples of diagnostic and therapeutic uses for gp330, or biologically active fragments thereof, are disclosed in EP 358,977, the entire contents of which are incorporated herein by reference. For example, human gp330, or fragment thereof, may be used in assays for detecting autoantibodies associated with human membranous glomerulonephritis. Examples of suitable assays include immunoassays, such as ELISA. Alternatively, synthetic peptides based on the human gp330 sequence may be used to localize immunodominent B- or T-lymphocyte recognition sites. Therefore, the invention enables detection of gp330 specific autoantibodies and helper, cytotoxic or suppressor T-cells. The invention permits identification of patients who may develop idiopathic autoimmune membranous glomerulonephritis and patients susceptible to autoimmune membranous glomerulonephritis following a renal allograft.

Human gp330 is useful for treatment of human membranous glomerulonephritis according to a variety of methods, For example, gp330 may be coupled to a polyphenol followed by immunization of a patient according to U.S. Pat. No. 4,702,907, the entire contents of which are incorporated herein by reference. Treatment in this manner results in selective immunosupression of antibodies specific for gp330. As an alternative method of treatment, it is also possible to selectively remove gp330-reactive autoantibodies from sera by immobilizing gp330, or fragment thereof, on a solid support and pass the sera over the support, thereby effectively removing autoantibodies characteristic of human membranous glomerulonephritis. Alternatively, human gp330, or a fragment thereof, can be directly administered to a patient in order to perturb formation of immune complexes. Synthetic peptides based on the sequence of human gp330 are also useful therapetically. Administration of immunogenic peptides inhibits activation or function of gp330 specific helper and cytotoxic T-cells.

The structure of human gp330 includes 16 growth factor repeats separated by 8 YWTD spacer regions and 1 epidermal growth factor repeat in the immediate extracellular juxtamembrane region (FIG. 11). Therefore, administration of gp330, or a fragment thereof having growth factor activity, is useful in the treatment of wounds, such as burns and abrasions. Epidermal growth factor is also a potent inhibitor of gastric acid secretion. Therefore, gp330, or a fragment thereof having epidermal growth factor activity, is useful for treatment or prevention of gastric ulcers. Determination of effective amounts of therapeutic agent for administration is within the skill of the practitioner.

A further object of this invention is a method for treating disorders of the central nervous system characterized by amyloid beta protein accumulation. Human gp330 mediates the cellular uptake and transport of amyloid beta protein at the blood-brain barrier and blood cerebrospinal fluid barriers (71). This process is inhibited by proteins capable of binding gp330. Selective inhibition of gp330 expression or function in cells at the cerebrovascular endothelium and/or choroid epithelium will serve to slow or halt the accumulation of amyloid beta protein, such as in senile plaques, a hallmark of Alzheimer disease. This invention provides several embodiments for specifically inhibiting gp330 activity at selected tissues in a patient suffering from abnormal amyloid beta protein accumulation.

As a first embodiment, gp330 expression is inhibited by nucleic acids comprising a sequence complementary to the sequence encoding human gp330 and down-regulating or blocking expression of gp330. A preferred embodiment comprises an antisense polynucleotide molecule. Preparation and use of antisense polynucleotides, DNA encoding antisense RNA molecules and use of oligo and genetic antisense is disclosed in WO 92/15680, the entire contents of which are incorporated herein by reference.

Antisense nucleic acids of the invention are preferably RNA capable of specifically hybridizing with all or part of the sequence selected from the group consisting of SEQ ID No. 3, SEQ ID No. 11, SEQ ID No. 83, SEQ ID No. 85, SEQ ID No. 87, and SEQ ID No. 89 or the corresponding messenger RNA. The antisense sequence of the present invention may be derived from DNA sequences whose expression in the cell produces RNA complementary to all or part of human gp330 mRNA. These antisense sequences can be prepared by expression of all or part of the sequence selected from the group consisting of SEQ ID No. 3, SEQ ID No. 11, SEQ ID No. 83, SEQ ID No. 85, SEQ ID No. 87, and SEQ ID No. 89 in the opposite orientation (EP 140 308). Any length of the antisense sequence is suitable for practice of the invention so long as it is capable of down-regulating or blocking expression of gp330. Preferably, the antisense sequence is at least 20 nucleotides in length.

In another aspect of this preferred embodiment the nucleic acid encodes antisense RNA molecules. In this embodiment, the nucleic acid is operably linked to signals enabling expression of the nucleic acid sequence and is introduced into a cell utilizing, preferably, recombinant vector constructs, which will express the antisense nucleic acid once the vector is introduced into the cell. Examples of suitable vectors includes plasmids, adenoviruses, adeno-associated viruses, retroviruses, and herpes viruses. Preferably, the vector is an adenovirus. Most preferably, the vector is a replication defective adenovirus comprising a deletion in the E1 and/or E3 regions of the virus. Examples of viruses capable of infecting cells of the central nervous system are disclosed in WO 94/08026, the entire contents of which are incorporated herein by reference.

Suitable expression signals include transcriptional promoter and termination sequences. Among the promoter sequences useful for practice of this invention are tetracycline-regulated transcriptional modulators and CMV, SV-40, E1a, MLP, and LTR promoters. Tetracycline-regulated transcriptional modulators and CMV promoters are described in WO 96/01313, U.S. Pat. No. 5,168,062 and 5,385,839, the entire contents of which are incorporated herein by reference.

The nucleic acid constructs of this invention are capable of down-regulating or blocking expression of human gp330, and are delivered, in a preferred aspect of the invention, locally to cells of the central nervous system. Alternatively, the nucleic acid is delivered stereotaxically to specific sites in the brain. WO 94/08026 discloses methods for localized delivery of replication defective adenoviruses to specific cells of the central nervous system, including stereotaxic delivery to sites in the brain.

A second embodiment of the present invention's method of specifically inhibiting human gp330 activity at selected sites, comprises inhibiting gp330 function by expression of a nucleic acid sequence encoding an intracellular binding protein capable of selectively interacting with gp330 within a transfected cell. WO 94/29446 and WO 94/02610, the entire contents of which are incorporated herein by reference, disclose cellular transfection with genes encoding an intracellular binding protein. An intracellular binding protein includes any protein capable of selectively interacting, or binding, with human gp330 in the cell in which it is expressed and of neutralizing the function of bound human gp330. Preferably, the intracellular binding protein is an antibody or a fragment of an antibody. More preferably, the antibody or fragment thereof binds the cytoplasmic domain of gp330. Most preferably, the intracellular binding protein is a single chain antibody capable of inhibiting cellular uptake and transport of amyloid beta protein at the blood-brain barrier and blood cerebrospinal fluid barriers by binding the cytoplasmic domain of gp330.

WO 94/02610 discloses preparation of antibodies and identification of the nucleic acid encoding a particular antibody. Using gp330 or a fragment thereof, a monoclonal antibody specific for the cytoplasmic domain is prepared by according to techniques known to those skilled in the art. A vector comprising the nucleic acid encoding an intracellular binding protein, or a portion thereof, and capable of expression in a host cell is subsequently prepared for use in the method of this invention. Suitable vectors and methods of delivering nucleic acids encoding intracellular binding proteins to cells containing gp330 include those discussed above for delivery of antisense nucleic acids.

In a preferred aspect of this second embodiment, the nucleic acid sequence encoding a gp330 intracellular binding protein additionally comprises a sequence encoding a localization signal for targeting the intracellular binding protein to the cellular location of gp330 and/or a sequence enabling insertion of the intracellular binding protein in the plasma membrane. The localization signal or insertion sequence can be located anywhere on the intracellular binding protein, so long as it does not interfere with binding to gp330. Examples of localization signals are disclosed in WO 94/02610. Preferably, the localization signal targets the intracellular binding protein to the plasma membrane.

Discussion

The important role of the parathyroid as key regulator of the calcium homeostasis has been related to its exquisite capacity to sense and respond to variation in the extracellular $Ca^{2+}$ ion concentration. Essential for recognition of changes in external calcium is a cation receptor or sensor of the parathyroid cell membrane, the presence of which was implicated by a series of in vitro studies on parathyroid cell regulation (9, 10, 21–24). The concept of a cell membrane receptor was further substantiated when monoclinal antiparathyroid antibodies were found to recognize and interfere with the calcium sensing of parathyroid cells (1–6). Another crucial piece of evidence was obtained when cytotrophoblast cells of the human placenta, selected by their reactivity with the antiparathyroid antibodies, displayed parathyroid-like sensing of changes in external calcium, a function which also could be blocked by one of the anti-parathyroid antibodies (7,8). The calcium sensor of the placenta was subsequently isolated by immunosorbent and ion exchange chromatographies and shown to consist of a large glycoprotein of approximately 500 kDa molecular size (7). It was also demonstrated by irmunoprecipitation that a protein of the same size reacted with the antiparathyroid antibodies within the parathyroid and kidney tubule cells (to be published, (25).

The parathyroid calcium sensor or receptor is known to have features in common with most other classical receptors for cellular activation, although it exhibits the unusual ability to bind and be activated by divalent cations. Cation binding triggers biphasic rise in $[Ca^{2+}i]$ and concomittant activation of phospholipase C, possibly via a coupled G-protein, with a resulting accumulation of inositol phosphates (2,5,9,10). An initial transient rise in $[Ca^{2+}i]$ is due to inositoltrisphosphate (Ip3)induced mobilization of $Ca^{2+}$ from intracellular sources, while an ensuing steady-state elevation in [$Ca^{2+}i$] is caused by calcium gating through plasma membrane channels, possibly mediated by increase in inositol-tetraphosphate (Ip4) (9,10,23).

Sequence analysis of a partial cDNA clone and data-base comparison of the deduced amino acid sequence showed that the placental calcium sensor protein belongs to the LDL-receptor superfamily of proteins, and available sequences showed close similarity with the rat Heymann nephritis antigen (11,15,16). This antigen was originally described in the rat as a 330 kDa glycoprotein (gp 330), present within the proximal kidney tubule brush border, and in placental and epididymal cells, but by special staining techniques also demonstrated to occur sparsely on rat kidney glomerular cells, as well as on pneumocytes II in the lung and sporadic cells of the liver and small intestine (17–19). It has later been proposed that the molecular size of the protein was underestimated and actually should be in the range of 500 kDa (20). The Heymann antigen has been revealed as the dominating antigen causing membranous, autoimmune glomerulonephritis in the rat after immunization with a crude tubular protein fraction (17,19). Using anti-gp 330 antibodies a protein with an estimated molecular size larger than 400 kDa has been identified in man (20). The sequence identity of 77% between the human placental 500 kDa calcium sensor protein and the rat Heymann nephritis antigen indicates that they represent related forms of the calcium sensor protein in two different species. This view is supported by close similarities in tissue distribution of the two proteins, as revealed by the immunohistochemistry of the present study. The antibodies E11 and G11, reacting with the calcium sensor protein, thus stain parathyroid cells, proximal kidney tubule cells, placental cytotrophoblasts and also epididymal cells. Furthermore, we have recently reported staining with one of the antiparathyroid antibodies preferentially within coated pits and the base of the proximal tubule microvilli, which equals that previously described with antibodies against the gp 330 protein (19,26). A recognized glycoprotein of similar size within the tubule brush border, renal maltase, has been located mainly to microvillar membranes and not within the coated invaginations (18).

Thus far recognized members of the LDL-receptor superfamily, the LDL-receptor, the LDL-receptor-related protein and the Heymann antigen, have been thought to function as receptors for proteins, but all exhibit functionally important $Ca^{2+}$-binding ability (16,27,28). Thus, $Ca^{2+}$ binding is necessary for the interaction of the LDL-receptor with apo-B (27). The LDL-receptor related protein ($\alpha_2$-macroglobulin receptor) is also known to bind $Ca^{2+}$, which induces conformational changes, and $Ca^{2+}$ is necessary for binding of activated $\alpha_2$-macroglobulin to the receptor (16). Recently, the rat Heymann antigen was shown by a blotting technique to interact with $Ca^{2+}$ (28).

The $Ca^{2+}$ binding motifs of the calcium sensor protein remain to be identified. The sensor protein (as well as the Heymann antigen) contains EGF-like modules, like other members of the LDL-receptor superfamily (11,16,27), which may represent putative $Ca^{2+}$ binding sites. Thus, when present in the coagulation factors IX, X and protein C, each EGF-like module is known to bind one $Ca^{2+}$ ion (29–34), and the EGF-like modules have also been demonstrated to mediate $Ca^{2+}$ dependent protein/protein interaction (35). Kinetic data have suggested that the calcium sensor displays positive cooperativity in its interaction with $Ca^{2+}$, a phenomenon which appears essential for the sigmoidal regulation of [$Ca^{2+}i$] and PTH release, with a steep relation within the physiological range of extracellular calcium (9,10). The positive cooperativity should require multiple binding sites for $Ca^{2+}$, possibly resulting from the repetitive EGF-like modules, generally present in molecules of the LDL-receptor superfamily (11,16,27). However, $Ca^{2+}$ binding to EGF-like domains are known to induce only minor, localized pertubations of the three-dimensional structure (32), and it is possible that the calcium sensor contains also other $Ca^{2+}$ binding sites.

A 43 kDa membrane protein ($\alpha_2$-macroglobulin receptor-associated protein, or Heparin-binding protein) (28,36) is known to interact both with the LDL-receptor-related protein and with the rat Heymann antigen in a $Ca^{2+}$ dependent manner (28). No physiological function has yet been assigned to this protein, but it appears also in tissues where the Heymann antigen and the LDL-receptorrelated proteins are not expressed (28). An intriguing observation is the presence of a putative leucine-zipper motif in the aminoterminal part of the 43 kDa protein (36), considering that such motifs have been suggested to influence the opening and closure of membrane ion channels (37). Since the 43 kDa protein interacts with the Heymann antigen, it can be assumed to form a complex also with the calcium sensor protein in a $Ca^{2+-}$ dependent manner. Interaction with the 43 kDa protein might be important for the transmission of $Ca^{2+}$ induced conformational changes within the extracellular portion of the molecule to the cell interior. It is also possible that additional proteins interact with the calcium sensor in a $Ca^{2+}$ dependent manner, and that such an interaction is important for the modulation of the sensor response. The mechanisms by which an activated calcium sensor triggers further signalling to the cell interior is unknown, although we have in preliminary experiments utilized immunoprecipitation to isolate a phosphorylated form of the sensor protein in dispersed parathyroid cells loaded with [$^{32}p$]-orthophosphate (unpublished observation).

The calcium sensor protein of the placenta may be involved in maintenance of a feto-maternal $Ca^{2+}$ gradient and placental $Ca^{2+}$ transport, possibly by mediating calcium regulation of the parathyroid hormone related peptide (PTHrP) production and/or 1,25 $(OH)_2D_3$ metabolism (8). Its presence already within the blastocyst (unpublished observation) may indicate a function also as adhesion molecule, or implicate involvement in differentiation or growth regulation, as suggested for the Heymann antigen (38). The function of a calcium sensor within the kidney tubule brush border is less well explored. However, it should be noted that the enzyme 1-$\alpha$-hydroxylase present in the placenta and proximal kidney tubule, is regulated by extracellular calcium, and the calcium sensor might accordingly regulate 1,25 $(OH)_2D_3$ metabolism, but it may possibly also influence $Ca^{2+}$ reabsorption from the glomerular filtrate (7–9). The significance of the presence of the calcium sensor protein on epididymal cells, as well as rat pneumocytes, liver and intestinal cells as implicated by the distribution of the Heymann antigen (18,19), yet remains unknown. It has, however, been proposed that several cell types may exhibit $Ca^{2+}$ sensing ability for regulation of various functions, separate from the general calcium homeostasis, either during development or in the differentiated state (10).

The association with autoimmune nephritis substantiates that the Heymann antigen is an immunogen molecule. This may have implication also in parathyroid disorder, as we have recently reported the presence of circulating parathyroid autoantibodies and induction of class II transplantation antigen in the pathological parathyroid tissue of patients with primary HPT. These findings suggested that autoimmune phenomena may be involved in HPT (39) and autoimmunity has also been implicated in the pathogenesis of rare idiopathic hypoparathyroidism (10). The availability of cDNA clones for the calcium sensor should, enable extended studies on the pathophysiology in parathyroid disorder, and also in vestigation of a possible genetic abberration affecting the calcium sensing function of the parathyroid and kidney tubule in kindreds with familial hypocalciuric hypercalcemia (FHH) (40,41).

The skilled person within this art realizes that the information obtainable from the nucleotide sequences of SEQ ID No. 3, SEQ ID No. 11, SEQ ID No. 83, SEQ ID No. 85, SEQ ID No. 87, and SEQ ID No. 89 can be used for isolating the genomic sequence encoding the calcium sensor. Preferably, an analysis of overlapping cDNA clones in conjunction with PCR techniques is used. The genomic sequence can be obtained from the analysis of overlapping genomic cosmid and/or lambda phage clones.

References

1. Juhlin, C., Holmdahl, R., Johansson, H., Rastad, J., Akerström, G., Klareskog, L., (1987) Proc. Natl. Acad. Sci. USA. 84, 2990–2994.

2. Juhlin, C., Johansson, H., Holmdahl, R., Gylfe, E., Larsson, R., Rastad, J., Akerström, G., Klareskog, L., (1987) Biochem. Biophys. Res. Commun. 143, 570–574.

3. Juhlin, C., Klareskog, L., Nygren, P., Gylfe, E., Ljunghall, S., Rastad, J., Akerström, G., (1988) Endocrinol. 122, 2999–3001.

4. Juhlin, C., Akerström, G., Klareskog, L., Gylfe, E., Holmdahl, R., Johansson, H., Ljunghall, S., Larsson, R., Nygren, P., Rastad, J., (1988) World. J. Surg. 12, 552–558.

5. Gylfe, E., Juhlin, C., Akerstr6m, G., Klareskog, L., Rask, L., Rastad, J., (1990) Cell Calcium. 11, 329–332.

6. Juhlin, C., Rastad, J., Klareskog, L., Grimelius, L., Akerström, G., (1989) Am. J. Pathol. 135, 321–328.

7. Juhlin, C., Lundgren, S., Johansson, H., Lorenzon, J., Rask, L., Larsson, E., Rastad, J., Akerström, G., Klareskog, L., (1990) J. Biol. Chem. 265, 8275–8279.

8. Hellman, P., Ridefelt, P., Juhlin, C., Akerström, G., Rastad, J., Gylfe, E., (1992) Arch. Biochem. Ciophys. 293, 174–180.

9. Akerström, G., Rastad, J., Ljunghall, S., Ridefelt, P., Juhlin, C., Gylfe, E., (1991) World. J. Surg. 15, 672–680.

10. Brown, E. M., (1991) Phys. Rev. 71, 371–411.

11. Raychowdury, R., Niles, J. L., Mc Cluskey, R. T., Smith, J. A., (1989) Science, 244, 1163–1165.

12. Denhardt, D. T., (1966) Biochem. Biophys. Res. Commun. 23, 641–646.

13. Pearson, W. R., Lipman, D. J., (1988) Proc. Natl. Acad. Sci. USA. 85, 2444–2448.

14. Holmdahl, R., Rubin, K., Klareskog, L., Larsson, E., Wigzell, H., (1986) Arthritis. Rheum. 29, 400–410.

15. Yamamoto, T., Davis, C. G., Brown, M. S., Schneider, W. J., Casey, M. L., Goldstein, J. L., Russel, D. W., (1984) Cell. 39, 27–38.

16. Herz, J., Haman, U., Rogne, S., Myklebost, O., Gausepohl, H., Stanley, K. K., (1988) EMBO. J. 7, 4119–4127.

17. Chatelet, F., Brianti, E., Ronco, P., Roland, J., Verroust, P., (1986) Am. J. Pathol. 122, 500–511.

18. Chatelet, F., Brianti, E., Ronco, P., Roland, J., Verroust, P., (1986) Am. J. Pathol. 122, 512–519.

19. Kerjaschki, D., Farquhar, M. G., (1984) in Nephrology ed Robinsson R.R., New York Springer-Verlag pp 560–574.

20. Kerjaschki, D., Horvat, R., Binder, S., Susani, M., Dekan, G., Ojha, P. P., Hillermans, P., Ulrich, W., Doninn, U., (1987) Am. J. Pathol. 129, 183–191.

21. Wallfelt, C., Larsson, R., Johansson, H., Rastad, J., Akerström, G., Ljunghall, S., Gylfe, E., (1985) Acta. Physiol. Scand. 124, 239–245.

22. Gylfe, E., Larsson, R., Johansson, H., Nygren, P., Rastad, J., Wallfelt, C., Akerström, G.,(1986) Febs. lett. 205, 132–136.

23. Nemeth, E., Scarpa, A., (1987) J. Biol. Chem. 262, 5188–5196.

24. Gylfe, E., Akerström, G., Juhlin, C., Klareskog, L., Rastad, J., (1990) In: Hormones and Cell Regulation. Eds: Dumont, J. E., Nunez, J., King, R. J. B., John Libhey Eurotext Ltd., London pp 5–15. 25.Lundgren, S., Juhlin, C., Rastad, J., Klareskog, L., Akerström, G., Rask, L., Submitted.

26. Bjerneroth, G., Juhlin, C., Akerström, G., Rastad, J., (1992) J. Submicrosc.Cytol. Pathol. 24, 179–186.

27. Brown, M. S., Goldstein, J. L., (1986) Science. 232, 34–47. 28.Christensen, E. J., Glieman, J., Moestrup, S. K., (1992) J. Histochem. Cytochem.40, 1481–1490.

29. Handford, P. A., Baron, M., Mayhew, M., Willis, A., Beasly, T., Brownlee, G. G., Campbell, I. D., (1990) EMBO J. 9, 475–480.

30. Huang, L. H., Ke, X-H., Sweeny, W., Tam, I. P., (1989) Biochem. Biophys. Res. Commun. 160, 133–139.

31. Persson, E., Selander, M., Linse, S., Drakenberg, T., Ohlin, A. K., Stenflo,J., (1989) J. Biol. Chem. 264, 16897–16904.

32. Ohlin, A. K., Linse, S., Stenflo, J., (1988) J. Biol. Chem. 263, 7411–7417.Urukawa, T., 33.Öhlin, A. K., Landes, G., Bourdan, P., Oppenheimer, C., Wydro, L., Stenflo, J., (1988) J. Biol. Chem. 263, 19240–19248.

34. Selander - Sunnerhagen, M., Ullner, M., Persson, C., Teleman, O., Stenflo, J., Drakenberg, T., (1992) J. Biol. Chem. 267, 19642–19649.

35. Rebay, I., Fleming, R. J., Felion, R. G., Cherbas, L., Cherbas, P., Artavanis -Tsakonas, S., (1991) Cell. 67, 687–699.

36. Furukawa,T., Ozawa, M., Hvang, R. P., Muramatsu, T., (1990) J. Biochem. 108, 297–302.

37. McCormack, K., Campanelli, I. T., Ramaswami, M., Mathew M. K., Tanoye, M. A., Iverson, L.E., Rudy, B., (1989) Nature. 340, 103.

38. Mendrick, D. L., Chung, D. C., Remcke, H. G., (1990) Exp. Cell. Research. 188, 23–25.

39. Bjerneroth, G., (1992) Comprehensive summaries of Uppsala Disertations from the Faculty of Medicine 360, ISBN. 91–54–2928–9.

40. Marx, S.J., Attie, M. F., Levine, M. A., Spiegel, A. M., Downs, R. W., Lasker, R. D., (1981) Medicine 60, 397–412.

41. Choo, Y-H. W., Brown, E. H., Levi, T., Crowe, G. B., Atkinson, A. B., Arnqvist, H. J., Toss, G., Fuleihan, G. E-H., Seidman, J. G., Seidman, C. E., (1992) Nature Genetics. 1, 298–300.

42. Cantley, L. C., Auger, K. R>, Carpenter, C., Duckworth, B., Graziani, A., Kapeller, R., Íoltoff, S., (1991) Cell 64, 281–302

43. Koch, C. A., Anderson, D., Moran, M.F., Elllis, C., Pawson, T. (1991) Science 252, 668–74

44. Mayer, B. J., Hamagucchi, M., Hanafusa, H. (1088) Nature 332, 272–275

45. Musacchio, A., Gibson, T., Lehto, V. P., Saraste, M. (1992) Febs Lett 307, 55–61

46. Clark, S. G., Stern, M. J., Horvitz, H. R. (1992) Nature 356, 340–4

47. Lowenstein, E. J., Daly, R. J., Batzer, A. G., Li, W., Margolis, B., Lammers, R., Ullrich, A., Skolnik, E. Y., Bar-Sagi, D., Schlessinger, J. (1992) *Cell* 70, 431–42

48. Chardin, P., Camonis, J. H., Gale, N. W., van Aelst, L., Schlessinger, J., Wigler, M.H., Bar-Sagi, D. (1993) *Science* 260, 1338–43

49. Olivier, J. P., Raabe, T., Henkemeyer, M., Dickson, B., Mbamalu, G., Margolis, B., Schlessinger, J., Hafen, E., Pawson, T. (1993) *Cell* 73, 179–91

50. Rozakis-Adcock, M., Fernley, R., Wade, J., Pawson, T., Bowtell, D. (1993) Nature 363, 83–5

51. Sambrook, J., Fritsch, E. F., Maniatis, T. (1989) *Molecular Cloning: A Laboratory Manual* (Cold Spring Harbor Lab. Press, Plainview, N.Y.).

52. Lundgren, S., Hjalm, G., Hellman, P., Juhlin, C., Rastad, J., Klareskog, L., Akerstrom, G., Rask, L. (1994) *Experimental Cell Research* 212, 001–07

53. Yu, H., Chen, J. K., Feng, S., Dalgarno, D. C., Brauer, A. W., Schreiber, S. L. (1994) *Cell* 76, 933–945

54. Stephens, L. R., Jackson, T. r., Hawkins, P. T. (1993) *Biochimica et Biophysica Acta* 1179, 27–75

55. Dhand, R., Hiles, I., Panayotou, G., Roche, S., Fry, M. J., Gout, I., Totty, NF., Truong, O., Vicendo, P., Yonezawa, K., Kasuga, M., Courtneidge, S. A., Waterfield, M. D. (1994) *The EMBO Journal* 13,(3), 522–533

56. Marshall, I. C. B., Taylor, C. W. (1993) *J. Exp. Biol.* 184, 161–182

57. Prasad, K. V., Janssen, O., Kapeller, R., Raab, M., Cantley, L. C., Rudd, C. E. (1993) *Proc. Natl. Acad. Sci. U.S.A.* 90, 7366–7370

58. Wasenius, V. M., Merilainen, J., Lehto, V. P. (1993) Gene 134, 299–300

59. Trahey, M., Wong, G., Halenbeck, R., Rubinfeld, B., Martin, G. A., Ladner, M., Long, C. M., Crosier, W. J., Watt, K., Koths, K., McCormick F. (1988) *Science* 242, 1697–1700

60. Hsieh, C. L., Vogel, U. S., Dixon, R. A., Francke, U. (1989) *Somat. Cell Mol. Genet.* 15, 579–90

61. Kenney, R. T., Leto, T. L. (1990) *Nucleic Acids Res* 18, 7193

62. Francke, U., Hsieh, C. L., Foellmer, B. E., Lomax, K. J., Malech, H. L. Leto, T. L. (1990) *Am J Hum Genet* 47, 483,492

63. Songyang, Z., Shoelson, S. E., Chaudhuri, M., Gish, G., Pawson, T., Haser, W. G., King, F., Roberts, T., Ratnofsky, S., Lechleider, R. J., Neel, B. G.,. Birge, R. B., Fajardo, J. E., Chou, M. M., Hanafusa, H. Schaffhausen, B., Cantley, L. C. (1993) *Cell* 72, 767–778

64. Brown, E. M. (1991) *Physiological Reviews* 71(2), 371–411

65. Brown, E. M. (1993) *Current Opinion in Nephrology and hypertension* 2 541–551

66. Juhlin, C., Akerström, G., Klareskog, L., Gylfe, E., Johansson, H., Larsson, R., Ljunghall, S., Nygren, P., Rastad, J. (1988) *World J. Surg.* 12, 552–558

67. Saito, A., Pietromonaco, S., Loo, A., Farquhar, M. (1994) *Proc. Natl. Acad. Sci. USA* 91, 9725–9729.

68. Farquhar, M. et al. (1994) *Ann. NY Acad. Sci.* 737, 96–113.

69. Kounnas, M. et al. (1994) *Ann. NY Acad. Sci.* 737, 114–123.

70. Moestrup, S. et al. (1994) *Ann. NY Acad. Sci.* 737, 124–137.

71. Zlokovic, B. et al. (1996) *Proc. Natl. Acad. Sci.* 93(9), 4229–4234.

What is claimed is:

1. A method of identifying a compound that either blocks or enhances the activity of human gp330, comprising:
   (A) expressing in a heterologous host cell a nucleic acid encoding a protein comprising an amino acid sequence selected from the group consisting of SEQ ID No. 4, SEQ ID No. 12, SEQ ID No.84, SEQ ID No.86, SEQ ID No.88, and SEQ ID No. 90;
   (B) contacting the compound with said host cell; and
   (C) determining the ability of said compound to block or enhance the activity of said gp330.

2. The method of claim 1, wherein said activity is uptake and transport of amyloid protein.

* * * * *